US009630922B2

(12) United States Patent
Ng et al.

(10) Patent No.: US 9,630,922 B2
(45) Date of Patent: Apr. 25, 2017

(54) 3-SPIRO-7-HYDROXAMIC ACID TETRALINS AS HDAC INHIBITORS

(71) Applicant: Forma Therapeutics, Inc., Watertown, MA (US)

(72) Inventors: Pui Yee Ng, Waltham, MA (US); Heather Davis, Haverhill, MA (US); Kenneth W. Bair, Wellesley, MA (US); David S. Millan, Watertown, MA (US); Aleksandra Rudnitskaya, Roslindale, MA (US); Xiaozhang Zheng, Lexington, MA (US); Bingsong Han, North Haven, CT (US); Nicholas Barczak, Waterford, CT (US); David R. Lancia, Jr., Boston, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 15/130,613

(22) Filed: Apr. 15, 2016

(65) Prior Publication Data

US 2016/0304462 A1    Oct. 20, 2016

Related U.S. Application Data

(60) Provisional application No. 62/149,360, filed on Apr. 17, 2015.

(51) Int. Cl.
| | | |
|---|---|---|
| *C07D 221/20* | (2006.01) | |
| *C07D 403/04* | (2006.01) | |
| *C07D 209/96* | (2006.01) | |
| *C07D 401/04* | (2006.01) | |
| *C07D 417/06* | (2006.01) | |
| *C07D 519/00* | (2006.01) | |
| *C07D 401/06* | (2006.01) | |
| *C07D 413/06* | (2006.01) | |
| *C07D 405/04* | (2006.01) | |
| *C07D 471/04* | (2006.01) | |
| *C07D 497/10* | (2006.01) | |
| *C07D 491/107* | (2006.01) | |
| *C07D 405/06* | (2006.01) | |
| *C07D 403/06* | (2006.01) | |
| *C07D 405/10* | (2006.01) | |

(52) U.S. Cl.
CPC ......... *C07D 209/96* (2013.01); *C07D 221/20* (2013.01); *C07D 401/04* (2013.01); *C07D 401/06* (2013.01); *C07D 403/04* (2013.01); *C07D 403/06* (2013.01); *C07D 405/04* (2013.01); *C07D 405/06* (2013.01); *C07D 405/10* (2013.01); *C07D 413/06* (2013.01); *C07D 417/06* (2013.01); *C07D 471/04* (2013.01); *C07D 491/107* (2013.01); *C07D 497/10* (2013.01); *C07D 519/00* (2013.01)

(58) Field of Classification Search
None
See application file for complete search history.

(56) References Cited

U.S. PATENT DOCUMENTS

| 6,992,077 B2 | 1/2006 | Radeke et al. |
| 7,951,795 B2 | 5/2011 | Bell et al. |
| 8,658,641 B2 | 2/2014 | Barvian et al. |

FOREIGN PATENT DOCUMENTS

| WO | WO 2009/127609 | 10/2009 |
| WO | WO 2010/042475 | 4/2010 |
| WO | WO 2011/045265 | 4/2011 |
| WO | WO 2012/088015 | 6/2012 |
| WO | WO 2012/117421 | 9/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Benedetti R, Conte M, Altucci L. "Targeting Histone Deacetylases in Diseases: Where Are We?" *Antioxidants & Redox Signaling*, 23(1), pp. 99-126, 2015.
Dallavalle S, Pisano C, Zunino F. "Development and therapeutic impact of HDAC6-selective inhibitors",*Biochemical Pharmacology*, Sep. 15, 2012; 84(6):756-65.
Kalin JH, Bergman JA. "Development and therapeutic implications of selective histone deacetylase 6 inhibitors", *J Med Chem.* Aug. 22, 2013; 56(16):6297-313.
Tang J, Yan H, Zhuang S. "Histone deacetylases as targets for treatment of multiple diseases", *Clinical Science* (Lond), Jun. 2013; 124(11):651-62.
Varasi, Mario et al. "Discovery, Synthesis, and Pharmacological Evaluation of Spiropiperidine Hydroxamic Acid Based Derivatives as Structurally Novel Histone Deacetylase (HDAC) Inhibitors", *Journal of Medicinal Chemistry*, vol. 54, No. 8, 2011, p. 3051-3064.
West AC, Johnstone RW, "New and emerging HDAC inhibitors for cancer treatment", *Journal of Clinical Investigation*, Jan. 2, 2014; 124(1):30-9.

* cited by examiner

*Primary Examiner* — Kristin Vajda
(74) *Attorney, Agent, or Firm* — Cooley LLP; J. Dean Farmer; Serge Banini

(57) ABSTRACT

The present invention is directed to inhibitors of histone deacetylases (HDACs) such as HDAC6, and their use in the treatment of diseases such as cell proliferative diseases (e.g., cancer), neurological (e.g., neurodegenerative disease or neurodevelopmental disease), inflammatory or autoimmune disease, infection, metabolic disease, hematologic disease, or cardiovascular disease.

33 Claims, 1 Drawing Sheet

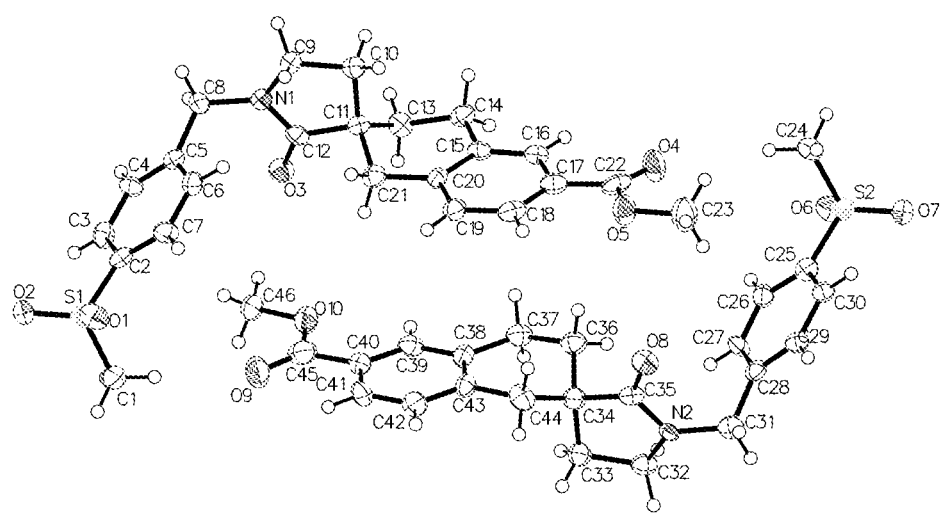

3-SPIRO-7-HYDROXAMIC ACID TETRALINS AS HDAC INHIBITORS

CROSS-REFERENCE TO RELATED APPLICATIONS

This application claims the benefit of priority of U.S. Provisional Application No. 62/149,360, filed Apr. 17, 2015, the contents of which are hereby incorporated by reference.

FIELD OF THE INVENTION

The present invention relates to inhibitors of zinc-dependent histone deacetylases (HDACs) useful in the treatment of diseases or disorders associated with HDACs including cell proliferation diseases (e.g., cancer), neurological and inflammatory diseases. Specifically, this invention is concerned with compounds and compositions inhibiting HDACs, methods of treating diseases associated with HDACs, and methods of synthesizing these compounds.

BACKGROUND OF THE INVENTION

Many members of the HDAC family require zinc (Zn) to function properly. For instance, the isozyme histone deacetylase 6 (HDAC6) is a zinc-dependent histone deacetylase that possesses histone deacetylase activity. Other family members include HDACs 1-5 and 7-11. (De Ruijter et al, *Biochem. J.* 2003. 370; 737-749).

HDAC6 is known to deacetylate and associate with α-tubulin, cortactin, heat shock protein 90, β-catenin, glucose-regulated protein 78 kDa, myosin heavy chain 9, heat shock cognate protein 70, and dnaJ homolog subfamily A member 1 (reviewed in Li et al, *FEBS J.* 2013, 280: 775-93; Zhang et al, *Protein Cell.* 2015, 6(1): 42-54). Diseases in which HDAC6 inhibition could have a potential benefit include cancer (reviewed in Aldana-Masangkay et al, *J. Biomed. Biotechnol.* 2011, 875824), specifically: multiple myeloma (Hideshima et al, *Proc. Natl. Acad. Sci. USA* 2005, 102(24):8567-8572); lung cancer (Kamemura et al, *Biochem. Biophys. Res. Commun.* 2008, 374(1):84-89); ovarian cancer (Bazzaro et al, *Clin. Cancer Res.* 2008, 14(22):7340-7347); breast cancer (Lee et al, *Cancer Res.* 2008, 68(18): 7561-7569; Park et al, *Oncol. Rep.* 2011, 25: 1677-81; Rey et al, *Eur. J. Cell Biol.* 2011, 90: 128-35); prostate cancer (Seidel et al, *Biochem. Pharmacol.* 2015 (15)00714-5); pancreatic cancer (Nawrocki et al, *Cancer Res.* 2006, 66(7): 3773-3781); renal cancer (Cha et al, *Clin. Cancer Res.* 2009, 15(3): 840-850); hepatocellular cancer (Ding et al, *FEBS Lett.* 2013, 587:880-6; Kanno et al, *Oncol. Rep.* 2012, 28: 867-73); lymphomas (Ding et al, *Cancer Cell Int.* 2014, 14:139; Amengual et al, *Clin Cancer Res.* 2015, 21(20): 4663-75); and leukemias such as acute myeloid leukemia (AML) (Fiskus et al, *Blood* 2008, 112(7):2896-2905) and acute lymphoblastic leukemia (ALL) (Rodriguez-Gonzalez et al, *Blood* 2008, 112(11): Abstract 1923)).

Inhibition of HDAC6 may also have a role in cardiovascular disease, including pressure overload, chronic ischemia, and infarction-reperfusion injury (Tannous et al, *Circulation* 2008, 1 17(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Alzheimer's, Parkinson's and Huntington's disease (reviewed in Simoes-Pires et al, *Mol. Neurodegener.* 2013, 8: 7) or central nervous system trauma caused by tissue injury, oxidative-stress induced neuronal or axomal degeneration (Rivieccio et al, *Proc. Natl. Acad. Sci. USA* 2009, 106(46):19599-195604); and inflammation and autoimmune diseases through enhanced T cell-mediated immune tolerance at least in part through effects on regulatory T cells, including rheumatoid arthritis, psoriasis, spondylitis arthritis, psoriatic arthritis, multiple sclerosis, lupus, colitis and graft versus host disease (reviewed in Wang et al, *Nat. Rev. Drug Disc.* 2009 8(12):969-981; Vishwakarma et al, *Int. Immunopharmacol.* 2013, 16:72-8; Kalin et al, *J. Med. Chem.* 2012, 55:639-51); and fibrotic disease, including kidney fibrosis (Choi et al, *Vascul. Pharmacol.* 2015 72:130-140).

Four HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus there is a need for HDAC inhibitors with an improved safety-efficacy profile.

SUMMARY OF THE INVENTION

One aspect of the invention relates to compounds of Formula I:

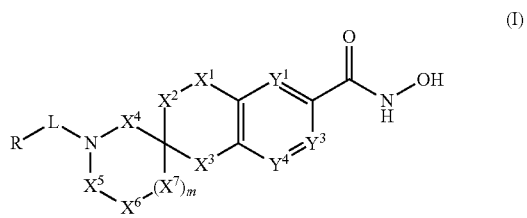

and pharmaceutically acceptable salts, prodrugs, solvates, hydrates, tautomers, or isomers or thereof, wherein:

$X^1$, $X^2$, $X^3$, $X^6$, and $X^7$ are each independently —$CR^1R^2$—, —$NR^3$—, —O—, —C(O)—, —$SO_2$—, —S(O)—, or —S—;

$X^4$ and $X^5$ are each independently —$CR^1R^2$—, —C(O)—, —$SO_2$—, —S(O)—, or —S—;

$Y^1$, $Y^3$ and $Y^4$ are each independently N or $CR^1$;

L is a bond, —$(CR^1R^2)_n$—, —$C(O)NR^3$—, —$S(O)_2$—, —$S(O)_2NR^3$—, —S(O)—, —$S(O)NR^3$—, —$C(O)(CR^1R^2)_nO$—, or —$C(O)(CR^1R^2)_n$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl;

$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, —N(C$_1$-C$_6$alkyl)S(O)$_2$C$_1$-C$_6$alkyl, or (CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^3$, —NHR$^3$, NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ can combine with the carbon atom to which they are both attached to form a cycloalkyl, heterocycle, spirocycle, spiroheterocycle, or spirocycloalkenyl;

or R$^1$ and R$^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, or —(CHR$^5$)$_n$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkly)$_2$, —S(O)$_2$N(C$_1$-C$_6$alkyl)$_2$, —S(O)$_2$NHC$_1$-C$_6$alkyl, —C(O)C$_1$-C$_6$alkyl, —CO$_2$C$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —CO$_2$C$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_n$N(C$_1$-C$_6$alkyl)$_2$;

n is an integer from 0 to 6; and m is 0, 1, 2 or 3.

In another aspect, the invention relates to compounds of Formula II:

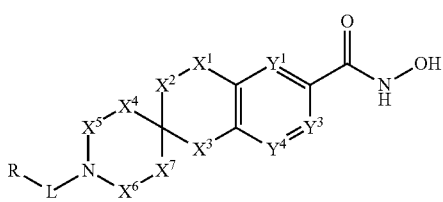

(II)

and pharmaceutically acceptable salts, prodrugs, solvates, hydrates, tautomers or isomers thereof, wherein:

X$^1$ is independently —CR$^1$R$^2$—, —NR$^3$—, —O—, —SO$_2$—, —S(O)—, or —S—;

X$^2$, X$^3$, X$^4$, and X$^7$ are each independently —CR$^1$R$^2$—, —NR$^3$—, —O—, —C(O)—, —SO$_2$—, —S(O)—, or —S—;

X$^5$ and X$^6$ are each independently —CR$^1$R$^2$—, —C(O)—, —SO$_2$—, —S(O)—, or —S—;

Y$^1$, Y$^3$ and Y$^4$ are each independently N or CR$^1$;

L is a bond, —(CR$^1$R$^2$)$_n$—, —C(O)NR$^3$—, —S(O)$_2$—, —S(O)$_2$NR$^3$—, —S(O)—, —S(O)NR$^3$—, —C(O)(CR$^1$R$^2$)$_n$O—, or —C(O)(CR$^1$R$^2$)$_n$—;

R is independently —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —C$_5$-C$_{12}$spirocycle, heterocyclyl, spiroheterocyclyl, aryl, or heteroaryl containing 1-5 heteroatoms selected from the group consisting of N, S, P, or O, wherein each -alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl;

R$^1$ and R$^2$ are independently, and at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P, or O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, —N(C$_1$-C$_6$alkyl)S(O)$_2$C$_1$-C$_6$alkyl, or (CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more substituents selected from —OH, halogen, —NO$_2$, oxo, —CN, —R$^5$, —OR$^3$, —NHR$^3$, NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ can combine with the carbon atom to which they are both attached to form a cycloalkyl, heterocycle, spirocycle, spiroheterocycle, or spirocycloalkenyl;

or R$^1$ and R$^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, or —(CHR$^5$)$_n$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkly)$_2$, —S(O)$_2$N(C$_1$-C$_6$alkyl)$_2$, —S(O)$_2$NHC$_1$-C$_6$alkyl, —C(O)C$_1$-C$_6$alkyl, —CO$_2$C$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

each R$^5$ is independently —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, O and P, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —CO$_2$C$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_n$N(C$_1$-C$_6$alkyl)$_2$; and n is an integer from 0 to 6.

Another aspect of the invention relates to a method of treating a disease or disorder associated with HDAC6 modulation in a subject in need thereof, comprising administering to the subject an effective amount of a compound of Formula I or Formula II.

Another aspect of the invention is directed to a method of inhibiting HDAC6. The method involves administering to a patient in need thereof an effective amount of a compound of Formula I or Formula II.

Another aspect of the invention is directed to pharmaceutical compositions comprising a compound of Formula I or Formula II and a pharmaceutically acceptable carrier. The pharmaceutically acceptable carrier can further include an excipient, diluent, or surfactant. The pharmaceutical composition can be effective for treating a disease or disorder associated with HDAC6 modulation in a subject in need thereof. The pharmaceutical compositions can comprise the compounds of the present invention for use in treating diseases described herein.

The compositions can contain at least one compound of the invention and a pharmaceutically acceptable carrier. The invention also provides the use of the compounds described herein in the manufacture of a medicament for the treatment of a disease associated with HDACs.

The present invention also provides methods for the treatment of human diseases or disorders including, without limitation, oncological, neurological, inflammatory, autoimmune, infectious, metabolic, hematologic, or cardiovascular diseases or disorders.

The present invention also provides compounds that are useful in inhibiting of zinc-dependent HDAC enzymes, and in particular HDAC6. These compounds can also be useful in the treatment of diseases including cancer, The present invention further provides compounds that can inhibit HDAC6. In some embodiments, the efficacy-safety profile of the compounds of the current invention can be improved relative to other known HDAC (e.g. HDAC6) inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Invention, below.

BRIEF DESCRIPTION OF THE DRAWINGS

FIG. 1 shows an X-ray crystal structure of methyl (R)-1'-[(4-methanesulfonylphenyl)methyl]-2'-oxo-3,4-dihydro-1H-spiro[naphthalene-2,3'-pyrrolidine]-6-carboxylate.

DETAILED DESCRIPTION OF THE INVENTION

HDAC6 is a zinc-dependent histone deacetylase that has two catalytic domains. HDAC6 can interact with and deacetylate non-histone proteins, including HSP90 and α-tubulin. Acetylation of HSP90 is associated with loss of function of HSP90. HDAC6 is also implicated in the degradation of misfolded proteins as part of the aggresome. Accordingly, inhibition of HDAC6 can have downstream effects that can play a role in the development of certain diseases such as cancer. The present invention provides inhibitors of HDAC6 and methods for using the same to treat disease.

In a first aspect of the invention, compounds of the Formula I are described:

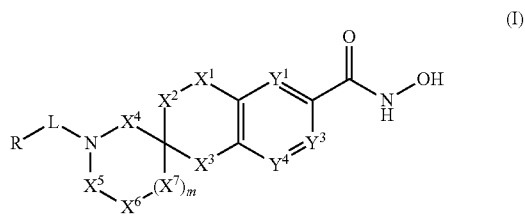

(I)

and pharmaceutically acceptable salts, prodrugs, solvates, hydrates, tautomers, and isomers thereof, wherein m, R, L, X$^1$, X$^2$, X$^3$, X$^4$, X$^5$, X$^6$, X$^7$, Y$^1$, Y$^3$, and Y$^4$ are described as above.

In a second aspect of the invention, compounds of the Formula II are described:

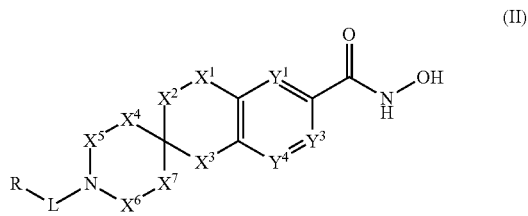

(II)

and pharmaceutically acceptable salts, prodrugs, solvates, hydrates, tautomers, and isomers thereof, wherein R, L, X$^1$, X$^2$, X$^3$, X$^4$, X$^5$, X$^6$, X$^7$, Y$^1$, Y$^3$, and Y$^4$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen.

For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof.

Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, phosphorous nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I or Formula II may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In one embodiments of the compounds of Formula I or Formula II, $X^4$ is —C(O)—.

In one or more embodiments of the compounds of Formula I, m is 0 or 1.

In one or more embodiments of the compounds of Formula I and Formula II, $Y^1$, $Y^3$ and $Y^4$ are each $CR^1$.

In one embodiment of the compound of Formula I, the compound is of the Formula I-a, I-b, I-c, I-d, I-e, I-f, I-g, I-h, I-j, I-k, or I-m:

In one embodiment of the compound of Formula II, the compound is of the Formula II-a, II-b, II-c, II-d or II-e:

-continued

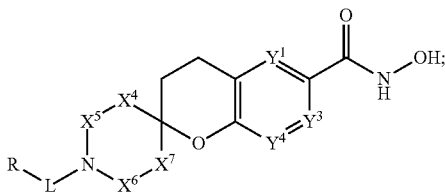
(II-c)

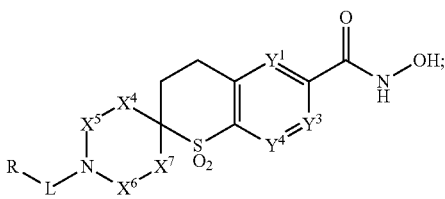
(II-d)

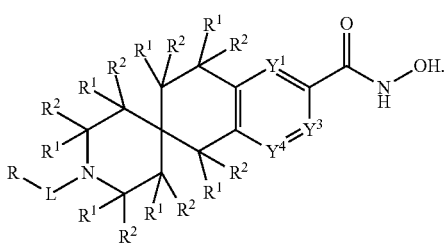
(II-e)

In an illustrative embodiment, a compound of Formula I can be selected from:

1'-((1H-benzo[d]imidazol-2-yl)methyl)-N-hydroxy-3,4-dihydro-1H-spiro[naphthalene-2,3'-pyrrolidine]-6-carboxamide (I-1);
N-hydroxy-1'-(4-methoxyphenethyl)-3,4-dihydro-1H-spiro[naphthalene-2,3'-pyrrolidine]-6-carboxamide (I-2);
N-hydroxy-1'-(4-methoxybenzyl)-3,4-dihydro-1H-spiro[naphthalene-2,3'-pyrrolidine]-6-carboxamide (I-3);
N-hydroxy-1'-(4-methoxyphenethyl)-2'-oxo-3,4-dihydro-1H-spiro[naphthalene-2,3'-pyrrolidine]-6-carboxamide (I-4);
1'-(1H-benzo[d]imidazol-2-yl)-N-hydroxy-2'-oxo-3,4-dihydro-1H-spiro[naphthalene-2,3'-pyrrolidine]-6-carboxamide (I-5);
1'-(3,4-dichlorobenzyl)-N-hydroxy-2'-oxo-3,4-dihydro-1H-spiro[naphthalene-2,3'-pyrrolidine]-6-carboxamide (I-6);
1'-(cyclohexylmethyl)-N-hydroxy-2'-oxo-3,4-dihydro-1H-spiro[naphthalene-2,3'-pyrrolidine]-6-carboxamide (I-7);
N-hydroxy-1'-(4-methylbenzyl)-2'-oxo-3,4-dihydro-1H-spiro[naphthalene-2,3'-pyrrolidine]-6-carboxamide (I-8);
1'-(3-(dimethylamino)propyl)-N-hydroxy-2'-oxo-3,4-dihydro-1H-spiro[naphthalene-2,3'-pyrrolidine]-6-carboxamide (I-9);
(R)-N-hydroxy-2'-oxo-1'-(pyridin-3-yl)-3,4-dihydro-1H-spiro[naphthalene-2,3'-pyrrolidine]-6-carboxamide (I-10);
(S)-N-hydroxy-2'-oxo-1'-(pyridin-3-yl)-3,4-dihydro-1H-spiro[naphthalene-2,3'-pyrrolidine]-6-carboxamide (I-11);
(R)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-12);
(S)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-13);
(R)-N-hydroxy-2'-oxo-1'-(pyridin-4-ylmethyl)-3,4-dihydro-1H-spiro[naphthalene-2,3'-pyrrolidine]-6-carboxamide (I-14);
(S)-N-hydroxy-2'-oxo-1'-(pyridin-4-ylmethyl)-3,4-dihydro-1H-spiro[naphthalene-2,3'-pyrrolidine]-6-carboxamide (I-15);
(R)-N-hydroxy-2'-oxo-1'-(pyridin-4-yl)-3,4-dihydro-1H-spiro[naphthalene-2,3'-pyrrolidine]-6-carboxamide (I-16);
(S)-N-hydroxy-2'-oxo-1'-(pyridin-4-yl)-3,4-dihydro-1H-spiro[naphthalene-2,3'-pyrrolidine]-6-carboxamide (I-17);
(R)-N-hydroxy-2'-oxo-1'-(pyridin-3-ylmethyl)-3,4-dihydro-1H-spiro[naphthalene-2,3'-pyrrolidine]-6-carboxamide (I-18);
(S)-N-hydroxy-2'-oxo-1'-(pyridin-3-ylmethyl)-3,4-dihydro-1H-spiro[naphthalene-2,3'-pyrrolidine]-6-carboxamide (I-19);
(R)-N-hydroxy-2'-oxo-1'-(pyridin-2-yl)-3,4-dihydro-1H-spiro[naphthalene-2,3'-pyrrolidine]-6-carboxamide (I-20);
(S)-N-hydroxy-2'-oxo-1'-(pyridin-2-yl)-3,4-dihydro-1H-spiro[naphthalene-2,3'-pyrrolidine]-6-carboxamide (I-21);
(R)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide (I-22);
(S)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide (I-23);
(R)-N-hydroxy-1'-isopropyl-2'-oxo-3,4-dihydro-1H-spiro[naphthalene-2,3'-pyrrolidine]-6-carboxamide (I-24);
(S)-N-hydroxy-1'-isopropyl-2'-oxo-3,4-dihydro-1H-spiro[naphthalene-2,3'-pyrrolidine]-6-carboxamide (I-25);
(R)-N-hydroxy-2'-oxo-1'-phenyl-3,4-dihydro-1H-spiro[naphthalene-2,3'-pyrrolidine]-6-carboxamide (I-26);
(R)-N-hydroxy-2'-oxo-3,4-dihydro-1H-spiro[naphthalene-2,3'-pyrrolidine]-6-carboxamide (I-27);
(S)-N-hydroxy-2'-oxo-3,4-dihydro-1H-spiro[naphthalene-2,3'-pyrrolidine]-6-carboxamide (I-28);
(S)-N-hydroxy-2'-oxo-1'-phenyl-3,4-dihydro-1H-spiro[naphthalene-2,3'-pyrrolidine]-6-carboxamide (I-29);
(R)-1'-((2-chlorothiazol-5-yl)methyl)-N-hydroxy-2'-oxo-3,4-dihydro-1H-spiro[naphthalene-2,3'-pyrrolidine]-6-carboxamide (I-30);
(R)-N-hydroxy-1'-((2-hydroxythiazol-5-yl)methyl)-2'-oxo-3,4-dihydro-1H-spiro[naphthalene-2,3'-pyrrolidine]-6-carboxamide (I-31);
(R)-N-hydroxy-2'-oxo-1'-propyl-3,4-dihydro-1H-spiro[naphthalene-2,3'-pyrrolidine]-6-carboxamide (I-32);
(R)-1'-(cyclobutylmethyl)-N-hydroxy-2'-oxo-3,4-dihydro-1H-spiro[naphthalene-2,3'-pyrrolidine]-6-carboxamide (I-33);
(R)-N-hydroxy-1'-isopentyl-2'-oxo-3,4-dihydro-1H-spiro[naphthalene-2,3'-pyrrolidine]-6-carboxamide (I-34);
(R)-1'-(but-2-yn-1-yl)-N-hydroxy-2'-oxo-3,4-dihydro-1H-spiro[naphthalene-2,3'-pyrrolidine]-6-carboxamide (I-35);
(R)-N-hydroxy-1'-(2-methoxyethyl)-2'-oxo-3,4-dihydro-1H-spiro[naphthalene-2,3'-pyrrolidine]-6-carboxamide (I-36);
(R)-1'-cinnamyl-N-hydroxy-2'-oxo-3,4-dihydro-1H-spiro[naphthalene-2,3'-pyrrolidine]-6-carboxamide (I-37);
(R)-N-hydroxy-1'-(2-methylbenzyl)-2'-oxo-3,4-dihydro-1H-spiro[naphthalene-2,3'-pyrrolidine]-6-carboxamide (I-38);
(R)-N-hydroxy-1'-(2-(trifluoromethyl)benzyl)-3,4-dihydro-1H-spiro[naphthalene-2,3'-pyrrolidine]-6-carboxamide (I-39);

(R)-1'-(2-chlorobenzyl)-N-hydroxy-2'-oxo-3,4-dihydro-1H-spiro[naphthalene-2,3'-pyrrolidine]-6-carboxamide (I-40);

(R)-N-hydroxy-2'-oxo-1'-(2-(trifluoromethoxy)benzyl)-3,4-dihydro-1H-spiro[naphthalene-2,3'-pyrrolidine]-6-carboxamide (I-41);

(R)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide (I-42);

(R)-N-hydroxy-1'-(2-morpholino-2-oxoethyl)-2'-oxo-3,4-dihydro-1H-spiro[naphthalene-2,3'-pyrrolidine]-6-carboxamide (I-43);

(R)-N-hydroxy-1'-(2-methoxybenzyl)-2'-oxo-3,4-dihydro-1H-spiro[naphthalene-2,3'-pyrrolidine]-6-carboxamide (I-44);

(R)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide (I-45);

(R)-N-hydroxy-1'-((1-methyl-1H-benzo[d]imidazol-2-yl)methyl)-2'-oxo-3,4-dihydro-1H-spiro[naphthalene-2,3'-pyrrolidine]-6-carboxamide (I-46);

(R)-N-hydroxy-1'-(2-methylallyl)-2'-oxo-3,4-dihydro-1H-spiro[naphthalene-2,3'-pyrrolidine]-6-carboxamide (I-47);

(R)-1'-(2,5-dichlorobenzyl)-N-hydroxy-2'-oxo-3,4-dihydro-1H-spiro[naphthalene-2,3'-pyrrolidine]-6-carboxamide (I-48);

(R)-1'-(2,6-dichlorobenzyl)-N-hydroxy-2'-oxo-3,4-dihydro-1H-spiro[naphthalene-2,3'-pyrrolidine]-6-carboxamide (I-49);

(R)-1'-benzyl-N-hydroxy-2'-oxo-3,4-dihydro-1H-spiro[naphthalene-2,3'-pyrrolidine]-6-carboxamide (I-50);

(R)-N-hydroxy-1'-(3-methoxybenzyl)-2'-oxo-3,4-dihydro-1H-spiro[naphthalene-2,3'-pyrrolidine]-6-carboxamide (I-51);

(R)-N-hydroxy-2'-oxo-1'-(pyridin-2-ylmethyl)-3,4-dihydro-1H-spiro[naphthalene-2,3'-pyrrolidine]-6-carboxamide (I-52);

(R)-1'-(3-fluorobenzyl)-N-hydroxy-2'-oxo-3,4-dihydro-1H-spiro[naphthalene-2,3'-pyrrolidine]-6-carboxamide (I-53);

(R)-1'-(3-chlorobenzyl)-N-hydroxy-2'-oxo-3,4-dihydro-1H-spiro[naphthalene-2,3'-pyrrolidine]-6-carboxamide (I-54);

(R)-1'-(4-chlorobenzyl)-N-hydroxy-2'-oxo-3,4-dihydro-1H-spiro[naphthalene-2,3'-pyrrolidine]-6-carboxamide (I-55);

(R)-N-hydroxy-1'-(4-methoxybenzyl)-2'-oxo-3,4-dihydro-1H-spiro[naphthalene-2,3'-pyrrolidine]-6-carboxamide (I-56);

(R)-1'-(2-fluorobenzyl)-N-hydroxy-2'-oxo-3,4-dihydro-1H-spiro[naphthalene-2,3'-pyrrolidine]-6-carboxamide (I-57);

(R)-N-hydroxy-1'-(naphthalen-2-ylmethyl)-2'-oxo-3,4-dihydro-1H-spiro[naphthalene-2,3'-pyrrolidine]-6-carboxamide (I-58);

(R)-1'-(2-(difluoromethoxy)benzyl)-N-hydroxy-2'-oxo-3,4-dihydro-1H-spiro[naphthalene-2,3'-pyrrolidine]-6-carboxamide (I-59);

(S)-N-hydroxy-2'-oxo-1'-propyl-3,4-dihydro-1H-spiro[naphthalene-2,3'-pyrrolidine]-6-carboxamide (I-60);

(S)-1'-(cyclobutylmethyl)-N-hydroxy-2'-oxo-3,4-dihydro-1H-spiro[naphthalene-2,3'-pyrrolidine]-6-carboxamide (I-61);

(S)-N-hydroxy-1'-isopentyl-2'-oxo-3,4-dihydro-1H-spiro[naphthalene-2,3'-pyrrolidine]-6-carboxamide (I-62);

(S)-1'-(but-2-yn-1-yl)-N-hydroxy-2'-oxo-3,4-dihydro-1H-spiro[naphthalene-2,3'-pyrrolidine]-6-carboxamide (I-63);

(S)-N-hydroxy-1'-(2-methoxyethyl)-2'-oxo-3,4-dihydro-1H-spiro[naphthalene-2,3'-pyrrolidine]-6-carboxamide (I-64);

(S)-1'-cinnamyl-N-hydroxy-2'-oxo-3,4-dihydro-1H-spiro[naphthalene-2,3'-pyrrolidine]-6-carboxamide (I-65);

(S)-N-hydroxy-1'-(2-methylbenzyl)-2'-oxo-3,4-dihydro-1H-spiro[naphthalene-2,3'-pyrrolidine]-6-carboxamide (I-66);

(S)-N-hydroxy-2'-oxo-1'-(2-(trifluoromethyl)benzyl)-3,4-dihydro-1H-spiro[naphthalene-2,3'-pyrrolidine]-6-carboxamide (I-67);

(S)-1'-(2-chlorobenzyl)-N-hydroxy-2'-oxo-3,4-dihydro-1H-spiro[naphthalene-2,3'-pyrrolidine]-6-carboxamide (I-68);

(S)-N-hydroxy-2'-oxo-1'-(2-(trifluoromethoxy)benzyl)-3,4-dihydro-1H-spiro[naphthalene-2,3'-pyrrolidine]-6-carboxamide (I-69);

(S)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide (I-70);

(S)-N-hydroxy-1'-(2-morpholino-2-oxoethyl)-2'-oxo-3,4-dihydro-1H-spiro[naphthalene-2,3'-pyrrolidine]-6-carboxamide (I-71);

(S)-N-hydroxy-1'-(2-methoxybenzyl)-2'-oxo-3,4-dihydro-1H-spiro[naphthalene-2,3'-pyrrolidine]-6-carboxamide (I-72);

(S)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide (I-73);

(S)-1'-(2,5-dichlorobenzyl)-N-hydroxy-2'-oxo-3,4-dihydro-1H-spiro[naphthalene-2,3'-pyrrolidine]-6-carboxamide (I-74);

(S)-1'-(2,6-dichlorobenzyl)-N-hydroxy-2'-oxo-3,4-dihydro-1H-spiro[naphthalene-2,3'-pyrrolidine]-6-carboxamide (I-75);

(S)-1'-benzyl-N-hydroxy-2'-oxo-3,4-dihydro-1H-spiro[naphthalene-2,3'-pyrrolidine]-6-carboxamide (I-76);

(S)-N-hydroxy-1'-(3-methoxybenzyl)-2'-oxo-3,4-dihydro-1H-spiro[naphthalene-2,3'-pyrrolidine]-6-carboxamide (I-77);

(S)-N-hydroxy-2'-oxo-1'-(pyridin-2-ylmethyl)-3,4-dihydro-1H-spiro[naphthalene-2,3'-pyrrolidine]-6-carboxamide (I-78);

(S)-1'-(3-fluorobenzyl)-N-hydroxy-2'-oxo-3,4-dihydro-1H-spiro[naphthalene-2,3'-pyrrolidine]-6-carboxamide (I-79);

(S)-N-hydroxy-2'-oxo-1'-(4-(trifluoromethoxy)benzyl)-3,4-dihydro-1H-spiro[naphthalene-2,3'-pyrrolidine]-6-carboxamide (I-80);

(S)-1'-(3-chlorobenzyl)-N-hydroxy-2'-oxo-3,4-dihydro-1H-spiro[naphthalene-2,3'-pyrrolidine]-6-carboxamide (I-81);

(S)-1'-(4-chlorobenzyl)-N-hydroxy-2'-oxo-3,4-dihydro-1H-spiro[naphthalene-2,3'-pyrrolidine]-6-carboxamide (I-82);

(S)-N-hydroxy-1'-(4-methoxybenzyl)-2'-oxo-3,4-dihydro-1H-spiro[naphthalene-2,3'-pyrrolidine]-6-carboxamide (I-83);

(S)-1'-(2-fluorobenzyl)-N-hydroxy-2'-oxo-3,4-dihydro-1H-spiro[naphthalene-2,3'-pyrrolidine]-6-carboxamide (I-84);

(S)-1'-(4-(tert-butyl)benzyl)-N-hydroxy-2'-oxo-3,4-dihydro-1H-spiro[naphthalene-2,3'-pyrrolidine]-6-carboxamide (I-85);

(S)-N-hydroxy-1'-(naphthalen-2-ylmethyl)-2'-oxo-3,4-dihydro-1H-spiro[naphthalene-2,3'-pyrrolidine]-6-carboxamide (I-86);

(S)-1'-(2-(difluoromethoxy)benzyl)-N-hydroxy-2'-oxo-3,4-dihydro-1H-spiro[naphthalene-2,3'-pyrrolidine]-6-carboxamide (I-87);

(R)-N-hydroxy-1'-(4-(methylsulfonyl)benzyl)-2'-oxo-3,4-dihydro-1H-spiro[naphthalene-2,3'-pyrrolidine]-6-carboxamide (I-88);

(R)-N-hydroxy-1'-(naphthalen-1-yl)-2'-oxo-3,4-dihydro-1H-spiro[naphthalene-2,3'-pyrrolidine]-6-carboxamide (I-89);

(R)-1'-(3-fluoro-4-methoxyphenyl)-N-hydroxy-2'-oxo-3,4-dihydro-1H-spiro[naphthalene-2,3'-pyrrolidine]-6-carboxamide (I-90);

(R)-1'-(benzo[d][1,3]dioxol-5-yl)-N-hydroxy-2'-oxo-3,4-dihydro-1H-spiro[naphthalene-2,3'-pyrrolidine]-6-carboxamide (I-91);

(R)-N-hydroxy-1'-(3-(methylthio)phenyl)-2'-oxo-3,4-dihydro-1H-spiro[naphthalene-2,3'-pyrrolidine]-6-carboxamide (I-92);

(R)-1'-(4-(dimethylamino)phenyl)-N-hydroxy-2'-oxo-3,4-dihydro-1H-spiro[naphthalene-2,3'-pyrrolidine]-6-carboxamide (I-93);

(R)-N-hydroxy-1'-(6-isopropylpyridin-3-yl)-2'-oxo-3,4-dihydro-1H-spiro[naphthalene-2,3'-pyrrolidine]-6-carboxamide (I-94);

(R)-N-hydroxy-2'-oxo-1'-(quinolin-3-yl)-3,4-dihydro-1H-spiro[naphthalene-2,3'-pyrrolidine]-6-carboxamide (I-95);

(R)-1'-(2,3-dihydrobenzofuran-7-yl)-N-hydroxy-2'-oxo-3,4-dihydro-1H-spiro[naphthalene-2,3'-pyrrolidine]-6-carboxamide (I-96);

(R)-1'-(6-(tert-butylamino)pyrimidin-4-yl)-N-hydroxy-2'-oxo-3,4-dihydro-1H-spiro[naphthalene-2,3'-pyrrolidine]-6-carboxamide (I-97);

(R)-1'-(1,3-dimethyl-1H-pyrazol-4-yl)-N-hydroxy-2'-oxo-3,4-dihydro-1H-spiro[naphthalene-2,3'-pyrrolidine]-6-carboxamide (I-98);

(R)-N-hydroxy-1'-(imidazo[1,2-a]pyridin-6-yl)-2'-oxo-3,4-dihydro-1H-spiro[naphthalene-2,3'-pyrrolidine]-6-carboxamide (I-99);

(S)-1'-(2,4-dimethylphenyl)-N-hydroxy-2'-oxo-3,4-dihydro-H-spiro[naphthalene-2,3'-pyrrolidine]-6-carboxamide (I-100);

(S)-N-hydroxy-1'-(6-isopropylpyridin-3-yl)-2'-oxo-3,4-dihydro-1H-spiro[naphthalene-2,3'-pyrrolidine]-6-carboxamide (I-101);

(S)-N-hydroxy-2'-oxo-1'-(quinolin-3-yl)-3,4-dihydro-1H-spiro[naphthalene-2,3'-pyrrolidine]-6-carboxamide (I-102);

(S)-N-hydroxy-1'-(imidazo[1,2-a]pyridin-6-yl)-2'-oxo-3,4-dihydro-1H-spiro[naphthalene-2,3'-pyrrolidine]-6-carboxamide (I-103);

(R)-N-hydroxy-1'-methyl-2'-oxo-3,4-dihydro-1H-spiro[naphthalene-2,3'-pyrrolidine]-6-carboxamide (I-104);

(S)-N-hydroxy-1'-methyl-2'-oxo-3,4-dihydro-1H-spiro[naphthalene-2,3'-pyrrolidine]-6-carboxamide (I-105);

(R)-N-hydroxy-2'-oxo-1'-(4-((trifluoromethyl)sulfonyl)benzyl)-3,4-dihydro-1H-spiro[naphthalene-2,3'-pyrrolidine]-6-carboxamide (I-106);

(S)-N-hydroxy-2'-oxo-1'-(4-((trifluoromethyl)sulfonyl)benzyl)-3,4-dihydro-1H-spiro[naphthalene-2,3'-pyrrolidine]-6-carboxamide (I-107);

(R)-N-hydroxy-1'-(3-methoxyphenyl)-2'-oxo-3,4-dihydro-1H-spiro[naphthalene-2,3'-pyrrolidine]-6-carboxamide (I-108);

(R)-1'-cyclopropyl-N-hydroxy-2'-oxo-3,4-dihydro-H-spiro[naphthalene-2,3'-pyrrolidine]-6-carboxamide (I-109);

(R)-1'-(5-fluoropyridin-3-yl)-N-hydroxy-2'-oxo-3,4-dihydro-1H-spiro[naphthalene-2,3'-pyrrolidine]-6-carboxamide (I-110);

(R)-N-hydroxy-1'-(2-methoxyphenyl)-2'-oxo-3,4-dihydro-1H-spiro[naphthalene-2,3'-pyrrolidine]-6-carboxamide (I-111);

(R)-1'-(3-cyanophenyl)-N-hydroxy-2'-oxo-3,4-dihydro-1H-spiro[naphthalene-2,3'-pyrrolidine]-6-carboxamide (I-112);

(R)-1'-(3-fluorophenyl)-N-hydroxy-2'-oxo-3,4-dihydro-1H-spiro[naphthalene-2,3'-pyrrolidine]-6-carboxamide (I-113);

(R)-N-hydroxy-1'-(6-methoxypyridin-3-yl)-2'-oxo-3,4-dihydro-1H-spiro[naphthalene-2,3'-pyrrolidine]-6-carboxamide (I-114);

(S)-N-hydroxy-1'-(2-methoxyphenyl)-2'-oxo-3,4-dihydro-1H-spiro[naphthalene-2,3'-pyrrolidine]-6-carboxamide (I-115);

(S)-1'-(3-cyanophenyl)-N-hydroxy-2'-oxo-3,4-dihydro-1H-spiro[naphthalene-2,3'-pyrrolidine]-6-carboxamide (I-116);

(S)-1'-(3-fluorophenyl)-N-hydroxy-2'-oxo-3,4-dihydro-1H-spiro[naphthalene-2,3'-pyrrolidine]-6-carboxamide (I-117);

(S)-N-hydroxy-1'-(6-methoxypyridin-3-yl)-2'-oxo-3,4-dihydro-1H-spiro[naphthalene-2,3'-pyrrolidine]-6-carboxamide (I-118);

(R)-1'-(3,4-difluorophenyl)-N-hydroxy-2'-oxo-3,4-dihydro-1H-spiro[naphthalene-2,3'-pyrrolidine]-6-carboxamide (I-119);

(R)-1'-(4-fluorophenyl)-N-hydroxy-2'-oxo-3,4-dihydro-1H-spiro[naphthalene-2,3'-pyrrolidine]-6-carboxamide (I-120);

(R)-1'-(2-fluorophenyl)-N-hydroxy-2'-oxo-3,4-dihydro-1H-spiro[naphthalene-2,3'-pyrrolidine]-6-carboxamide (I-121);

(S)-N-hydroxy-1'-(oxetan-3-ylmethyl)-2'-oxo-3,4-dihydro-1H-spiro[naphthalene-2,3'-pyrrolidine]-6-carboxamide (I-122);

(R)-1'-(2,3-difluorophenyl)-N-hydroxy-2'-oxo-3,4-dihydro-1H-spiro[naphthalene-2,3'-pyrrolidine]-6-carboxamide (I-123);

(R)-N-hydroxy-1'-(4-methoxyphenyl)-2'-oxo-3,4-dihydro-1H-spiro[naphthalene-2,3'-pyrrolidine]-6-carboxamide (I-124);

(R)-1'-(2-fluoro-3-methoxyphenyl)-N-hydroxy-2'-oxo-3,4-dihydro-1H-spiro[naphthalene-2,3'-pyrrolidine]-6-carboxamide (I-125);

(S)-1'-(2-fluoro-3-methoxyphenyl)-N-hydroxy-2'-oxo-3,4-dihydro-1H-spiro[naphthalene-2,3'-pyrrolidine]-6-carboxamide (I-126);

(S)-1'-(2-fluoro-4-methoxyphenyl)-N-hydroxy-2'-oxo-3,4-dihydro-1H-spiro[naphthalene-2,3'-pyrrolidine]-6-carboxamide (I-127);

(R)-1'-(4-fluoro-3-methoxyphenyl)-N-hydroxy-2'-oxo-3,4-dihydro-1H-spiro[naphthalene-2,3'-pyrrolidine]-6-carboxamide (I-128);

(S)-1'-(4-fluoro-3-methoxyphenyl)-N-hydroxy-2'-oxo-3,4-dihydro-1H-spiro[naphthalene-2,3'-pyrrolidine]-6-carboxamide (I-129);

(S)-1'-(5-chloropyridin-2-yl)-N-hydroxy-2'-oxo-3,4-dihydro-1H-spiro[naphthalene-2,3'-pyrrolidine]-6-carboxamide (I-130);

(R)-N-hydroxy-1'-(2-methylpyridin-3-yl)-2'-oxo-3,4-dihydro-1H-spiro[naphthalene-2,3'-pyrrolidine]-6-carboxamide (I-131);
(S)-N-hydroxy-1'-(2-methylpyridin-3-yl)-2'-oxo-3,4-dihydro-1H-spiro[naphthalene-2,3'-pyrrolidine]-6-carboxamide (I-132);
(R)-N-hydroxy-1'-(6-methylpyridin-3-yl)-2'-oxo-3,4-dihydro-1H-spiro[naphthalene-2,3'-pyrrolidine]-6-carboxamide (I-133);
(S)-N-hydroxy-1'-(6-methylpyridin-3-yl)-2'-oxo-3,4-dihydro-1H-spiro[naphthalene-2,3'-pyrrolidine]-6-carboxamide (I-134);
(R)-N-hydroxy-1'-(5-methylpyridin-3-yl)-2'-oxo-3,4-dihydro-1H-spiro[naphthalene-2,3'-pyrrolidine]-6-carboxamide (I-135);
(R)-N-hydroxy-1'-(4-methylpyridin-3-yl)-2'-oxo-3,4-dihydro-1H-spiro[naphthalene-2,3'-pyrrolidine]-6-carboxamide (I-136);
(S)-N-hydroxy-1'-(4-methylpyridin-3-yl)-2'-oxo-3,4-dihydro-1H-spiro[naphthalene-2,3'-pyrrolidine]-6-carboxamide (I-137);
(R)-1'-(5-chloropyridin-3-yl)-N-hydroxy-2'-oxo-3,4-dihydro-1H-spiro[naphthalene-2,3'-pyrrolidine]-6-carboxamide (I-138);
(S)-1'-(5-chloropyridin-3-yl)-N-hydroxy-2'-oxo-3,4-dihydro-1H-spiro[naphthalene-2,3'-pyrrolidine]-6-carboxamide (I-139);
(R)-1'-(3-chloropyridin-4-yl)-N-hydroxy-2'-oxo-3,4-dihydro-1H-spiro[naphthalene-2,3'-pyrrolidine]-6-carboxamide (I-140);
(S)-1'-(3-chloropyridin-4-yl)-N-hydroxy-2'-oxo-3,4-dihydro-1H-spiro[naphthalene-2,3'-pyrrolidine]-6-carboxamide (I-141);
(S)-N-hydroxy-1'-(4-methoxypyridin-3-yl)-2'-oxo-3,4-dihydro-1H-spiro[naphthalene-2,3'-pyrrolidine]-6-carboxamide (I-142);
(R)-N-hydroxy-1'-(5-methoxypyridin-3-yl)-2'-oxo-3,4-dihydro-1H-spiro[naphthalene-2,3'-pyrrolidine]-6-carboxamide (I-143);
(S)-N-hydroxy-1'-(5-methoxypyridin-3-yl)-2'-oxo-3,4-dihydro-1H-spiro[naphthalene-2,3'-pyrrolidine]-6-carboxamide (I-144);
(R)-N-hydroxy-1'-(2-methoxypyridin-3-yl)-2'-oxo-3,4-dihydro-1H-spiro[naphthalene-2,3'-pyrrolidine]-6-carboxamide (I-145);
(S)-N-hydroxy-1'-(2-methoxypyridin-3-yl)-2'-oxo-3,4-dihydro-1H-spiro[naphthalene-2,3'-pyrrolidine]-6-carboxamide (I-146);
(S)-1'-(2-fluoro-5-methoxyphenyl)-N-hydroxy-2'-oxo-3,4-dihydro-1H-spiro[naphthalene-2,3'-pyrrolidine]-6-carboxamide (I-147);
(S)-1'-(3-fluoro-5-methoxyphenyl)-N-hydroxy-2'-oxo-3,4-dihydro-1H-spiro[naphthalene-2,3'-pyrrolidine]-6-carboxamide (I-148);
(R)-N-hydroxy-1'-(2-methoxypyridin-4-yl)-2'-oxo-3,4-dihydro-1H-spiro[naphthalene-2,3'-pyrrolidine]-6-carboxamide (I-149);
(S)-N-hydroxy-1'-(2-methoxypyridin-4-yl)-2'-oxo-3,4-dihydro-1H-spiro[naphthalene-2,3'-pyrrolidine]-6-carboxamide (I-150);
(R)-1'-(6-(dimethylamino)pyridin-3-yl)-N-hydroxy-2'-oxo-3,4-dihydro-H-spiro[naphthalene-2,3'-pyrrolidine]-6-carboxamide (I-151);
(S)-1'-(6-(dimethylamino)pyridin-3-yl)-N-hydroxy-2'-oxo-3,4-dihydro-1H-spiro[naphthalene-2,3'-pyrrolidine]-6-carboxamide (I-152);
(S)-1'-(5-fluoropyridin-3-yl)-N-hydroxy-2'-oxo-3,4-dihydro-H-spiro[naphthalene-2,3'-pyrrolidine]-6-carboxamide (I-153);
(S)-1'-(4-fluorophenyl)-N-hydroxy-2'-oxo-3,4-dihydro-1H-spiro[naphthalene-2,3'-pyrrolidine]-6-carboxamide (I-154);
(S)-1'-(3,4-difluorophenyl)-N-hydroxy-2'-oxo-3,4-dihydro-H-spiro[naphthalene-2,3'-pyrrolidine]-6-carboxamide (I-155);
(S)-1'-(2,3-difluorophenyl)-N-hydroxy-2'-oxo-3,4-dihydro-H-spiro[naphthalene-2,3'-pyrrolidine]-6-carboxamide (I-156);
(S)-1'-(2-fluorophenyl)-N-hydroxy-2'-oxo-3,4-dihydro-1H-spiro[naphthalene-2,3'-pyrrolidine]-6-carboxamide (I-157);
(S)-N-hydroxy-1'-(3-methoxyphenyl)-2'-oxo-3,4-dihydro-1H-spiro[naphthalene-2,3'-pyrrolidine]-6-carboxamide (I-158);
(R)-N-hydroxy-1'-isobutyl-2'-oxo-3,4-dihydro-1H-spiro[naphthalene-2,3'-pyrrolidine]-6-carboxamide (I-159);
(S)-N-hydroxy-1'-isobutyl-2'-oxo-3,4-dihydro-1H-spiro[naphthalene-2,3'-pyrrolidine]-6-carboxamide (I-160);
(R)-1'-ethyl-N-hydroxy-2'-oxo-3,4-dihydro-1H-spiro[naphthalene-2,3'-pyrrolidine]-6-carboxamide (I-161);
(S)-1'-ethyl-N-hydroxy-2'-oxo-3,4-dihydro-H-spiro[naphthalene-2,3'-pyrrolidine]-6-carboxamide (I-162);
(R)-1'-cyclopentyl-N-hydroxy-2'-oxo-3,4-dihydro-1H-spiro[naphthalene-2,3'-pyrrolidine]-6-carboxamide (I-163);
(S)-1'-cyclopentyl-N-hydroxy-2'-oxo-3,4-dihydro-1H-spiro[naphthalene-2,3'-pyrrolidine]-6-carboxamide (I-164);
(R)-N-hydroxy-2'-oxo-1'-(2,2,2-trifluoroethyl)-3,4-dihydro-1H-spiro[naphthalene-2,3'-pyrrolidine]-6-carboxamide (I-165);
(S)-N-hydroxy-2'-oxo-1'-(2,2,2-trifluoroethyl)-3,4-dihydro-1H-spiro[naphthalene-2,3'-pyrrolidine]-6-carboxamide (I-166);
(R)-1'-(2, 5-difluorophenyl)-N-hydroxy-2'-oxo-3,4-dihydro-1H-spiro[naphthalene-2,3'-pyrrolidine]-6-carboxamide (I-167);
(R)-N-hydroxy-1'-(1-methyl-1H-pyrazol-4-yl)-2'-oxo-3,4-dihydro-1H-spiro[naphthalene-2,3'-pyrrolidine]-6-carboxamide (I-168);
(S)-1'-(2,5-difluorophenyl)-N-hydroxy-2'-oxo-3,4-dihydro-1H-spiro[naphthalene-2,3'-pyrrolidine]-6-carboxamide (I-169);
(S)-N-hydroxy-1'-(1-methyl-1H-pyrazol-4-yl)-2'-oxo-3,4-dihydro-1H-spiro[naphthalene-2,3'-pyrrolidine]-6-carboxamide (I-170);
(R)-1'-cyclobutyl-N-hydroxy-2'-oxo-3,4-dihydro-1H-spiro[naphthalene-2,3'-pyrrolidine]-6-carboxamide (I-171);
(S)-1'-cyclobutyl-N-hydroxy-2'-oxo-3,4-dihydro-1H-spiro[naphthalene-2,3'-pyrrolidine]-6-carboxamide (I-172);
(S)-1'-(4-cyanophenyl)-N-hydroxy-2'-oxo-3,4-dihydro-1H-spiro[naphthalene-2,3'-pyrrolidine]-6-carboxamide (I-173);
(S)-1'-(2-cyanophenyl)-N-hydroxy-2'-oxo-3,4-dihydro-1H-spiro[naphthalene-2,3'-pyrrolidine]-6-carboxamide (I-174);
(R)-1'-(2-cyanophenyl)-N-hydroxy-2'-oxo-3,4-dihydro-1H-spiro[naphthalene-2,3'-pyrrolidine]-6-carboxamide (I-175);
1'-benzyl-N-hydroxy-2'-oxo-3,4-dihydro-1H-spiro[naphthalene-2,3'-piperidine]-6-carboxamide (I-176);
N-hydroxy-2'-oxo-3,4-dihydro-1H-spiro[naphthalene-2,3'-piperidine]-6-carboxamide (I-177);
N-hydroxy-1'-methyl-2'-oxo-3,4-dihydro-1H-spiro[naphthalene-2,3'-piperidine]-6-carboxamide (I-178);

(R)-N-hydroxy-1'-methyl-2'-oxo-3,4-dihydro-1H-spiro [naphthalene-2,3'-piperidine]-6-carboxamide (I-179);
(S)-N-hydroxy-1'-methyl-2'-oxo-3,4-dihydro-1H-spiro [naphthalene-2,3'-piperidine]-6-carboxamide (I-180);
(R)-N-hydroxy-2'-oxo-1'-phenyl-3,4-dihydro-1H-spiro [naphthalene-2,3'-piperidine]-6-carboxamide (I-181);
(S)-N-hydroxy-2'-oxo-1'-phenyl-3,4-dihydro-1H-spiro [naphthalene-2,3'-piperidine]-6-carboxamide (I-182);
(S)-1'-cyclopropyl-N-hydroxy-2'-oxo-3,4-dihydro-1H-spiro [naphthalene-2,3'-piperidine]-6-carboxamide (I-183);
(S)-1'-ethyl-N-hydroxy-2'-oxo-3,4-dihydro-1H-spiro[naphthalene-2,3'-piperidine]-6-carboxamide (I-184);
(R)-1'-(cyclobutylmethyl)-N-hydroxy-2'-oxo-3,4-dihydro-1H-spiro[naphthalene-2,3'-piperidine]-6-carboxamide (I-185);
(S)-1'-(cyclobutylmethyl)-N-hydroxy-2'-oxo-3,4-dihydro-1H-spiro[naphthalene-2,3'-piperidine]-6-carboxamide (I-186);
(R)-N-hydroxy-1'-(3-methoxypropyl)-2'-oxo-3,4-dihydro-1H-spiro[naphthalene-2,3'-piperidine]-6-carboxamide (I-187);
(S)-N-hydroxy-1'-(3-methoxypropyl)-2'-oxo-3,4-dihydro-1H-spiro[naphthalene-2,3'-piperidine]-6-carboxamide (I-188);
(R)-N-hydroxy-1'-isobutyl-2'-oxo-3,4-dihydro-1H-spiro [naphthalene-2,3'-piperidine]-6-carboxamide (I-189);
(S)-N-hydroxy-1'-isobutyl-2'-oxo-3,4-dihydro-1H-spiro [naphthalene-2,3'-piperidine]-6-carboxamide (I-190);
(R)-N-hydroxy-1'-isopropyl-2'-oxo-3,4-dihydro-1H-spiro [naphthalene-2,3'-piperidine]-6-carboxamide (I-191);
(S)-N-hydroxy-1'-isopropyl-2'-oxo-3,4-dihydro-1H-spiro [naphthalene-2,3'-piperidine]-6-carboxamide (I-192);
(R)-1'-cyclopropyl-N-hydroxy-2'-oxo-3,4-dihydro-H-spiro [naphthalene-2,3'-piperidine]-6-carboxamide (I-193);
(R)-1'-ethyl-N-hydroxy-2'-oxo-3,4-dihydro-1H-spiro[naphthalene-2,3'-piperidine]-6-carboxamide (I-194);
(S)-N-hydroxy-1'-(oxetan-3-ylmethyl)-2'-oxo-3,4-dihydro-1H-spiro[naphthalene-2,3'-piperidine]-6-carboxamide (I-195);
(R)-N-hydroxy-1'-(oxetan-3-ylmethyl)-2'-oxo-3,4-dihydro-H-spiro[naphthalene-2,3'-piperidine]-6-carboxamide (I-196);
(R)-1'-cyclobutyl-N-hydroxy-2'-oxo-3,4-dihydro-1H-spiro [naphthalene-2,3'-piperidine]-6-carboxamide (I-197);
(S)-1'-cyclobutyl-N-hydroxy-2'-oxo-3,4-dihydro-1H-spiro [naphthalene-2,3'-piperidine]-6-carboxamide (I-198);
(R)-1'-cyclopentyl-N-hydroxy-2'-oxo-3,4-dihydro-1H-spiro [naphthalene-2,3'-piperidine]-6-carboxamide (I-199);
(S)-1'-cyclopentyl-N-hydroxy-2'-oxo-3,4-dihydro-1H-spiro [naphthalene-2,3'-piperidine]-6-carboxamide (I-200);
(R)-N-hydroxy-1'-methyl-5'-oxo-3,4-dihydro-1H-spiro [naphthalene-2,3'-pyrrolidine]-6-carboxamide (I-201);
(S)-N-hydroxy-1'-methyl-5'-oxo-3,4-dihydro-1H-spiro [naphthalene-2,3'-pyrrolidine]-6-carboxamide (I-202);
(R)-N-hydroxy-5'-oxo-1'-phenyl-3,4-dihydro-1H-spiro [naphthalene-2,3'-pyrrolidine]-6-carboxamide (I-203);
(S)-N-hydroxy-5'-oxo-1'-phenyl-3,4-dihydro-1H-spiro [naphthalene-2,3'-pyrrolidine]-6-carboxamide (I-204);
(R)-1'-(cyclobutylmethyl)-N-hydroxy-5'-oxo-3,4-dihydro-1H-spiro[naphthalene-2,3'-pyrrolidine]-6-carboxamide (I-205);
(R)-1'-ethyl-N-hydroxy-5'-oxo-3,4-dihydro-1H-spiro[naphthalene-2,3'-pyrrolidine]-6-carboxamide (I-206);
(R)-N-hydroxy-1'-isobutyl-5'-oxo-3,4-dihydro-1H-spiro [naphthalene-2,3'-pyrrolidine]-6-carboxamide (I-207);
(R)-N-hydroxy-1'-isopropyl-5'-oxo-3,4-dihydro-1H-spiro [naphthalene-2,3'-pyrrolidine]-6-carboxamide (I-208);
(R)-1'-cyclopropyl-N-hydroxy-5'-oxo-3,4-dihydro-H-spiro [naphthalene-2,3'-pyrrolidine]-6-carboxamide (I-209);
(S)-1'-(cyclobutylmethyl)-N-hydroxy-5'-oxo-3,4-dihydro-1H-spiro[naphthalene-2,3'-pyrrolidine]-6-carboxamide (I-210);
(S)-1'-ethyl-N-hydroxy-5'-oxo-3,4-dihydro-1H-spiro[naphthalene-2,3'-pyrrolidine]-6-carboxamide (I-211);
(S)-N-hydroxy-1'-isobutyl-5'-oxo-3,4-dihydro-1H-spiro [naphthalene-2,3'-pyrrolidine]-6-carboxamide (I-212);
(S)-N-hydroxy-1'-isopropyl-5'-oxo-3,4-dihydro-1H-spiro [naphthalene-2,3'-pyrrolidine]-6-carboxamide (I-213);
(S)-1'-cyclopropyl-N-hydroxy-5'-oxo-3,4-dihydro-1H-spiro [naphthalene-2,3'-pyrrolidine]-6-carboxamide (I-214);
(R)-N-hydroxy-1'-(oxetan-3-ylmethyl)-5'-oxo-3,4-dihydro-H-spiro[naphthalene-2,3'-pyrrolidine]-6-carboxamide (I-215);
(R)-1'-benzyl-N-hydroxy-5'-oxo-3,4-dihydro-1H-spiro [naphthalene-2,3'-pyrrolidine]-6-carboxamide (I-216);
(S)-N-hydroxy-1'-(oxetan-3-ylmethyl)-5'-oxo-3,4-dihydro-1H-spiro[naphthalene-2,3'-pyrrolidine]-6-carboxamide (I-217);
(S)-1'-benzyl-N-hydroxy-5'-oxo-3,4-dihydro-1H-spiro [naphthalene-2,3'-pyrrolidine]-6-carboxamide (I-218);
(R)-N-hydroxy-1'-(3-methoxypropyl)-5'-oxo-3,4-dihydro-1H-spiro[naphthalene-2,3'-pyrrolidine]-6-carboxamide (I-219);
(R)-N-hydroxy-5'-oxo-1'-(2,2,2-trifluoroethyl)-3,4-dihydro-1H-spiro[naphthalene-2,3'-pyrrolidine]-6-carboxamide (I-220);
(R)-N-hydroxy-5'-oxo-1'-(pyridin-3-yl)-3,4-dihydro-1H-spiro[naphthalene-2,3'-pyrrolidine]-6-carboxamide (I-221);
(S)-N-hydroxy-1'-(3-methoxypropyl)-5'-oxo-3,4-dihydro-1H-spiro[naphthalene-2,3'-pyrrolidine]-6-carboxamide (I-222);
(S)-N-hydroxy-5'-oxo-1'-(2,2,2-trifluoroethyl)-3,4-dihydro-1H-spiro[naphthalene-2,3'-pyrrolidine]-6-carboxamide (I-223);
(S)-N-hydroxy-5'-oxo-1'-(pyridin-3-yl)-3,4-dihydro-1H-spiro[naphthalene-2,3'-pyrrolidine]-6-carboxamide (I-224);
(R)-N-hydroxy-1'-(2-methylbenzyl)-5'-oxo-3,4-dihydro-1H-spiro[naphthalene-2,3'-pyrrolidine]-6-carboxamide (I-225);
(R)-N-hydroxy-5'-oxo-1'-(pyridin-3-ylmethyl)-3,4-dihydro-1H-spiro[naphthalene-2,3'-pyrrolidine]-6-carboxamide (I-226);
(R)-1'-(4-fluorophenyl)-N-hydroxy-5'-oxo-3,4-dihydro-1H-spiro[naphthalene-2,3'-pyrrolidine]-6-carboxamide (I-227);
(R)-N-hydroxy-5'-oxo-1'-(pyridin-4-yl)-3,4-dihydro-1H-spiro[naphthalene-2,3'-pyrrolidine]-6-carboxamide (I-228);
(R)-N-hydroxy-5'-oxo-1'-(pyridin-2-yl)-3,4-dihydro-1H-spiro[naphthalene-2,3'-pyrrolidine]-6-carboxamide (I-229);
N-hydroxy-2'-oxo-1'-(pyridin-4-ylmethyl)spiro[chromane-2,3'-pyrrolidine]-6-carboxamide (I-230);
N-hydroxy-2'-oxo-1'-phenylspiro[chromane-2,3'-pyrrolidine]-6-carboxamide (I-231);
1'-benzyl-N-hydroxy-2'-oxospiro[chromane-2,3'-pyrrolidine]-6-carboxamide (I-232);
N-hydroxy-2'-oxo-1'-(pyridin-3-yl)spiro[chromane-2,3'-pyrrolidine]-6-carboxamide (I-233);
N-hydroxy-2'-oxo-1'-((tetrahydro-2H-pyran-4-yl)methyl) spiro[chromane-2,3'-pyrrolidine]-6-carboxamide (I-234);

N-hydroxy-1'-isopropyl-2'-oxospiro[chromane-2,3'-pyrrolidine]-6-carboxamide (I-235);
N-hydroxy-2'-oxospiro[chromane-2,3'-pyrrolidine]-6-carboxamide (I-236);
N-hydroxy-1'-methyl-2'-oxospiro[chromane-2,3'-pyrrolidine]-6-carboxamide (I-237);
N-hydroxy-2-oxo-1-phenylspiro[pyrrolidine-3,2'-thiochromane]-6'-carboxamide 1',1'-dioxide (I-238);
1-benzyl-N-hydroxy-2-oxospiro[pyrrolidine-3,2'-thiochromane]-6'-carboxamide 1',1'-dioxide (I-239);
N-hydroxy-2-oxo-1-(pyridin-3-yl)spiro[pyrrolidine-3,2'-thiochromane]-6'-carboxamide 1',1'-dioxide (I-240);
N-hydroxy-2-oxo-1-((tetrahydro-2H-pyran-4-yl)methyl)spiro[pyrrolidine-3,2'-thiochromane]-6'-carboxamide 1',1'-dioxide (I-241);
N-hydroxy-2-oxo-1-(pyridin-4-ylmethyl)spiro[pyrrolidine-3,2'-thiochromane]-6'-carboxamide 1',1'-dioxide (I-242);
N-hydroxy-2-oxospiro[pyrrolidine-3,2'-thiochromane]-6'-carboxamide 1',1'-dioxide (I-243); and
N-hydroxy-1-methyl-2-oxospiro[pyrrolidine-3,2'-thiochromane]-6'-carboxamide 1',1'-dioxide (I-244).

In one or more embodiments, the compound of Formula II can be selected from:
N-hydroxy-1'-(4-methoxybenzyl)spiro[chromane-2,4'-piperidine]-6-carboxamide (II-1);
1'-((1H-benzo[d]imidazol-2-yl)methyl)-N-hydroxyspiro[chromane-2,4'-piperidine]-6-carboxamide (II-2);
1'-(cyclohexanecarbonyl)-N-hydroxyspiro[chromane-2,4'-piperidine]-6-carboxamide (II-3);
N-hydroxy-1'-(4-methoxybenzoyl)spiro[chromane-2,4'-piperidine]-6-carboxamide (II-4);
N-hydroxy-1'-((4-methoxyphenyl)sulfonyl)spiro[chromane-2,4'-piperidine]-6-carboxamide (II-5);
1'-(cyclohexylsulfonyl)-N-hydroxyspiro[chromane-2,4'-piperidine]-6-carboxamide (II-6);
N6-hydroxy-N1'-phenylspiro[chromane-2,4'-piperidine]-1',6-dicarboxamide (II-7);
1'-cyclohexyl-N-hydroxyspiro[chromane-2,4'-piperidine]-6-carboxamide (II-8); and
N-hydroxy-1'-(2',3',5',6'-tetrahydrospiro[indoline-3,4'-pyran]-1-carbonyl)spiro[chromane-2,4'-piperidine]-6-carboxamide (II-9).

In one or more embodiments, the compound of Formula I can be selected from:
N-hydroxy-1'-methyl-3,4-dihydro-1H-spiro[naphthalene-2,3'-piperidine]-6-carboxamide (I-245);
N-hydroxy-1-methyl-3',4'-dihydro-1'H-spiro[azepane-3,2'-naphthalene]-6'-carboxamide (I-246);
N-hydroxy-1-methyl-3',4'-dihydro-1'H-spiro[azocane-3,2'-naphthalene]-6'-carboxamide (I-247);
N-hydroxy-1-methyl-2-oxo-3',4'-dihydro-1'H-spiro[azepane-3,2'-naphthalene]-6'-carboxamide (I-248);
N-hydroxy-1-methyl-2-oxo-3',4'-dihydro-1'H-spiro[azocane-3,2'-naphthalene]-6'-carboxamide (I-249);
N-hydroxy-1'-methyl-6'-oxo-3,4-dihydro-1H-spiro[naphthalene-2,3'-piperidine]-6-carboxamide (I-250);
N-hydroxy-1-methyl-7-oxo-3',4'-dihydro-1'H-spiro[azepane-3,2'-naphthalene]-6'-carboxamide (I-251);
N-hydroxy-1-methyl-8-oxo-3',4'-dihydro-1'H-spiro[azocane-3,2'-naphthalene]-6'-carboxamide (I-252);
N-hydroxy-1'-methyl-2'-oxospiro[chromane-2,3'-piperidine]-6-carboxamide (I-253);
N-hydroxy-1-methyl-2-oxospiro[azepane-3,2'-chromane]-6'-carboxamide (I-254);
N-hydroxy-1-methyl-2-oxospiro[azocane-3,2'-chromane]-6'-carboxamide (I-255);
N-hydroxy-1-methyl-2-oxospiro[piperidine-3,2'-thiochromane]-6'-carboxamide 1',1'-dioxide (I-256);
N-hydroxy-1-methyl-2-oxospiro[azepane-3,2'-thiochromane]-6'-carboxamide 1',1'-dioxide (I-257); and
N-hydroxy-1-methyl-2-oxospiro[azocane-3,2'-thiochromane]-6'-carboxamide 1',1'-dioxide (I-258).

In one embodiment of the compounds of Formulae I and II, $Y^1$, $Y^3$, and $Y^4$ are each $CR^1$. In other embodiments, $Y^1$ is N and $Y^3$ and $Y^4$ are each $CR^1$. In other embodiments, $Y^3$ is N and $Y^1$ and $Y^4$ are each $CR^1$. In other embodiments, $Y^4$ is N and $Y^1$ and $Y^3$ are each $CR^1$.

In some embodiments of the compounds of Formulae I and II, $Y^1$, $Y^3$, and $Y^4$ are each $CR^1$ and $X^1$, $X^2$, $X^3$, $X^4$, $X^5$, $X^6$, and $X^7$ are each independently —$CR^1R^2$—. In some embodiments, $X^1$ is —C(O)—, and $X^2$, $X^3$, $X^4$, $X^5$, $X^6$, and $X^7$ are each independently —$CR^1R^2$—. In some embodiments, $X^2$ is —C(O)—, and $X^1$, $X^3$, $X^4$, $X^5$, $X^6$, and $X^7$ are each independently —$CR^1R^2$—. In some embodiments, $X^3$ is —C(O)—, and $X^1$, $X^2$, $X^4$, $X^5$, $X^6$, and $X^7$ are each independently —$CR^1R^2$—. In some embodiments, $X^4$ is —C(O)—, and $X^1$, $X^2$, $X^3$, $X^5$, $X^6$, and $X^7$ are each independently —$CR^1R^2$—. In some embodiments, $X^5$ is —C(O)—, and $X^1$, $X^2$, $X^3$, $X^4$, $X^6$, and $X^7$ are each independently —$CR^1R^2$—. In some embodiments, $X^6$ is —C(O)—, and $X^1$, $X^2$, $X^3$, $X^4$, $X^5$, and $X^7$ are each independently —$CR^1R^2$—. In some embodiments, $X^7$ is —C(O)—, and $X^1$, $X^2$, $X^3$, $X^5$, $X^5$, and $X^6$ are each independently —$CR^1R^2$—.

In other embodiments of the compounds of Formulae I and II, $X^1$ is —$NR^3$—, and $X^2$, $X^3$, $X^4$, $X^5$, $X^6$, and $X^7$ are each independently —$CR^1R^2$—. In some embodiments, $X^2$ is —$NR^3$—, and $X^1$, $X^3$, $X^4$, $X^5$, $X^6$, and $X^7$ are each independently —$CR^1R^2$—. In some embodiments, $X^3$ is —$NR^3$—, and $X^1$, $X^2$, $X^4$, $X^5$, $X^6$, and $X^7$ are each independently —$CR^1R^2$—. In some embodiments, $X^4$ is —$NR^3$—, and $X^1$, $X^2$, $X^3$, $X^5$, $X^6$, and $X^7$ are each independently —$CR^1R^2$—. In some embodiments, $X^5$ is —$NR^3$—, and $X^1$, $X^2$, $X^3$, $X^4$, $X^6$, and $X^7$ are each independently —$CR^1R^2$—. In some embodiments, $X^6$ is —$NR^3$—, and $X^1$, $X^2$, $X^3$, $X^4$, $X^5$, and $X^7$ are each independently —$CR^1R^2$—. In some embodiments, $X^7$ is —$NR^3$—, and $X^1$, $X^2$, $X^3$, $X^4$, $X^5$, and $X^6$ are each independently —$CR^1R^2$—.

In other embodiments of the compounds of Formula I, $X^1$ is —O—, —$SO_2$—, —S(O)—, or —S—, and $X^2$, $X^3$, $X^4$, $X^5$, $X^6$, and $X^7$ are each independently —$CR^1R^2$—. In some embodiments, $X^2$ is —O—, —$SO_2$—, —S(O)—, or —S—, and $X^1$, $X^3$, $X^4$, $X^5$, $X^6$, and $X^7$ are each independently —$CR^1R^2$—. In some embodiments, $X^3$ is —O—, —$SO_2$—, —S(O)—, or —S—, and $X^1$, $X^2$, $X^4$, $X^5$, $X^6$, and $X^7$ are each independently —$CR^1R^2$—. In some embodiments, $X^4$ is —S—, —$SO_2$— or —S(O)—, and $X^1$, $X^2$, $X^3$, $X^5$, $X^6$, and $X^7$ are each independently —$CR^1R^2$—. In some embodiments, $X^5$ is —S—, —$SO_2$— or —S(O)—, and $X^1$, $X^2$, $X^3$, $X^4$, $X^6$, and $X^7$ are each independently —$CR^1R^2$—. In some embodiments, $X^6$ is —O—, —$SO_2$—, —S(O)—, or —S—, and $X^1$, $X^2$, $X^3$, $X^4$, $X^5$, and $X^7$ are each independently —$CR^1R^2$—. In some embodiments, $X^7$ is —O—, —$SO_2$—, —S(O)—, or —S—, and $X^1$, $X^2$, $X^3$, $X^4$, $X^5$, and $X^6$ are each independently —$CR^1R^2$—.

In other embodiments of the compounds of Formula II, $X^1$ is —O—, —$SO_2$—, —S(O)—, or —S—, and $X^2$, $X^3$, $X^5$, $X^6$, and $X^7$ are each independently —$CR^1R^2$—. In some embodiments, $X^2$ is —O—, —$SO_2$—, —S(O)—, or —S—, and $X^1$, $X^3$, $X^4$, $X^5$, $X^6$, and $X^7$ are each independently —$CR^1R^2$—. In some embodiments, $X^3$ is —O—, —$SO_2$—, —S(O)—, or —S—, and $X^1$, $X^2$, $X^4$, $X^5$, $X^6$, and $X^7$ are each independently —$CR^1R^2$—. In some embodiments, $X^4$ is —O—, —$SO_2$—, —S(O)—, or —S—, and $X^1$, $X^2$, $X^3$, $X^5$, $X^6$, and $X^7$ are each independently —$CR^1R^2$—. In some embodiments, $X^5$ is —S—, —$SO_2$— or —S(O)—, and $X^1$, $X^2$, $X^3$, $X^4$, $X^6$, and $X^7$ are each independently —$CR^1R^2$—. In some embodiments, $X^6$ is —S—, —$SO_2$— or —S(O)—, and $X^1$, $X^2$, $X^3$, $X^4$, $X^5$, and $X^7$ are each independently —$CR^1R^2$—. In some embodiments, $X^7$ is —O—, —$SO_2$—, —S(O)—, or —S—, and $X^1$, $X^2$, $X^3$, $X^4$, $X^5$, and $X^6$ are each independently —$CR^1R^2$—.

In other embodiments of the compounds of Formulae I and II, L is a bond. In other embodiments, L is —$(CR^1R^2)_n$—. In other embodiments, L is —$S(O)_2$—. In other embodiments, L is —$S(O)_2NR^3$—, —S(O)—, or —$S(O)NR^3$—. In other embodiments, L is —$C(O)(CR^1R^2)_nO$—. In other embodiments, L is —$C(O)(CR^1R^2)_n$— and n is 0. In other embodiments, L is —$C(O)NR^3$—.

In other embodiments of the compounds of Formulae I and II, R is —$C_1$-$C_6$alkyl optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl. In other embodiments, R is —$C_2$-$C_6$alkenyl or —$C_2$-$C_6$alkynyl optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl. In other embodiments, R is aryl or heteroaryl optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl. In other embodiments, R is —$C_4$-$C_8$cycloalkenyl, —$C_3$-$C_8$cycloalkyl, —$C_5$-$C_{12}$spirocycle, heterocyclyl, or spiroheterocyclyl, optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl.

In other embodiments of the compounds of Formula I, m is 0, 1, 2, or 3. In another embodiment m is 0. In yet another embodiment, m is 1. In yet another embodiment, m is 2. In yet another embodiment, m is 3.

In some embodiments of the invention, the compounds of Formula I or Formula II are enantiomers. In some embodiments the compounds are the (S)-enantiomer. In other embodiments the compounds are the (R)-enantiomer. In yet other embodiments, the compounds of Formula I or Formula II may be (+) or (−) enantiomers. As used herein, a chemical structure that is labelled as "R/S" indicates that the structure represents one enantiomer, the stereochemistry of which is not defined.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Methods of Synthesizing the Disclosed Compounds

The compounds of the present invention may be made by a variety of methods, including standard chemistry. Suitable synthetic routes are depicted in the schemes given below.

The compounds of Formula I or Formula II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I or Formula II. Those skilled in the art will recognize if a stereocenter exists in the compounds of Formula I or Formula II. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the Formula I (e.g., Formula I-m, I-n, I-p, I-q, I-r and II-g) can be synthesized using the methods described below, together with synthetic methods known in the art of synthetic organic chemistry, or variations thereon as appreciated by those skilled in the art. These methods include but are not limited to those methods described below.

Scheme 1. General synthesis of compounds of Formula (I-n) and (I-p).

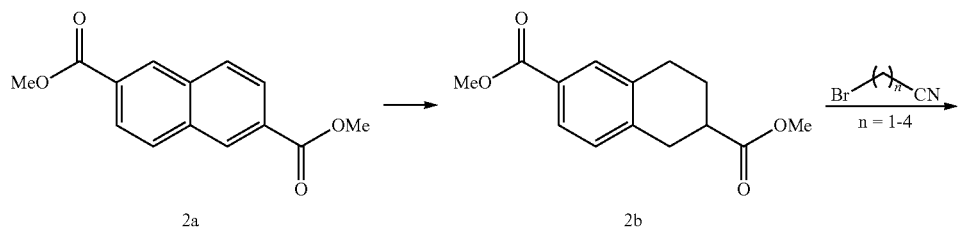

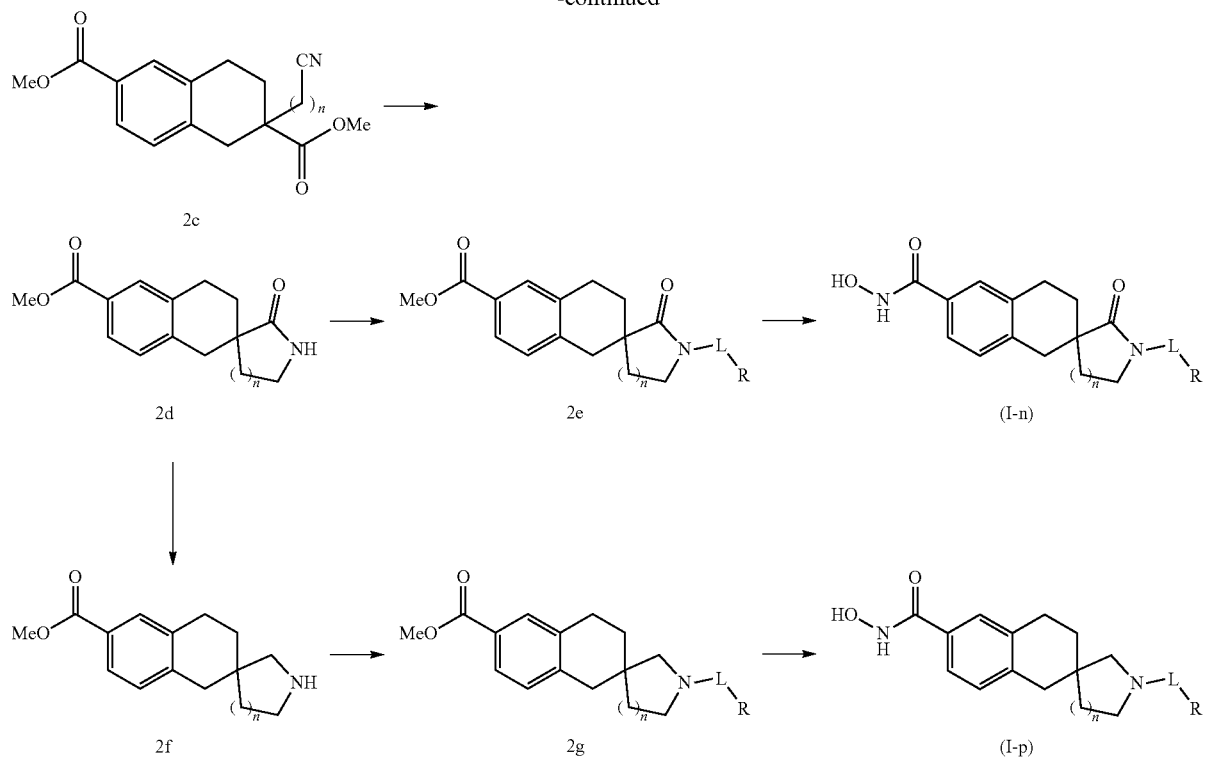

wherein L and R are defined as in Formula (I).

The general way of preparing target molecules of Formula (I-n) by using intermediates 2a, 2b, 2c, 2d, and 2e is outlined in General Scheme 1. Hydrogenation of 2,6-dimethyl naphthalene-2,6-dicarboxylate (2a) in the presence of palladium on carbon under standard conditions affords 2b. Deprotonation of 2b with a base, followed by alkylation with a halo-nitrile provides intermediates 2c. Spiro-lactams 2d can be obtained by treatment of 2c with platinum (IV) oxide ($PtO_2$) in the presence of hydrogen ($H_2$) gas and ammonia ($NH_3$). Addition of the R-L moiety can be achieved via standard methods of alkylation or arylation. For example, alkylation of 2d with an alkyl halide in the presence of a base, e.g. sodium hydride, can provide compounds of intermediates 2e. Alternatively, arylation of 2d with an aryl bromide or aryl iodide in the presence of a metal catalyst, e.g. copper (I) iodide (CuI), and a base, e.g. cesium carbonate ($Cs_2CO_3$), can also provide compounds of intermediates 2e. Treatment of 2e with hydroxylamine and a base, e.g, sodium hydroxide, provides compounds of Formula (I-n).

The general way of preparing target molecules of Formula (I-p) by using intermediates 2a, 2b, 2c, 2d, 2f, and 2g is also outlined in General Scheme 1. Spiro-amines 2f can be obtained by treatment of 2d with borane-tetrahydrofuran complex under standard reduction conditions. Addition of the R-L moiety can be achieved via standard methods of alkylation, arylation, acylation, urea formation, or sulfonation. Treatment of 2g with hydroxylamine and a base, e.g, sodium hydroxide, provides compounds of Formula (I-p).

Scheme 2. General synthesis of sulfone compounds of the Formula (I-q).

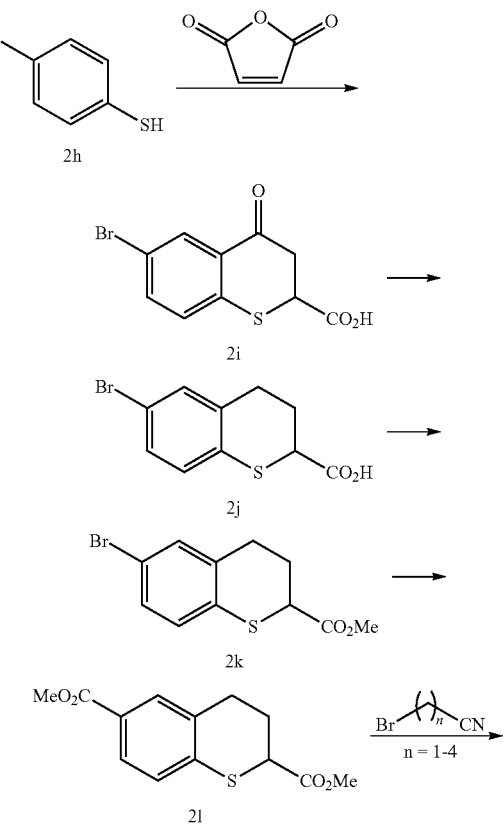

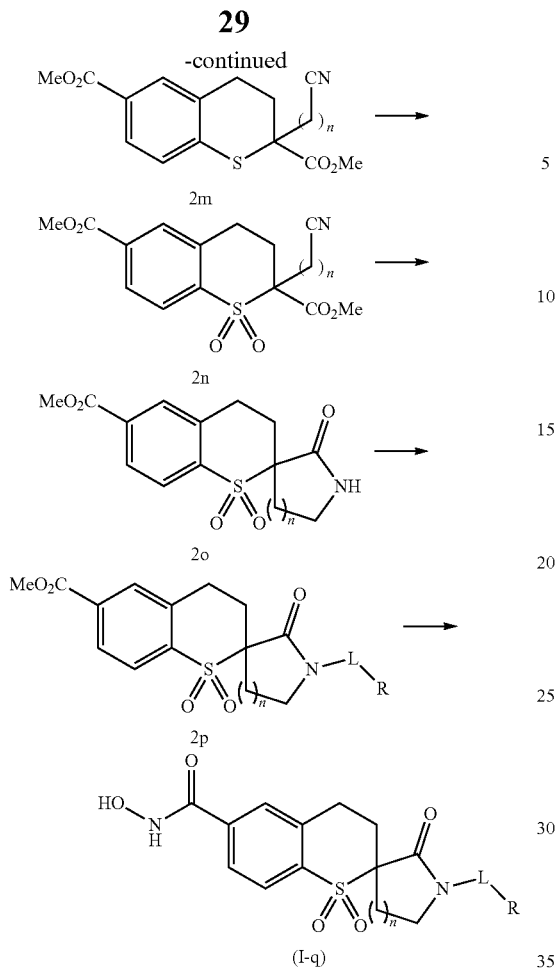

wherein L and R are defined as in Formula (I).

The general way of preparing target molecules of Formula (I-q) by using intermediates 2h, 2i, 2j, 2k, 2l, 2m, 2n, 2o, and 2p is outlined in General Scheme 2. Treatment of 4-bromobenzenethiol (2h) with 2,5-dihydrofuran-2,5-dione and a base, e.g. triethylamine, followed by aluminum chloride, affords 2i. Treatment of 2i with triethylsilane in the presence of an acid, e.g. trifluoroacetic acid, provides 2j. Standard esterification methods afford methyl ester 2k. Carbonylation of 2k with carbon monoxide gas in the presence of a metal catalyst, e.g. [1,1'-bis(diphenylphosphino)ferrocene]dichloropalladium(II) (Pd(dppf)Cl$_2$), a base, e.g. triethylamine, and methanol, affords 2l. Deprotonation of 2l with a base, followed by alkylation with a halo-nitrile provides intermediates 2m, which can be readily oxidized to the sulfones 2n with m-chloroperoxybenzoic acid. Spiro-lactams 2o can be obtained by treatment of 2n with PtO$_2$ in the presence of H$_2$ gas and NH$_3$. Addition of the R-L moiety can be achieved via standard methods of alkylation or arylation. For example, alkylation of 2o with an alkyl halide in the presence of a base, e.g. sodium hydride, can provide compounds of intermediates 2p. Alternatively, arylation of 2o with an aryl bromide or aryl iodide in the presence of a metal catalyst, e.g. palladium (II) acetate (Pd(OAc)$_2$), a ligand, e.g. 4,5-Bis(diphenylphosphino)-9,9-dimethylxanthene (Xant-Phos), and a base, e.g. Cs$_2$CO$_3$, can also provide compounds of intermediates 2p. Treatment of 2p with hydroxylamine and a base, e.g, sodium hydroxide, provides compounds of Formula (I-q).

Scheme 3. General synthesis of amide compounds of the Formula (I-r).

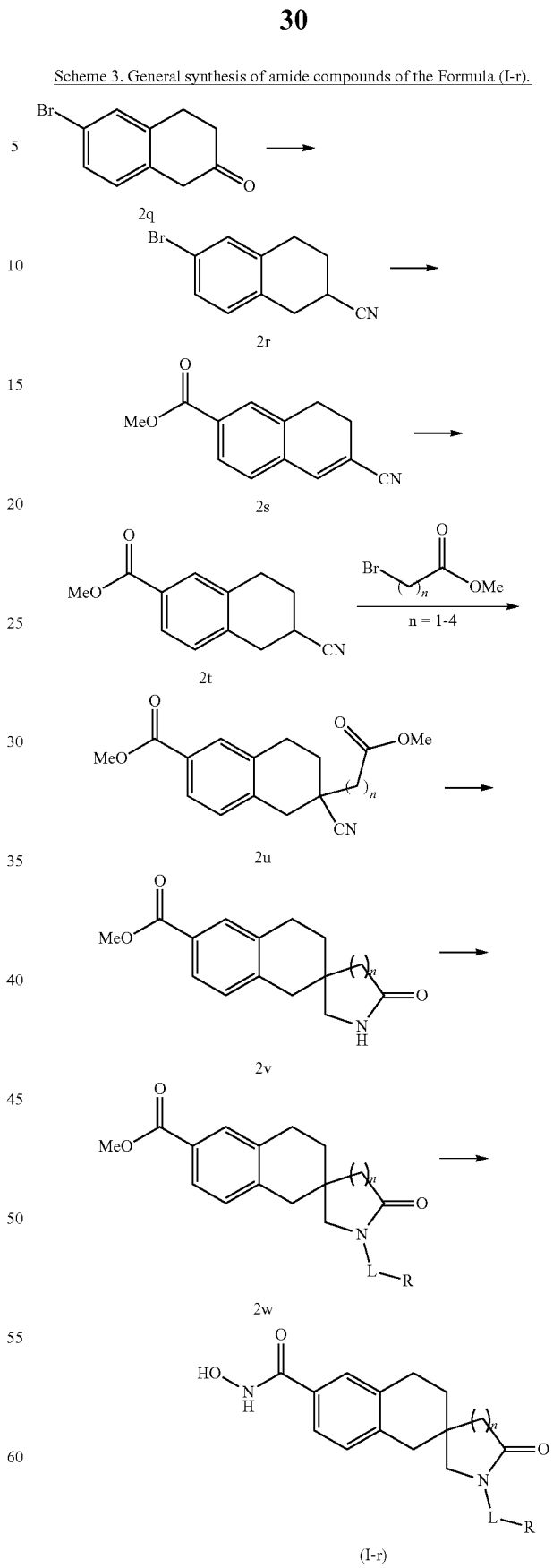

wherein L and R are defined as in Formula (I).

The general way of preparing target molecules of Formula (I-r) by using intermediates 2q, 2r, 2s, 2t, 2u, 2v, and 2w is outlined in General Scheme 3. Nitrile addition to 6-bromo-3,4-dihydronaphthalen-2(1H)-one (2q), for example with trimethylsilyl cyanide in the presence of zinc diiodide, followed by dehydration, for example with phosphorus (V) oxychloride, provides 2r. Carbonylation of 2r with carbon monoxide gas in the presence of a metal catalyst, e.g. Pd(dppf)Cl$_2$, a base, e.g. triethylamine, and methanol, affords methyl ester 2s. Treatment of 2s with magnesium provides affords 2t, which can be deprotonated with a base, and alkylated with a halo-ester to provide intermediates 2u. Spiro-lactams 2v can be obtained by treatment of 2u with PtO$_2$ in the presence of H$_2$ gas and NH$_3$. Addition of the R-L moiety can be achieved via standard methods of alkylation or arylation. For example, alkylation of 2v with an alkyl halide in the presence of a base, e.g. sodium hydride, can provide compounds of intermediates 2w. Alternatively, coupling of 2v with an aryl boronic acid in the presence of a metal catalyst, e.g. copper (II) acetate (Cu(OAc)$_2$), and a base, e.g. triethylamine, can also provide compounds of intermediates 2w. Treatment of 2w with hydroxylamine and a base, e.g, sodium hydroxide, provides compounds of Formula (I-r).

Scheme 4. General synthesis of ether compounds of the Formula (I-s).

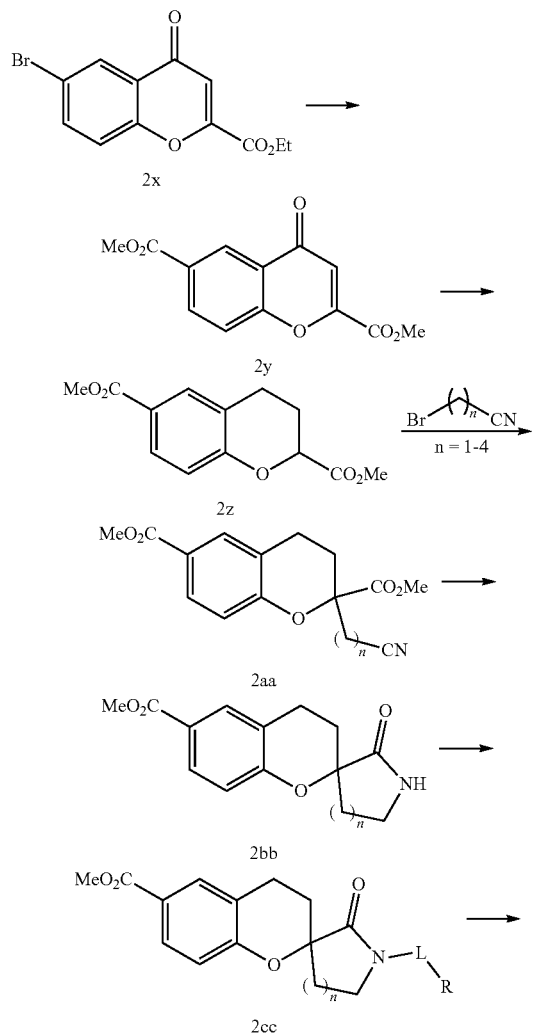

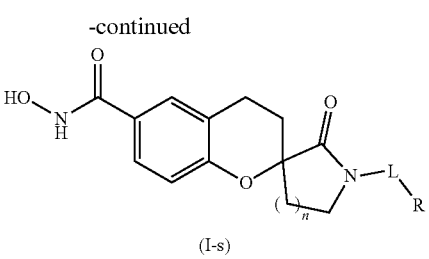

(I-s)

wherein L and R are defined as in Formula (I).

The general way of preparing target molecules of Formula (I-s) by using intermediates 2x, 2y, 2z, 2aa, 2bb, and 2cc is outlined in General Scheme 4. Carbonylation of ethyl 6-bromo-4-oxo-4H-chromene-2-carboxylate (2x) can be achieved by treatment with carbon monoxide gas in the presence of a metal catalyst, e.g. Pd(dppf)Cl$_2$, a base, e.g. triethylamine, and methanol, to afford methyl ester 2y. Reduction of the chromenone, for example by treatment with H$_2$ gas in the presence of palladium on carbon and acetic acid, provides chromane 2z. Deprotonation of 2z with a base, followed by alkylation with a halo-nitrile provides intermediates 2aa. Spiro-lactams 2bb can be obtained by treatment of 2aa with PtO$_2$ in the presence of H$_2$ gas and NH$_3$. Addition of the R-L moiety can be achieved via standard methods of alkylation or arylation. For example, alkylation of 2bb with an alkyl halide in the presence of a base, e.g. sodium hydride, can provide compounds of intermediates 2cc. Alternatively, coupling of 2bb with an aryl bromide or aryl iodide in the presence of a metal catalyst, e.g. Pd(OAc)$_2$, a ligand, e.g. XantPhos, and a base, e.g. Cs$_2$CO$_3$, can also provide compounds of intermediates 2cc. Treatment of 2cc with hydroxylamine and a base, e.g, sodium hydroxide, provides compounds of Formula (I-s).

Scheme 5. General synthesis of compounds of the Formula (II-f).

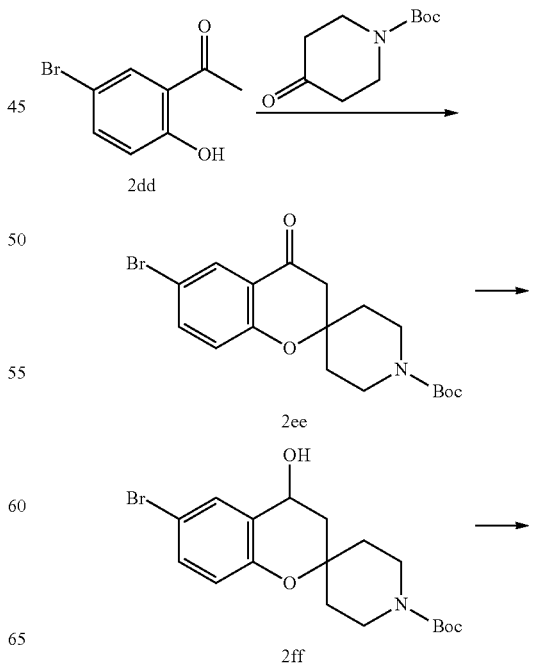

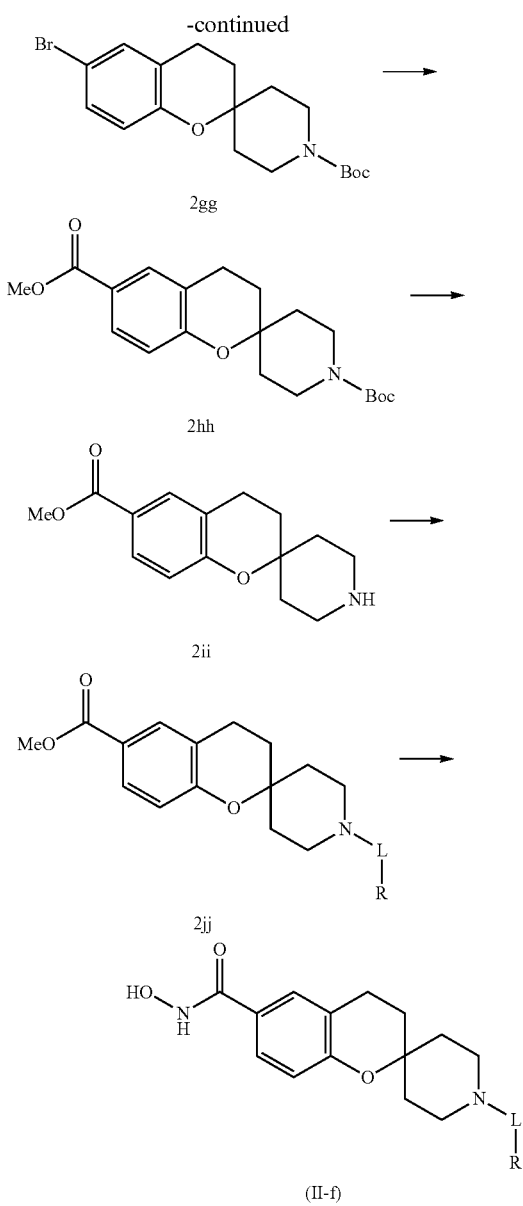

wherein L and R are defined as in Formula (II).

The general way of preparing target molecules of Formula (II-f) by using intermediates 2dd, 2ee, 2ff, 2gg, 2hh, 2ii, and 2jj is outlined in General Scheme 5. Treatment of 1-(5-bromo-2-hydroxyphenyl)ethan-1-one (2dd) with tert-butyl 4-oxopiperidine-1-carboxylate in the presence of a base affords 2ee, which can be reduced by stepwise treatment with sodium borohydride, followed by triethylsilane and trifluroacetic acid to afford 2gg. Carbonylation of 2gg can be achieved by metal exchange, e.g. with n-butyl lithium, followed by treatment with methyl chloroformate, to afford methyl ester 2hh. Spiro-amine 2ii can be readily obtained by standard Boc deprotection methods. Addition of the R-L moiety can be achieved via standard methods of alkylation, arylation, acylation, urea formation, or sulfonation. Treatment of 2jj with hydroxylamine and a base, e.g. sodium hydroxide, provides compounds of Formula (II-f).

Methods of Using the Disclosed Compounds

Another aspect of the invention relates to a method of treating a disease associated with HDAC6 modulation in a subject in need thereof. The method involves administering to a patient in need of treatment for diseases or disorders associated with HDAC6 modulation an effective amount of a compound of Formula I or Formula II. In an embodiment, the disease can be, but is not limited to, cancer, neurodegenerative disease, neurodevelopmental disease, inflammatory or autoimmune disease, infection, metabolic disease, hematologic disease, or cardiovascular disease.

Another aspect of the invention is directed to a method of inhibiting HDAC6. The method involves administering to a patient in need thereof an effective amount of Formula I or Formula II.

The present invention relates to compositions capable of modulating the activity of (e.g., inhibiting) HDACs, and in particular HDAC6. The present invention also relates to the therapeutic use of such compounds.

One therapeutic use of the compounds of the present invention is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), Hodgkin lymphoma, melanoma and multiple myeloma. In other embodiments, treating proliferative diseases or disorders can include any cancer where there is evidence of an increase in Treg/effector T cell ratio or in an absolute Treg number, either in the periphery or in the tumor microenvironment or tertiary lymphoid structures, or increased expression of T cell tolerance-related genes. Such proliferative diseases or disorders can include but are not limited to: any Kras mutant carrying tumor (http://cancerimmunolres.aacrjournals.org/content/early/2016/02/13/2326-6066.CIR-15-0241.long); renal cell carcinoma; lung carcinoma; cervical cancer; prostate cancer; ovarian cancer; head and neck cancer; lymphoma; colorectal cancer, non-small cell lung carcinoma; breast cancers (Gobert, M. et al. (2009) Cancer Res. 69, 2000-2009); and bladder cancer.

One therapeutic use of the compounds of the present disclosure is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, amyotrophic lateral sclerosis, spinal muscular atrophy, essential tremor, central nervous system trauma caused by tissue injury, oxidative stress-induced neuronal or axomal degeneration, and multiple sclerosis.

Another therapeutic use of the compounds of the present disclosure is to treat neurodevelopmental disorders. Neurodevelopmental disorders can include, but are not limited to, Rett syndrome, intellectual disability, intellectual and developmental disability, autism spectrum disorder, fetal alcohol syndrome, developmental coordination disorder, stereotypic movement disorder, Tourette syndrome, cerebral palsy, fragile X syndrome, attention deficit hyperactivity disorder, and Mendelsohn's syndrome.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-10, and increased expression of the FOXP3 transcription factor. In some embodiments, the inflammatory diseases include fibrosis or fibrotic diseases. Types of fibrotic diseases include but are not limited to lung fibrosis or pulmonary fibrosis, Liver fibrosis; Heart fibrosis; Mediastinal fibrosis; Retroperitoneal cavity fibrosis; Bone marrow fibrosis; Skin fibrosis; and Scleroderma or systemic sclerosis.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to rheumatoid arthritis, Crohn's disease, type-1 diabetes, systemic juvenile idiopathic arthritis; inflammatory bowel disease; allograft transplantation; eczema, psoriasis, idiopathic thrombocytopenic purpra, autoimmune thrombocytopenia, acquired immune thrombocytopenia, autoimmune neutropenia, autoimmune hemolyitic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lamber-Eaton myasthenic syndrome, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atomic dermatitis, systemic and diffuse sclerosis, primary biliary cirrhosis, Celiac disease, dermatitis herpetiformis, cryptogenic cirrhosis, reactive arthritis, Hashimoto's thryroditis, Wegner's granulomoatosis, micropolyarterits, Churg-Strauss syndrome Type I and Type II autoimmune polygalndular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Bechet's syndrome temporal arteritis, Takayasu's arteritis, autoimmune urticaria, and Kawasaki's disease.

Another therapeutic use of the compounds of the present invention is also to treat infectious diseases or disorders. Infections or infectious diseases are caused by the invasion of a foreign pathogen. The infection may be caused by, for instance, a bacteria, a fungus, or virus. Bacterial infections include, but are not limited to *streptococcus* infections, mycobacterial infections, *bacillus* infections, *Salmonella* infections, *Vibrio* infections, spirochete infections, and *Neisseria* infections. Viral infections include, but are not limited to herpes virus infections, hepatitis virus infections, west nile virus infections, flavivrus infections, influenza virus infections, rhinovirus infections, papillomavirus infections, paromyxovirus infections, parainfluenza virus infections, and retrovirus infections. In particular embodiments, the compounds of the present invention are useful for treating infections which result in an inflammatory cytokine burst. Nonlimiting examples of such infections include Ebola and othe viral hemorghagic fever-causing viruses, and Malaria.

Another therapeutic use of the compounds of the present invention is also to treat and/or prevent allergy and unwanted immune responses associated with allergy. A non-limiting list of allergies and related conditions includes, pollen allergy (e.g. Japanese Cedar Pollen), mold allergy, food allergies (including, but not limited to peanut, tree nut, milk, soy, gluten, and egg allergies), animal allergies (e.g. allergies to dogs, cats, rabbits), dust mite allergy, atopic dermatitis, allergic rhinitis, allergic otitis, allergic asthma, dry eye, ocular allergy, allergic urticaria, contact dermatitis, anaphalaxis, eosinophilic esophagitis.

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, non-alcoholic fatty liver disease and heart failure.

Yet another therapeutic use of the compounds of the present invention is also to treat hematologic disorders. Hematologic diseases primarily affect the blood. Hematologic disorders can include but are not limited to anemia, multiple myeloma, lymphoma, and leukemia.

Yet another therapeutic use of the compounds of the present invention is also to prevent and/or treat transplant rejection. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, and heart failure.

Another therapeutic use of the compounds of the present invention is for purging the reservoir of latently infected memory CD4+ T cells in HIV+ patients (Matalon, et al., Mol Med. 2011; 17(5-6): 466-472).

The disclosed compound can be administered in effective amounts to treat or prevent a disorder and/or prevent the development thereof in subjects.

Another aspect of the present disclosure relates to a compound of Formula I or Formula II, or a pharmaceutically acceptable salt, hydrate, solvate, prodrug, stereoisomer, or tautomer thereof, for use in treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In another aspect, the present disclosure relates to the use of a compound of Formula (I) or Formula (II), or a pharmaceutically acceptable salt, hydrate, solvate, prodrug, stereoisomer, or tautomer thereof, in the manufacture of a medicament for treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In some embodiments, the cancer is melanoma, cutaneous T-cell lymphoma, peripheral T-cell lymphoma, Hodgkin lymphoma, multiple myeloma, leukemia, lung, ovarian, breast, prostate, pancreatic, hepatocellular or renal cancer. In other embodiments, the neurodegenerative disease is Alzheimer's, Huntington's, Parkinson's, Amyotrophic Lateral Sclerosis, or spinal muscular atrophy. In other embodiments, the neurodevelopmental disorder is Rett syndrome. In yet other embodiments, the inflammatory or autoimmune disease is rheumatoid arthritis, spondylitis arthritis, psoriatic arthritis, psoriasis, multiple sclerosis, systemic lupus erythematosus, inflammatory bowel diseases, graft versus host disease, transplant rejection or fibrotic disease.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanami dephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formula I or Formula II and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present invention can inhibit HDACs such as HDAC6 by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present invention includes a number of unique features and advantages compared with other inhibitors of HDAC enzymes, in particular HDAC6. For instance, the present invention features a unique class of small molecule therapeutic agents of Formula I or Formula II. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:
AcOH Acetic acid
$AlCl_3$ Aluminum chloride
$CH_2Cl_2$ Methylene chloride, Dichloromethane
$CH_3CN$ Acetonitrile
CO (g) Carbon monoxide gas
$CH_3I$ Iodomethane
$CO_2$ Carbon dioxide
$Cs_2CO_3$ Cesium carbonate
$Cu(OAc)_2$ Copper (II) acetate
CuI Copper (I) iodide
CuBr Copper (I) bromide
DCE 1,2-Dichloroethane
DMA Dimethylacetamide
DIEA Diisopropylethylamine
DMC 2-Chloro-1,3-dimethylimidazolinium chloride
DMF N,N-Dimethylformamide
DMSO Dimethylsulfoxide
$Et_3N$ Triethylamine
$Et_2O$ Diethyl ether
EtOAc Ethyl acetate
EtOH Ethanol
h hours
$H_2$ (g) Hydrogen (gas)
$H_2O$ Water
HBTU N,N,N',N'-Tetramethyl-O-(1H-benzotriazol-1-yl)uronium hexafluorophosphate
HCl Hydrochloric acid
$K_2CO_3$ Potassium carbonate
$K_3PO_4$ Potassium phosphate tribasic
LDA Lithium diisopropylamide
m-CPBA 3-Chloroperbenzoic acid MeOH Methanol
$MgSO_4$ Magnesium sulfate
min minutes
$NaBH(OAc)_3$ Sodium triacetoxyborohydride
$Na_2CO_3$ Sodium carbonate
$Na_2SO_4$ Sodium sulfate
$NH_4Cl$ Ammonium chloride
$NH_4HCO_3$ Ammonium bicarbonate
NaH Sodium hydride
$NaHCO_3$ Sodium bicarbonate
$NH_3$ Ammonia
NaI Sodium iodide
NaOH Sodium hydroxide
$NH_2OH$ Hydroxylamine
NMM 4-Methylmorpholine
$Pd(dppf)Cl_2$ [1,1'-Bis(diphenylphosphino)ferrocene]dichloropalladium(II)
$Pd(dppf)Cl_2 \cdot CH_2Cl_2$ [1,1'-Bis(diphenylphosphino)ferrocene]dichloropalladium(II)-dichloromethane adduct
$Pd(OAc)_2$ Palladium (II) acetate
$Pd_2(dba)_3$ Tris(dibenzylideneacetone)dipalladium(0)
$POCl_3$ Phosphorus (V) oxychloride
$PtO_2$ Platinum (IV) oxide
PTSA p-Toluenesulfonic acid monohydrate
RuPhos 2-Dicyclohexylphosphino-2',6'-diisopropoxybiphenyl
RuPhos Pd G2 Chloro(2-dicyclohexylphosphino-2',6'-diisopropoxy-1,1'-biphenyl) [2-(2'-amino-1,1'-biphenyl)]palladium(II)
TFA Trifluoroacetic acid
THF Tetrahydrofuran
TMSCN Trimethylsilyl cyanide
XantPhos 4,5-Bis(diphenylphosphino)-9,9-dimethylxanthene
$ZnI_2$ Zinc diiodide Example 1

Preparation of 1'-benzyl-N-hydroxy-2'-oxo-3,4-dihydro-1H-spiro[naphthalene-2,3'-piperidine]-6-carboxamide (I-176)

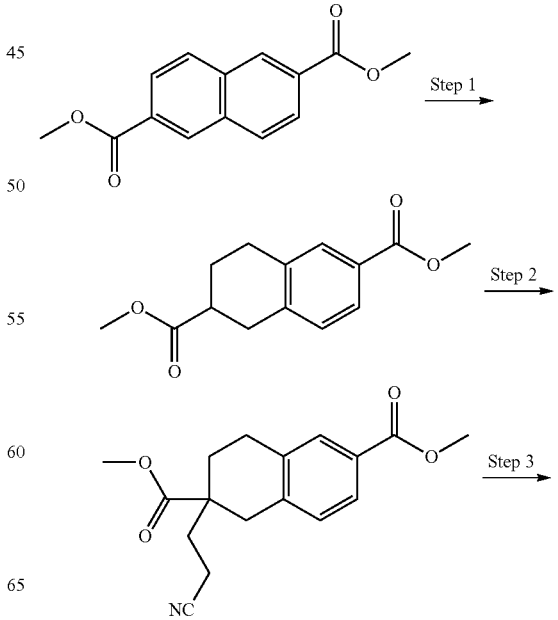

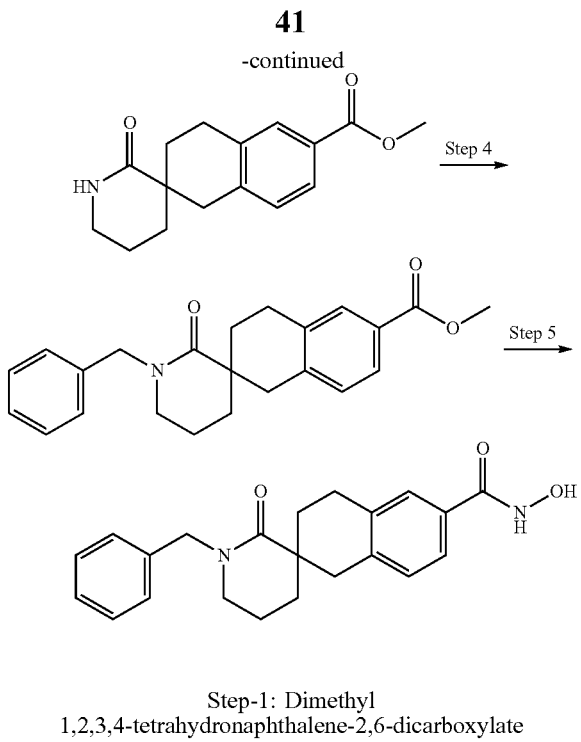

Step-1: Dimethyl 1,2,3,4-tetrahydronaphthalene-2,6-dicarboxylate

Into a 2-L pressure tank reactor was placed 2,6-dimethyl naphthalene-2,6-dicarboxylate (50 g, 204.71 mmol, 1 equiv) in isopropanol (1.2 L), palladium on carbon (9.5 g) and acetic acid (5 g, 83.26 mmol, 0.41 equiv). Hydrogen gas (50 atm) was introduced. The resulting solution was stirred for 2 days at 40° C. The solids were filtered off. The filter cake was washed with 2×200 mL of CH$_2$Cl$_2$ and 2×200 mL of MeOH. The combined filtrate was concentrated under vacuum. The residue was dissolved with 300 mL of EtOAc. The pH was adjusted to 8 using aq. Na$_2$CO$_3$. The organic layer was washed with 3×100 mL of H$_2$O and dried with anhydrous Na$_2$SO$_4$, filtered and concentrated under vacuum to give 40 g (79% yield) of the title compound as a white solid. MS: (ES, m/z): 249 [M+H]$^+$.

Step-2: Dimethyl 2-(2-cyanoethyl)-1,2,3,4-tetrahydronaphthalene-2,6-dicarboxylate Into a 500-mL 3-necked round-bottom flask purged and maintained with N$_2$, was placed dimethyl 1,2,3,4-tetrahydronaphthalene-2,6-dicarboxylate (6 g, 24.17 mmol, 1 equiv) in THF (50 mL, 1 equiv). The solution was cooled to −78° C. and LDA (2M in THF/hexanes, 24.2 mL 2 equiv) was added dropwise to the stirring solution. After 30 min, 3-bromopropanenitrile (4.8 g, 35.83 mmol, 1.5 equiv) was added at −78° C. The resulting solution was stirred for additional 2 h. The reaction was then quenched by the addition of 30 mL of NH$_4$Cl. The resulting solution was extracted with 3×20 mL of EtOAc. The combined extracts were dried over anhydrous Na$_2$SO$_4$, filtered and concentrated under vacuum. The residue was purified by normal phase chromatography on silica gel with EtOAc/petroleum ether (1/1). The collected fractions were concentrated to give 1.6 g (22% yield) of the title compound as a white solid. MS: (ES, m/z): 302 [M+H]$^+$.

Step-3: Methyl 2′-oxo-3,4-dihydro-1H-spiro[naphthalene-2,3′-piperidine]-6-carboxylate Into a 250-mL 3-necked round-bottom flask was placed dimethyl 2-(2-cyanoethyl)-1,2,3,4-tetrahydronaphthalene-2,6-dicarboxylate (1.6 g, 5.31 mmol, 1 equiv) in MeOH (50 mL), PtO$_2$ (0.4 g) and NH$_3$/MeOH (8 mL). To the above mixture, H$_2$ (g) was introduced and the resulting mixture was stirred for 16 h at room temperature under H$_2$ atmosphere. The solids were filtered out and the filtrate was concentrated under vacuum. The crude product was purified by re-crystallization from EtOAc. This provided 1 g (69% yield) of the title compound as an off-white solid. MS: (ES, m/z): 274 [M+H]$^+$.

Step-4: Methyl 1′-benzyl-2′-oxo-3,4-dihydro-1H-spiro[naphthalene-2,3′-piperidine]-6-carboxylate Into a 100-mL round-bottom flask was placed methyl 2′-oxo-3,4-dihydro-1H-spiro[naphthalene-2,3′-piperidine]-6-carboxylate (100 mg, 0.37 mmol, 1 equiv) in DMF (5 mL, 1 equiv). The resulting mixture was cooled to 0° C. in an ice-water bath. NaH (60% dispersion in oil, 29.3 mg, 1.22 mmol, 3 equiv) was added and the mixture stirred at 0° C. for 30 min. Then (bromomethyl)benzene (68.4 mg, 0.40 mmol, 1.1 equiv) was added to the reaction. The resulting mixture was stirred for 1h at room temperature. The reaction was then quenched by the addition of 10 mL of water and was extracted with 3×10 mL of EtOAc. The combined organics were dried over anhydrous Na$_2$SO$_4$, filtered and concentrated under vacuum to give 120 mg (90% yield) of the title compound as a yellow solid. MS: (ES, m/z): 364[M+H]$^+$.

Step-5: 1′-Benzyl-N-hydroxy-2′-oxo-3,4-dihydro-1H-spiro[naphthalene-2,3′-piperidine]-6-carboxamide Into a 50-mL round-bottom flask was placed methyl 1′-benzyl-2′-oxo-3,4-dihydro-1H-spiro[naphthalene-2,3′-piperidine]-6-carboxylate (120 mg, 0.33 mmol, 1 equiv), THF/MeOH (4:1, 2 mL), NH$_2$OH (50% in water, 326.7 mg, 30 equiv), and 1N aq. NaOH (26.4 mg, 2 equiv). The resulting solution was stirred for 1h at room temperature. The pH of the solution was adjusted to 6 with 1N aq. HCl. The crude product was purified by Prep-HPLC with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 18.1 mg (15% yield) of the title compound as a pink solid. $^1$H-NMR (400 MHz, DMSO-d6) δ (ppm): 11.09 (s, 1H), 7.51 (s, 1H), 7.46-7.48 (d, J=8 Hz, 1H), 7.34-7.38 (m, 2H), 7.21-7.29 (m, 3H), 7.14-7.16 (d, J=8 Hz, 1H), 4.53 (s, 2H), 3.15-3.25 (m, 3H), 2.70-2.80 (m, 3H), 2.08-2.18 (m, 1H), 1.74-1.77 (m, 3H), 1.58-1.61 (m, 2H). MS: (ES, m/z): 365[M+H]$^+$.

Example 2

Preparation of N-hydroxy-2′-oxo-3,4-dihydro-1H-spiro[naphthalene-2,3′-piperidine]-6-carboxamide (I-177)

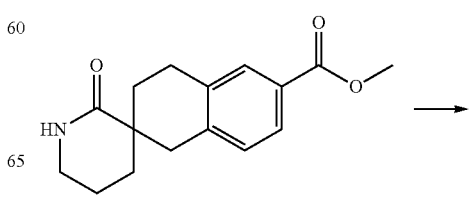

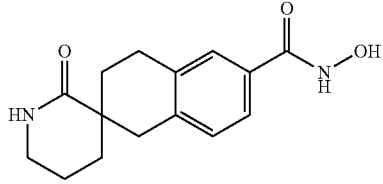

Into an 8-mL vial, was placed a solution of methyl 2'-oxo-3,4-dihydro-1H-spiro[naphthalene-2,3'-piperidine]-6-carboxylate (70 mg, 0.26 mmol, 1 equiv) in THF/MeOH (4:1, 1.5 mL), $NH_2OH$ (50% in water, 0.51 mL, 2 equiv) and 1N aq. NaOH (0.51 mL, 30 equiv). The resulting solution was stirred for 3 h at room temperature. The crude product was purified by Prep-HPLC with the following conditions: Column: Sunfire C18, 19×150, 5 μm; Mobile Phase A: Water/0.05% TFA, Mobile Phase B: $CH_3CN$/0.05% TFA; Flow rate: 25 mL/min; Gradient: 5% B to 52% B in 6 min); Detector: UV 254 nm, 220 nm. The collected fractions were lyophilized to give 39.2 mg (56% yield) of the title compound as an off-white solid. $^1$H-NMR (400 MHz, DMSO-d6) δ (ppm): 11.08 (br s, 1H), 7.50-7.41 (m, 3H), 7.13-7.12 (m, 1H), 3.16-3.06 (m, 3H), 2.82-2.71 (m, 2H), 2.70-2.65 (m, 1H), 2.08-2.00 (m, 1H), 1.70-1.66 (m, 3H), 1.59-1.58 (m, 2H). MS: (ES, m/z): 275 [M+H]$^+$.

Example 3

Preparation of N-hydroxy-1'-methyl-2'-oxo-3,4-dihydro-1H-spiro[naphthalene-2,3'-piperidine]-6-carboxamide (I-178)

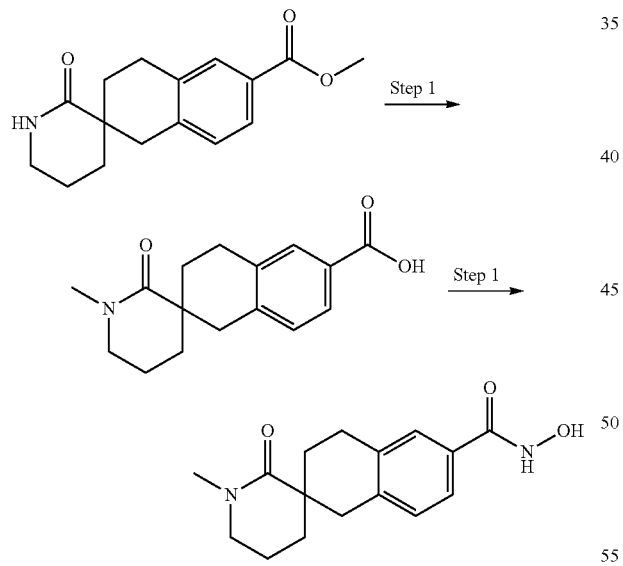

Step-1: 1'-Methyl-2'-oxo-3,4-dihydro-1H-spiro[naphthalene-2,3'-piperidine]-6-carboxylic acid Into an 8-mL vial, was placed a solution of methyl 2'-oxo-3,4-dihydro-1H-spiro[naphthalene-2,3'-piperidine]-6-carboxylate (100 mg, 0.37 mmol, 1 equiv) in DMF (4 mL). This was followed by the addition of NaH (60% dispersion in oil, 44 mg, 1.83 mmol, 3 equiv), in portions at 0° C. over 10 min. To this was added $CH_3I$ (104 mg, 0.73 mmol, 2 equiv). The resulting mixture was stirred for 18 h at room temperature. The reaction was then quenched by the addition of 10 mL of $NH_4Cl$ (aq.) at 0° C. The resulting solution was extracted with 2×20 mL of EtOAc. The aqueous layers were combined and the pH of the solution was adjusted to 4 with 1N aq. HCl. The resulting solution was extracted with 3×30 mL of $CH_2Cl_2$, dried over anhydrous magnesium sulfate, filtered and concentrated under vacuum to give 137.6 mg (crude) of the title compound as a light yellow oil which was used in the next step without purification. MS: (ES, m/z): 274 [M+H]$^+$.

Step-2: N-Hydroxy-1'-methyl-2'-oxo-3,4-dihydro-1H-spiro[naphthalene-2,3'-piperidine]-6-carboxamide Into an 8-mL vial, was placed a solution of 1'-methyl-2'-oxo-3,4-dihydro-1H-spiro[naphthalene-2,3'-piperidine]-6-carboxylic acid (135 mg, 0.49 mmol, 1 equiv) in DMA (3 mL). This was followed by the addition of isopropyl chloroformate (311 mg, 2.47 mmol, 5 equiv) and NMM (250 mg, 2.47 mmol, 5 equiv) at 0° C. over 10 min. To this was added a solution of $NH_2OH.HCl$ (173 mg, 2.47 mmol, 5 equiv) in DMA (1.5 mL). The resulting solution was stirred for 18 h at room temperature. The crude product was purified by Prep-HPLC with the following conditions: Column: Sunfire C18, 5 μm, 19×100 mm; Mobile Phase A: Water/0.05% TFA, Mobile Phase B: $CH_3CN$/0.05% TFA; Flow rate: 25 mL/min; Gradient: 5% B to 52% B in 6 min; Detector: UV 254 nm, 220 nm. The collected fractions were lyophilized to give 46.4 mg (33% yield) of the title compound as an off-white solid. $^1$H-NMR (400 MHz, DMSO-d6) δ (ppm): 11.08 (br s, 1H), 7.50-7.45 (m, 2H), 7.12-7.10 (d, J=8.0 Hz, 1H), 3.32-3.25 (m, 2H), 3.11-3.07 (m, 1H), 2.83 (s, 3H), 2.79-2.69 (m, 2H), 2.66-2.62 (m, 1H), 2.10-2.02 (m, 1H), 1.79-1.78 (m, 2H), 1.74-1.63 (m, 1H), 1.62-1.53 (m, 2H). MS: (ES, m/z): 289 [M+H]$^+$.

Example 4

Preparation of (R)-N-hydroxy-1'-methyl-2'-oxo-3,4-dihydro-1H-spiro[naphthalene-2,3'-piperidine]-6-carboxamide (I-179) and (S)-N-hydroxy-1'-methyl-2'-oxo-3,4-dihydro-1H-spiro[naphthalene-2,3'-piperidine]-6-carboxamide (I-180)

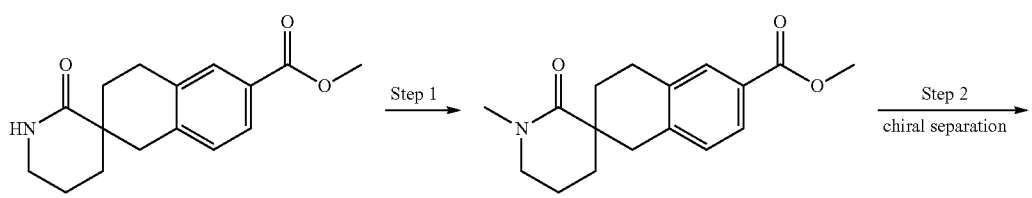

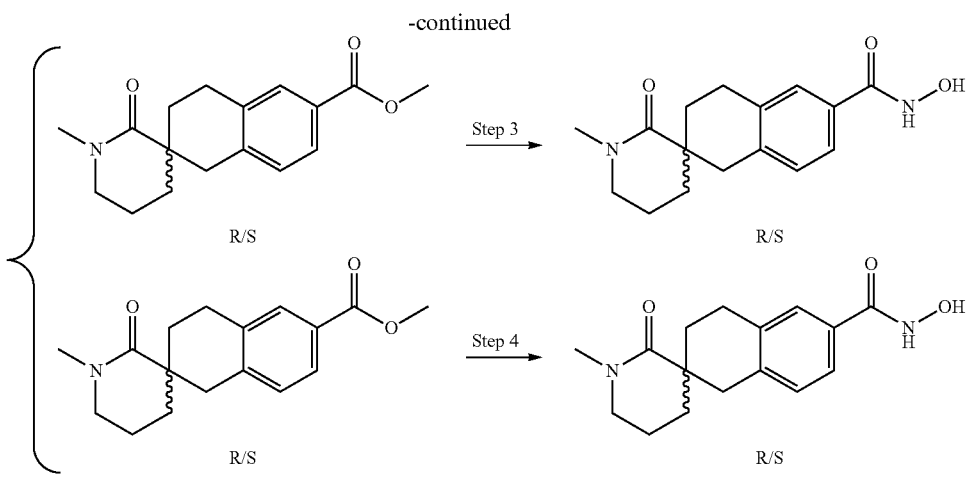

Step-1: Methyl 1'-methyl-2'-oxo-3,4-dihydro-1H-spiro[naphthalene-2,3'-piperidine]-6-carboxylate Into an 8-mL vial, was placed a solution of methyl 2'-oxo-3,4-dihydro-1H-spiro[naphthalene-2,3'-piperidine]-6-carboxylate (100 mg, 0.37 mmol, 1 equiv) in DMF (4 mL). This was followed by the addition of NaH (60% dispersion in oil, 44 mg, 1.83 mmol, 3 equiv), in portions at 0° C. over 10 min. To this was added $CH_3I$ (104 mg, 0.73 mmol, 2 equiv). The resulting solution was stirred for 18 h at room temperature. The reaction was then quenched by the addition of 10 mL of $NH_4Cl$ (aq.). The resulting solution was extracted with 3×30 mL of $CH_2Cl_2$. The organic layers were combined, dried over anhydrous magnesium sulfate, filtered and concentrated under vacuum to provide 137.6 mg (crude) of the title compound as a light yellow oil. MS: (ES, m/z): 288 $[M+H]^+$.

Step-2: Chiral separation of the racemate to obtain methyl (R)-1'-methyl-2'-oxo-3,4-dihydro-1H-spiro [naphthalene-2,3'-piperidine]-6-carboxylate and methyl (S)-1'-methyl-2'-oxo-3,4-dihydro-1H-spiro [naphthalene-2,3'-piperidine]-6-carboxylate The racemate of methyl 1'-methyl-2'-oxo-3,4-dihydro-1H-spiro[naphthalene-2,3'-piperidine]-6-carboxylate (137.6 mg, 47.9 mmol, 1 equiv) was purified by Prep-SFC with the following conditions: Column: Chiralpak IC 2×25 cm, 5 μm; Mobile Phase A: Hexanes, Mobile Phase B: EtOH; Flow rate: 18 mL/min; Gradient: 25% B in 26 min; Detector: UV 254 nm, 220 nm. The first peak (Rt 18.65 min) was collected and concentrated to give 60 mg of a yellow solid which was assigned as the R isomer of methyl 1'-methyl-2'-oxo-3,4-dihydro-1H-spiro[naphthalene-2,3'-piperidine]-6-carboxylate. MS: (ES, m/z): 288 $[M+H]^+$. The second peak (Rt 22.25 min) was collected and concentrated to give 40 mg of a yellow solid which was assigned as the S isomer of methyl 1'-methyl-2'-oxo-3,4-dihydro-1H-spiro[naphthalene-2,3'-piperidine]-6-carboxylate. MS: (ES, m/z): 288 $[M+H]^+$.

Step-3: (R)-N-Hydroxy-1'-methyl-2'-oxo-3,4-dihydro-1H-spiro[naphthalene-2,3'-piperidine]-6-carboxamide Into an 8-mL vial, was placed a solution of the first eluted isomer from Step 2, which was assigned as methyl (R)-1'-methyl-2'-oxo-3,4-dihydro-1H-spiro[naphthalene-2,3'-piperidine]-6-carboxylate as described above, (60 mg, 0.21 mmol, 1 equiv) in THF/MeOH (4:1, 1.5 mL), $NH_2OH$ (50% in water, 0.41 mL, 30 equiv) and 1N aq. NaOH (0.42 mL, 2 equiv). The resulting solution was stirred for 2 h at room temperature. The crude product was purified by Prep-HPLC with the following conditions: Column: XBridge Prep C18 OBD, 19×150 mm, 5 μm; Mobile Phase A: Water/0.1% Formic Acid, Mobile Phase B: $CH_3CN$/0.1% Formic Acid; Flow rate: 20 mL/min; Gradient: 5% B to 40% B in 8 min; Detector: UV 254 nm, 220 nm. The collected fractions were lyophilized to give 38.7 mg (64% yield) of the title compound as an off-white solid. $^1$H-NMR (400 MHz, DMSO-d6) δ (ppm): 11.08 (br s, 1H), 8.94 (br s, 1H), 7.50-7.45 (m, 2H), 7.12-7.10 (m, 1H), 3.32-3.25 (m, 2H), 3.12-3.07 (m, 1H), 2.83-2.2.79 (m, 3H), 2.78-2.76 (m, 2H), 2.74-2.72 (m, 1H), 2.10-2.02 (m, 1H), 1.79-1.73 (m, 2H), 1.69-1.61 (m, 1H), 1.59-1.51 (m, 2H). MS: (ES, m/z): 289 $[M+H]^+$.

Step-4: (S)-N-Hydroxy-1'-methyl-2'-oxo-3,4-dihydro-1H-spiro[naphthalene-2,3'-piperidine]-6-carboxamide Into an 8-mL vial, was placed a solution of the second eluted isomer from Step 2, which was assigned as methyl (S)-1'-methyl-2'-oxo-3,4-dihydro-1H-spiro[naphthalene-2,3'-piperidine]-6-carboxylate as described above, (40 mg, 0.14 mmol, 1 equiv) in THF/MeOH (4:1, 1.5 mL), $NH_2OH$ (50% in water, 0.27 mL, 30 equiv) and 1N aq. NaOH (0.29 mL, 2 equiv). The resulting solution was stirred for 2 h at room temperature. The crude product was purified by Prep-HPLC with the following conditions: Column: XBridge Prep C18 OBD, 19×150 mm, 5 μm; Mobile Phase A: Water/0.1% Formic Acid, Mobile Phase B: $CH_3CN$/0.1% Formic Acid; Flow rate: 20 mL/min; Gradient: 5% B to 40% B in 8 min; Detector: UV 254 nm, 220 nm. The collected fractions were lyophilized to give 33.7 mg (84% yield) of the title compound as an off-white solid. $^1$H-NMR (400 MHz, DMSO-d6) δ (ppm): 11.06 (br s, 1H), 8.92 (br s, 1H), 7.48-7.43 (m, 2H), 7.10-7.08 (m, 1H), 3.31-3.25 (m, 2H), 3.10-3.06 (m, 1H), 2.81-2.61 (m, 6H), 2.08-2.00 (m, 2H), 1.78-1.72 (m, 2H), 1.68-1.64 (m, 1H), 1.57-1.50 (m, 2H). MS: (ES, m/z): 289 $[M+H]^+$.

Example 5

Preparation of (R)-N-hydroxy-2'-oxo-1'-phenyl-3,4-dihydro-1H-spiro[naphthalene-2,3'-piperidine]-6-carboxamide (I-181) and (S)-N-hydroxy-2'-oxo-1'-phenyl-3,4-dihydro-1H-spiro[naphthalene-2,3'-piperidine]-6-carboxamide (I-182)

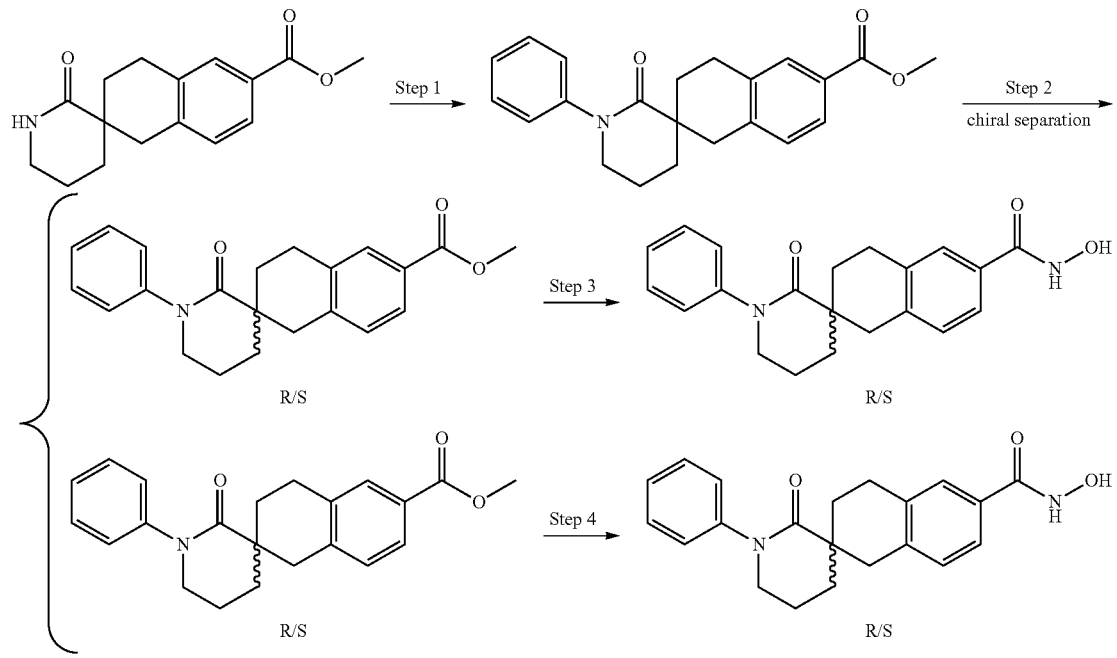

Step-1: Methyl 2'-oxo-1'-phenyl-3,4-dihydro-1H-spiro[naphthalene-2,3'-piperidine]-6-carboxylate Into a 25-mL round-bottom flask, was placed methyl 2'-oxo-3,4-dihydro-1H-spiro[naphthalene-2,3'-piperidine]-6-carboxylate (500 mg, 1.83 mmol, 1 equiv) in DMSO (8 mL), iodobenzene (448 mg, 2.20 mmol, 1.2 equiv), CuI (70 mg, 0.37 mmol, 0.2 equiv), $Cs_2CO_3$ (1.78 g, 5.46 mmol, 3 equiv), and methyl[2-(methylamino)ethyl]amine (65 mg, 0.74 mmol, 0.4 equiv). The resulting mixture was stirred overnight at 130° C. The reaction was then quenched by the addition of 20 mL of water, extracted with 3×50 mL of $CH_2Cl_2$, washed with 100 mL of brine, dried over anhydrous $Na_2SO_4$, filtered and concentrated under vacuum. The residue was purified by normal phase column chromatography on silica gel with EtOAc/petroleum ether (1:5). The collected fractions were concentrated under vacuum to give 150 mg (23% yield) of the title compound as an off-white solid. MS: (ES, m/z): 350 [M+H]$^+$.

Step-2: Chiral separation of methyl (R)-2'-oxo-1'-phenyl-3,4-dihydro-1H-spiro[naphthalene-2,3'-piperidine]-6-carboxylate and methyl (S)-2'-oxo-1'-phenyl-3,4-dihydro-1H-spiro[naphthalene-2,3'-piperidine]-6-carboxylate The racemate was purified by Chiral-HPLC with the following conditions: Column: CHIRALPAK IC 2×25 cm, 5 μm; Mobile Phase A: Hexanes, Mobile Phase B: EtOH; Flow rate: 15 mL/min; Gradient: 50% B to 50% B in 21 min; Detector: UV 254 nm, 220 nm. The first eluting isomer (Rt 12.37 min) was collected and concentrated under vacuum to give 55 mg (37% yield) of an off-white solid which was assigned as the R isomer of methyl 2'-oxo-1'-phenyl-3,4-dihydro-1H-spiro[naphthalene-2,3'-piperidine]-6-carboxylate. MS: (ES, m/z): 350 [M+H]$^+$. The second eluting isomer (Rt 15.78 min) was collected and concentrated under vacuum to give 48 mg (32% yield) of an off-white solid which was assigned as the S isomer of methyl 2'-oxo-1'-phenyl-3,4-dihydro-1H-spiro[naphthalene-2,3'-piperidine]-6-carboxylate. MS: (ES, m/z): 350 [M+H]$^+$.

Step-3: (R)-N-Hydroxy-2'-oxo-1'-phenyl-3,4-dihydro-1H-spiro[naphthalene-2,3'-piperidine]-6-carboxamide Into a 25-mL round-bottom flask, was placed the first eluted isomer from Step 2, which was assigned as methyl (R)-2'-oxo-1'-phenyl-3,4-dihydro-1H-spiro[naphthalene-2,3'-piperidine]-6-carboxylate as described above, (55 mg, 0.16 mmol, 1 equiv), THF/MeOH (4:1, 3 mL), $NH_2OH$ (50% in $H_2O$, 1560 mg, 30.56 mmol, 150 equiv) and 1N aq. NaOH (0.3 mL, 2 equiv). The resulting solution was stirred for 2 h at room temperature. The solids were filtered out and the crude product was purified by Prep-HPLC with the following conditions: Column: XBridge Prep C18 OBD, 5 μm, 19×150 mm; Mobile Phase A: Water/0.01% $NH_4HCO_3$, Mobile Phase B: $CH_3CN$; Gradient: 15% B to 60% B in 6 min; Detector: UV 254 nm, 220 nm. The collected fractions were lyophilized to give 38.6 mg (70% yield) of the title compound as an off-white solid. $^1$H-NMR (300 MHz, DMSO-d6) δ(ppm): 10.56 (s, 1H), 8.95 (s, 1H), 7.52-7.47 (t, J=8.3 Hz, 2H), 7.41-7.36 (m, 2H), 7.27-7.22 (m, 3H), 7.16-7.14 (d, J=8 Hz, 1H), 3.66-3.62 (t, J=5.9 Hz, 2H), 3.19-3.14 (d, J=16.8 Hz, 1H), 2.88-2.73 (m, 3H), 2.18-2.08 (m, 1H), 1.96-1.70 (m, 5H). MS: (ES, m/z): 351 [M+H]$^+$.

Step-4: (S)-N-Hydroxy-2'-oxo-1'-phenyl-3,4-dihydro-1H-spiro[naphthalene-2,3'-piperidine]-6-carboxamide Into a 25-mL round-bottom flask, was placed the second eluted isomer from Step 2, which was assigned as methyl (S)-2'-oxo-1'-phenyl-3,4-dihydro-1H-spiro[naphthalene-2,3'-piperidine]-6-carboxylate as described above, (43 mg, 0.12 mmol, 1 equiv), THF/MeOH (4:1, 2 mL), NH$_2$OH (50% in H$_2$O, 1220 mg, 23.90 mmol, 150 equiv), 1N aq. NaOH (0.25 mL, 2 equiv). The resulting solution was stirred for 2 h at room temperature. The solids were filtered out and the crude product was purified by Prep-HPLC with the following conditions: Column: XBridge Prep C18 OBD, 5 μm, 19×150 mm; Mobile Phase A: Water/0.01% NH$_4$HCO$_3$, Mobile Phase B: CH$_3$CN; Gradient: 15% B to 60% B in 6 min; Detector: UV 254 nm, 220 nm. The collected fractions were lyophilized to give 39.4 mg (91% yield) of the title compound as an off-white solid. $^1$H-NMR (400 MHz, DMSO-d6) δ (ppm): 11.07 (br s, 1H), 8.97 (s, 1H), 7.53 (s, 1H), 7.50-7.48 (d, J=8 Hz, 1H), 7.42-7.38 (t, J=7.8 Hz, 2H), 7.28-7.24 (m, 3H), 7.17-7.15 (d, J=8 Hz, 1H), 3.67-3.64 (t, J=6 Hz, 2H), 3.19-3.15 (d, J=16.8 Hz, 1H), 2.88-2.75 (m, 3H), 2.18-2.09 (m, 1H), 1.96-1.84 (m, 3H), 1.79-1.66 (m, 2H). MS: (ES, m/z): 351 [M+H]$^+$.

Example 6

Preparation of (R)-1'-(cyclobutylmethyl)-N-hydroxy-2'-oxo-3,4-dihydro-1H-spiro[naphthalene-2,3'-piperidine]-6-carboxamide (I-185)

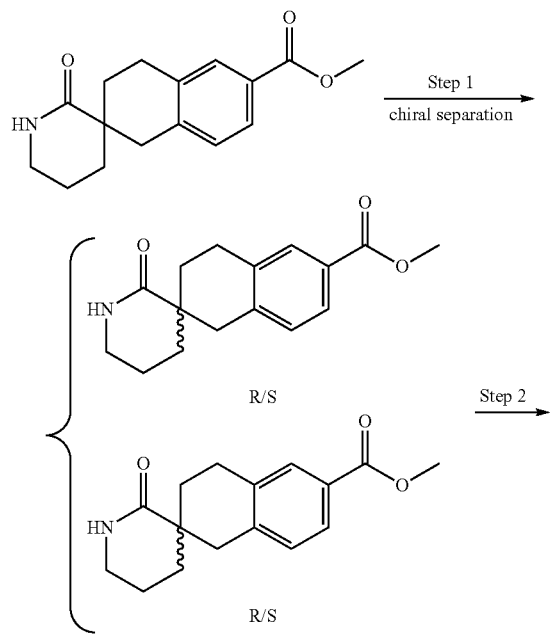

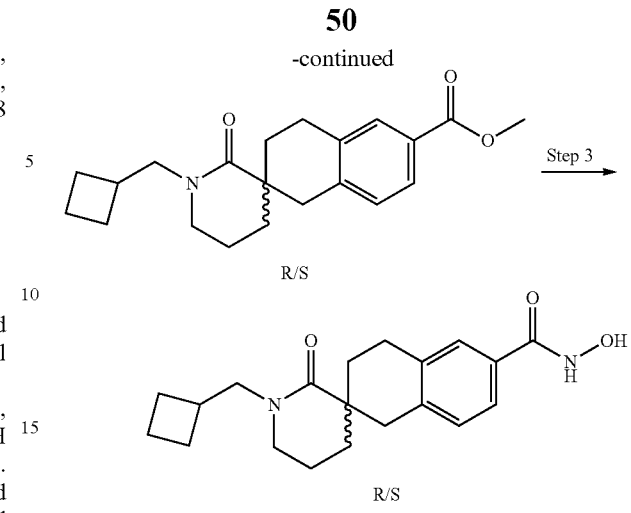

Step-1: Chiral separation of methyl (R)-2'-oxo-3,4-dihydro-1H-spiro[naphthalene-2,3'-piperidine]-6-carboxylate and methyl (S)-2'-oxo-3,4-dihydro-1H-spiro[naphthalene-2,3'-piperidine]-6-carboxylate 5 g of the racemate methyl 2'-oxo-3,4-dihydro-1H-spiro[naphthalene-2,3'-piperidine]-6-carboxylate was purified by Prep-SFC with the following conditions: Column: CHIRALPAK IA-SFC-02, 5 cm×25 cm; Mobile Phase A: CO$_2$: 50%, Mobile Phase B: MeOH/CH$_2$Cl$_2$ (1:1) 50%; Flow rate: 180 mL/min; Detector: UV 220 nm. The first eluting isomer (Rt 3.53 min) was collected and concentrated under vacuum to give 2.4 g (29% yield) of a white solid which was assigned as the R isomer of methyl 2'-oxo-3,4-dihydro-1H-spiro[naphthalene-2,3'-piperidine]-6-carboxylate as a white solid. MS: (ES, m/z): 274 [M+H]+. The second eluting isomer (Rt 4.49 min) was collected and concentrated under vacuum to give 2.4 g (29% yield) of a white solid which was assigned as the S isomer of methyl 2'-oxo-3,4-dihydro-1H-spiro[naphthalene-2,3'-piperidine]-6-carboxylate as a white solid. MS: (ES, m/z): 274 [M+H]+.

Step-2: Methyl (R)-1'-(cyclobutylmethyl)-2'-oxo-3,4-dihydro-1H-spiro[naphthalene-2,3'-piperidine]-6-carboxylate Into a 25-mL round-bottom flask, was placed the first eluted isomer from Step 1, which was assigned as methyl (R)-2'-oxo-3,4-dihydro-1H-spiro[naphthalene-2,3'-piperidine]-6-carboxylate as described above, (120 mg, 0.44 mmol, 1 equiv) in DMF (5 mL). This was followed by the addition of NaH (60% dispersion in oil, 70 mg, 2.92 mmol, 4 equiv) at 0° C. The mixture was stirred for 30 min at room temperature. Then (bromomethyl)cyclobutane (262 mg, 1.76 mmol, 1 equiv) was added. The resulting solution was stirred for 5 h at room temperature. The reaction was then quenched by the addition of 20 mL of water, extracted with 3×30 mL of CH$_2$Cl$_2$, washed with 50 mL of brine, dried over anhydrous Na$_2$SO$_4$, filtered and concentrated under vacuum. The residue was purified by normal phase column chromatography on silica gel with EtOAc/petroleum ether (1:1). The collected fractions were concentrated under vacuum to give 60 mg (40% yield) of the title compound as a yellow oil. MS: (ES, m/z): 342 [M+H]$^+$.

Step-3: (R)-1'-(Cyclobutylmethyl)-N-hydroxy-2'-oxo-3,4-dihydro-1H-spiro[naphthalene-2,3'-piperidine]-6-carboxamide Into a 10-mL sealed tube, was placed a solution of the product from Step 2, which was assigned as methyl (R)-1'-(cyclobutylmethyl)-2'-oxo-3,4-dihydro-1H-spiro[naphthalene-2,3'-piperidine]-6-carboxylate as described above, (60 mg, 0.18 mmol, 1 equiv) in THF/MeOH (4:1, 4 mL), NH$_2$OH (50% in H$_2$O, 1394 mg, 42.20 mmol, 120 equiv), 1N aq. NaOH (0.35 mL, 2 equiv). The resulting solution was stirred for 2 h at 28° C. The solids were filtered out. The crude product was purified by Prep-HPLC with the following conditions: Column: XBridge Prep C18 OBD, 5 μm, 19×150 mm; Mobile Phase A: Water/0.1% Formic acid, Mobile Phase B: CH$_3$CN; Gradient: 5% B to 65% B in 8 min; Detector: UV 254 nm, 220 nm. The collected fractions were lyophilized to give 34.8 mg (58% yield) of the title compound as an off-white solid. $^1$H-NMR (400 MHz, DMSO-d6), δ (ppm): 11.09 (s, 1H), 8.94 (s, 1H), 7.50-7.45 (t, J=18.8 Hz, 2H), 7.13-7.11 (d, J=8 Hz, 1H), 3.45-3.40 (m, 1H), 3.32-3.25 (m, 3H), 3.13-3.08 (d, J=20 Hz, 1H), 2.74-2.65 (m, 2H), 2.61-2.51 (m, 2H), 2.08-2.06 (t, J=8 Hz, 1H), 1.99-1.96 (m, 2H), 1.85-1.80 (m, 2H), 1.79-1.64 (m, 5H), 1.57-1.51 (m, 2H). MS: (ES, m/z): 343 [M+H]$^+$.

TABLE 1

The following compounds were prepared according to the method of Example 6 using the first eluted enantiomer from Step 1.

| Ex. | Structure | $^1$H-NMR δ (ppm) | Found (ES, m/z) [M + H]$^+$ |
| --- | --- | --- | --- |
| I-196 | R/S | (300 MHz, DMSO-d6): 9.57 (s, 1H), 7.49-7.45 (t, J = 14.1 Hz, 2H), 7.12-7.09 (t, J = 8.1 Hz, 1H), 4.64-61 (t, J = 7.2 Hz, 2H), 4.37-4.31 (m, 2H), 3.70-3.51(m, 2H), 3.32-3.19 (m, 3H), 3.12-3.06 (d, J = 16.5 Hz, 1H), 2.76-2.71 (m, 2H), 2.65-2.60 ( d, J = 16.5 Hz, 1H), 2.08-2.00 (m, 1H), 1.78-1.61 (m, 3H), 1.57-1.50 (m, 2H) | 345 |
| I-187 | R/S | (300 MHz, DMSO-d6): 7.47-7.43 (t, J = 12 Hz, 2H), 7.13-7.10 (d, J = 7.8 Hz, 1H), 3.63-3.32 (m, 6H), 3.30-3.27 (m, 3H), 3.23-3.14 (t, J = 13.7 Hz, 1H), 2.89-2.76 (m, 2H), 2.71-2.66 (d, J = 16.8 Hz, 1H), 2.24-2.13 (m, 1H), 1.89-1.68 (m, 5H), 1.67-1.51 (m, 2H) | 347 |
| I-189 | R/S | (400 MHz, DMSO-d6): 11.09 (s, 1H), 8.95 (s, 1H), 7.50 (s, 1H), 7.47-7.45 (d, J = 8 Hz, 1H), 7.13-7.11 (d, J = 7.6 Hz, 1H), 3.32-3.26 (m, 2H), 3.25-3.18 (m, 1H), 3.14-3.02 (m, 2H), 2.77-2.73 (t, J = 8.4 Hz, 2H), 2.70-2.63 (d, J = 16.8 Hz, 1H), 2.12-2.04 (m, 1H), 1.99-1.92 (m, 1H), 1.78-1.74 (m, 2H), 1.69-1.62 (t, J = 15.6 Hz, 1H), 1.60-1.52 (m, 2H), 0.86-0.83 (t, J = 2.8 Hz, 6H) | 331 |
| I-191 | R/S | (300 MHz, DMSO-d6): 11.07 (s, 1H), 8.94 (s, 1H), 7.50-7.44 (t, J = 15.3 Hz, 2H), 7.12-7.10 (t, J = 8.1 Hz, 1H), 4.72-4.63 (m, 1H), 3.31-3.08 (m, 3H), 2.77-2.60 (m, 3H), 2.12-2.01 (m, 1H), 1.69-1.48 (m, 5H), 1.06-1.04 (d, J = 6.9 Hz, 6H) | 317 |
| I-194 | R/S | (400 MHz, DMSO-d6): 11.08 (s, 1H), 8.92 (s, 1H), 7.48-7.43 (t, J = 9.6 Hz, 2H), 7.11-7.09 (d, J = 7.6 Hz, 1H), 3.30-3.25 (m, 4H), 3.11-3.06 (d, J = 16.8 Hz, 1H), 2.77-2.60 (m, 3H), 2.08-2.00 (m, 1H), 1.77-1.71 (m, 2H), 1.66-1.59 (m, 1H), 1.57-1.48 (m, 2H), 1.03-1.00 (t, J = 7.2 Hz, 3H) | 303 |

TABLE 2

The following compounds were prepared according to the method of Example 6, with the following modification: In Step 2, the second eluted product from Step 1 was used.

| Ex. | Structure | ¹H-NMR δ (ppm) | Found (ES, m/z) [M + H]⁺ |
|---|---|---|---|
| I-186 | R/S | (300 MHz, DMSO-d6): 11.06 (s, 1H), 8.93 (s, 1H), 7.49-7.44 (m, 2H), 7.12-7.10 (m, 1H), 3.46-3.39 (m, 1H), 3.31-3.24 (m, 3H), 3.12-3.07 (m, 1H), 2.82-2.71 (m, 2H), 2.64-2.50 (m, 2H), 2.27-1.95 (m, 3H), 1.87-1.60 (m, 7H), 1.57-1.46 (m, 2H) | 343 |
| I-195 | R/S | (400 MHz, DMSO-d6): 8.94 (br s, 1H), 7.49-7.45 (m, 2H), 7.11-7.09 (d, J = 7.6 Hz, 1H), 4.63-4.59 (m, 2H), 4.37-4.32 (m, 2H), 3.69-3.64 (m, 1H), 3.58-3.52 (m, 1H), 3.27-3.19 (m, 3H), 3.11-3.06 (d, J = 16.8 Hz, 1H), 2.80-2.73 (m, 2H), 2.64-2.60 (d, J = 16.4 Hz, 1H), 2.10-2.01 (m, 1H), 1.75-1.72 (m, 2H), 1.70-1.61 (m, 1H), 1.58-1.54 (m, 2H) | 345 |
| I-188 | R/S | (300 MHz, CD₃OD): 7.50-7.46 (m, 2H), 7.16-7.13 (m, 1H), 3.51-3.38 (m, 6H), 3.33-3.31 (m, 3H), 3.26-3.21 (m, 1H), 2.91-2.83 (m, 2H), 2.75-2.70 (m, 2H), 2.27-2.16 (m, 1H), 1.88-1.77 (m, 7H) | 347 |
| I-190 | R/S | (300 MHz, DMSO-d6): 11.06 (br s, 1H), 8.93 (br s, 1H), 7.49-7.41 (m, 2H), 7.13-7.10 (d, J = 8.10 Hz, 1H), 3.28-3.14 (m, 3H), 3.08-3.01 (m, 3H), 2.76-2.61 (m, 3H), 2.12-1.90 (m, 2H), 1.78-1.51 (m, 5H), 0.92-0.82 (m, 6H) | 331 |
| I-192 | R/S | (300 MHz, DMSO-d6): 11.07 (s, 1H), 8.93 (s, 1H), 7.49-7.44 (m, 2H), 7.12-7.10 (m, 1H), 4.72-4.62 (m, 1H), 3.31-3.08 (m, 3H), 2.81-2.60 (m, 3H), 2.12-2.01 (m, 1H), 1.73-1.54 (m, 5H), 1.10-1.00 (m, 6H) | 317 |
| I-184 | R/S | (300 MHz, DMSO-d6): 11.04 (s, 1H), 8.94 (s, 1H), 7.50-7.45 (m, 2H), 7.12-7.10 (m, 1H), 3.32-3.25 (m, 4H), 3.13-3.07 (m, 1H), 2.81-2.66 (m, 2H), 2.60-2.50 (m, 1H), 2.11-2.00 (m, 1H), 1.80-1.58 (m, 5H), 1.08-0.96 (m, 3H) | 303 |

Example 7

Preparation of (R)-1'-cyclopropyl-N-hydroxy-2'-oxo-3,4-dihydro-1H-spiro[naphthalene-2,3'-piperidine]-6-carboxamide (I-193)

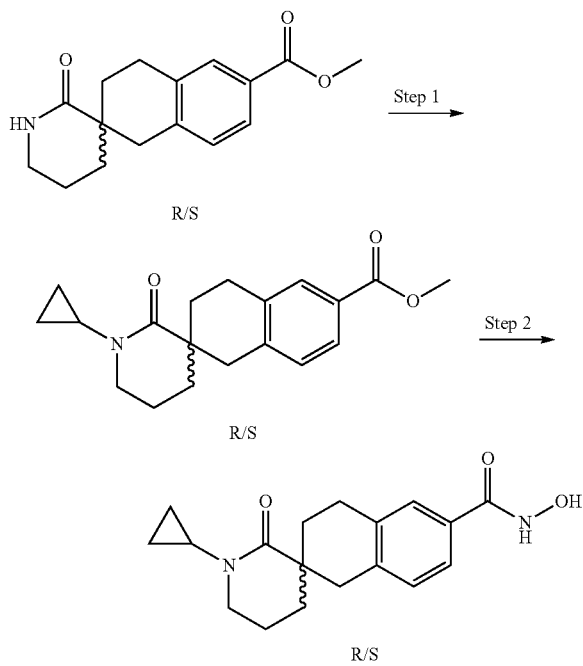

Step-1: Methyl (R)-1'-cyclopropyl-2'-oxo-3,4-dihydro-1H-spiro[naphthalene-2,3'-piperidine]-6-carboxylate Into a 25-mL round-bottom flask purged and maintained with an inert atmosphere of $O_2$, was placed the first eluted isomer from Example 6, Step 1, which was assigned as methyl (R)-2'-oxo-3,4-dihydro-1H-spiro[naphthalene-2,3'-piperidine]-6-carboxylate as described above, (100 mg, 0.37 mmol, 1 equiv) in THF (5 mL), Cu(OAc)$_2$ (80 mg, 0.44 mmol, 1 equiv), Et$_3$N (120 mg, 1.19 mmol, 3 equiv), pyridine (40 mg, 0.51 mmol, 1.5 equiv), and cyclopropylboronic acid (105 mg, 1.22 mmol, 3 equiv). The resulting solution was stirred overnight at 60° C. The solids were filtered out and the filtrate was quenched by the addition of 50 mL of water, extracted with 3×20 mL of CH$_2$Cl$_2$, washed with 100 mL of brine, dried over anhydrous Na$_2$SO$_4$, filtered and concentrated under vacuum. The residue was purified by normal phase column chromatography on silica gel with CH$_2$Cl$_2$/MeOH (10:1). The collected fractions were concentrated under vacuum to give 90 mg (78% yield) of the title compound as a yellow oil. MS: (ES, m/z): 314 [M+H]$^+$.

Step-2: (R)-1'-Cyclopropyl-N-hydroxy-2'-oxo-3,4-dihydro-1H-spiro[naphthalene-2,3'-piperidine]-6-carboxamide Into a 25-mL round-bottom flask, was placed a solution of the product from Step 1, which was assigned as methyl (R)-1'-cyclopropyl-2'-oxo-3,4-dihydro-1H-spiro[naphthalene-2,3'-piperidine]-6-carboxylate as described above, (70 mg, 0.22 mmol, 1 equiv) in THF/MeOH (4:1, 3 mL), NH$_2$OH (50% in H$_2$O, 1771 mg, 53.62 mmol, 120 equiv), 1N aq. NaOH (5 mL, 2 equiv). The resulting solution was stirred for 2 h at 28° C. The solids were filtered out and the crude product was purified by Prep-HPLC with the following conditions: Column: XBridge Prep C18 OBD, 5 μm, 19×150 mm; Mobile Phase A: Water/0.1% Formic acid, Mobile Phase B: CH$_3$CN; Flow rate: 20 mL/min; Gradient: 28% B to 39% B in 8 min; Detector: UV 254 nm, 220 nm. The collected fractions were lyophilized to give 22.2 mg (32% yield) of the title compound as an off-white solid. $^1$H-NMR (300 MHz, DMSO-d6) δ(ppm): 11.04 (s, 1H), 8.92 (s, 1H), 7.49-7.44 (t, J=14.4 Hz, 2H), 7.12-7.09 (d, J=7.8 Hz, 1H), 3.31-3.18 (m, 2H), 3.10-3.05 (d, J=16.8 Hz, 1H), 2.75-2.59 (m, 4H), 2.08-1.98 (m, 1H), 1.73-1.58 (m, 3H), 1.54-1.48 (m, 2H), 0.72-0.61 (m, 2H), 0.56-0.48 (m, 2H). MS: (ES, m z): 315 [M+H]$^+$.

TABLE 3

The following compound was prepared according to the method of Example 7, with the following modification: In Step 1, the second eluted product from Example 6, Step 1 was used.

| Ex. | Structure | $^1$H-NMR δ (ppm) | Found (ES, m/z) [M + H]$^+$ |
|---|---|---|---|
| I-183 | 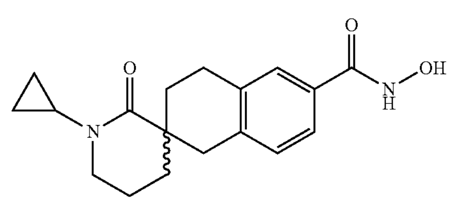 | (300 MHz, DMSO-d6): 11.06 (s, 1H), 8.96-8.89 (m, 1H), 7.52-7.40 (m, 2H), 7.10 (d, J = 7.9 Hz, 1H), 3.20 (t, J = 6.1 Hz, 2H), 3.07 (d, J = 16.7 Hz, 1H), 2.86-2.52 (m, 4H), 2.11-1.94 (m, 1H), 1.80-1.48 (m, 3H), 1.47-1.40 (m, 2H), 0.75-0.58 (m, 2H), 0.57-0.42 (m, 2H) | 315 |

Example 8

Preparation of (R)-1'-cyclobutyl-N-hydroxy-2'-oxo-3,4-dihydro-1H-spiro[naphthalene-2,3'-piperidine]-6-carboxamide (I-197) and (S)-1'-cyclobutyl-N-hydroxy-2'-oxo-3,4-dihydro-1H-spiro[naphthalene-2,3'-piperidine]-6-carboxamide (I-198)

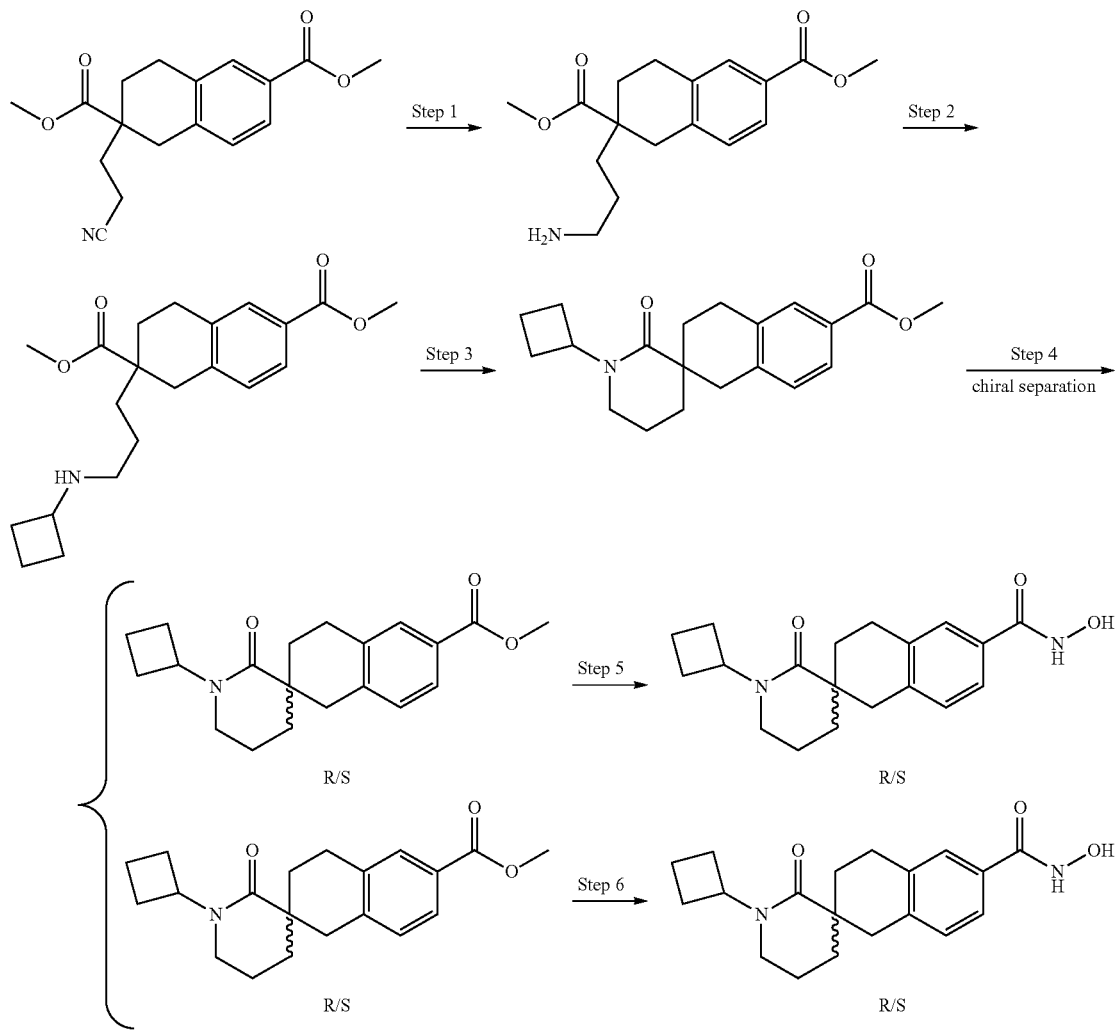

Step-1: Dimethyl 2-(3-aminopropyl)-1,2,3,4-tetrahydronaphthalene-2,6-dicarboxylate Into a 100-mL round-bottom flask, was placed dimethyl 2-(2-cyanoethyl)-1,2,3,4-tetrahydronaphthalene-2,6-dicarboxylate (250 mg, 0.83 mmol, 1 equiv), MeOH (25 mL), AcOH (8 mL), and $PtO_2$ (135 mg). $H_2$ (g) was introduced into the flask. The resulting solution was stirred for 1 h at 25° C. The solid was filtered out and the filtrate was concentrated under vacuum to give 200 mg (74% yield) of the title compound as a yellow oil. MS: (ES, m/z): 306 [M+H]$^+$.

Step-2: Dimethyl 2-(3-(cyclobutylamino)propyl)-1,2,3,4-tetrahydronaphthalene-2,6-dicarboxylate Into a 25-mL round-bottom flask, was placed dimethyl 2-(3-aminopropyl)-1,2,3,4-tetrahydronaphthalene-2,6-dicarboxylate (200 mg, 0.65 mmol, 1 equiv) in $CH_2Cl_2$ (6 mL), AcOH (0.2 mL) and cyclobutanone (46 mg, 0.66 mmol, 1 equiv). The resulting solution was stirred for 1 h at 28° C. Then NaBH(OAc)$_3$ (695 mg, 3.28 mmol, 5 equiv) was added. The resulting solution was allowed to stir for an additional 2 h at 28° C. The reaction was then quenched by the addition of 15 mL of water. The solids were filtered out and the filtrate was extracted with 3×30 mL of $CH_2Cl_2$, dried over anhydrous $Na_2SO_4$, filtered and concentrated under vacuum. The residue was purified by normal phase column chromatography on silica gel with EtOAc/petroleum ether (1:2). The collected fractions were concentrated under vacuum to give 97 mg (41% yield) of the title compound as an off-white solid. MS: (ES, m/z): 360 [M+H]$^+$.

Step-3: Methyl 1'-cyclobutyl-2'-oxo-3,4-dihydro-1H-spiro[naphthalene-2,3'-piperidine]-6-carboxylate Into a 20-mL pressure tank reactor, was placed a solution of dimethyl 2-(3-(cyclobutylamino)propyl)-1,2,3,4-tetrahydronaphthalene-2,6-dicarboxylate (200 mg, 0.56 mmol, 1 equiv) in NH$_3$(g)/MeOH (7M, 10 mL). The resulting solution was stirred overnight at 90° C. The reaction was then cooled to room temperature and quenched by the addition of 15 mL of water. The resulting solution was extracted with 3×30 mL of CH$_2$Cl$_2$, dried over anhydrous Na$_2$SO$_4$, filtered and concentrated under vacuum. The residue was purified by normal phase column chromatography on silica gel with EtOAc/petroleum ether (1:1). The collected fractions were concentrated under vacuum to give 80 mg (44% yield) of the title compound as a yellow oil. MS: (ES, m/z): 328 [M+H]$^+$.

Step-4: Chiral separation of methyl (R)-1'-cyclobutyl-2'-oxo-3,4-dihydro-1H-spiro[naphthalene-2,3'-piperidine]-6-carboxylate and methyl (S)-1'-cyclobutyl-2'-oxo-3,4-dihydro-1H-spiro[naphthalene-2,3'-piperidine]-6-carboxylate Methyl 1'-cyclobutyl-2'-oxo-3,4-dihydro-1H-spiro[naphthalene-2,3'-piperidine]-6-carboxylate was separated by Chiral-Prep-HPLC with the following conditions: Column: Chiralpak IC, 2×25 cm, 5 μm; Mobile Phase A: hexanes, Mobile Phase B: isopropanol; Gradient: hold 30% B over 36 min; Detector: UV 254 nm, 220 nm. The first eluting isomer (Rt 4.876 min) was collected and concentrated under vacuum to give 32 mg (40% yield) of an off-white solid which was assigned as the R isomer of methyl 1'-cyclobutyl-2'-oxo-3,4-dihydro-1H-spiro[naphthalene-2,3'-piperidine]-6-carboxylate. MS: (ES, m/z): 328 [M+H]$^+$. The second eluting isomer (Rt 6.071 min) was collected and concentrated under vacuum to give 33 mg (41% yield) of an off-white solid which was assigned as the S isomer of methyl 1'-cyclobutyl-2'-oxo-3,4-dihydro-1H-spiro[naphthalene-2,3'-piperidine]-6-carboxylate. MS: (ES, m/z): 328 [M+H]$^+$.

Step-5: (R)-1'-Cyclobutyl-N-hydroxy-2'-oxo-3,4-dihydro-1H-spiro[naphthalene-2,3'-piperidine]-6-carboxamide Into a 10-mL vial, was placed a solution of the first eluted isomer from Step 4, which was assigned as methyl (R)-1'-cyclobutyl-2'-oxo-3,4-dihydro-1H-spiro[naphthalene-2,3'-piperidine]-6-carboxylate as described above, (30 mg, 0.09 mmol, 1 equiv) in THF/MeOH (4:1, 3 mL), NH$_2$OH (50% in H$_2$O, 691 mg, 20.92 mmol, 120 equiv), and 1N aq. NaOH (0.2 mL, 2 equiv). The resulting solution was stirred for 2 h at 28° C. The solids were filtered out and the crude product was purified by Prep-HPLC with the following conditions: Column: XBridge Prep C18 OBD, 5 μm, 19×150 mm; Mobile Phase A: Water/0.01% NH$_4$HCO$_3$, Mobile Phase B: CH$_3$CN; Gradient: 5% B to 60% B in 7 min; Detector: UV 254 nm, 220 nm. The collected fractions were lyophilized to give 15.9 mg (53% yield) of the title compound as an off-white solid. $^1$H-NMR (300 MHz, DMSO-d6), δ (ppm): 10.88 (s, 1H), 8.94-8.92 (d, J=5.4 Hz, 1H), 7.49-7.44 (t, J=7.2 Hz, 2H), 7.11-7.08 (d, J=7.8 Hz, 1H), 4.81-4.75 (t, J=9 Hz, 1H), 3.28-3.24 (t, J=6.6 Hz, 2H), 3.09-3.04 (d, J=16.5 Hz, 1H), 2.76-2.60 (m, 3H), 2.17-1.97 (m, 5H), 1.76 (s, 2H), 1.66-1.58 (m, 3H), 1.54-1.42 (m, 2H). MS: (ES, m/z): 329 [M+H]$^+$.

Step-6: (S)-1'-Cyclobutyl-N-hydroxy-2'-oxo-3,4-dihydro-1H-spiro[naphthalene-2,3'-piperidine]-6-carboxamide Into a 8-mL vial, was placed a solution of the second eluted isomer from Step 4, which was assigned as methyl (S)-1'-cyclobutyl-2'-oxo-3,4-dihydro-1H-spiro[naphthalene-2,3'-piperidine]-6-carboxylate as described above, (34 mg, 0.10 mmol, 1 equiv) in THF/MeOH (4:1, 2.0 mL), NH$_2$OH (50% in water, 0.21 mL, 30 equiv) and 1N aq. NaOH (0.21 mL, 2 equiv). The resulting solution was stirred for 1 h at room temperature. The crude product was purified by Prep-HPLC with the following conditions: Column: XBridge Prep C18 OBD, 19×150 mm, 5 μm; Mobile Phase A: Water/0.1% Formic acid; Mobile Phase B: CH$_3$CN; Flow rate: 20 mL/min; Gradient: 5% B to 64% B in 7 min; Detector: UV 254 nm, 220 nm. The collected fractions were lyophilized to give 19.5 mg (57% yield) of title compound as a white solid. $^1$H NMR (400 MHz, DMSO-d6) δ (ppm): 11.05 (s, 1H), 8.92 (s, 1H), 7.45-7.43 (m, 2H), 7.10-7.08 (m, 1H), 4.80-4.70 (m, 1H), 3.36-3.19 (m, 1H), 3.07-3.03 (d, J=16.7 Hz, 1H), 2.75-2.59 (m, 3H), 2.14-1.96 (m, 5H), 1.74-1.71 (m, 2H), 1.64-1.56 (m, 3H), 1.53-1.47 (m, 2H). MS: (ES, m/z): 329 [M+H]$^+$.

TABLE 4

The following compounds were prepared according to the method of Example 8.

| Ex. | Structure | $^1$H-NMR δ (ppm) | Found (ES, m/z) [M + H]$^+$ |
|---|---|---|---|
| I-199 | 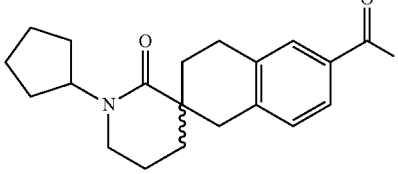 R/S | (300 MHz, DMSO-d6): 11.06 (s, 1H), 8.96 (s, 1H), 7.50-7.44 (t, J = 7.7 Hz, 2H), 7.12-7.10 (d, J = 7.8 Hz, 1H), 4.81-4.75 (t, J = 7.8 Hz, 1H), 3.22-3.07 (m, 3H), 2.81-2.61 (m, 3H), 2.12-2.01 (m, 1H), 1.72-1.53 (m, 13H) | 343 |

TABLE 4-continued

The following compounds were prepared according to the method of Example 8.

| Ex. | Structure | ¹H-NMR δ (ppm) | Found (ES, m/z) [M + H]⁺ |
|---|---|---|---|
| I-200 | 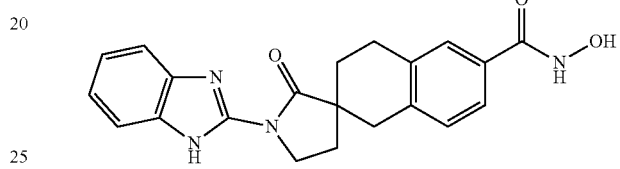<br>R/S | (300 MHz, DMSO-d6): 11.07 (s, 1H), 8.95 (s, 1H), 7.50-7.44 (t, J = 8 Hz, 2H), 7.12-7.10 (d, J = 8.1 Hz, 1H), 4.81-4.76 (d, J = 7.2 Hz, 1H), 3.22-3.07 (m, 3H), 2.77-2.61 (m, 3H), 2.12-2.01 (m, 1H), 1.72-1.51 (m, 13H) | 343 |

Example 9

Preparation of 1'-(1H-benzo[d]imidazol-2-yl)-N-hydroxy-2'-oxo-3,4-dihydro-1H-spiro[naphthalene-2,3'-pyrrolidine]-6-carboxamide (I-5)

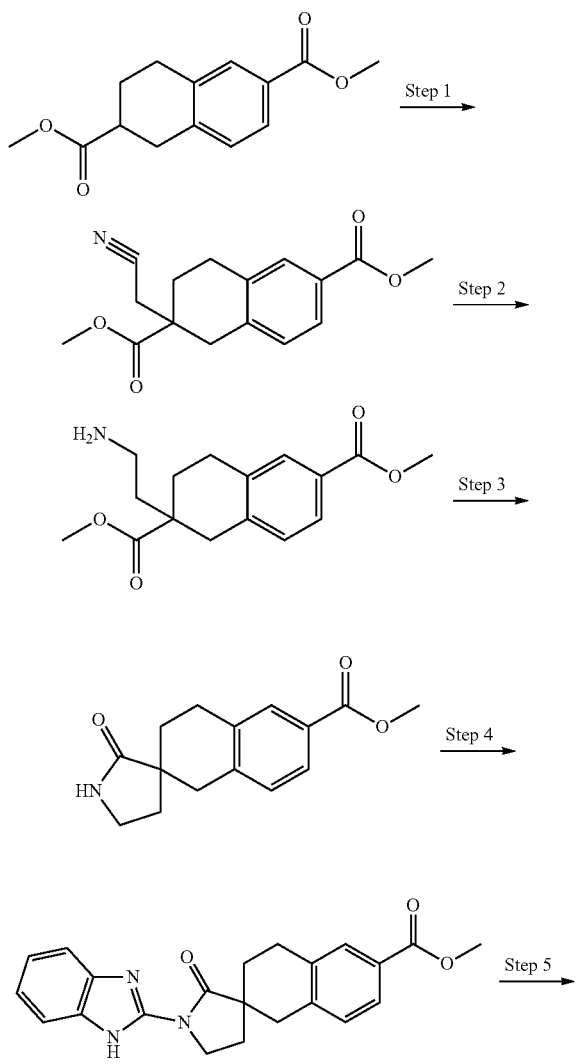

Step-1: Dimethyl 2-(cyanomethyl)-1,2,3,4-tetrahydronaphthalene-2,6-dicarboxylate Into a 1-L 3-necked round-bottom flask was placed dimethyl 1,2,3,4-tetrahydronaphthalene-2,6-dicarboxylate (20 g, 80.56 mmol, 1 equiv) in THF (400 mL). This was followed by the dropwise addition of LDA (2 M in THF, 53 mL, 106 mmol, 1.32 equiv) with stirring at −78° C. over 30 min. To this was added 2-bromoacetonitrile (9 mL, 129 mmol, 1.6 equiv) dropwise with stirring at −78° C. over 30 min. The resulting mixture was stirred overnight at room temperature. The reaction was quenched by adding 300 mL of H₂O. The resulting solution was extracted with 3×300 mL of EtOAc. The combined organics were washed with 2×300 mL of H₂O, dried over anhydrous Na₂SO₄, filtered and concentrated. The residue was purified by normal phase chromatography on silica gel with EtOAc/petroleum ether (3:20). The collected fractions were concentrated to give 14 g (60% yield) of the title compound as a yellow oil. ¹H NMR (300 MHz, CDCl₃) δ (ppm): 7.83 (dq, J=3.5, 1.7 Hz, 2H), 7.20 (d, J=8.4 Hz, 1H), 3.93 (s, 3H), 3.79 (s, 3H), 3.42 (d, J=16.9 Hz, 1H), 3.06-2.83 (m, 3H), 2.69 (s, 2H), 2.39-2.23 (m, 1H), 2.15-2.00 (m, 1H).

Step-2: Dimethyl 2-(2-aminoethyl)-1,2,3,4-tetrahydronaphthalene-2,6-dicarboxylate Into a 1000-mL 3-necked round-bottom flask was placed dimethyl 2-(cyanomethyl)-1,2,3,4-tetrahydronaphthalene-2,6-dicarboxylate (14 g, 48.73 mmol, 1 equiv) in MeOH (440 mL), acetic acid (220 mL) and PtO₂ (6 g). Hydrogen gas was introduced. The resulting solution was stirred overnight at room temperature. The solids were filtered out. The filter cake was washed with 2×100 mL of MeOH and 100 mL of CH₂Cl₂. The combined filtrate was concentrated under vacuum. The residue was dissolved in 200 mL of EtOAc and the pH was adjusted to 9 with aq. Na₂CO₃. The resulting solution was extracted with 3×200 mL of EtOAc. The combined organics were dried over anhydrous Na₂SO₄, filtered and concentrated under vacuum to give 10 g (70% yield) of the title compound as a yellow oil. MS: (ES, m/z): 292 [M+H]+.

Step-3: Methyl 2'-oxo-3,4-dihydro-1H-spiro[naphthalene-2,3'-pyrrolidine]-6-carboxylate Into a 500-mL round-bottom flask was placed dimethyl 2-(2-aminoethyl)-1,2,3,4-tetrahydronaphthalene-2,6-dicarboxylate (10 g, 34.32 mmol, 1 equiv) in MeOH (80 mL) and NH$_3$ (7M in MeOH, 40 mL). The resulting solution was stirred overnight at room temperature. The resulting mixture was concentrated under vacuum to give 9.1 g (crude) of the title compound as a solid. $^1$H-NMR (300 MHz, CDCl$_3$) δ (ppm): 7.81 (s, 1H), 7.78 (d, J=8.1 Hz, 2H), 7.15 (d, J=8.1 Hz, 1H), 6.01 (s, 1H), 3.90 (s, 3H), 3.41-3.37 (t, J=6.6 Hz, 2H), 3.16-2.65 (m, 4H), 2.14-1.78 (m, 4H). MS: (ES, m/z): 260 [M+H]+.

Step-4: Methyl 1'-(1H-benzo[d]imidazol-2-yl)-2'-oxo-3,4-dihydro-1H-spiro[naphthalene-2,3'-pyrrolidine]-6-carboxylate Into a 100-mL round-bottom flask purged and maintained with an inert atmosphere of nitrogen, was placed methyl 2'-oxo-3,4-dihydro-1H-spiro[naphthalene-2,3'-pyrrolidine]-6-carboxylate (150 mg, 0.58 mmol, 1 equiv), 2-bromo-1H-1,3-benzodiazole (171 mg, 0.87 mmol, 1.5 equiv), CuI (220 mg, 1.16 mmol, 2 equiv), K$_3$PO$_4$ (492 mg, 2.32 mmol, 4.01 equiv), 1-N, 2-N-dimethylcyclohexane-1,2-diamine (124 mg, 0.87 mmol, 1.51 equiv), and DMF (3 mL). The resulting solution was degassed three times with N$_2$, and stirred overnight at 100° C. The reaction was quenched by adding 50 mL of H$_2$O. The resulting solution was extracted with 3×50 mL of EtOAc. The organic layers were combined, dried over anhydrous Na$_2$SO$_4$, filtered and concentrated. The residue was purified by normal phase chromatography on silica gel with EtOAc/petroleum ether (1:9). The collected fractions were concentrated to give 63 mg (29% yield) of the title compound as a yellow oil. MS: (ES, m/z): 376 [M+H]+.

Step-5: 1'-(1H-Benzo[d]imidazol-2-yl)-N-hydroxy-2'-oxo-3,4-dihydro-1H-spiro[naphthalene-2,3'-pyrrolidine]-6-carboxamide Into a 50-mL round-bottom flask was placed methyl 1'-(1H-benzo[d]imidazol-2-yl)-2'-oxo-3,4-dihydro-1H-spiro[naphthalene-2,3'-pyrrolidine]-6-carboxylate (63 mg, 0.17 mmol, 1 equiv), THF/MeOH (4:1, 2.5 mL), NH$_2$OH (50% in water, 498 mg, 15.08 mmol, 89.85 equiv), and 1N aq. NaOH (0.5 mL, 2.94 equiv). The resulting solution was stirred for 2 h at room temperature. The crude product was purified by Prep-HPLC with the following conditions: Column: Xbridge C18, 19×150 mm; Mobile phase A: Water/0.05% TFA, Mobile Phase B: CH$_3$CN/0.05% TFA; Gradient: 19% B to 51% B in 7 min; Detector: UV 254 nm, 220 nm. The collected fractions were lyophilized to give 23.6 mg (37% yield) of the title compound as a pink solid. $^1$H-NMR (400 MHz, DMSO-d6) δ (ppm): 11.11 (br s, 1H), 7.56-7.50 (m, 4H), 7.22-7.15 (m, 3H), 4.08-4.05 (t, J=6 Hz, 2H), 3.05-2.88 (m, 4H), 2.19-1.93 (m, 4H). MS: (ES, m/z): 377 [M+H]+.

Example 10

Preparation of N-hydroxy-1'-(4-methoxyphenethyl)-2'-oxo-3,4-dihydro-1H-spiro[naphthalene-2,3'-pyrrolidine]-6-carboxamide (I-4)

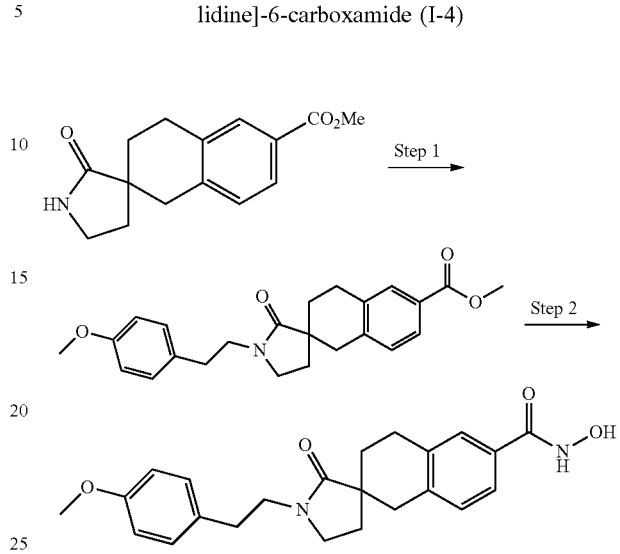

Step-1: Methyl 1'-(4-methoxyphenethyl)-2'-oxo-3,4-dihydro-1H-spiro[naphthalene-2,3'-pyrrolidine]-6-carboxylate Into a 10 mL microwave vial was added methyl 2'-oxo-3,4-dihydro-1H-spiro[naphthalene-2,3'-pyrrolidine]-6-carboxylate (50.2 mg, 0.194 mmol, 1 equiv) and 1-(2-bromoethyl)-4-methoxybenzene (45.8 mg, 0.213 mmol, 1.1 equiv) in DMF (1.5 mL). Next, sodium bis(trimethylsilyl)amide (1M in THF, 0.25 mL, 1.3 equiv) was added and the mixture was heated in the microwave at 150° C. for 20 min. Water was added and the reaction mixture was extracted with three portions of EtOAc. The organic phases were combined, washed with brine, dried over anhydrous Na$_2$SO$_4$, filtered and concentrated. The residue was purified by column chromatography on silica gel (Biotage SP1, 10 g Snap column, 10-50% EtOAc/hexanes) to afford 15.8 mg (21% yield) of the title compound as a colorless oil. MS: (ES m/z) 394 [M+H]+.

Step-2: N-hydroxy-1'-(4-methoxyphenethyl)-2'-oxo-3,4-dihydro-1H-spiro[naphthalene-2,3'-pyrrolidine]-6-carboxamide Methyl 1'-(4-methoxyphenethyl)-2'-oxo-3,4-dihydro-1H-spiro[naphthalene-2,3'-pyrrolidine]-6-carboxylate (20 mg, 0.051 mmol, 1 equiv) was dissolved in a solution of THF/MeOH (4:1, 1.38 mL). NH$_2$OH (50% in water, 0.279 mL, 4.6 mmol, 90 equiv) was added followed by 2N aq. NaOH (0.076 mL, 3 equiv). The reaction was stirred at room temperature for 48 h and was purified directly by reverse-phase chromatography using the following conditions: Column: XTerra Prep MS C18 OBD, 5 mM, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyophilized to afford 6.2 mg (31% yield) the title compound. $^1$H NMR (300 MHz, DMSO-d6) δ (PPM): 11.10 (br s, 1H), 8.97 (br s, 2H), 7.34-7.54 (m, 2H), 6.97-7.29 (m, 3H), 6.86 (d, J=8.5 Hz, 2H), 3.73 (s, 3H), 3.30-3.52 (m, 4H), 3.10-3.30 (m, 2H), 2.62-2.97 (m, 4H), 1.47-1.85 (m, 4H). MS: (ES m/z) 395 [M+H]+.

Example 11

Preparation of 1'-(3,4-dichlorobenzyl)-N-hydroxy-2'-oxo-3,4-dihydro-1H-spiro[naphthalene-2,3'-pyrrolidine]-6-carboxamide (I-6)

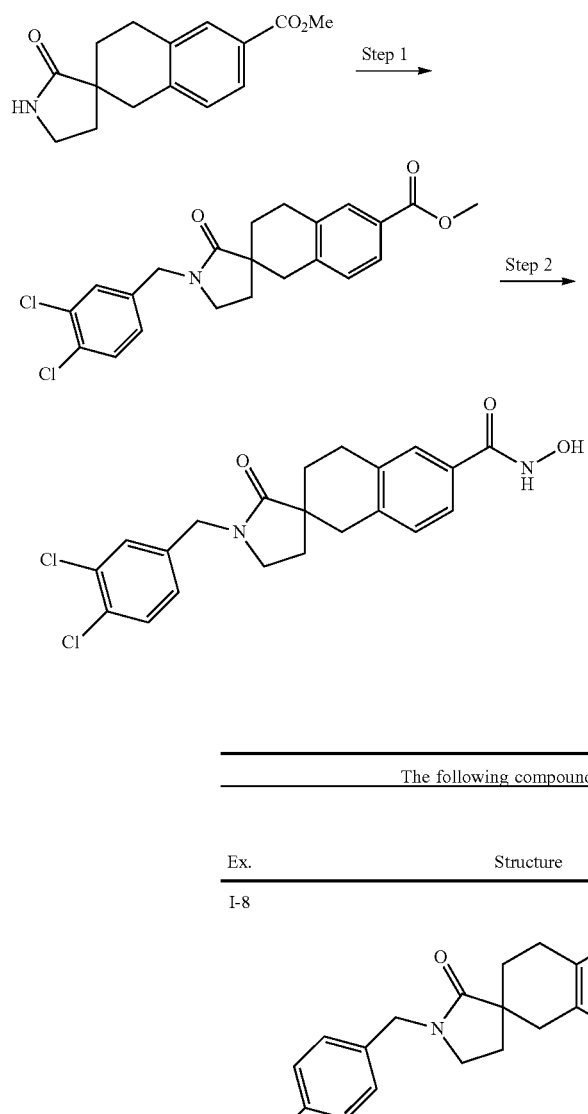

Step-1: Methyl 1'-(3,4-dichlorobenzyl)-2'-oxo-3,4-dihydro-1H-spiro[naphthalene-2,3'-pyrrolidine]-6-carboxylate Into a 100-mL round-bottom flask was placed methyl 2'-oxo-3,4-dihydro-1H-spiro[naphthalene-2,3'-pyrrolidine]-6-carboxylate (150 mg, 0.58 mmol, 1 equiv), DMF (5 mL), NaH (29 mg, 1.21 mmol, 2.09 equiv), and 4-(bromomethyl)-1,2-dichlorobenzene (193 mg, 0.80 mmol, 1.39 equiv). The resulting solution was stirred for 3 h at room temperature. The resulting mixture was quenched with 30 mL of $H_2O$ and extracted with 2×50 mL of EtOAc. The combined organics were washed with 2×30 mL of $H_2O$, dried over anhydrous $Na_2SO_4$, filtered and concentrated. The residue was purified by normal phase chromatography on silica gel with EtOAc/petroleum ether (1:3). The collected fractions were concentrated to give 277 mg (crude) of the title compound as a yellow solid. MS: (ES, m/z): 418 [M+H]+.

Step-2: 1'-(3,4-Dichlorobenzyl)-N-hydroxy-2'-oxo-3,4-dihydro-1H-spiro[naphthalene-2,3'-pyrrolidine]-6-carboxamide Into a 100-mL round-bottom flask was placed methyl 1'-(3,4-dichlorobenzyl)-2'-oxo-3,4-dihydro-1H-spiro[naphthalene-2,3'-pyrrolidine]-6-carboxylate (277 mg, 0.66 mmol, 1 equiv), THF/MeOH (4:1, 2.5 mL), $NH_2OH$ (50% in water, 4.57 g, 68.55 mmol, 104 equiv), and 1N aq. NaOH (1 mL, 1.51 equiv). The resulting solution was stirred for 5 h at room temperature. The pH of the solution was adjusted to 6 with 4N aq. HCl. The crude product was purified by Prep-HPLC with the following conditions: Column: SunFire Prep C18, 5 μm, 19×100 mm; Mobile Phase A: Water/10% $NH_4HCO_3$, Mobile Phase B: $CH_3CN$/10% $NH_4HCO_3$; Gradient: 10% B to 50% B in 6 min; Detector: UV 254 nm, 220 nm. The collected fractions were lyophilized to give 30.2 mg (10% yield) of the title compound as a pink solid. 1H-NMR (400 MHz, DMSO-d6) δ (ppm): 11.10 (br s, 1H), 8.96 (br s, 1H), 7.65-7.63 (d, J=8 Hz, 1H), 7.53-7.44 (m, 3H), 7.26-7.12 (m, 2H), 4.43 (s, 2H), 3.27-3.24 (t, J=8 Hz, 2H), 2.95-2.77 (m, 3H), 2.67-2.61 (m, 1H), 1.95-1.82 (m, 2H), 1.73-1.63 (m, 2H). MS: (ES, m/z): 419 [M+H]+.

TABLE 5

The following compounds were prepared according to the method of Example 11.

| Ex. | Structure | 1H-NMR δ (ppm) | Found (ES, m/z) [M + H]+ |
|---|---|---|---|
| I-8 | ![structure] | (400 MHz, DMSO-d6): 11.09 (br s, 1H), 9.12-8.78 (br s, 1H), 7.53-7.46 (m, 2H), 7.18-7.11 (m, 5H), 4.37( s, 2H), 3.20-3.16 (t, J = 8 Hz, 2H), 2.93-2.76 (m, 3H), 2.62-2.58 (m, 1H), 2.33 (s, 3H), 1.92-1.83 (m, 2H), 1.71-1.63 (m, 2H). | 365 |
| I-7 | ![structure] | (400 MHz, DMSO-d6): 11.09 (br s, 1H), 7.51-7.45 (m, 2H), 7.15-7.13 (d, J = 8 Hz, 1H), 3.32-3.29 (t, J = 4 Hz, 2H), 3.06-3.04 (d, J = 8 Hz, 2H), 2.91-2.74 (m, 3H), 2.62-2.55 (m, 1H), 1.91-1.78 (m, 2H), 1.71-1.57 (m, 7H), 1.27-1.11 (m, 3H), 0.92-0.83 (m, 2H). | 357 |

TABLE 5-continued

The following compounds were prepared according to the method of Example 11.

| Ex. | Structure | ¹H-NMR δ (ppm) | Found (ES, m/z) [M + H]⁺ |
|---|---|---|---|
| I-9 | 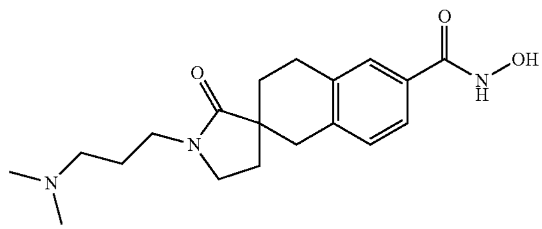 [SMILES: CN(C)CCCN1CCC2(CCc3cc(C(=O)NO)ccc3C2)C1=O] | (300 MHz, DMSO-d6): 11.10 (br s, 1H), 10.28-9.82 (m, 2H), 9.05-8.95 (br, 1H), 7.54-7.44 (m, 2H), 7.15-7.12 (d, J = 9 Hz, 1H), 3.37-3.27 (m, 4H), 3.02-2.96 (m, 2H), 2.96-2.83 (m, 3H), 2.77 (s, 6H), 2.68-2.59 (m, 1H), 1.96-1.59 (m, 6H). | 346 |

Example 12

Preparation of (R)-1'-cyclobutyl-N-hydroxy-2'-oxo-3,4-dihydro-1H-spiro[naphthalene-2,3'-pyrrolidine]-6-carboxamide (I-171) and (S)-1'-cyclobutyl-N-hydroxy-2'-oxo-3,4-dihydro-1H-spiro[naphthalene-2,3'-pyrrolidine]-6-carboxamide (I-172)

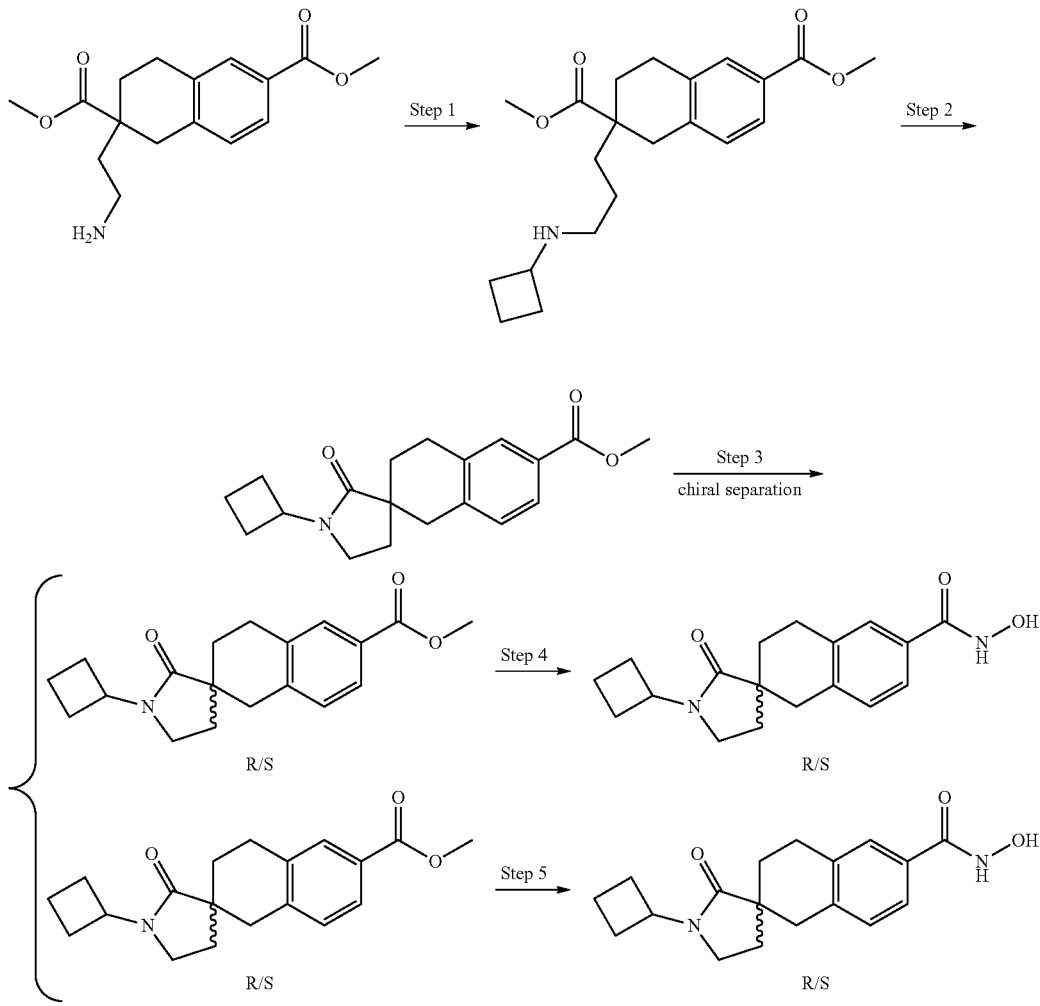

Step-1: Dimethyl 2-(2-(cyclobutylamino)ethyl)-1,2,3,4-tetrahydronaphthalene-2,6-dicarboxylate Into a 250-mL round-bottom flask, was placed a mixture of 2,6-dimethyl 2-(2-aminoethyl)-1,2,3,4-tetrahydronaphthalene-2,6-dicarboxylate (2 g, 6.86 mmol, 1 equiv) and cyclobutanone (433.3 mg, 6.18 mmol, 0.9 equiv) in $CH_2Cl_2$ (50 mL) and AcOH (1 mL). The mixture was stirred for 15 min at 0° C. After that $NaBH(OAc)_3$ (4.37 g, 20.58 mmol, 3 equiv) was slowly added at 0° C. The resulting solution was stirred overnight while the temperature warmed to room temperature. The solids were filtered out. The filtrate was concentrated under vacuum. The residue was purified by normal phase chromatography on silica gel with $CH_2Cl_2$/MeOH (92:8). The collected fractions were concentrated to give 800 mg (34% yield) of the title compound as a light yellow oil. MS: (ES, m/z): 346 $[M+H]^+$.

Step-2: Methyl 1'-cyclobutyl-2'-oxo-3,4-dihydro-1H-spiro[naphthalene-2,3'-pyrrolidine]-6-carboxylate Into a 100-mL round-bottom flask, was placed a solution of dimethyl 2-(2-(cyclobutylamino)ethyl)-1,2,3,4-tetrahydronaphthalene-2,6-dicarboxylate (700 mg, 2.03 mmol, 1 equiv) and 7M $NH_3$ in MeOH (20 mL, 8 equiv). The resulting solution was stirred for 18 h at 25° C. The resulting mixture was concentrated under vacuum. The residue was purified by normal phase column chromatography on silica gel column with EtOAc/petroleum ether (1:5). The collected fractions were concentrated to give 300 mg (47% yield) of the title compound as a light yellow oil. MS: (ES, m/z): 314 $[M+H]^+$.

Step-3: Chiral separation of methyl (R)-1'-cyclobutyl-2'-oxo-3,4-dihydro-1H-spiro[naphthalene-2,3'-pyrrolidine]-6-carboxylate and methyl (S)-1'-cyclobutyl-2'-oxo-3,4-dihydro-1H-spiro[naphthalene-2,3'-pyrrolidine]-6-carboxylate The racemate of methyl 1'-cyclobutyl-2'-oxo-3,4-dihydro-1H-spiro[naphthalene-2,3'-pyrrolidine]-6-carboxylate (300 mg) was purified by Prep-SFC with the following conditions: Column: Chiralpak AS-H 2×25 cm; Mobile Phase A: $CO_2$ (70%), Mobile Phase B: isopropanol (30%); Flow rate: 40 mL/min; Detector: UV 220 nm. The first eluting isomer (Rt 4.22 min) was collected and concentrated to give 120 mg of a white solid which was tentatively assigned as the R isomer of methyl 1'-cyclobutyl-2'-oxo-3,4-dihydro-1H-spiro[naphthalene-2,3'-pyrrolidine]-6-carboxylate. MS: (ES, m/z): 314 $[M+H]^+$. The second eluting isomer (Rt 6.06 min) was collected and concentrated to give 130 mg of a white solid which was tentatively assigned as the S isomer of methyl 1'-cyclobutyl-2'-oxo-3,4-dihydro-1H-spiro[naphthalene-2,3'-pyrrolidine]-6-carboxylate. MS: (ES, m/z): 314 $[M+H]^+$.

Step-4: (R)-1'-Cyclobutyl-N-hydroxy-2'-oxo-3,4-dihydro-1H-spiro[naphthalene-2,3'-pyrrolidine]-6-carboxamide Into a 25-mL round-bottom flask, was placed a solution of the first eluted isomer from Step 3, which was assigned as methyl (R)-1'-cyclobutyl-2'-oxo-3,4-dihydro-1H-spiro[naphthalene-2,3'-pyrrolidine]-6-carboxylate as described above, (50 mg, 0.16 mmol, 1 equiv), $NH_2OH$ (50% in water, 1.2 mL, 120 equiv) and 1N aq. NaOH (0.32 mL, 2 equiv) in THF/MeOH (5:1, 1.25 mL). The reaction was stirred for 5 h at 25° C. The resulting mixture was concentrated under vacuum. The residue was dissolved in 3 mL of THF and purified by Prep-HPLC with the following conditions: Column: XBridge Prep C18 OBD, 5 μm, 19×150 mm; Mobile Phase A: Water/0.1% Formic acid, Mobile Phase B: $CH_3CN$/0.1% Formic Acid; Gradient: 20% B to 38% B in 8 min; Detector: UV 254 nm, 220 nm. The collected fractions were lyophilized to give 25 mg (50% yield) of the title compound as a white solid. $^1$H-NMR (400 MHz, DMSO-d6) δ (ppm): 1.68-1.70 (m, 4H), 1.78-1.90 (m, 2H), 2.00-2.01 (m, 2H), 2.04-2.24 (m, 2H), 2.59 (d, J=6 Hz, 1H), 2.81 (d, J=12 Hz, 3H), 3.41 (t, J=12 Hz, 2H), 4.47-4.52 (m, 1H), 7.13 (m, J=6 Hz, 1H), 7.46-7.51 (m, 2H), 8.95 (s, 1H), 11.10 (s, 1H). MS: (ES, m/z): 315 $[M+H]^+$.

Step-5: (S)-1'-Cyclobutyl-N-hydroxy-2'-oxo-3,4-dihydro-1H-spiro[naphthalene-2,3'-pyrrolidine]-6-carboxamide (S)-1'-Cyclobutyl-N-hydroxy-2'-oxo-3,4-dihydro-1H-spiro[naphthalene-2,3'-pyrrolidine]-6-carboxamide was prepared according to the method of (R)-1'-Cyclobutyl-N-hydroxy-2'-oxo-3,4-dihydro-1H-spiro[naphthalene-2,3'-pyrrolidine]-6-carboxamide. $^1$H-NMR (400 MHz, DMSO-d6) δ (ppm): 1.56-1.69 (m, 4H), 1.70-1.86 (m, 2H), 1.96-2.01 (m, 2H), 2.17-2.22 (m, 2H), 2.55-2.60 (m, 1H), 2.77-2.83 (m, 3H), 3.33-3.39 (m, 2H), 4.46-4.49 (m, 1H), 7.11 (d, J=7.6 Hz, 1H), 7.46-7.49 (m, 2H), 8.93 (br s, 1H), 11.09 (br s, 1H). MS: (ES, m/z): 315 $[M+H]^+$.

Example 13

Preparation of methyl (R)-2'-oxo-3,4-dihydro-1H-spiro[naphthalene-2,3'-pyrrolidine]-6-carboxylate and methyl (S)-2'-oxo-3,4-dihydro-1H-spiro[naphthalene-2,3'-pyrrolidine]-6-carboxylate

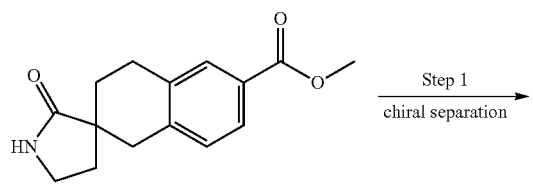

-continued

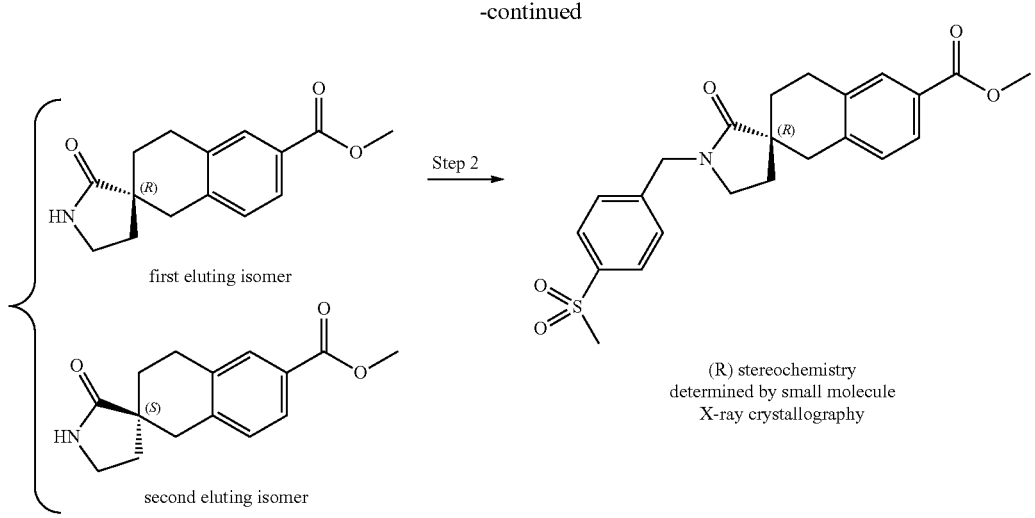

first eluting isomer second eluting isomer (R) stereochemistry
determined by small molecule
X-ray crystallography Step-1: Chiral separation of methyl (R)-2'-oxo-3,4-dihydro-1H-spiro[naphthalene-2,3'-pyrrolidine]-6-carboxylate and methyl (S)-2'-oxo-3,4-dihydro-1H-spiro[naphthalene-2,3'-pyrrolidine]-6-carboxylate The racemate of methyl 2'-oxo-3,4-dihydro-1H-spiro[naphthalene-2,3'-pyrrolidine]-6-carboxylate (22 g, 75.51 mmol, 1 equiv) was purified by Prep-SFC with the following conditions: Column: Chiralpak AS-H, 5×25 cm, 5 μm; Mobile Phase: $CO_2$ (50%), MeOH:$CH_2Cl_2$ (2:1)/0.2% DIEA; Detector: UV 220 nm. The first eluting isomer (Rt 6.56 min) was collected and concentrated to give 10 g of a yellow solid. $^1$H NMR (400 MHz, DMSO-d6) δ (ppm): 7.74-7.64 (m, 3H), 7.23 (d, J=8.0 Hz, 1H), 3.21 (t, J=6.8 Hz, 2H), 2.99-2.75 (m, 3H), 2.71-2.62 (m, 1H), 1.93 (m, 1H), 1.87-1.59 (m, 3H). MS: (ES, m/z): 260 [M+H]$^+$. The second eluting isomer (Rt 8.26 min) was collected and concentrated to give 10 g of a yellow solid. $^1$H NMR (400 MHz, DMSO-d6) δ(ppm): 7.74-7.64 (m, 3H), 7.23 (d, J=8.0 Hz, 1H), 3.21 (t, J=6.8 Hz, 2H), 2.98-2.75 (m, 3H), 2.71-2.62 (m, 1H), 1.93 (m, 1H), 1.87-1.59 (m, 3H). MS: (ES, m/z): 260 [M+H]$^+$.

Step-2: Determination of the Absolute Stereochemistry of methyl (R)-2'-oxo-3,4-dihydro-1H-spiro[naphthalene-2,3'-pyrrolidine]-6-carboxylate Into a 50-mL round-bottom flask, was placed a solution of the first eluting isomer from Step 1 (400 mg, 1.54 mmol, 1 equiv) in DMF (5 mL). This was followed by the addition of NaH (124 mg, 5.17 mmol, 1.5 equiv) at 0° C. over 10 min. To this was added 1-(bromomethyl)-4-methanesulfonylbenzene (572 mg, 2.30 mmol, 2 equiv) dropwise with stirring at 0° C. The resulting solution was stirred for 2 h at 0° C. in a water-ice bath. The reaction was then quenched by the addition of 40 mL of water. The resulting solution was extracted with 3×100 mL of EtOAc and the combined organic layers were concentrated. The residue was purified on a C18 column eluting with 45% $CH_3CN$/water/0.05% TFA to afford 501 mg (60% yield) of a single isomer of methyl 1'-[(4-methanesulfonylphenyl)methyl]-2'-oxo-3,4-dihydro-1H-spiro[naphthalene-2,3'-pyrrolidine]-6-carboxylate.TFA as a white solid. $^1$H NMR (400 MHz, DMSO-d6) δ (ppm): 7.92-7.94 (dd, J=8 Hz, 2H), 7.70-7.72 (m, 2H), 7.49-7.51 (dd, J=8 Hz, 2H), 7.23-7.25 (dd, J=8 Hz, 1H), 4.53 (s, 2H), 3.82 (s, 3H), 3.28-3.24 (t, J=8 Hz, 2H), 3.22 (s, 3H), 2.92-2.97 (m, 2H), 2.80-2.89 (m, 1H), 2.70-2.74 (m, 1H), 1.84-1.97 (m, 2H), 1.76-1.74 (m, 2H). MS: (ES, m/z): 428 [M+H]$^+$. A sample was recrystallized from EtOAc/hexanes (~1:1) and submitted for small molecule X-ray crystallography, which showed the material to be methyl (R)-1'-[(4-methanesulfonylphenyl)methyl]-2'-oxo-3,4-dihydro-1H-spiro[naphthalene-2,3'-pyrrolidine]-6-carboxylate (see Example 52). Thus, the first eluting isomer of Step 1 was assigned as methyl (R)-2'-oxo-3,4-dihydro-1H-spiro[naphthalene-2,3'-pyrrolidine]-6-carboxylate and the second eluting isomer of Step 1 was assigned as methyl (S)-2'-oxo-3,4-dihydro-1H-spiro[naphthalene-2,3'-pyrrolidine]-6-carboxylate.

Example 14

Preparation of (R)-N-hydroxy-2'-oxo-1'-(pyridin-2-yl)-3,4-dihydro-1H-spiro[naphthalene-2,3'-pyrrolidine]-6-carboxamide (I-20)

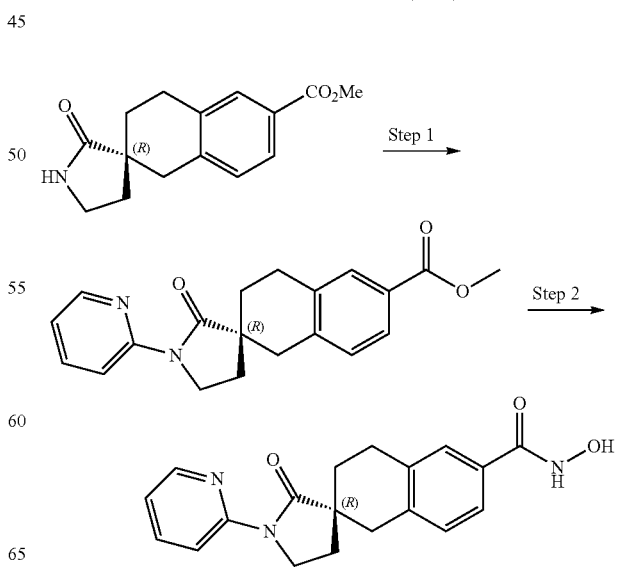

Step-1: Methyl (R)-2'-oxo-1'-(pyridin-2-yl)-3,4-dihydro-1H-spiro[naphthalene-2,3'-pyrrolidine]-6-carboxylate Into a 100-mL round-bottom flask maintained with the atmosphere of nitrogen, was placed methyl (R)-2'-oxo-3,4-dihydro-H-spiro[naphthalene-2,3'-pyrrolidine]-6-carboxylate (100 mg, 0.39 mmol, 1 equiv) in toluene (5 mL), Pd₂(dba)₃ (7.9 mg, 0.01 mmol, 0.02 equiv), XantPhos (66.0 mg, 0.11 mmol, 0.3 equiv), Cs₂CO₃ (248.0 mg, 0.76 mmol, 1.97 equiv), and 2-bromopyridine (91.0 mg, 0.58 mmol, 1.49 equiv). The resulting mixture was stirred overnight at 110° C. and then concentrated under vacuum. The residue was purified by normal phase chromatography on silica gel with EtOAc/petroleum ether (1:5). The collected fractions were concentrated to give 40 mg (31% yield) of the title compound as a white solid. MS: (ES, m/z): 337 [M+H]⁺.

Step-2: (R)-N-Hydroxy-2'-oxo-1'-(pyridin-2-yl)-3,4-dihydro-1H-spiro[naphthalene-2,3'-pyrrolidine]-6-carboxamide Into a 100-mL round-bottom flask was placed methyl (R)-2'-oxo-1'-(pyridin-2-yl)-3,4-dihydro-1H-spiro[naphthalene-2,3'-pyrrolidine]-6-carboxylate (40 mg, 0.12 mmol, 1 equiv) in THF/MeOH (4:1, 1.25 mL), NH₂OH (50% in water, 786 mg, 23.8 mmol, 200 equiv) and 1N aq. NaOH (0.2 mL, 1.67 equiv). The resulting solution was stirred for 4 h at room temperature. The resulting mixture was adjusted to pH 7 with 4N aq. HCl. The crude product was purified by Prep-HPLC with the following conditions: Column: X Bridge C18, 19×150 mm, 5 µm; Mobile Phase A: Water/0.05% TFA, Mobile Phase B: CH₃CN/0.05% TFA; Flow rate: 28 mL/min; Gradient: 10% B to 40% B in 7 min; Detector: UV 254 nm. The collected fractions were lyophilized to give 36 mg (90% yield) of the title compound as a pink solid. ¹H-NMR (400 MHz, DMSO-d6) δ (ppm): 11.10 (br s, 1H), 8.42-8.33 (m, 2H), 7.86-7.82 (m, 1H), 7.55-7.49 (m, 2H), 7.18-7.15 (m, 2H), 4.03-3.96 (m, 2H), 2.98-2.80 (m, 4H), 2.07-1.80 (m, 4H). MS: (ES, m/z): 338 [M+H]⁺.

TABLE 6

The following compounds were prepared according to the method of Example 14.

| Ex. | Structure | ¹H-NMR δ (ppm) | Found (ES, m/z) [M + H]⁺ |
|---|---|---|---|
| I-10 | 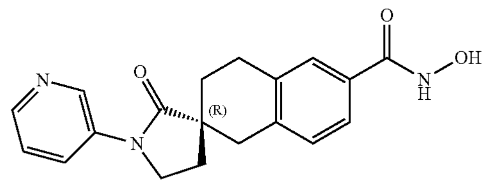 | (400 MHz, DMSO-d6): 11.13 (s, 1H), 9.08 (s, 1H), 8.47-8.46 (d, J = 4.4 MHz, 1H), 8.35-8.33 (d, J = 7.2 MHz, 1H), 7.66-7.49 (m, 3H), 7.23-7.11 (m, 1H), 3.94-3.91 (t, J = 7.2 MHz, 2H), 2.98-2.80 (m, 4H), 2.14-1.82 (m, 4H). | 338 |
| I-16 | 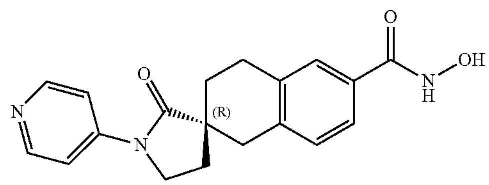 | (300 MHz, DMSO-d6): 11.14 (s, 1H), 8.78 (s, 2H), 8.19 (s, 2H), 7.56-7.50 (m, 2H), 7.18-7.16 (d, J = 7.8 Hz, 1H), 4.02-3.97 (t, J = 6.9 Hz, 2H), 3.01-2.84 (m, 4H), 2.18-2.11 (m, 1H), 2.09-1.92 (m, 3H). | 338 |
| I-26 | 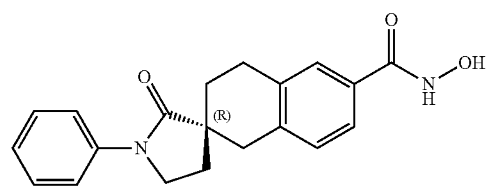 | (400 MHz, DMSO-d6): 11.10 (br s, 1H), 7.73-7.71 (d, J = 8 Hz, 2H), 7.58-7.38 (m, 4H), 7.18-7.12 (m, 2H), 3.88-3.86 (t, J = 4 Hz, 2H), 2.97-2.78 (m, 4H), 2.09-2.02 (m, 1H), 1.96-1.79 (m, 3H). | 337 |

Example 15

Preparation of (R)-N-hydroxy-1'-methyl-2'-oxo-3,4-dihydro-1H-spiro[naphthalene-2,3'-pyrrolidine]-6-carboxamide (I-104)

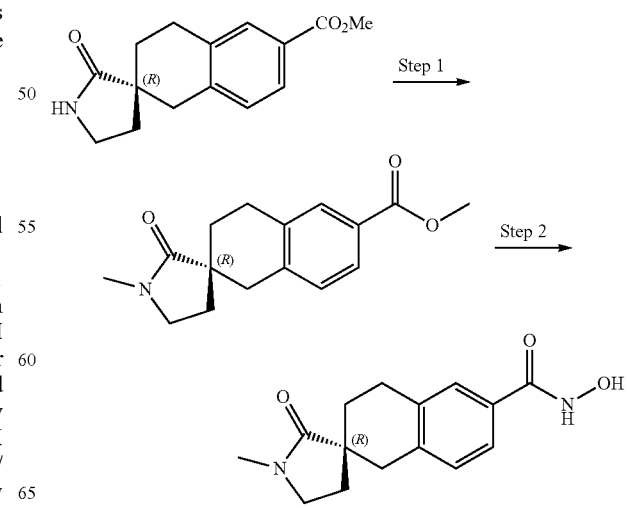

Step-1: Methyl (R)-1'-methyl-2'-oxo-3,4-dihydro-1H-spiro[naphthalene-2,3'-pyrrolidine]-6-carboxylate Into a 100-mL round-bottom flask was placed a solution of methyl (R)-2'-oxo-3,4-dihydro-1H-spiro[naphthalene-2,3'-pyrrolidine]-6-carboxylate (200 mg, 0.77 mmol, 1 equiv) in DMF (5 mL). NaH (60 mg, 2.50 mmol, 2 equiv) was added in portions at 0° C. After stirring for 10 min, iodomethane (219 mg, 1.54 mmol, 2 equiv) was added dropwise at 0° C. The resulting solution was stirred for 2.5 h at 0° C. The reaction was quenched with 30 mL of water. The resulting solution was extracted 3×100 mL with EtAOc. The organic layers were combined and concentrated under reduced pressure. The crude product was purified by normal phase column chromatography on silica gel with EtOAc/petroleum ether (1:5). The collected fractions were concentrated to give 230 mg of the title compound as a yellow oil. MS: (ES, m/z): 274 [M+H]+.

Step-2: (R)-N-Hydroxy-1'-methyl-2'-oxo-3,4-dihydro-1H-spiro[naphthalene-2,3'-pyrrolidine]-6-carboxamide Into a 50-mL round-bottom flask was placed a solution of methyl (R)-1'-methyl-2'-oxo-3,4-dihydro-1H-spiro[naphthalene-2,3'-pyrrolidine]-6-carboxylate (130 mg, 0.48 mmol, 1 equiv) in THF (2.0 mL), NH$_2$OH (50% in water, 1.87 mL, 60 equiv) and 1N aq. NaOH (0.95 mL, 2 equiv). The resulting solution was stirred for 4 h at room temperature. The crude product was purified by Prep-HPLC with the following conditions: Column: X-bridge C18 190×50 mm 5 µm; Mobile Phase A: Water/0.05% TFA, Mobile Phase B: CH$_3$CN/0.05% TFA; Gradient: 20% B to 60% B in 7 min; Detector: UV 254 nm. The collected fractions were lyophilized to give 43.5 mg (24% yield) of the title compound as a light yellow solid. $^1$H-NMR (400 MHz, DMSO-d6) δ(ppm): 11.09 (s, 1H), 8.95 (s, 1H), 7.45-7.51 (m, 2H), 7.11-7.13 (d, J=8 Hz, 1H), 3.28-3.32 (t, J=8 Hz, 2H), 2.76-2.89 (m, 6H), 2.50-2.56 (m, 1H), 1.81-1.90 (m, 2H), 1.63-1.80 (m, 2H). MS: (ES, m/z): 275 [M+H]+.

TABLE 7

The following compounds were prepared according to the method of Example 15, with the following modification: In Step 1, the halide can be an iodide, a chloride, or a bromide.

| Ex. | Structure | $^1$H-NMR δ (ppm) | Found (ES, m/z) [M + H]+ |
|---|---|---|---|
| I-88 | 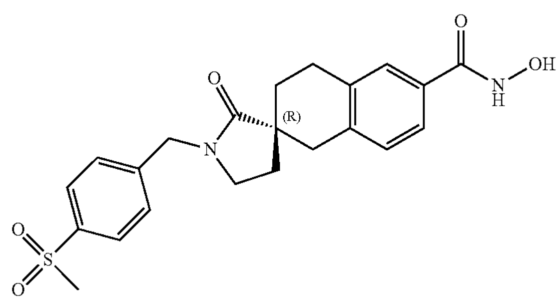 | (400 MHz, DMSO-d6): 11.09 (s, 1H), 9.00 (s, 1H), 7.92-7.94 (dd, J = 8 Hz, 2H), 7.46-7.52 (m, 4H), 7.15-7.17 (dd, J = 8 Hz, 1H), 4.54(s, 2H), 3.22-3.28 (m, 5H), 2.81-2.95 (m, 3H), 2.65-2.70 (m, 1H), 1.86-1.97 (m, 2H), 1.60-1.71 (m, 2H) | 429 |
| I-30 | 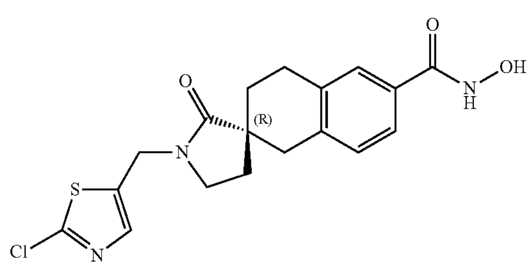 | (400 MHz, DMSO-d6): 11.09 (s, 1H), 7.64 (s, 1H), 7.50 (s, 1H), 7.45-7.47 (dd, J = 8Hz, 1H), 7.13-7.15 (dd, J = 8 Hz, 1H), 4.60 (s, 2H), 3.29-3.22 (t, J = 6.8 Hz, 2H), 2.79-2.90 (m, 3H), 2.50-2.58 (m, 1H), 1.90-1.94 (m, 1H), 1.80-1.89 (m, 1H), 1.77-1.80 (m, 2H) | 392 |
| I-22 | 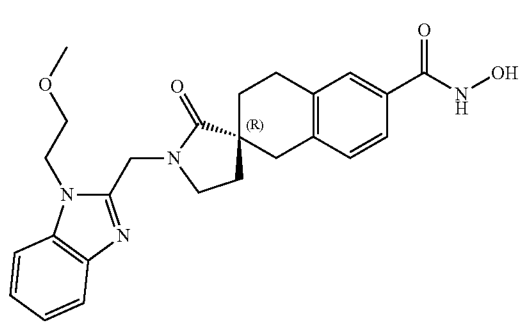 | (400 MHz, DMSO-d6): 11.11 (br s, 1H), 7.79-7.72 (m, 2H), 7.532-7.37 (m, 4H), 7.17-7.15 (d, J = 8.0 Hz, 1H), 4.88 (s, 2H), 4.60 (s, 2H), 3.70-3.67 (t, J = 6 Hz, 2H), 3.45-3.41 (t, J = 8 Hz, 2H), 3.24 (s, 3H), 2.94-2.73 (m, 4H), 1.98-1.72 (m, 4H) | 449 |

TABLE 7-continued

The following compounds were prepared according to the method of Example 15, with the following modification: In Step 1, the halide can be an iodide, a chloride, or a bromide.

| Ex. | Structure | ¹H-NMR δ (ppm) | Found (ES, m/z) [M + H]⁺ |
|---|---|---|---|
| I-14 | 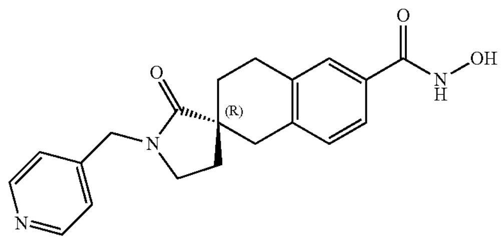 | (300 MHz, DMSO-d6): 11.14 (br s, 1H), 8.78-8.76 (d, J = 6 Hz 2H), 7.65-7.63 (d, J = 6 Hz, 2H), 7.56-7.48 (m, 2H), 7.18-7.15 (d, J = 9 Hz 1H), 4.64 (s, 2H) 3.37-3.32 (t, J = 7.5 Hz, 2H), 2.96-2.70 (m, 4H), 2.04-1.72 (m, 4H) | 352 |
| I-18 | 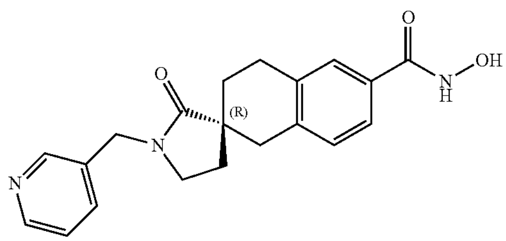 | (300 MHz, DMSO-d6): 11.12 (br s, 1H), 8.71-8.67 (m, 2H), 8.04-8.01 (d, J = 9 Hz, 1H), 7.76-7.71 (m, 1H), 7.53-7.42 (m, 2H), 7.16-7.13 (d, J = 9 Hz, 1H), 4.56 (s, 2H), 3.32-3.28 (t, J = 6 Hz, 2H), 2.94-2.75 (m, 3H), 2.70-2.64 (m, 1H), 1.98-1.81 (m, 2H), 1.77-1.60 (m, 2H) | 352 |
| I-24 | 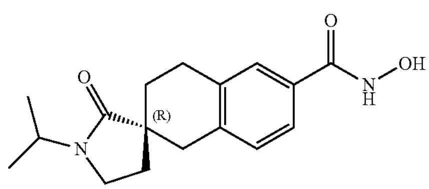 | (400 MHz, DMSO-d6): 11.08 (s, 1H), 7.51-7.46 (m, 2H), 7.15-7.09 (m, 1H), 4.18-4.10 (m, 1H), 3.28-3.24 (t, 2H, J = 6.8 Hz), 2.89-2.60 (m, 4H), 1.88-1.58 (m, 4H), 1.15-1.05 (m, 6H) | 303 |
| I-163 | 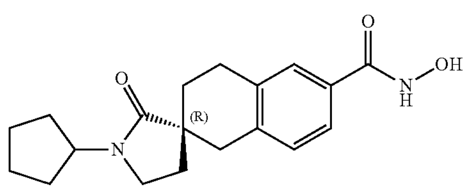 | (400 MHz, DMSO-d6): 11.09 (s, 1H), 8.95 (s, 1H), 7.46-7.51 (m, 2H), 7.12-7.14 (d, J = 8.0 Hz, 1H), 4.31-4.35 (m, 1H), 3.27-3.32 (m, 2H), 2.75-2.89 (m, 3H), 2.57-2.61 (m, 1H), 1.69-1.89 (m, 12H) | 329 |
| I-159 | 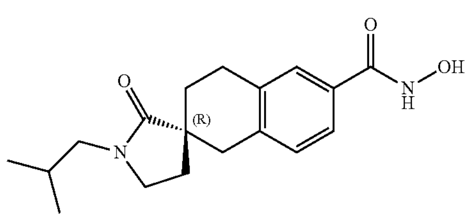 | (400 MHz, DMSO-d6): 11.09 (br s, 1H), 8.95 (br s, 1H), 7.51 (s, 1H), 7.47 (d, J = 8 Hz, 1H), 7.14 (d, J = 8 Hz, 1H), 2.32-2.29 (m, 2H), 3.04-3.01 (m, 2H), 2.88-2.78 (m, 2H), 2.61 (d, J = 16 Hz, 1H), 1.93-1.78 (m, 3H), 1.71-1.60 (m, 2H), 1.86 (d, J = 7 Hz, 6H) | 317 |
| I-161 | 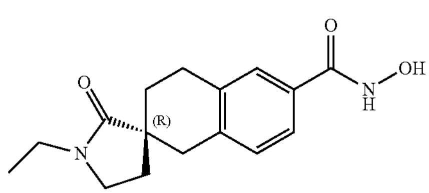 | (400 MHz, DMSO-d6): 11.08 (br s, 1H), 8.95 (br s, 1H), 7.51 (s, 1H), 7.46 (d, J = 7.6 Hz, 1H), 7.14 (d, J = 8 Hz, 1H), 3.33-3.29 (m, 2H), 3.27-3.23 (m, 2H), 2.89-2.75 (m, 3H), 2.59 (d, J = 17 Hz, 1H), 1.90-1.76 (m, 2H), 1.70-1.65 (m, 2H), 1.05 (t, J = 8.0 Hz, 3H) | 289 |
| I-165 | 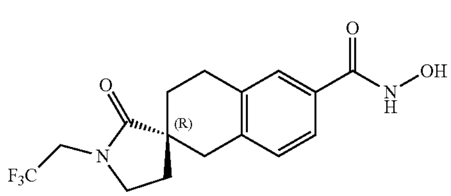 | (400 MHz, DMSO-d6): 11.08 (s, 1H), 8.97 (s, 1H), 7.47-7.52 (m, 2H), 7.15 (d, J = 8 Hz, 1H), 4.06-4.15 (m, 2H), 3.45-3.49 (m, 2H), 2.77-2.92 (m, 3H), 2.66 (d, J = 16 Hz, 3H), 1.95-2.00 (m, 1H), 1.77-1.95 (m, 3H) | 343 |

Example 16

Preparation of (R)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-12)

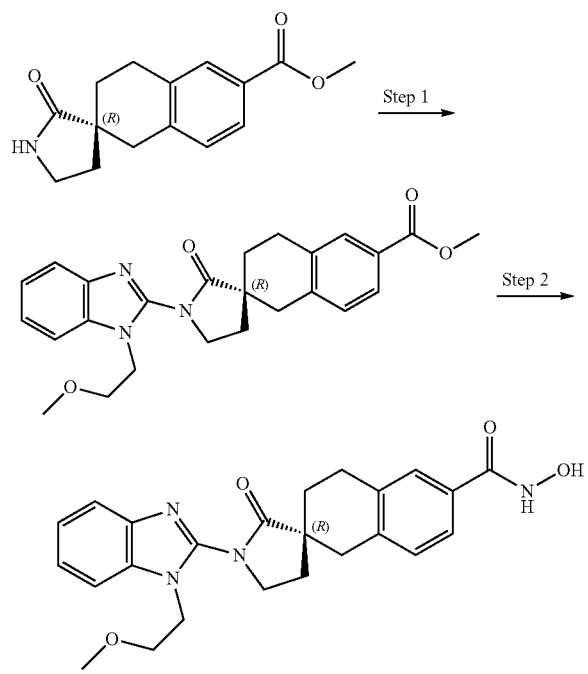

Step-1: Methyl (R)-1'-(1-(2-methoxyethyl)-1H-benzo[d]imidazol-2-yl)-2'-oxo-3,4-dihydro-1H-spiro[naphthalene-2,3'-pyrrolidine]-6-carboxylate Into a 10-mL sealed tube purged and maintained with an inert atmosphere of nitrogen, was placed methyl (R)-2'-oxo-3,4-dihydro-1H-spiro[naphthalene-2,3'-pyrrolidine]-6-carboxylate (60 mg, 0.23 mmol, 1 equiv), 2-bromo-1-(2-methoxyethyl)-1H-1,3-benzodiazole (103 mg, 0.40 mmol, 1.5 equiv) in toluene (4 mL), CuI (5 mg, 0.03 mmol, 0.1 equiv), $Cs_2CO_3$ (263 mg, 0.81 mmol, 3 equiv), and (1R, 2R)-1-N, 2-N-dimethylcyclohexane-1,2-diamine (8 mg, 0.06 mmol, 0.2 equiv). The resulting mixture was stirred for 10 h at 110° C. in an oil bath. The reaction mixture was cooled to 20° C. with a water bath. The solids were filtered out. The filtrate was concentrated under vacuum. The residue was purified by normal phase chromatography on silica gel with EtOAc/petroleum ether (1:1). The collected fractions were concentrated to give 50 mg (50% yield) of the title compound as a colorless oil. MS: (ES, m/z): 434 [M+H]+.

Step-2: (R)-N-Hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide Into a 10-mL round-bottom flask was placed methyl (R)-1'-(1-(2-methoxyethyl)-1H-benzo[d]imidazol-2-yl)-2'-oxo-3,4-dihydro-1H-spiro[naphthalene-2,3'-pyrrolidine]-6-carboxylate (50 mg, 0.12 mmol, 1 equiv), THF/MeOH (4:1, 2.5 mL), $NH_2OH$ (50% in water, 0.5 mL, 63 equiv), and 1N aq. NaOH (0.3 mL, 2.5 equiv). The resulting solution was stirred for 3 h at room temperature. The reaction mixture was cooled to 0° C. with an ice-water bath. The pH of the solution was adjusted to 7 with 1N aq. HCl. The crude product was purified by Prep-HPLC with the following conditions: Column: XBridge C18, 19×150 mm, 5 μm; Mobile Phase A: Water/10% $NH_4HCO_3$, Mobile Phase B: $CH_3CN$/10% $NH_4HCO_3$; Flow rate: 25 mL/min; Gradient: 5% B to 47% B in 7 min; Detector: UV 254 nm. The collected fractions were lyophilized to give 38.4 mg (77% yield) of the title compound as an off-white solid. $^1$H-NMR (400 MHz, DMSO-d6) δ (ppm): 11.14 (br s, 1H), 7.65-7.48 (m, 4H), 7.31-7.18 (m, 3H), 4.35-4.32 (t, J=6 Hz, 2H), 3.99-3.89 (m, 2H), 3.62-3.59 (t, J=6 Hz, 2H), 3.20 (s, 3H), 3.01-2.86 (m, 4H), 2.22-2.16 (m, 1H), 2.02-1.98 (m, 3H). MS: (ES, m/z): 435 [M+H]+.

Example 17

Preparation of (R)-N-hydroxy-2'-oxo-3,4-dihydro-1H-spiro[naphthalene-2,3'-pyrrolidine]-6-carboxamide (I-27)

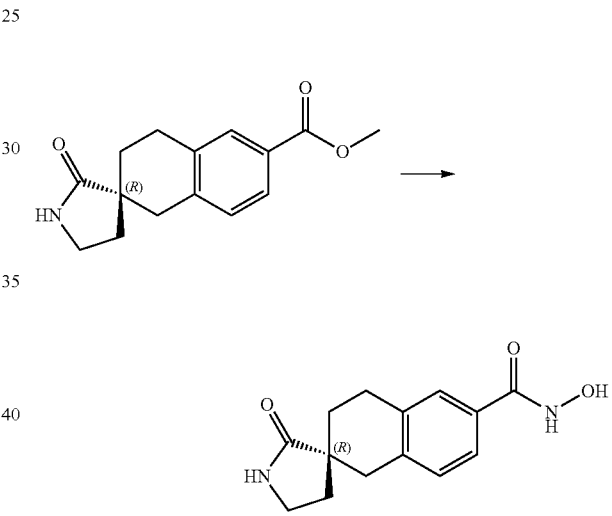

Into a 50-mL round-bottom flask was placed a solution of methyl (R)-2'-oxo-3,4-dihydro-1H-spiro[naphthalene-2,3'-pyrrolidine]-6-carboxylate (100 mg, 0.39 mmol, 1 equiv) in THF/MeOH (4:1, 2.5 mL), $NH_2OH$ (50% in water, 1.52 mL, 60 equiv), and 1N aq. NaOH (0.77 mL, 2 equiv). The resulting solution was stirred for 1.5 h at room temperature. The crude product was purified by Prep-HPLC with the following conditions: Column: Waters HSS C18, 2.1×50 mm, 1.8 μm; Mobile Phase A: Water/0.05% TFA, Mobile Phase B: $CH_3CN$/0.05% TFA; Flow rate: 0.7 mL/min; Gradient: 5% B to 95% B in 2.0 min hold 0.6 min; Detector: UV 254 nm. The collected fractions were lyophilized to give 40.6 mg (28% yield) of the title compound as a pink solid. $^1$H-NMR (400 MHz, DMSO-d6) δ (ppm): 11.09 (s, 1H), 8.94 (s, 1H), 7.66 (s, 1H), 7.45-7.50 (m, 2H), 7.13-7.15 (d, J=8 Hz, 1H), 318-3.22 (t, J=7 Hz, 2H), 2.74-2.90 (m, 3H), 2.63-2.67 (m, 1H), 1.90-1.95 (m, 1H), 1.68-1.80 (m, 2H), 1.60-1.64 (m, 1H). MS: (ES, m/z): 261 [M+H]+.

Example 18

Preparation of (R)-N-hydroxy-1'-((2-hydroxythiazol-5-yl)methyl)-2'-oxo-3,4-dihydro-1H-spiro[naphthalene-2,3'-pyrrolidine]-6-carboxamide (I-31)

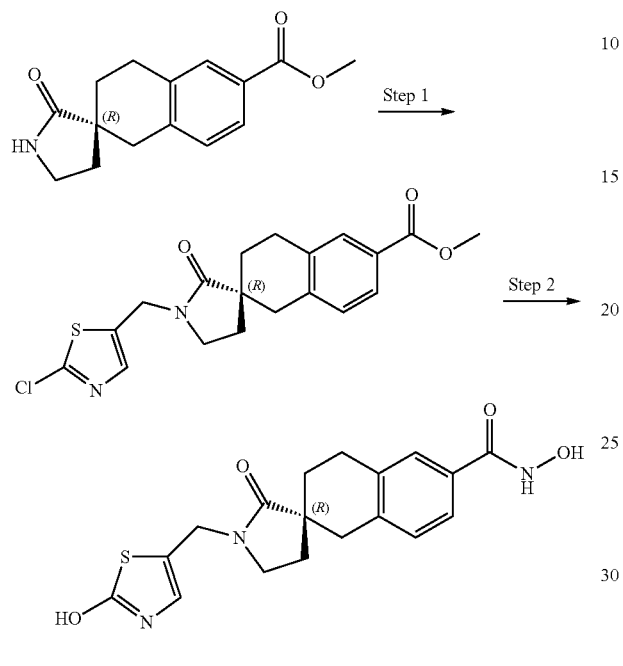

Step-1: Methyl (R)-1'-((2-chlorothiazol-5-yl)methyl)-2'-oxo-3,4-dihydro-1H-spiro[naphthalene-2,3'-pyrrolidine]-6-carboxylate Into a 100-mL round-bottom flask was placed a solution of methyl (R)-2'-oxo-3,4-dihydro-1H-spiro[naphthalene-2,3'-pyrrolidine]-6-carboxylate (250 mg, 0.96 mmol, 1 equiv) in DMF (5 mL). NaH (75 mg, 3.12 mmol, 2 equiv) and 2-chloro-5-(chloromethyl)-1,3-thiazole (242 mg, 1.44 mmol, 1.5 equiv) were added at 0° C. The resulting solution was stirred for 2.5 h at 0° C. The residue was purified by reverse-phase purification using the following conditions: C18 column; Mobile Phase A: Water/0.05% TFA, Mobile Phase B: $CH_3CN$/0.05% TFA; Gradient: 50% B to 60% B; Detector: UV 254 nm. The collected fractions were lyophilized to give 265 mg (54% yield) of the title compound as a light yellow oil. $^1$H-NMR (400 MHz, $CDCl_3$) δ (ppm): 7.80-7.82 (m, 2H), 7.50 (s, 1H), 7.14-7.16 (dd, J=8 Hz, 1H), 6.81 (s, 1H), 4.65 (s, 2H), 3.92 (s, 3H), 3.36-3.39 (t, J=12 Hz, 2H), 3.12-3.16 (m, 1H), 2.98-3.06 (m, 1H), 2.82-2.90 (m, 1H), 2.60-2.64 (m, 1H), 2.14-2.11 (m, 1H), 1.95-2.00 (m, 1H), 1.84-1.89 (m, 1H), 1.70-1.76 (m, 1H). MS: (ES, m/z): 391 [M+H]$^+$.

Step-2: (R)-N-Hydroxy-1'-((2-hydroxythiazol-5-yl)methyl)-2'-oxo-3,4-dihydro-1H-spiro[naphthalene-2,3'-pyrrolidine]-6-carboxamide Into a 50-mL round-bottom flask was placed a solution of methyl (R)-1'-((2-chlorothiazol-5-yl)methyl)-2'-oxo-3,4-dihydro-1H-spiro[naphthalene-2,3'-pyrrolidine]-6-carboxylate (150 mg, 0.38 mmol, 1 equiv) in THF/MeOH (4:1, 2.5 mL), $NH_2OH$ (50% in water, 1.6 mL, 60 equiv) and 1N aq. NaOH (1.0 mL, 3 equiv). The reaction was stirred for 6 h at room temperature. The crude product was purified by Prep-HPLC with the following conditions: Column: X-bridge C18 19×150 mm, Mobile Phase A: Water/0.05% TFA, Mobile Phase B: $CH_3CN$/0.05% TFA; Gradient: 5% B to 70% B in 7 min; Detector: UV 254 nm. The collected fractions were lyophilized to give 4.9 mg (4% yield) of the title compound as a pink solid. $^1$H-NMR (400 MHz, DMSO-d6) δ (ppm): 11.02-11.09 (m, 2H), 8.94 (s, 1H), 7.50-7.54 (m, 2H), 7.13-7.15 (d, J=8 Hz, 1H), 6.84 (s, 1H), 4.30 (s, 2H), 3.23-3.26 (t, J=7.2 Hz, 2H), 2.80-2.89 (m, 3H), 2.57-2.66 (m, 1H), 1.80-1.92 (m, 2H), 1.71-1.79 (m, 2H). MS: (ES, m/z): 374 [M+H]$^+$.

Example 19

Preparation of (R)-1'-cyclopropyl-N-hydroxy-2'-oxo-3,4-dihydro-1H-spiro[naphthalene-2,3'-pyrrolidine]-6-carboxamide (I-109)

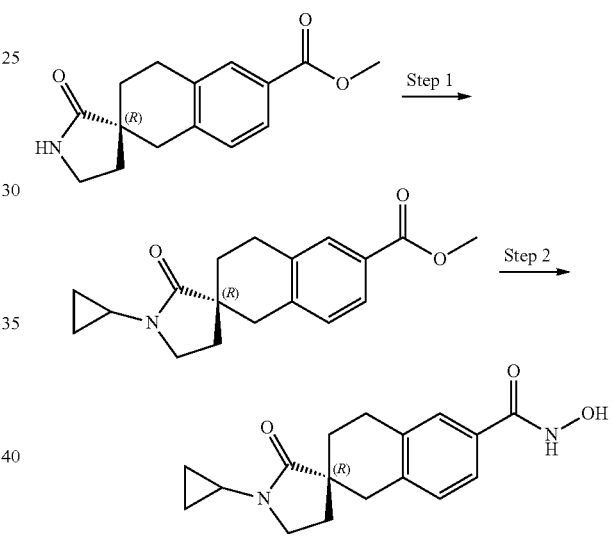

Step-1: Methyl (R)-1'-cyclopropyl-2'-oxo-3,4-dihydro-1H-spiro[naphthalene-2,3'-pyrrolidine]-6-carboxylate A 4 mL vial with a Teflon screw-cap was charged with a solution of methyl (R)-2'-oxo-3,4-dihydro-1H-spiro[naphthalene-2,3'-pyrrolidine]-6-carboxylate (0.2M in 4:1 toluene/pyridine, 0.15 mL, 0.03 mmol, 1 equiv). Then $Cu(OAc)_2$ (11 mg, 0.06 mmol, 2 equiv) was added, followed by $Cs_2CO_3$ (20 mg, 0.06 mmol, 2 equiv). Lastly a solution of 2-cyclopropyl-4,4,5,5-tetramethyl-1,3,2-dioxaborolane (0.2 M in toluene, 0.3 mL, 0.6 mmol, 2 equiv) was added. The vial was purged with $O_2$ and sealed. The vial was heated at 110° C. for 72 h. Then reaction mixture was then cooled to room temperature and diluted with 2 mL of EtOAc and 1 mL of 1N aq. HCl. The vial was shaken and the organic layer was separated. The aqueous layer was extracted once more with 2 mL EtOAc. The combined organic layers were washed with brine and concentrated to dryness. The title compound was carried forward as a residue without further purification. MS: (ES, m/z): 300 [M+H]$^+$.

Step-2: (R)-1'-Cyclopropyl-N-hydroxy-2'-oxo-3,4-dihydro-1H-spiro[naphthalene-2,3'-pyrrolidine]-6-carboxamide Into a vial was placed methyl (R)-1'-cyclopropyl-2'-oxo-3,4-dihydro-1H-spiro[naphthalene-2,3'-pyrrolidine]-6-carboxylate in THF/MeOH (3:1, 0.2 mL), NH$_2$OH (50% in water, 0.15 mL, 76 equiv), and 1N aq. NaOH (0.1 mL, 3.3 equiv). The reaction mixture was stirred at room temperature for 4 h. The reaction mixture was concentrated and purified by Prep-HPLC using the following conditions: Column: Waters Sunfire C18, 5 μm, 19×50 mm; Mobile Phase A: Water/0.1% Formic Acid, Mobile Phase B: CH$_3$CN/0.1% Formic Acid; Flow rate: 23 mL/min; Gradient 15% B to 100% B in 6 min; Detector: UV 254 nm, 220 nm. The collected fractions were lyophilized to afford 4 mg (37% yield) of the title compound. $^1$H NMR (400 MHz, DMSO-d$_6$) δ (ppm): 11.10 (s, 1H), 9.00 (s, 1H), 7.67 (d, J=8.3 Hz, 1H), 7.46 (d, J=7.7 Hz, 1H), 7.13 (d, J=7.8 Hz, 1H), 3.20 (t, J=8.0 Hz, 2H), 2.95-2.77 (m, 2H), 2.85 (d, J=16 Hz, 1H), 2.66-2.61 (m, 2H), 1.95-1.89 (m, 1H), 1.83-1.69 (m, 2H), 1.66-1.60 (m, 1H) 0.79-0.73 (m, 2H), 0.70-0.66 (m, 2H). MS: (ES, m/z): 301 [M+H]$^+$.

Example 20

Preparation of (R)-1'-(3-cyanophenyl)-N-hydroxy-2'-oxo-3,4-dihydro-1H-spiro[naphthalene-2,3'-pyrrolidine]-6-carboxamide (I-112)

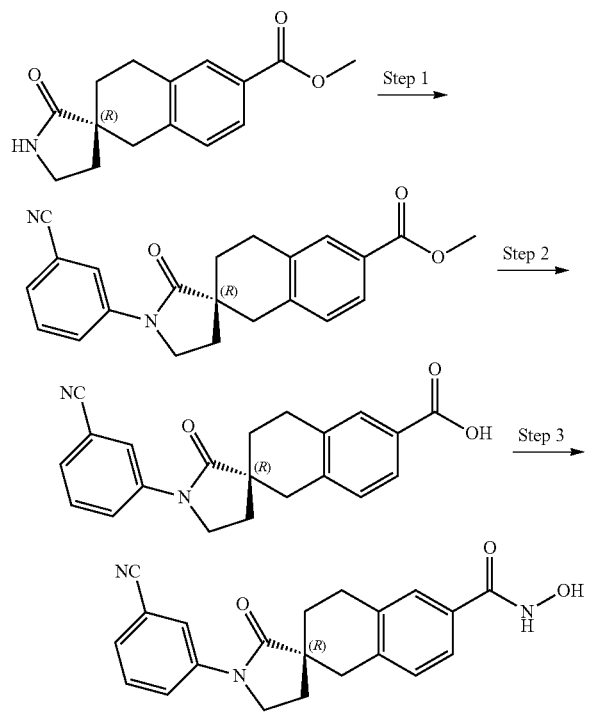

Step-1: Methyl-(R)-1'-(3-cyanophenyl)-2'-oxo-3,4-dihydro-1H-spiro[naphthalene-2,3'-pyrrolidine]-6-carboxylate A 7-mL vial with Teflon screw top and magnetic stir bar was charged with methyl-(R)-2'-oxo-3,4-dihydro-1H-spiro[naphthalene-2,3'-pyrrolidine]-6-carboxylate (41 mg, 0.160 mmol, 1 equiv), Cs$_2$CO$_3$ (210 mg, 0.640 mmol, 4 equiv), and a solution of 3-bromobenzonitrile in 1,4-dioxane (0.2M, 0.880 mL, 0.176 mmol, 1.1 equiv). The vial was sealed and brought into a nitrogen-filled glovebox where a solution of CuI and N,N'-dimethylethylenediamine in DMA (0.2M, 0.40 mL, 0.80 mmol, 0.5 equiv) was added. The vial was sealed and heated at 100° C. for 16 h. The reaction mixture was then cooled to room temperature and diluted with 30 mL of EtOAc and washed with sat. NH$_4$Cl (2×30 mL) and brine (1×30 mL). The organic phase was dried with Na$_2$SO$_4$, filtered and evaporated to dryness in vacuo to afford a pale yellow residue which was carried forward without any further purification (51 mg, 88% yield). $^1$H NMR (400 MHz, CDCl$_3$) δ (ppm): 8.07-8.05 (m, 1H), 7.99-7.96 (m, 1H), 7.88-7.82 (m, 1H), 7.80-7.77 (m, 1H), 7.49 (t, J=8.2 Hz, 1H), 7.41 (dt, J=7.8, 1.2 Hz, 1H), 7.22 (d, J=7.8 Hz, 1H), 3.91, (s, 3H), 3.86 (t, J=6.6 Hz, 2H), 3.20 (d, J=17 Hz, 1H), 3.12-3.05 (m, 1H), 2.99-2.90 (m, 1H), 2.78 (d, J=17 Hz, 1H), 2.24-2.00 (m, 3H), 1.92-1.86 (m, 1H). MS: (ES, m/z) 361 [M+H]$^+$.

Step-2: (R)-1'-(3-Cyanophenyl)-2'-oxo-3,4-dihydro-1H-spiro[naphthalene-2,3'-pyrrolidine]-6-carboxylic acid Methyl-(R)-1'-(3-cyanophenyl)-2'-oxo-3,4-dihydro-1H-spiro[naphthalene-2,3'-pyrrolidine]-6-carboxylate (51 mg, 0.140 mmol, 1 equiv) was dissolved in THF (1.0 mL). A solution of LiOH in water (0.2 M, 1.0 mL, 0.200 mmol, 1.42 equiv) was added and the reaction mixture stirred at room temperature for 16 h. The mixture was diluted with 30 mL of EtOAc and 10 mL of 1M HCl. The layers were separated and the organic layer was evaporated to dryness in vacuo to afford a white solid. The solid was recrystallized from 2-methyltetrahydrofuran/hexane (43 mg, 90% yield). $^1$H NMR (400 MHz, CDCl$_3$) δ (ppm): 8.04-8.00 (m, 2H), 7.92-7.87 (m, 2H), 7.52-7.43 (m, 2H), 7.22 (d, J=7.8 Hz, 1H), 3.87 (t, J=6.6 Hz, 2H), 3.24 (d, J=17 Hz, 1H), 3.12-3.05 (m, 1H), 2.99-2.90 (m, 1H), 2.80 (d, J=17 Hz, 1H), 2.24-2.00 (m, 3H), 1.92-1.86 (m, 1H). MS: (ES, m/z): 347 [M+H]$^+$.

Step-3: (R)-1'-(3-Cyanophenyl)-N-hydroxy-2'-oxo-3,4-dihydro-1H-spiro[naphthalene-2,3'-pyrrolidine]-6-carboxamide (R)-1'-(3-cyanophenyl)-2'-oxo-3,4-dihydro-1H-spiro[naphthalene-2,3'-pyrrolidine]-6-carboxylic acid (10 mg, 0.030 mmol, 1 equiv) was dissolved in 0.150 mL of CH$_3$CN. N-methylmorpholine (0.011 mL, 0.100 mmol, 3.33 equiv) was added followed by propylphosphonic anhydride solution (50% by weight in EtOAc, 0.070 mL, 7.8 equiv). The mixture stirred for 15 min at 50° C., then NH$_2$OH HCl (25 mg, 0.370 mmol, 12.33 equiv) was added. The mixture stirred vigorously at 50° C. for 48 h. The reaction mixture was then diluted with 3 mL of EtOAc and 2 mL of 1N aq HCl. The layers were separated and the organic layer was washed with 1N aq HCl once more. The organic layer was dried and the residue was purified by reverse-phase chromatography Prep-HPLC using the following conditions: Column: Waters Sunfire C18, 5 μm, 19×50 mm; Mobile Phase A: Water/0.1% Formic acid, Mobile Phase B: CH$_3$CN/0.1% Formic acid; Gradient: 15% B to 100% B in 6 min; Flow rate: 23 mL/min; Detector: UV 254 nm, 220 nm. The product containing fractions were combined and concentrated to afford 0.6 mg (5.5% yield) of the title compound. $^1$H NMR (400 MHz, CDCl$_3$) δ (ppm): 8.10 (br s, 2H), 8.04-8.00 (m, 2H), 7.92-7.87 (m, 2H), 7.52-7.43 (m, 2H), 7.22 (d, J=7.8 Hz, 1H), 3.87 (t, J=6.6 Hz, 2H), 3.24 (d, J=17 Hz, 1H), 3.12-3.05 (m, 1H), 2.99-2.90 (m, 1H), 2.80 (d, J=17 Hz, 1H), 2.24-2.00 (m, 3H), 1.92-1.86 (m, 1H). MS: (ES, m/z): 362 [M+H]$^+$.

TABLE 8

The following compound was prepared according to the method of Example 20.

| Ex. | Structure | $^1$H-NMR δ (ppm) | Found (ES, m/z) [M + H]$^+$ |
|---|---|---|---|
| I-175 | 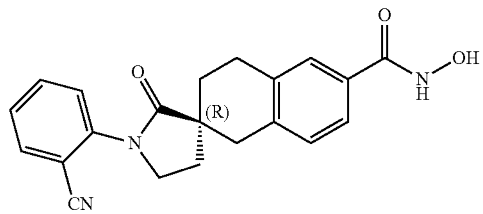 | (400 MHz, CDCl$_3$): 11.08 (br s, 1H), 8.91 (br s, 1H), 7.91 (s, 1H), 7.87 (d, J = 8.2 Hz, 1H), 7.75 (d, J = 12 Hz, 1H), 7.68 (t, J = 7.8 Hz, 1H), 7.48 (d, J = 7.8 Hz, 1H), 7.42 (t, J = 7.8 Hz, 1H), 3.97-3.89 (m, 2H), 3.30 (d, J = 17 Hz, 1H), 3.13-3.06 (m, 1H), 3.00-2.93 (m, 1H), 2.88 (d, J = 17 Hz, 1H), 2.27-2.04 (m, 3H), 2.00-1.94 (m, 1H) | 362 |

TABLE 9

The following compounds were prepared according to the method of Example 20, using methyl-(S)-2'-oxo-3,4-dihydro-1H-spiro[naphthalene-2,3'-pyrrolidine]-6-carboxylate in Step 1.

| Ex. | Structure | $^1$H-NMR δ (ppm) | Found (ES, m/z) [M + H]$^+$ |
|---|---|---|---|
| I-116 | 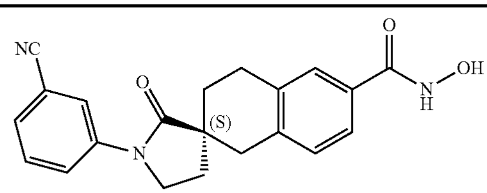 | (400 MHz, CDCl$_3$): 11.08 (br s, 1H). 8.90 (br s, 1H), 8.04-8.00 (m, 2H), 7.92-7.87 (m, 2H), 7.52-7.43 (m, 2H), 7.22 (d, J = 7.8 Hz, 1H), 3.87 (t, J = 6.6 Hz, 2H), 3.24 (d, J = 17 Hz, 1H), 3.12-3.05 (m, 1H), 2.99-2.90 (m, 1H), 2.80 (d, J = 17 Hz, 1H), 2.24-2.00 (m, 3H), 1.92-1.86 (m, 1H) | 362 |
| I-173 | 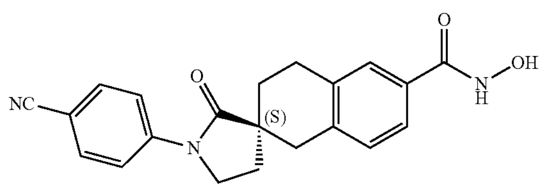 | (400 MHz, CDCl$_3$): 8.13 (br s, 2H), 7.90-7.85 (m, 4H), 7.69-7.66 (m, 2H), 7.20 (d, J = 7.8 Hz, 1H), 3.88 (t, J = 6.8 Hz, 2H), 3.23 (d, J = 17 Hz, 1H), 3.11-3.03 (m, 1H), 2.98-2.89 (m, 1H), 2.79 (d, J = 17 Hz, 1H), 2.22-1.99 (m, 3H), 1.91-1.85 (m, 1H) | 362 |
| I-174 | 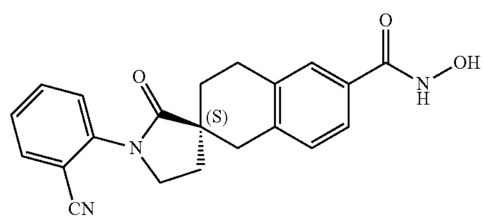 | (400 MHz, CDCl$_3$): 11.08 (br s, 1H), 8.90 (br s, 1H), 7.91 (s, 1H), 7.87 (d, J = 8.2 Hz, 1H), 7.75 (d, J = 12 Hz, 1H), 7.68 (t, J = 7.8 Hz, 1H), 7.48 (d, J = 7.8 Hz, 1H), 7.42 (t, J = 7.8 Hz, 1H), 3.97-3.89 (m, 2H), 3.30 (d, J = 17 Hz, 1H), 3.13-3.06 (m, 1H), 3.00-2.93 (m, 1H), 2.88 (d, J = 17 Hz, 1H), 2.27-2.04 (m, 3H), 2.00-1.94 (m, 1H) | 362 |

Example 21

Preparation of (S)-N-hydroxy-2'-oxo-1'-(pyridin-2-yl)-3,4-dihydro-1H-spiro[naphthalene-2,3'-pyrrolidine]-6-carboxamide (I-21)

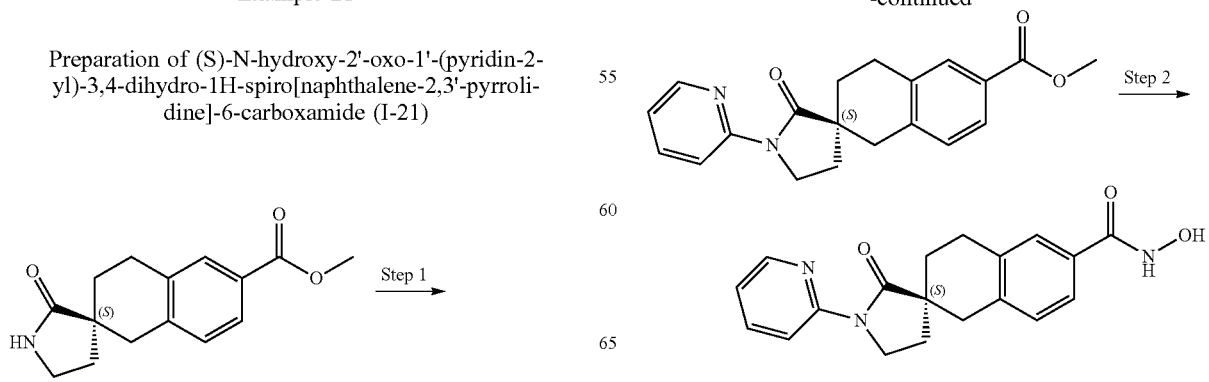

Step-1: Methyl (S)-2'-oxo-1'-(pyridin-2-yl)-3,4-dihydro-1H-spiro[naphthalene-2,3'-pyrrolidine]-6-carboxylate Into a 100-mL round-bottom flask maintained with the atmosphere of nitrogen, was placed methyl (S)-2'-oxo-3,4-dihydro-1H-spiro[naphthalene-2,3'-pyrrolidine]-6-carboxylate (100 mg, 0.39 mmol, 1 equiv) in toluene (5 mL), Pd$_2$(dba)$_3$ (7.9 mg, 0.01 mmol, 0.02 equiv), XantPhos (66 mg, 0.11 mmol, 0.3 equiv), Cs$_2$CO$_3$ (250 mg, 0.77 mmol, 1.99 equiv), and 2-bromopyridine (91 mg, 0.58 mmol, 1.49 equiv). The resulting solution was stirred overnight at 110° C. The solids were filtered out. The residue was purified by normal phase chromatography on silica gel with EtOAc/petroleum ether (1:5). The collected fractions were concentrated to give 60 mg (46% yield) of the title compound as a white solid. MS: (ES, m/z): 337 [M+H]⁺.

Step-2: (S)-N-hydroxy-2'-oxo-1'-(pyridin-2-yl)-3,4-dihydro-1H-spiro[naphthalene-2,3'-pyrrolidine]-6-carboxamide Into a 100-mL round-bottom flask was placed methyl (S)-2'-oxo-1'-(pyridin-2-yl)-3,4-dihydro-1H-spiro[naphthalene-2,3'-pyrrolidine]-6-carboxylate (60 mg, 0.18 mmol, 1 equiv), THF/MeOH (4:1, 1.25 mL), NH$_2$OH (50% in water, 1.18 g, 35.73 mmol, 60 equiv) and 1N aq. NaOH (0.4 mL, 2 equiv). The resulting solution was stirred for 5 h at room temperature. The resulting mixture was adjusted to pH 7 with 4N aq. HCl. The crude product was purified by Prep-HPLC with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 33 mg (55% yield) of the title compound as a pink solid. ¹H-NMR (400 MHz, DMSO-d6) δ (ppm): 11.10 (s, 1H), 8.42-8.33 (m, 2H), 7.86-7.82 (m, 1H), 7.55-7.49 (m, 2H), 7.18-7.15 (m, 2H), 4.03-3.96 (m, 2H), 2.98-2.80 (m, 4H), 2.07-1.81 (m, 4H). MS: (ES, m/z): 338 [M+H]⁺.

TABLE 10

The following compounds were prepared according to the method of Example 21.

| Ex. | Structure | ¹H-NMR δ (ppm) | Found (ES, m/z) [M + H]⁺ |
|---|---|---|---|
| I-11 | 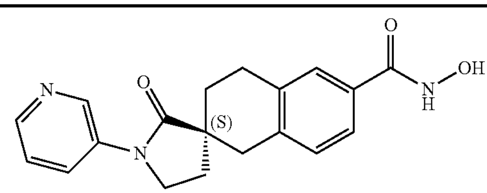 | (300 mHz, DMSO-d6): 11.13 (s, 1H), 9.09 (s, 1H), 8.47-8.46 (d, J = 4.4 Hz, 1H), 8.35-8.32 (d, J = 7.2 Hz, 1H), 7.67-7.49 (m, 3H), 7.23-7.11 (m, 1H), 3.94-3.91 (t, J = 7.2 Hz, 2H), 2.98-2.80 (m, 4H), 2.14-1.82 (m, 4H) | 338 |
| I-17 | 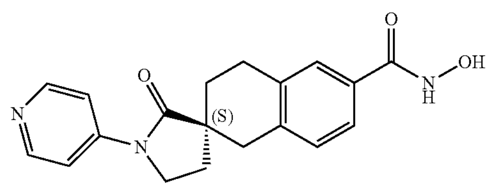 | (300 mHz, DMSO-d6): 11.14 (s, 1H), 8.77-8.75 (d, J = 9.9 Hz, 2H), 8.18-8.15 (d, J = 6.9 Hz, 2H), 7.56-7.50 (m, 2H), 7.18-7.13 (m, 1H), 4.01-3.97 (t, J = 6.9 Hz, 2H), 3.01-2.84 (m, 4H), 2.18-2.09 (m, 1H), 1.98-1.91 (m, 3H) | 338 |
| I-29 | 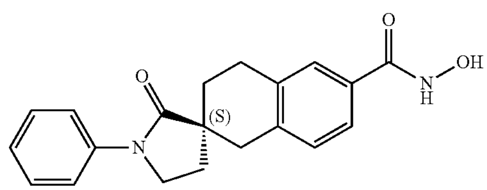 | (400 mHz, DMSO-d6): 11.14 (br s, 1H), 7.73-7.71 (d, J = 8 Hz, 2H), 7.55-7.36 (m, 4H), 7.20-7.12 (m, 2H), 3.88-3.86 (t, J = 4 Hz, 2H), 2.97-2.78 (m, 4H), 2.08-2.02 (m, 1H), 1.96-1.79 (m, 3H) | 337 |

Example 22

Preparation of (S)-N-hydroxy-1'-methyl-2'-oxo-3,4-dihydro-1H-spiro[naphthalene-2,3'-pyrrolidine]-6-carboxamide (I-105)

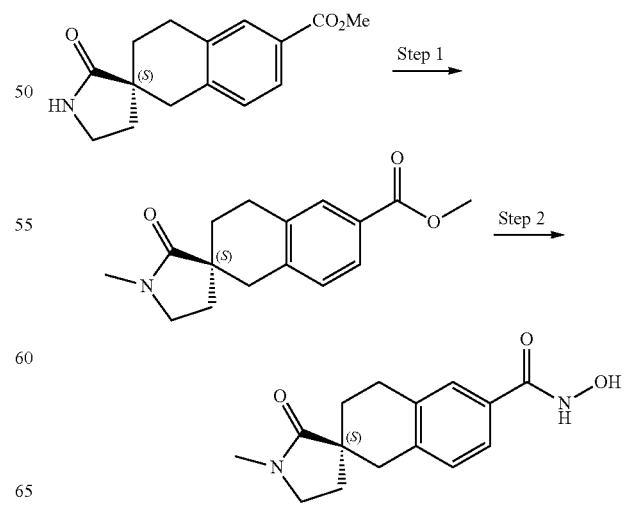

Step-1: Methyl (S)-1'-methyl-2'-oxo-3,4-dihydro-1H-spiro[naphthalene-2,3'-pyrrolidine]-6-carboxylate Into a 50-mL round-bottom flask, was placed a solution of methyl (S)-2'-oxo-3,4-dihydro-1H-spiro[naphthalene-2,3'-pyrrolidine]-6-carboxylate (100 mg, 0.39 mmol, 1 equiv) in DMF (5 mL). This was followed by the addition of NaH (60% dispersion in oil, 30 mg, 1.25 mmol, 2 equiv) at 0° C. over 10 min. Then CH₃I (109 mg, 0.77 mmol, 2 equiv) was added at 0° C. The resulting mixture was stirred for 2.5 h at the same temperature. The reaction was then quenched by the addition of 30 mL of water. The resulting solution was extracted with 3×80 mL of EtOAc. The organic layers were combined and concentrated. The residue was purified by normal phase chromatography on silica gel and eluted with EtOAc/petroleum ether (1:5). The collected fractions were concentrated to give 70 mg (66% yield) of the title compound as a yellow oil. MS: (ES, m/z): 274 [M+H]⁺.

Step-2: (S)-N-Hydroxy-1'-methyl-2'-oxo-3,4-dihydro-1H-spiro[naphthalene-2,3'-pyrrolidine]-6-carboxamide Into a 50-mL round-bottom flask, was placed a solution of methyl (S)-1'-methyl-2'-oxo-3,4-dihydro-1H-spiro[naphthalene-2,3'-pyrrolidine]-6-carboxylate (130 mg, 0.48 mmol, 1 equiv) in THF/MeOH (4:1, 2 mL), NH₂OH (50% in water, 0.1.87 mL, 28.8 mmol, 60 equiv), and 1N aq. NaOH (0.95 mL, 0.95 mmol, 2 equiv). The resulting solution was stirred for 4 h at room temperature. The crude product was purified by Prep-HPLC with the following conditions: Column: XBridge C18, 19×150 mm, 5 μm; Mobile Phase A: Water/0.05% TFA, Mobile Phase B: CH₃CN/0.05% TFA; Flow rate: 25 mL/min; Gradient: 20% B to 60% B in 7.0 min; Detector: UV 254 nm. The collected fractions were lyophilized to give 47.7 mg (26% yield) of the title compound as a light yellow solid. ¹H-NMR (400 MHz, DMSO-d6) δ (ppm): 11.09 (s, 1H), 8.95 (s, 1H), 7.45-7.51 (m, 2H), 7.11-7.13 (d, J=8 Hz, 1H), 3.28-3.32 (t, J=8 Hz, 2H), 2.76-2.89 (m, 6H), 2.50-2.56 (m, 1H), 1.81-1.91 (m, 2H), 1.65-1.80 (m, 2H). MS: (ES, m/z): 275 [M+H]⁺.

TABLE 11

The following compounds were prepared according to the method of Example 22, with the following modification: In Step 1, the halide can be an iodide, a chloride, or a bromide.

| Ex. | Structure | ¹H-NMR δ (ppm) | Found (ES, m/z) [M + H]⁺ |
| --- | --- | --- | --- |
| I-23 | 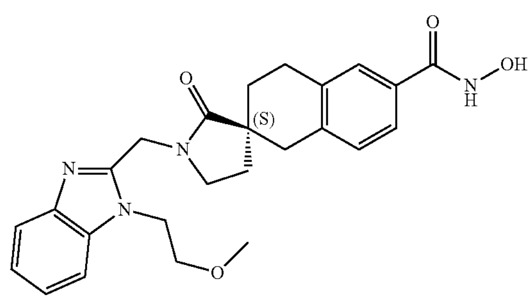 | (400 MHz, DMSO-d6): 11.12 (br s, 1H), 7.88-7.74 (m, 2H), 7.54-7.40 (m, 4H), 7.16-7.14 (d, J = 8 Hz, 1H), 4.94-4.89 (br, 2H), 4.64-4.56 (br, 2H), 3.70 (s, 2H), 3.45-3.43 (t, J = 4 Hz, 2H), 3.24 (s, 3H), 2.94-2.79 (m, 3H), 2.78-2.66 (m, 1H), 2.01-1.69 (m, 4H) | 449 |
| I-15 | 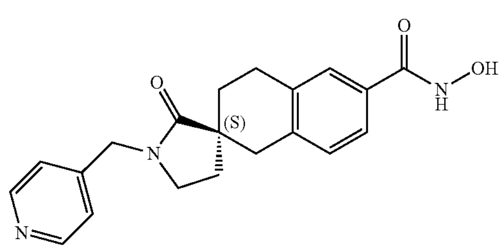 | (300 MHz, DMSO-d6): 11.14 (br s, 1H), 8.76-8.74 (d, J = 6 Hz, 2H), 7.62-7.60 (d, J = 6 Hz, 2H), 7.53-7.47 (m, 2H), 7.18-7.15 (d, J = 9 Hz 1H), 4.62 (s, 2H), 3.36-3.32 (t, J = 6 Hz, 2H), 2.96-2.67 (m, 4H), 2.07-1.72 (m, 4H) | 352 |
| I-19 | 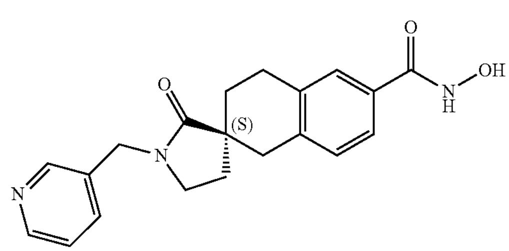 | (300 MHz, DMSO-d6): 11.11 (br s, 1H), 8.73-8.63 (m, 2H), 8.03-8.01 (d, J = 6 Hz, 1H), 7.75-7.71 (t, J = 6 Hz, 1H), 7.54-7.42 (m, 2H), 7.16-7.13 (d, J = 9 Hz, 1H), 4.56 (s, 2H), 3.32-3.28 (t, J = 6 Hz, 2H), 2.94-2.81 (m, 3H) 2.72-2.63 (m, 1H), 1.98-1.81 (m, 2H), 1.77-1.68 (m, 2H) | 352 |

TABLE 11-continued

The following compounds were prepared according to the method of Example 22,
with the following modification: In Step 1, the halide can be an iodide, a chloride, or a bromide.

| Ex. | Structure | $^1$H-NMR δ (ppm) | Found (ES, m/z) [M + H]$^+$ |
|---|---|---|---|
| I-25 | 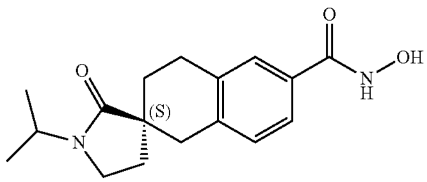 | (400 MHz, DMSO-d6): 11.09 (br s, 1H), 8.95 (br s, 1H), 7.53-7.45 (m, 2H), 7.14-7.12 (d, J = 8 Hz, 1H), 4.18-4.11 (m, 1H), 3.27-3.23 (t, J = 8 Hz, 2H), 2.92-2.76 (m, 3H), 2.62-2.54 (m, 1H), 1.88-1.68 (m, 2H), 1.66-1.57 (m, 2H), 1.11-1.08 (m, 6H) | 303 |
| I-164 | 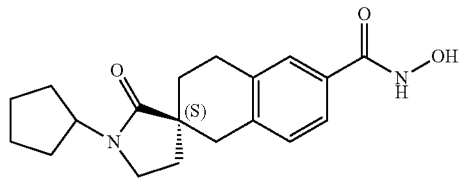 | (400 MHz, DMSO-d6): 11.09 (s, 1H), 8.96 (s, 1H), 7.47 (d, J = 27 Hz, 2H), 7.12 (d, J = 9 Hz, 1H), 4.29-4.36 (m, 1H), 329-3.34 (m, 2H), 3.27-3.33 (m, 3H), 2.53 (d, J = 18 Hz, 1H), 1.68-1.89 (m, 12H) | 329 |
| I-160 | 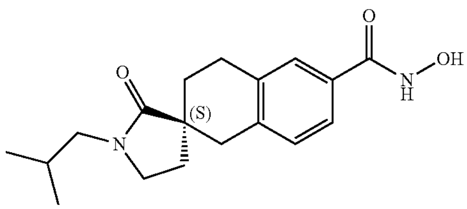 | (400 MHz, DMSO-d6): 11.08 (s, 1H), 8.96 (s, 1H), 7.43-7.50 (m, 2H), 7.15 (d, J = 9 Hz, 1H), 3.29-3.34 (m, 2H), 3.03 (d, J = 6 Hz, 2H), 2.80-2.89 (m, 3H), 2.51 (d, J = 3 Hz, 1H), 1.89-1.90 (m, 3H) 1.64-1.73 (m, 2H) 0.85 (d, J = 15 Hz, 6H) | 317 |
| I-162 | 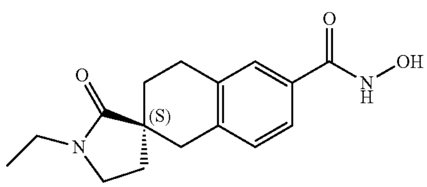 | (400 MHz, DMSO-d6): 11.05 (m, 1H), 9.03 (m, 1H), 7.46-7.44 (m, 2H), 7.12-7.10 (m, 1H), 3.31-3.30 (m, 2H), 3.28-3.20 (m, 2H), 2.88-2.78 (m, 3H), 2.59-2.49 (m, 1H), 1.89-1.76 (m, 2H), 1.74-1.56 (m, 2H), 1.04-1.01 (m, 3H) | 289 |
| I-166 | 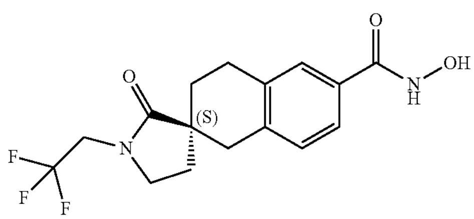 | (400 MHz, DMSO-d6): 11.03 (s, 1H), 7.50-7.44 (m, 2H), 7.14-7.11 (m, 1H), 4.11-4.02 (m, 2H), 3.46-3.43 (m, 2H), 2.90-2.75 (m, 3H), 2.65-2.61 (m, 1H), 1.97-1.91 (m, 1H), 1.85-1.70 (m, 2H), 1.66-1.63 (m, 1H) | 343 |

Example 23

Preparation of (S)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-13)

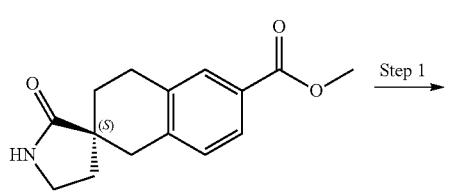

Step 1 →

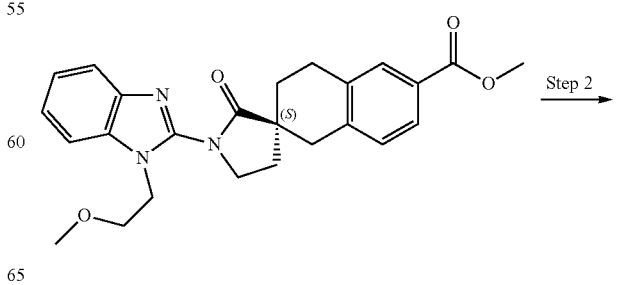

Step 2 →

93
-continued

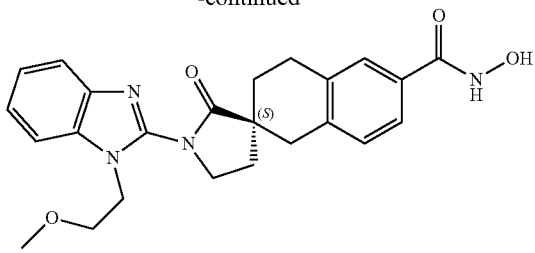

Step-1: Methyl (S)-1'-(1-(2-methoxyethyl)-1H-benzo[d]imidazol-2-yl)-2'-oxo-3,4-dihydro-1H-spiro[naphthalene-2,3'-pyrrolidine]-6-carboxylate Into a 10-mL sealed tube purged and maintained with an inert atmosphere of nitrogen, was placed methyl (S)-2'-oxo-3,4-dihydro-1H-spiro[naphthalene-2,3'-pyrrolidine]-6-carboxylate (60 mg, 0.23 mmol, 1 equiv), 2-bromo-1-(2-methoxyethyl)-1H-1,3-benzodiazole (103 mg, 0.40 mmol, 1.5 equiv), CuI (5.0 mg, 0.03 mmol, 0.1 equiv), $Cs_2CO_3$ (263 mg, 0.81 mmol, 3 equiv), toluene (2 mL), and (1R, 2R)-1-N, 2-N-dimethylcyclohexane-1,2-diamine (8 mg, 0.06 mmol, 0.2 equiv). The resulting solution was stirred for 10 h at 110° C. in an oil bath. The reaction mixture was cooled to 20° C. in a water bath. The solids were filtered out. The resulting mixture was concentrated under vacuum. The residue was purified by normal phase chromatography on silica gel with EtOAc/petroleum ether (1:1). The collected fractions were concentrated to give 30 mg (30% yield) of the title compound as a yellow oil. MS: (ES, m/z): 434 $[M+H]^+$.

Step-2: (S)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide Into a 10-mL round-bottom flask was placed methyl (S)-1'-(1-(2-methoxyethyl)-1H-benzo[d]imidazol-2-yl)-2'-oxo-3,4-dihydro-1H-spiro[naphthalene-2,3'-pyrrolidine]-6-carboxylate (30 mg, 0.07 mmol, 1 equiv), THF/MeOH (4:1, 2.5 mL), $NH_2OH$ (50% in water, 0.5 mL, 108 equiv), and 1N aq. NaOH (0.3 mL, 4.29 equiv). The resulting solution was stirred for 3 h at room temperature. The reaction mixture was cooled to 0° C. in an ice-water bath. The pH of the solution was adjusted to 7 with 1N aq. HCl. The crude product was purified by Prep-HPLC with the following conditions: Column: X Bridge C18, 19×150 mm, 5 μm; Mobile Phase A: Water/10% $NH_4HCO_3$, Mobile Phase B: $CH_3CN$/10% $NH_4HCO_3$; Flow rate: 25 mL/min; Gradient: 5% B to 47% B in 7.0 min; Detector: UV 254 nm. The collected fractions were lyophilized to give 29.6 mg (98% yield) of the title compound as an off-white solid. $^1$H-NMR (400 MHz, DMSO-d6) δ (ppm): 11.14 (br s, 1H), 7.65-7.48 (m, 4H), 7.28-7.17 (m, 3H), 4.35-4.33 (t, J=4 Hz, 2H), 3.99-3.89 (m, 2H), 3.62-3.60 (t, J=4 Hz, 2H), 3.20 (s, 3H), 3.02-2.86 (m, 4H), 2.22-2.15 (m, 1H), 2.02-1.97 (m, 3H). MS: (ES, m/z): 435 $[M+H]^+$.

94

Example 24

Preparation of (S)-N-hydroxy-2'-oxo-3,4-dihydro-1H-spiro[naphthalene-2,3'-pyrrolidine]-6-carboxamide (I-28)

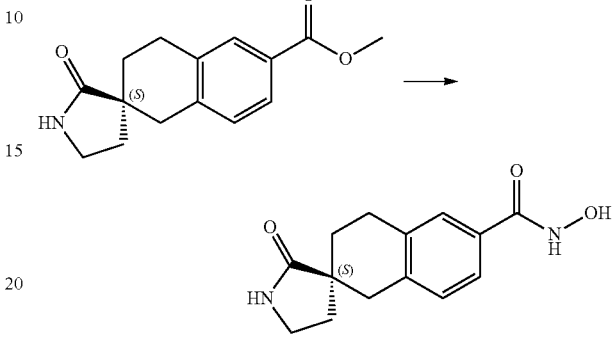

Into a 50-mL round-bottom flask was placed a solution of methyl (S)-2'-oxo-3,4-dihydro-1H-spiro[naphthalene-2,3'-pyrrolidine]-6-carboxylate (100 mg, 0.39 mmol, 1 equiv) in THF/MeOH (4:1, 1.25 mL), $NH_2OH$ (50% in water, 1.52 mL, 60 equiv), and 1N aq. NaOH (0.77 mL, 2 equiv). The resulting solution was stirred for 1.5 h at room temperature. The crude product was purified by Prep-HPLC with the following conditions: Column: Waters HSS C18, 2.1×50 mm, 1.8 m; Mobile Phase A: Water/0.05% TFA, Mobile Phase B: $CH_3CN$/0.05% TFA; Flow rate: 0.7 mL/min; Gradient: 5% B to 95% B in 2.0 min hold 0.6 min; Detector: UV 254 nm. The collected fractions were lyophilized to give 37.5 mg (38% yield) of the title compound as a pink solid. $^1$H-NMR (400 MHz, DMSO-d6) δ (ppm): 1.74-1.80 (m, 1H), 1.81-1.90 (m, 2H), 1.92-1.95 (m, 1H), 2.63-2.67 (m, 1H), 2.74-2.90 (m, 3H), 3.18-3.22 (t, J=7 Hz, 2H), 7.13-7.15 (d, J=8 Hz, 1H), 7.43-7.50 (m, 2H), 7.66 (s, 1H), 8.94 (s, 1H), 11.09 (s, 1H). MS: (ES, m/z): 261 $[M+H]^+$.

Example 25

Preparation of (S)-N-hydroxy-1'-(oxetan-3-ylmethyl)-2'-oxo-3,4-dihydro-1H-spiro[naphthalene-2,3'-pyrrolidine]-6-carboxamide (I-122)

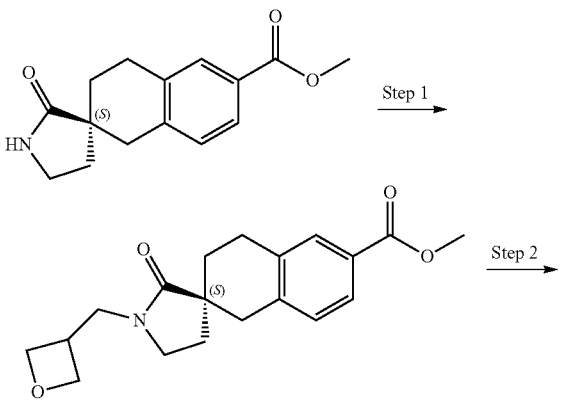

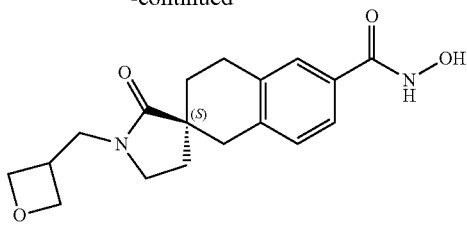

Step-1: Methyl (S)-1'-(oxetan-3-ylmethyl)-2'-oxo-3,4-dihydro-1H-spiro[naphthalene-2,3'-pyrrolidine]-6-carboxylate A 4-mL vial charged with methyl-(S)-2'-oxo-3,4-dihydro-1H-spiro[naphthalene-2,3'-pyrrolidine]-6-carboxylate (10 mg, 0.040 mmol) was dissolved in 0.20 mL of anhydrous DMA. Then NaH (60% dispersion in oil, 1 mg, 0.043 mmol, 1.1 equiv) was added. The reaction mixture was stirred for 5 min at room temperature. Next, a solution of 3-(bromomethyl)oxetane (0.20 mL, 0.040 mmol, 1 equiv) in CH$_3$CN was added. The reaction mixture was stirred at room temperature overnight. The solvent was removed under a stream of N$_2$. The residue was diluted with brine (0.50 mL) and extracted with EtOAc (2×0.50 mL). The combined organic layers were dried under a stream of N$_2$ and carried forward without further purification

Step-2: (S)-N-Hydroxy-1'-(oxetan-3-ylmethyl)-2'-oxo-3,4-dihydro-1H-spiro[naphthalene-2,3'-pyrrolidine]-6-carboxamide Methyl (S)-1'-(oxetan-3-ylmethyl)-2'-oxo-3,4-dihydro-1H-spiro[naphthalene-2,3'-pyrrolidine]-6-carboxylate was dissolved in THF/MeOH (3:1, 200 µL). The vial was sealed and shaken at 50° C. for 15 min to dissolve the residue, then cooled to room temperature. NH$_2$OH (50% v/v in water, 0.150 mL) was added, followed by 1N aq NaOH (0.10 mL, 0.10 mmol, 2.5 equiv). The mixture was sealed and then shaken at room temperature for 18 h. The reaction mixture was concentrated under a stream of N$_2$ at room temperature, then dissolved in 0.50 mL of DMSO and purified by reverse-phase chromatography Prep-HPLC Column: Waters Sunfire C18, 5 µm, 19×50 mm; Mobile Phase A: Water/0.1% Formic acid, Mobile Phase B: CH$_3$CN/0.1% Formic acid; gradient: 15% B to 100% B in 6 min; Flow rate: 23 mL/min; Detector: UV 254 nm, 220 nm. The product-containing fractions were combined and concentrated in to afford 0.6 mg (5% yield) of the title compound. $^1$H NMR (400 MHz, DMSO-d$_6$) δ (ppm): 11.10 (s, 1H), 9.00 (s, 1H), 7.67 (d, J=8.3 Hz, 1H), 7.46 (d, J=7.7 Hz, 1H), 7.13 (d, J=7.8 Hz, 1H), 4.80 (dd, J=7.4, 6.3 Hz, 2H), 4.41 (t, J=6.2 Hz, 2H), 3.64 (d, J=7.8 Hz, 2H), 3.37-3.25 (m, 1H), 3.23 (d, J=17 Hz, 1H), 3.11-3.03 (m, 1H), 2.98-2.89 (m, 1H), 2.79 (d, J=17 Hz, 1H), 2.22-1.99 (m, 3H), 1.91-1.85 (m, 1H). MS: (ES, m/z) 331 [M+H]$^+$.

Example 26

Preparation of (R)-N-hydroxy-2'-oxo-1'-propyl-3,4-dihydro-1H-spiro[naphthalene-2,3'-pyrrolidine]-6-carboxamide (I-32)

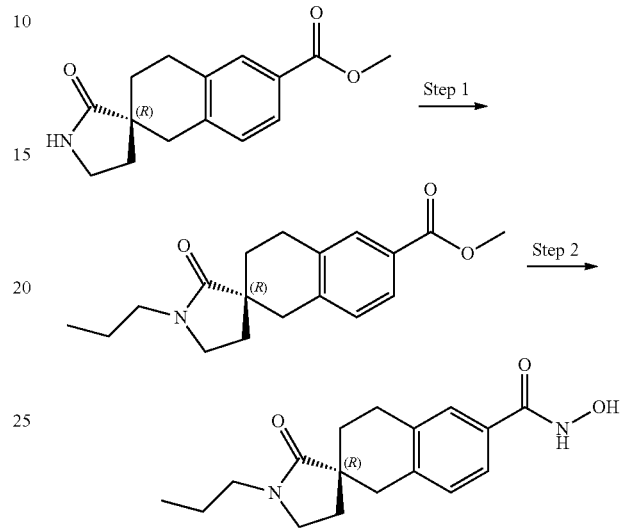

Step-1: Methyl (R)-2'-oxo-1'-propyl-3,4-dihydro-1H-spiro[naphthalene-2,3'-pyrrolidine]-6-carboxylate A solution of methyl (R)-2'-oxo-3,4-dihydro-1H-spiro[naphthalene-2,3'-pyrrolidine]-6-carboxylate (350 mg, 1.35 mmol, 1 equiv) in anhydrous DMF (6.75 mL) was deprotonated with NaH (60% dispersion in oil, 54 mg, 1.35 mmol, 1 equiv). This solution (0.15 mL, 0.30 mmol) was added to a solution of 1-iodopropane (0.2 M in acetonitrile, 0.30 mL, 0.06 mmol, 2 equiv) in a 2 dram vial. NaI (18 mg, 0.12 mmol, 4 equiv) was added and the vial was sealed and shaken at 80° C. for 48 h. The solvent was removed and the residue was diluted with brine (0.5 mL) and extracted with EtOAc (2×0.5 mL). The combined organic layers were concentrated under vacuum.

Step-2: (R)-N-Hydroxy-2'-oxo-1'-propyl-3,4-dihydro-1H-spiro[naphthalene-2,3'-pyrrolidine]-6-carboxamide The residue was dissolved in a solution of THF/MeOH (3:1, 0.2 mL). NH$_2$OH (50% in water, 0.15 mL, 76 equiv) was added, followed by addition of 1N aq NaOH (0.10 mL, 3.3 equiv). The mixture was sealed and shaken at room temperature for 18 h. The reaction mixture was concentrated and purified by reversed-phase chromatography Prep-HPLC Column: Waters Sunfire C18, 5 µm, 19×50 mm; Mobile Phase A: Water/0.1% Formic acid, Mobile Phase B: CH$_3$CN/0.1% Formic acid; Gradient: 15% B to 100% B in 6 min; Flow rate: 23 mL/min; Detector: UV 254 nm, 220 nm. The product-containing fractions were combined and concentrated to afford 3 mg (33% yield) of the title compound. MS: (ES, m/z) 303 [M+H]$^+$.

TABLE 12

The following compounds were prepared according to the parallel synthesis method of Example 26.

| Ex. | Name | Structure | Found (ES, m/z) [M + H]+ |
|---|---|---|---|
| I-33 | (R)-1'-(cyclobutylmethyl)-N-hydroxy-2'-oxo-3,4-dihydro-1H-spiro[naphthalene-2,3'-pyrrolidine]-6-carboxamide | 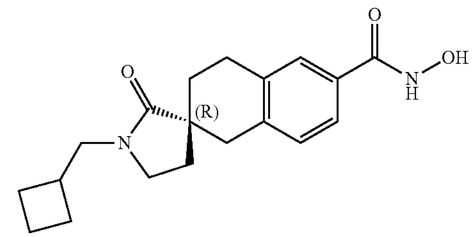 | 329 |
| I-34 | (R)-N-hydroxy-1'-isopentyl-2'-oxo-3,4-dihydro-1H-spirolnaphthalene-2,3'-pyrrolidine]-6-carboxamide | 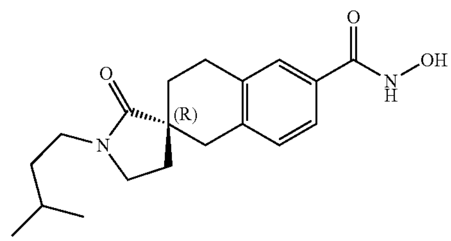 | 331 |
| I-35 | (R)-1'-(but-2-yn-1-yl)-N-hydroxy-2'-oxo-3,4-dihydro-1H-spiro[naphthalene-2,3'-pyrrolidine]-6-carboxamide | 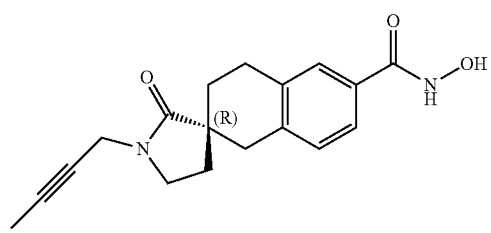 | 313 |
| I-36 | (R )-N-hydroxy-1'-(2-methoxyethyl)-2'-oxo-3,4-dihydro-1H-spiro[naphthalene-2,3'-pyrrolidine]-6-carboxamide | 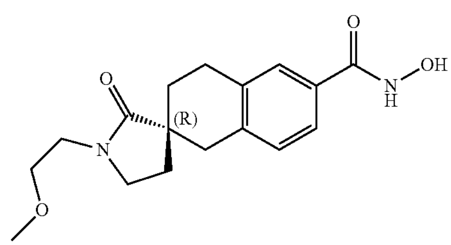 | 319 |
| I-37 | (R)-1'-cinnamyl-N-hydroxy-2'-oxo-3,4-dihydro-1H-spiro[naphthalene-2,3'-pyrrolidine]-6-carboxamide | 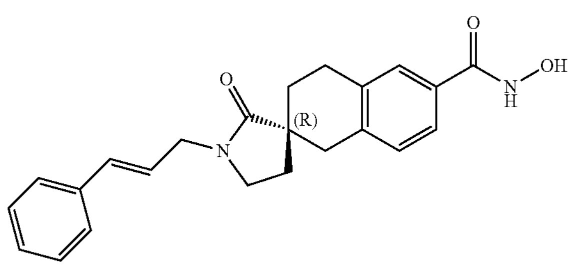 | 377 |
| I-38 | (R)-N-hydroxy-1'-(2-methylbenzyl)-2'-oxo-3,4-dihydro-1H-spiro[naphthalene-2,3'-pyrrolidine]-6-carboxamide | 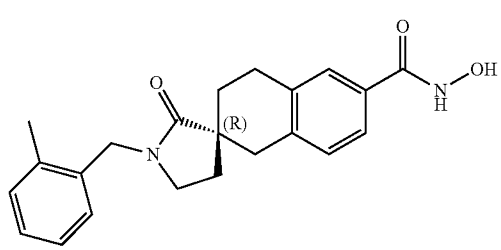 | 365 |

TABLE 12-continued

The following compounds were prepared according to the parallel synthesis method of Example 26.

| Ex. | Name | Structure | Found (ES, m/z) [M + H]+ |
|---|---|---|---|
| I-39 | (R)-N-hydroxy-2'-oxo-1'-(2-(trifluoromethyl)benzyl)-3,4-dihydro-1H-spiro[naphthalene-2,3'-pyrrolidine]-6-carboxamide | 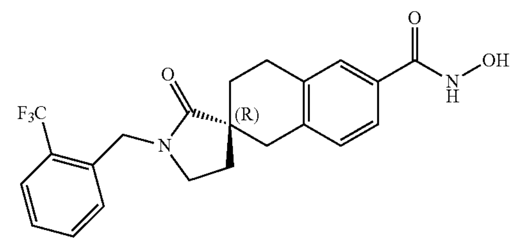 | 419 |
| I-40 | (R)-1'-(2-chlorobenzyl)-N-hydroxy-2'-oxo-3,4-dihydro-1H-spiro[naphthalene-2,3'-pyrrolidine]-6-carboxamide | 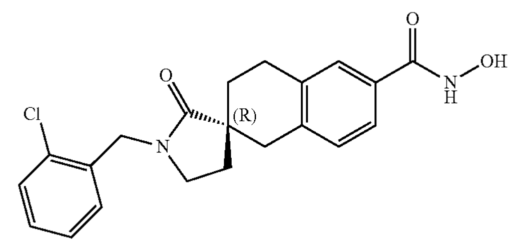 | 385 |
| I-41 | (R)-N-hydroxy-2'-oxo-1'-(2-(trifluoromethoxy)benzyl)-3,4-dihydro-1H-spiro[naphthalene-2,3'-pyrrolidine]-6-carboxamide | 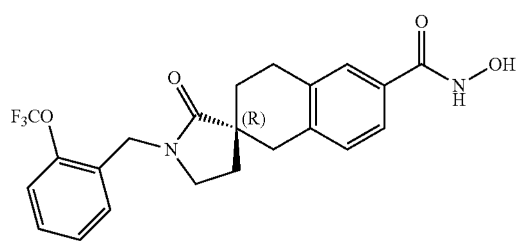 | 435 |
| I-42 | (R)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide | 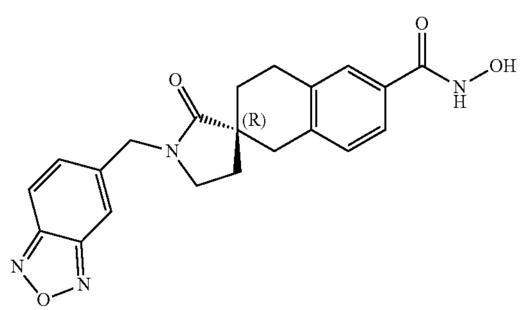 | 393 |
| I-43 | (R)-N-hydroxy-1'-(2-morpholino-2-oxoethyl)-2'-oxo-3,4-dihydro-1H-spiro[naphthalene-2,3'-pyrrolidine]-6-carboxamide | 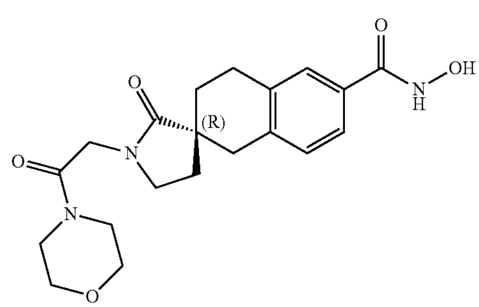 | 388 |

TABLE 12-continued

The following compounds were prepared according to the parallel synthesis method of Example 26.

| Ex. | Name | Structure | Found (ES, m/z) [M + H]+ |
|---|---|---|---|
| I-44 | (R)-N-hydroxy-1'-(2-methoxybenzyl)-2'-oxo-3,4-dihydro-1H-spiro[naphthalene-2,3'-pyrrolidine]-6-carboxamide | 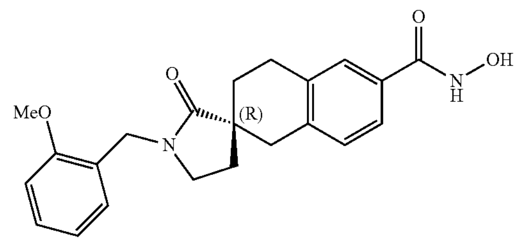 | 381 |
| I-45 | (R)-N-hydroxy-1'-((1-isopropyl-1H-benzo[d]imidazol-2-yl)methyl)-2'-oxo-3,4-dihydro-1H-spirofnaphthalene-2,3'-pyrrolidine]-6-carboxamide | 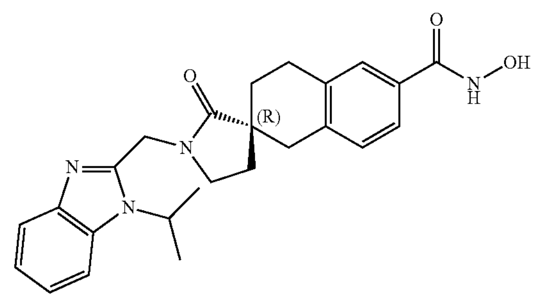 | 433 |
| I-46 | (R)-N-hydroxy-1'-((1-methyl-1H-benzo[d]imidazol-2-yl)methyl)-2'-oxo-3,4-dihydro-1H-spiro[naphthalene-2,3'-pyrrolidine]-6-carboxamide | 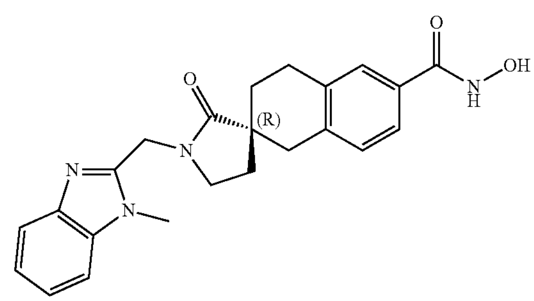 | 405 |
| I-47 | (R)-N-hydroxy-1'-(2-methylallyl)-2'-oxo-3,4-dihydro-1H-spiro[naphthalene-2,3'-pyrrolidine]-6-carboxamide | 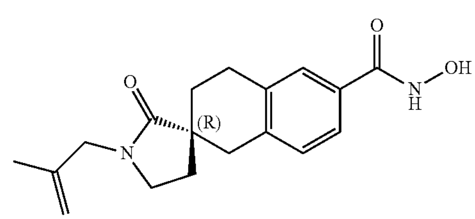 | 315 |
| I-48 | (R)-1'-(2,5-dichlorobenzyl)-N-hydroxy-2'-oxo-3,4-dihydro-1H-spiro[naphthalene-2,3'-pyrrolidine]-6-carboxamide | 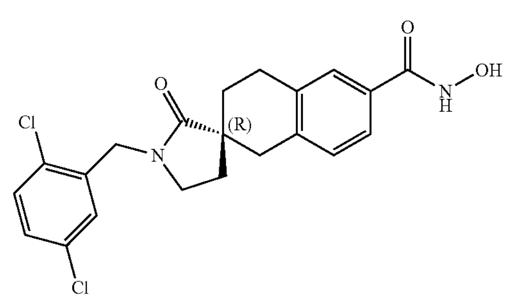 | 419 |

TABLE 12-continued

The following compounds were prepared according to the parallel synthesis method of Example 26.

| Ex. | Name | Structure | Found (ES, m/z) [M + H]+ |
|---|---|---|---|
| I-49 | (R)-1'-(2,6-dichlorobenzyl)-N-hydroxy-2'-oxo-3,4-dihydro-1H-spiro[naphthalene-2,3'-pyrrolidine]-6-carboxamide | 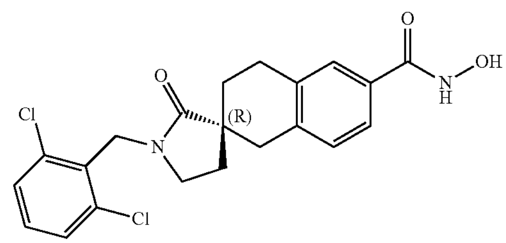 | 419 |
| I-50 | (R)-1'-benzyl-N-hydroxy-2'-oxo-3,4-dihydro-1H-spiro[naphthalene-2,3'-pyrrolidine]-6-carboxamide | 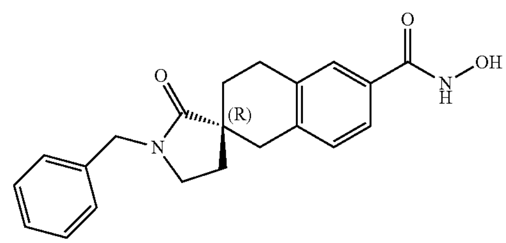 | 351 |
| I-51 | (R)-N-hydroxy-1'-(3-methoxybenzyl)-2'-oxo-3,4-dihydro-1H-spiro[naphthalene-2,3'-pyrrolidine]-6-carboxamide | 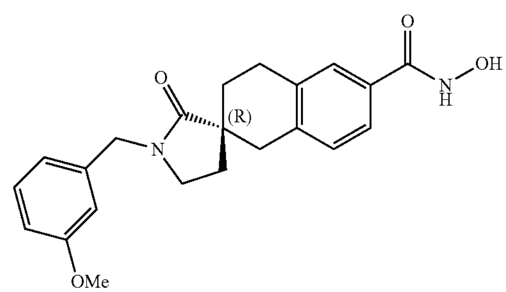 | 381 |
| I-52 | (R)-N-hydroxy-2'-oxo-1'-(pyridin-2-ylmethyl)-3,4-dihydro-1H-spiro[naphthalene-2,3'-pyrrolidine]-6-carboxamide | 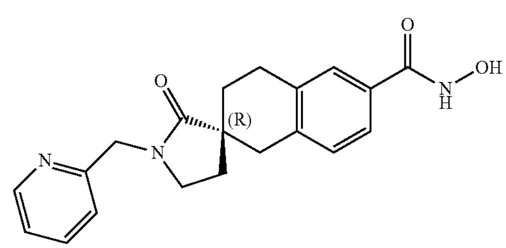 | 352 |
| I-53 | (R)-1'-(3-fluorobenzyl)-N-hydroxy-2'-oxo-3,4-dihydro-1H-spiro[naphthalene-2,3'-pyrrolidine]-6-carboxamide | 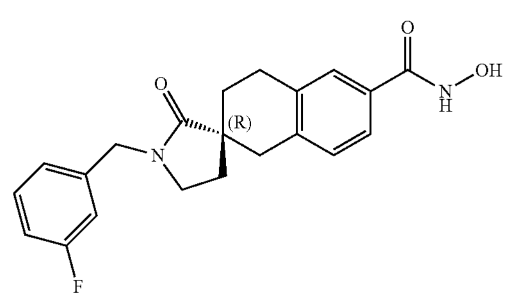 | 369 |

TABLE 12-continued

The following compounds were prepared according to the parallel synthesis method of Example 26.

| Ex. | Name | Structure | Found (ES, m/z) [M + H]+ |
|---|---|---|---|
| I-54 | (R)-1'-(3-chlorobenzyl)-N-hydroxy-2'-oxo-3,4-dihydro-1H-spiro[napthalene-2,3'-pyrrolidine]-6-carboxamide | 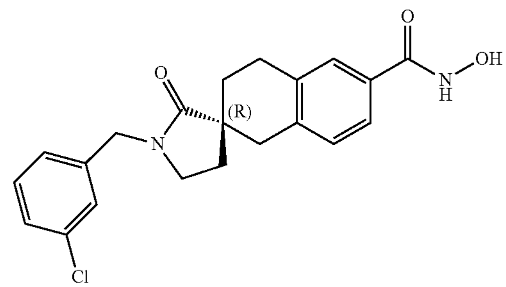 | 385 |
| I-55 | (R)-1'-(4-chlorobenzyl)-N-hydroxy-2'-oxo-3,4-dihydro-1H-spiro[naphthalene-2,3'-pyrrolidine]-6-carboxamide | 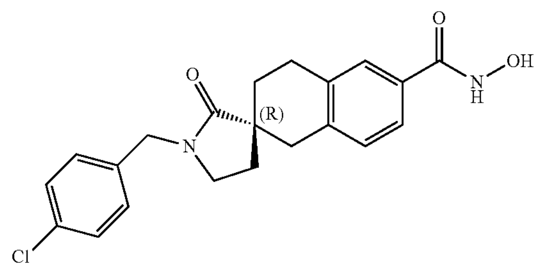 | 385 |
| I-56 | (R)-N-hydroxy-1'-(4-methoxybenzyl)-2'-oxo-3,4-dihydro-1H-spiro[naphthalene-2,3'-pyrrolidine]-6-carboxamide | 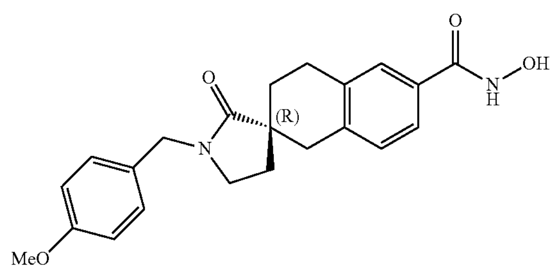 | 381 |
| I-57 | (R)-1'-(2-fluorobenzyl)-N-hydroxy-2'-oxo-3,4-dihydro-1H-spiro[naphthalene-2,3'-pyrrolidine]-6-carboxamide | 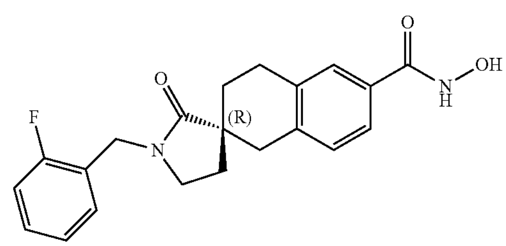 | 369 |
| I-58 | (R)-N-hydroxy-1'-(naphthalen-2-ylmethyl)-2'-oxo-3,4-dihydro-1H-spiro[naphthalene-2,3'-pyrrolidine]-6-carboxamide | 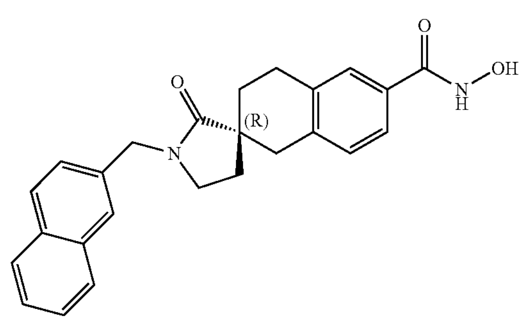 | 401 |

TABLE 12-continued

The following compounds were prepared according to the parallel synthesis method of Example 26.

| Ex. | Name | Structure | Found (ES, m/z) [M + H]+ |
|---|---|---|---|
| I-59 | (R)-1'-(2-(difluoromethoxy)benzyl)-N-hydroxy-2'-oxo-3,4-dihydro-1H-spiro[naphthalene-2,3'-pyrrolidine]-6-carboxamide | 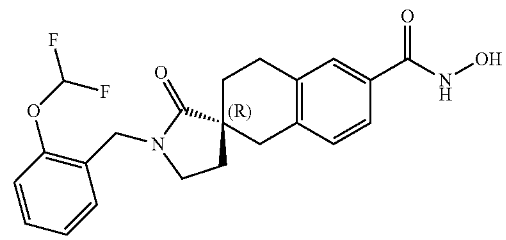 | 417 |
| I-106 | (R)-N-hydroxy-2'-oxo-1'-(4-((trifluoromethyl)sulfonyl)benzyl)-3,4-dihydro-1H-spiro[naphthalene-2,3'-pyrrolidine]-6-carboxamide | 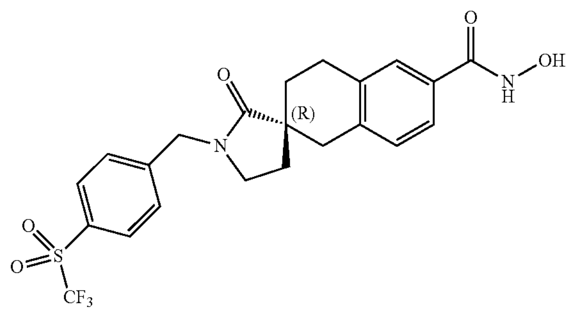 | 483 |

TABLE 13

The following compounds were prepared according to the synthesis method of Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-60 | (S)-N-hydroxy-2'-oxo-1'-propyl-3,4-dihydro-1H-spiro[naphthalene-2,3'-pyrrolidine]-6-carboxamide | 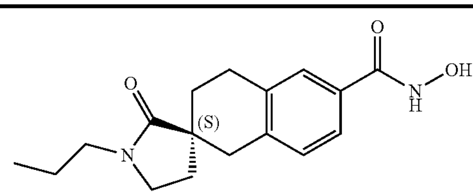 | 303 |
| I-61 | (S)-1'-(cyclobutylmethyl)-N-hydroxy-2'-oxo-3,4-dihydro-1H-spiro[naphthalene-2,3'-pyrrolidine]-6-carboxamide | 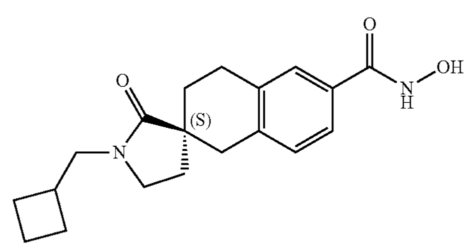 | 329 |
| I-62 | (S)-N-hydroxy-1'-isopentyl-2'-oxo-3,4-dihydro-1H-spiro[naphthalene-2,3'-pyrrolidine]-6-carboxamide | 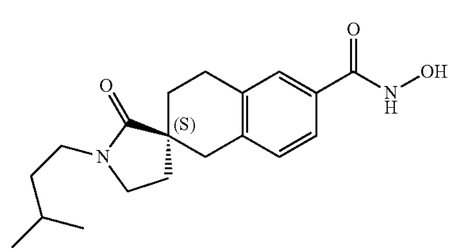 | 331 |

TABLE 13-continued

The following compounds were prepared according to the synthesis method of
Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-63 | (S)-1'-(but-2-yn-1-yl)-N-hydroxy-2'-oxo-3,4-dihydro-1H-spiro[naphthalene-2,3'-pyrrolidine]-6-carboxamide | 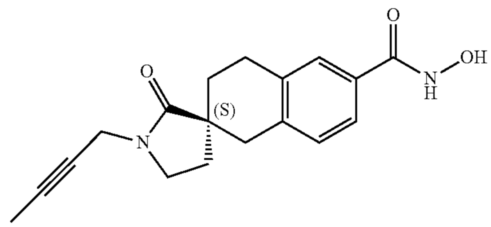 | 313 |
| I-64 | (S)-N-hydroxy-1'-(2-methoxyethyl)-2'-oxo-3,4-dihydro-1H-spiro[naphthalene-2,3'-pyrrolidine]-6-carboxamide | 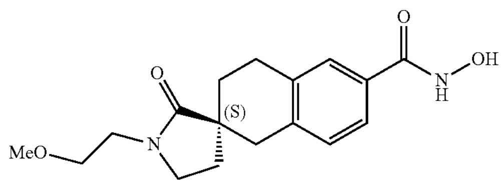 | 319 |
| I-65 | (S)-1'-cinnamyl-N-hydroxy-2'-oxo-3,4-dihydro-1H-spiro[naphthalene-2,3'-pyrrolidine]-6-carboxamide | 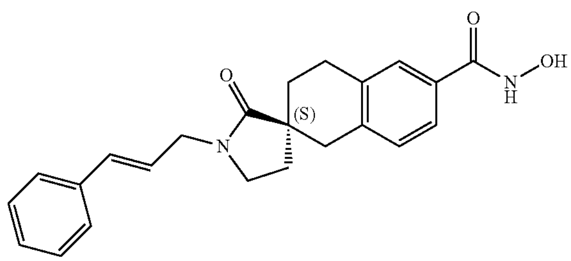 | 377 |
| I-66 | (S)-N-hydroxy-1'-(2-methylbenzyl)-2'-oxo-3,4-dihydro-1H-spiro[naphthalene-2,3'-pyrrolidine]-6-carboxamide | 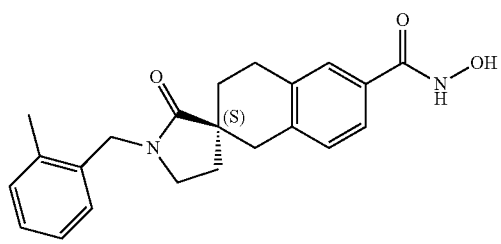 | 365 |
| I-67 | (S)-N-hydroxy-2'-oxo-1'-(2-(trifluoromethyl)benzyl)-3,4-dihydro-1H-spiro[naphthalene-2,3'-pyrrolidine]-6-carboxamide | 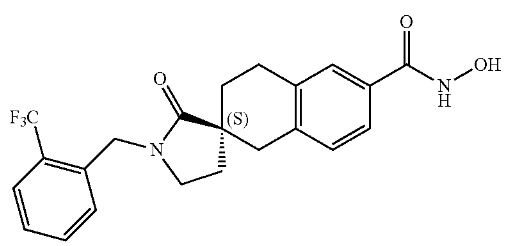 | 419 |
| I-68 | (S)-1'-(2-chlorobenzyl)-N-hydroxy-2'-oxo-3,4-dihydro-1H-spiro[naphthalene-2,3'-pyrrolidine]-6-carboxamide | 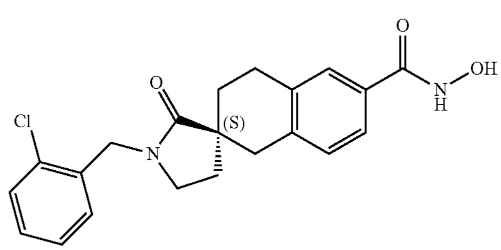 | 385 |

TABLE 13-continued

The following compounds were prepared according to the synthesis method of
Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-69 | (S)-N-hydroxy-2'-oxo-1'-(2-(trifluoromethoxy)benzyl)-3,4-dihydro-1H-spiro[naphthalene-2,3'-pyrrolidine]-6-carboxamide | 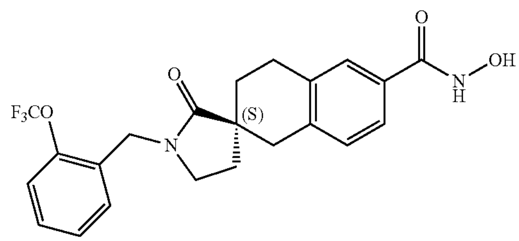 | 435 |
| I-70 | (S)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide | 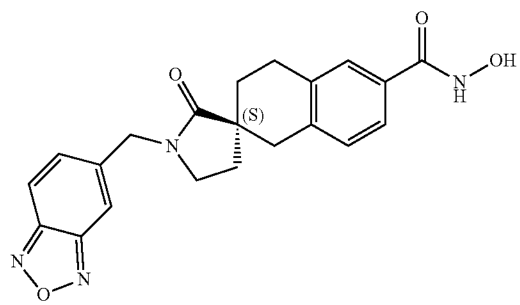 | 393 |
| I-71 | (S)-N-hydroxy-1'-(2-morpholino-2-oxoethyl)-2'-oxo-3,4-dihydro-1H-spiro[naphthalene-2,3'-pyrrolidine]-6-carboxamide | 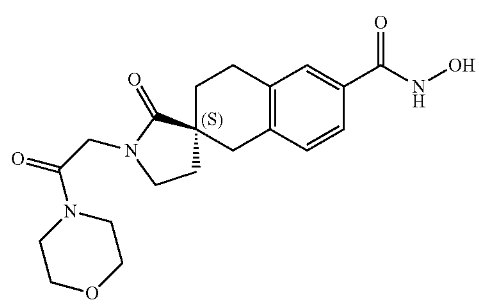 | 388 |
| I-72 | (S)-N-hydroxy-1'-(2-methoxybenzyl)-2'-oxo-3,4-dihydro-1H-spiro[naphthalene-2,3'-pyrrolidine]-6-carboxamide | 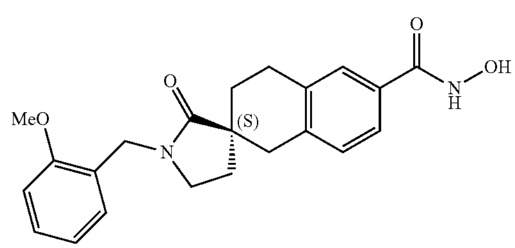 | 381 |
| I-73 | (S)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide | 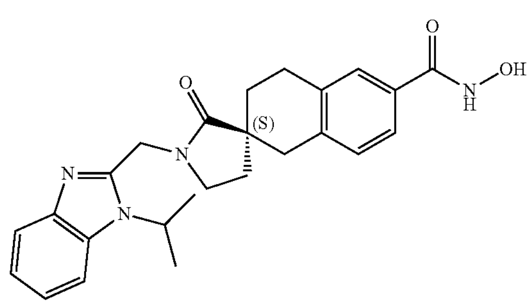 | 433 |

TABLE 13-continued

The following compounds were prepared according to the synthesis method of Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]$^+$ |
|---|---|---|---|
| I-74 | (S)-1'-(2,5-dichlorobenzyl)-N-hydroxy-2'-oxo-3,4-dihydro-1H-spiro[naphthalene-2,3'-pyrrolidine]-6-carboxamide | 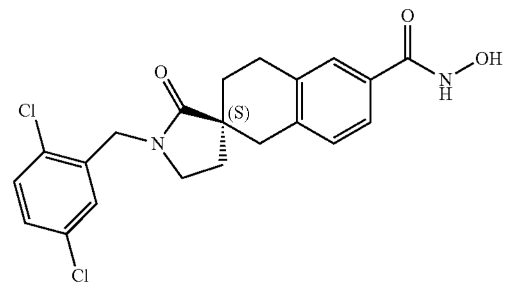 | 419 |
| I-75 | (S)-1'-(2,6-dichlorobenzyl)-N-hydroxy-2'-oxo-3,4-dihydro-1H-spiro[naphthalene-2,3'-pyrrolidine]-6-carboxamide | 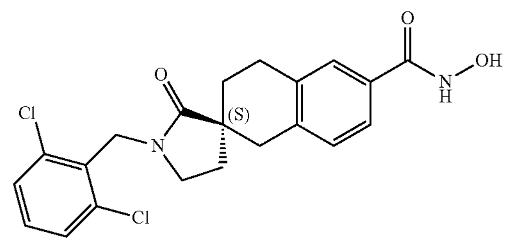 | 419 |
| I-76 | (S)-1'-benzyl-N-hydroxy-2'-oxo-3,4-dihydro-1H-spiro[naphthalene-2,3'-pyrrolidine]-6-carboxamide | 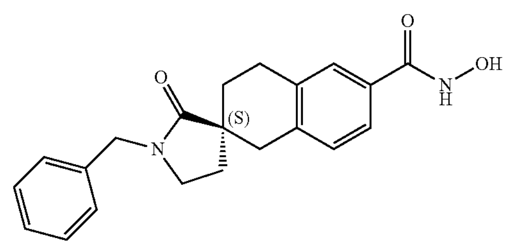 | 351 |
| I-77 | (S)-N-hydroxy-1'-(3-methoxybenzyl)-2'-oxo-3,4-dihydro-1H-spiro[naphthalene-2,3'-pyrrolidine]-6-carboxamide | 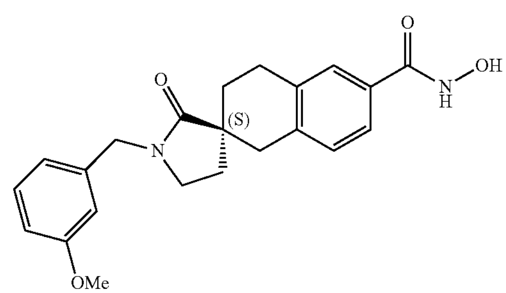 | 381 |
| I-78 | (S)-N-hydroxy-2'-oxo-1'-(pyridin-2-ylmethyl)-3,4-dihydro-1H-spiro[naphthalene-2,3'-pyrrolidine]-6-carboxamide | 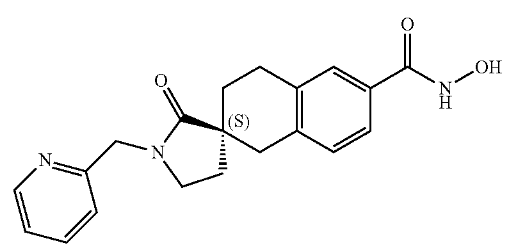 | 352 |

TABLE 13-continued

The following compounds were prepared according to the synthesis method of
Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-79 | (S)-1'-(3-fluorobenzyl)-N-hydroxy-2'-oxo-3,4-dihydro-1H-spiro[naphthalene-2,3'-pyrrolidine]-6-carboxamide | 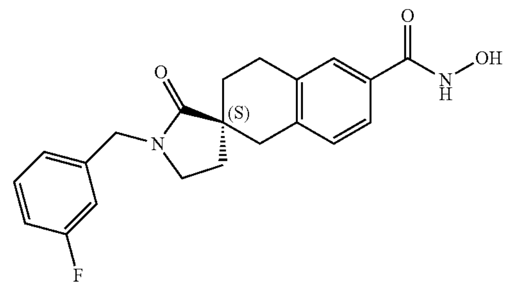 | 369 |
| I-80 | (S)-N-hydroxy-2'-oxo-1'-(4-(trifluoromethoxy)benzyl)-3,4-dihydro-1H-spiro[naphthalene-2,3'-pyrrolidine]-6-carboxamide | 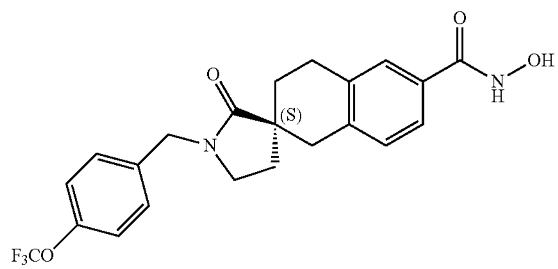 | 435 |
| I-81 | (S)-1'-[(3-chlorophenyl)methyl]-N-hydroxy-2'-oxo-3,4-dihydro-1H-spiro[naphthalene-2,3'-pyrrolidine]-6-carboxamide | 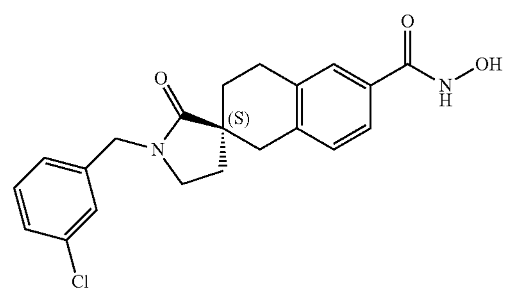 | 385 |
| I-82 | (S)-1'-(4-chlorobenzyl)-N-hydroxy-2'-oxo-3,4-dihydro-1H-spiro[naphthalene-2,3'-pyrrolidine]-6-carboxamide | 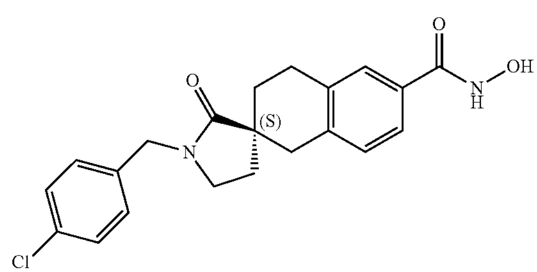 | 385 |
| I-83 | (S)-N-hydroxy-1'-(4-methoxybenzyl)-2'-oxo-3,4-dihydro-1H-spiro[naphthalene-2,3'-pyrrolidine]-6-carboxamide | 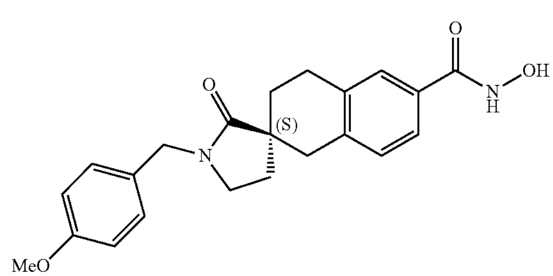 | 381 |

TABLE 13-continued

The following compounds were prepared according to the synthesis method of
Example 26, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-84 | (S)-1'-(2-fluorobenzyl)-N-hydroxy-2'-oxo-3,4-dihydro-1H-spiro[naphthalene-2,3'-pyrrolidine]-6-carboxamide | 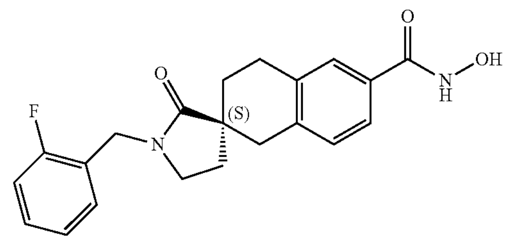 | 369 |
| I-85 | (S)-1'-(4-(tert-butyl)benzyl)-N-hydroxy-2'-oxo-3,4-dihydro-1H-spiro[naphthalene-2,3'-pyrrolidine]-6-carboxamide | 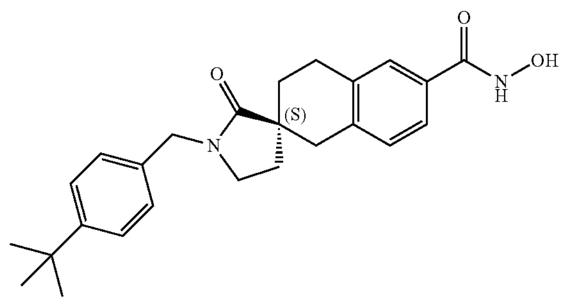 | 407 |
| I-86 | (S)-N-hydroxy-1'-(naphthalen-2-ylmethyl)-2'-oxo-3,4-dihydro-1H-spiro[naphthalene-2,3'-pyrrolidine]-6-carboxamide | 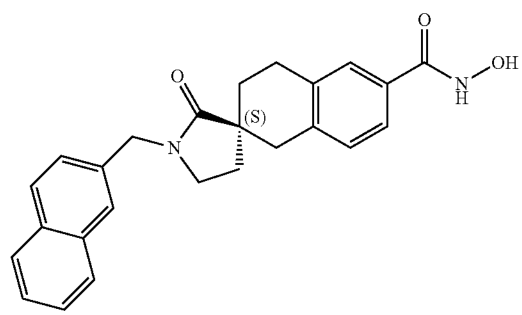 | 401 |
| I-87 | (S)-1'-(2-(difluoromethoxy)benzyl)-N-hydroxy-2'-oxo-3,4-dihydro-1H-spiro[naphthalene-2,3'-pyrrolidine]-6-carboxamide | 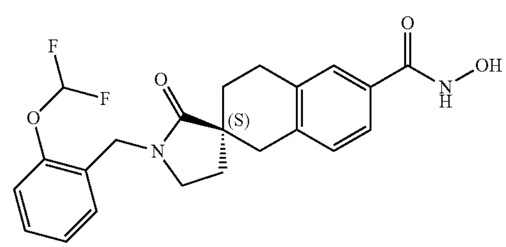 | 417 |
| I-107 | (S)-N-hydroxy-2'-oxo-1'-(4-((trifluoromethyl)sulfonyl)benzyl)-3,4-dihydro-1H-spiro[naphthalene-2,3'-pyrrolidine]-6-carboxamide | 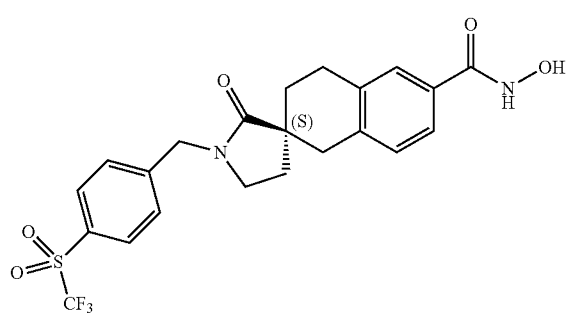 | 483 |

Example 27

Preparation of (R)-N-hydroxy-1'-(naphthalen-1-yl)-2'-oxo-3,4-dihydro-1H-spiro[naphthalene-2,3'-pyrrolidine]-6-carboxamide (I-89)

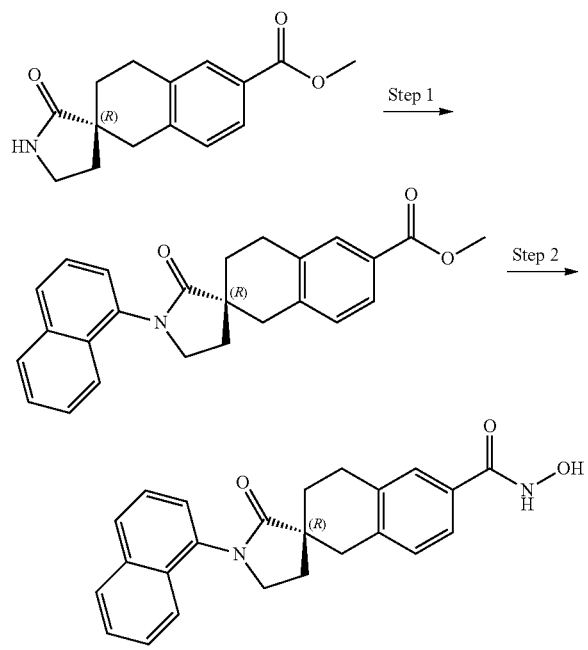

Step-1: Methyl (R)-1'-(naphthalen-1-yl)-2'-oxo-3,4-dihydro-1H-spiro[naphthalene-2,3'-pyrrolidine]-6-carboxylate A 2-mL vial was charged with methyl (R)-2'-oxo-3,4-dihydro-1H-spiro[naphthalene-2,3'-pyrrolidine]-6-carboxylate (0.2 M in 1,4-dioxane, 0.15 mL, 0.03 mmol, 1 equiv) and $Cs_2CO_3$ (39 mg, 0.12 mmol, 4 equiv). Then a solution of 1-bromonaphthalene (0.2 M in 1,4-dioxane, 0.30 mL, 0.06 mmol, 2 equiv) was added. The vial was sealed and brought into a glovebox. A degassed solution of CuBr (10 mol %) and N,N-dimethylethane-1,2-diamine (0.02 M in DMA, 0.15 mL, 0.003 mmol, 20 mol %) was added. The vial was sealed and heated at 110° C. for 18 h. The solvent was removed and the residue was diluted with brine (0.5 mL) and extracted with EtOAc (2×0.5 mL). The combined organic layers were concentrated under vacuum.

Step-2: (R)-N-Hydroxy-1'-(naphthalen-1-yl)-2'-oxo-3,4-dihydro-1H-spiro[naphthalene-2,3'-pyrrolidine]-6-carboxamide The residue was dissolved in THF/MeOH (3:1, 0.2 mL) and $NH_2OH$ (50% in water, 0.15 mL, 76 equiv) was added, followed by addition of 1N aq NaOH (0.1 mL, 3.3 equiv). The mixture was sealed and then shaken at room temperature for 18 h. The reaction mixture was concentrated and purified by reverse-phase Prep-HPLC Column: Waters Sunfire C18, 5 μm, 19×50 mm; Mobile Phase A: Water/0.1% Formic acid, Mobile Phase B: $CH_3CN$/0.1% Formic acid; Gradient: 15% B to 100% B in 6 min; Flow rate: 23 mL/min; Detector: UV 254 nm/220 nm. The product-containing fractions were combined and concentrated to afford 1 mg (8.6% yield) of the title compound. MS: (ES, m/z) 387 [M+H]⁺.

TABLE 14

The following compounds were prepared according to the parallel synthesis method of Example 27.

| Ex. | Name | Structure | Found (ES, m/z) [M + H]⁺ |
|---|---|---|---|
| I-90 | (R)-1'-(3-fluoro-4-methoxyphenyl)-N-hydroxy-2'-oxo-3,4-dihydro-1H-spiro[naphthalene-2,3'-pyrrolidine]-6-carboxamide | 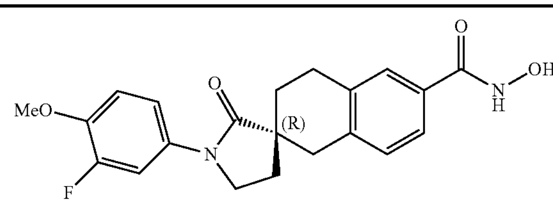 | 385 |
| I-91 | (R)-1'-(benzo[d][1,3]dioxol-5-yl)-N-hydroxy-2'-oxo-3,4-dihydro-1H-spiro[naphthalene-2,3'-pyrrolidine]-6-carboxamide | 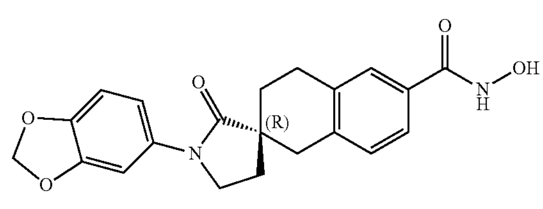 | 381 |
| I-92 | (R)-N-hydroxy-1'-(3-(methylthio)phenyl)-2'-oxo-3,4-dihydro-1H-spiro[naphthalene-2,3'-pyrrolidine]-6-carboxamide | 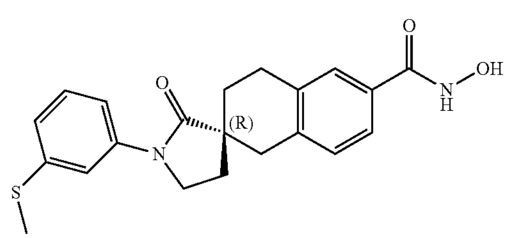 | 383 |

TABLE 14-continued

The following compounds were prepared according to the parallel synthesis method of Example 27.

| Ex. | Name | Structure | Found (ES, m/z) [M + H]+ |
|---|---|---|---|
| I-93 | (R)-1'-(4-(dimethylamino)phenyl)-N-hydroxy-2'-oxo-3,4-dihydro-1H-spiro[naphthalene-2,3'-pyrrolidine]-6-carboxamide | 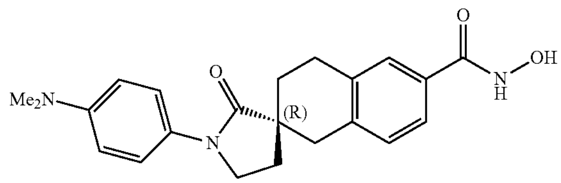 | 380 |
| I-94 | (R)-N-hydroxy-1'-(6-isopropylpyridin-3-yl)-2'-oxo-3,4-dihydro-1H-spiro[naphthalene-2,3'-pyrrolidine]-6-carboxamide | 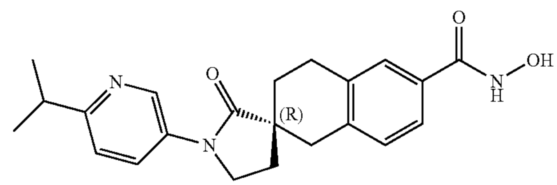 | 380 |
| I-95 | (R)-N-hydroxy-2'-oxo-1'-(quinolin-3-yl)-3,4-dihydro-1H-spiro[naphthalene-2,3'-pyrrolidine]-6-carboxamide | 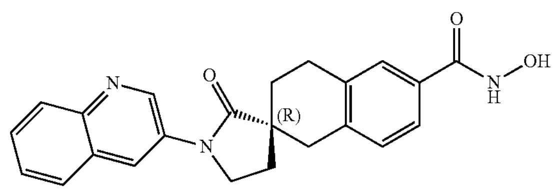 | 388 |
| I-96 | (R)-1'-(2,3-dihydrobenzofuran-7-yl)-N-hydroxy-2'-oxo-3,4-dihydro-1H-spiro[naphthalene-2,3'-pyrrolidine]-6-carboxamide | 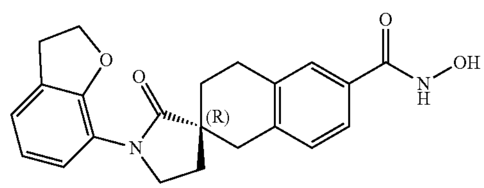 | 379 |
| I-97 | (R)-1'-(6-(tert-butylamino)pyrimidin-4-yl)-N-hydroxy-2'-oxo-3,4-dihydro-1H-spiro[naphthalene-2,3'-pyrrolidine]-6-carboxamide | 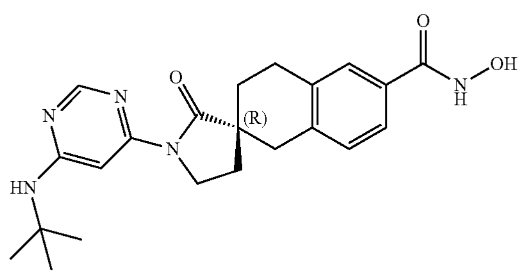 | 410 |
| I-98 | (R)-1'-(1,3-dimethyl-1H-pyrazol-4-yl)-N-hydroxy-2'-oxo-3,4-dihydro-1H-spiro[naphthalene-2,3'-pyrrolidine]-6-carboxamide | 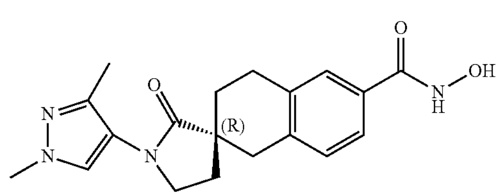 | 355 |
| I-99 | (R)-N-hydroxy-1'-(imidazo[1,2-a]pyridin-6-yl)-2'-oxo-3,4-dihydro-1H-spiro[naphthalene-2,3'-pyrrolidine]-6-carboxamide | 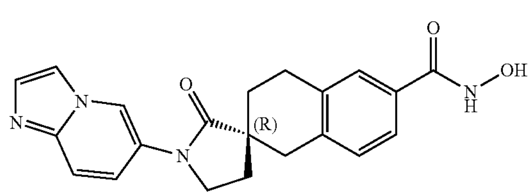 | 377 |

TABLE 14-continued

The following compounds were prepared according to the parallel synthesis method of Example 27.

| Ex. | Name | Structure | Found (ES, m/z) [M + H]+ |
|---|---|---|---|
| I-108 | (R)-N-hydroxy-1'-(3-methoxyphenyl)-2'-oxo-3,4-dihydro-1H-spiro[naphthalene-2,3'-pyrrolidine]-6-carboxamide | 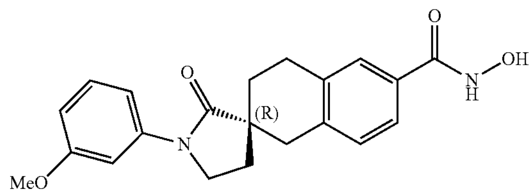 | 367 |
| I-110 | (R)-1'-(5-fluoropyridin-3-yl)-N-hydroxy-2'-oxo-3,4-dihydro-1H-spiro[naphthalene-2,3'-pyrrolidine]-6-carboxamide | 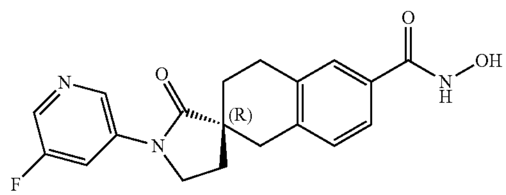 | 356 |
| I-124 | (R)-N-hydroxy-1'-(4-methoxyphenyl)-2'-oxo-3,4-dihydro-1H-spiro[naphthalene-2,3'-pyrrolidine]-6-carboxamide | 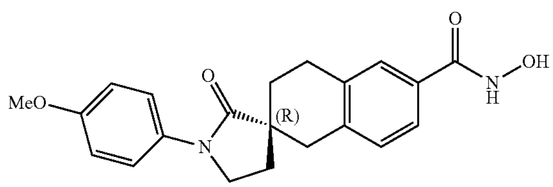 | 367 |
| I-131 | (R)-N-hydroxy-1'-(2-methylpyridin-3-yl)-2'-oxo-3,4-dihydro-1H-spiro[naphthalene-2,3'-pyrrolidine]-6-carboxamide | 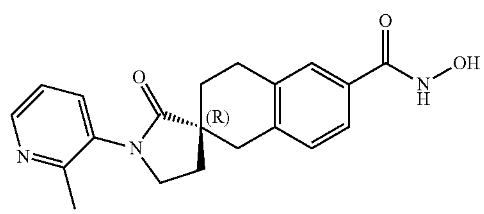 | 352 |
| I-133 | (R)-N-hydroxy-1'-(6-methylpyridin-3-yl)-2'-oxo-3,4-dihydro-1H-spiro[naphthalene-2,3'-pyrrolidine]-6-carboxamide | 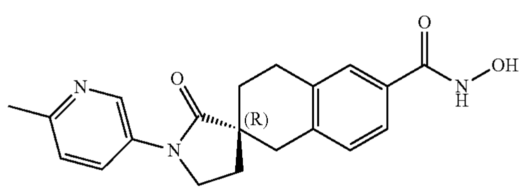 | 352 |
| I-135 | (R)-N-hydroxy-1'-(5-methylpyridin-3-yl)-2'-oxo-3,4-dihydro-1H-spiro[naphthalene-2,3'-pyrrolidine]-6-carboxamide | 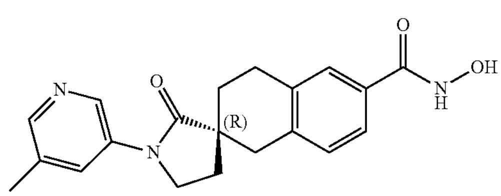 | 352 |
| I-136 | (R)-N-hydroxy-1'-(4-methylpyridin-3-yl)-2'-oxo-3,4-dihydro-1H-spiro[naphthalene-2,3'-pyrrolidine]-6-carboxamide | 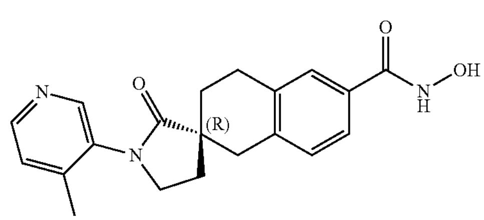 | 352 |

TABLE 14-continued

The following compounds were prepared according to the parallel synthesis method of Example 27.

| Ex. | Name | Structure | Found (ES, m/z) [M + H]+ |
|---|---|---|---|
| I-139 | (R)-1'-(5-chloropyridin-3-yl)-N-hydroxy-2'-oxo-3,4-dihydro-1H-spiro[naphthalene-2,3'-pyrrolidine]-6-carboxamide | 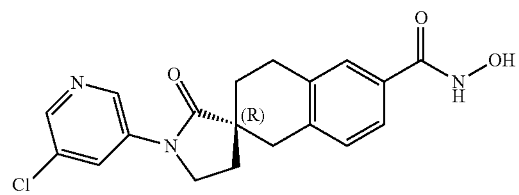 | 372 |
| I-140 | (R)-1'-(3-chloropyridin-4-yl)-N-hydroxy-2'-oxo-3,4-dihydro-1H-spiro[naphthalene-2,3'-pyrrolidine]-6-carboxamide | 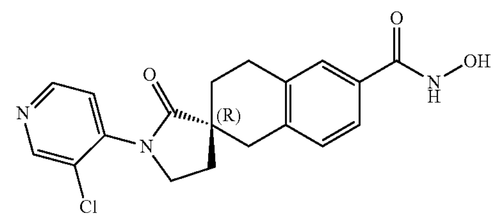 | 372 |
| I-143 | (R)-N-hydroxy-1'-(5-methoxypyridin-3-yl)-2'-oxo-3,4-dihydro-1H-spiro[naphthalene-2,3'-pyrrolidine]-6-carboxamide | 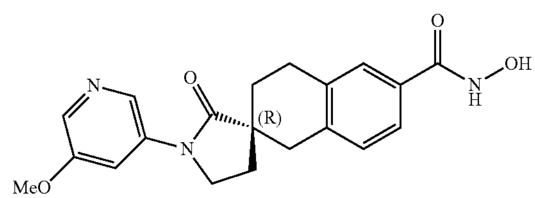 | 368 |
| I-145 | (R)-N-hydroxy-1'-(2-methoxypyridin-3-yl)-2'-oxo-3,4-dihydro-1H-spiro[naphthalene-2,3'-pyrrolidine]-6-carboxamide | 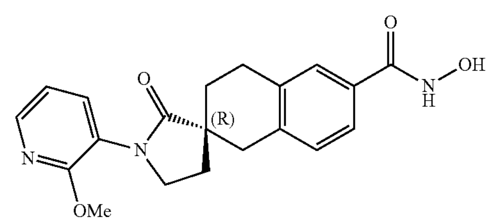 | 368 |
| I-149 | (R)-N-hydroxy-1'-(2-methoxypyridin-4-yl)-2'-oxo-3,4-dihydro-1H-spiro[naphthalene-2,3'-pyrrolidine]-6-carboxamide | 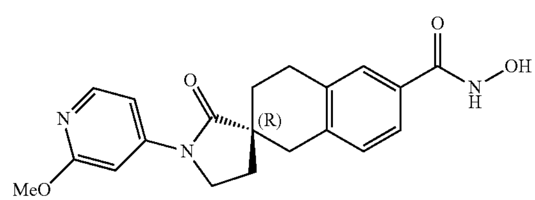 | 368 |
| I-168 | (R)-N-hydroxy-1'-(1-methyl-1H-pyrazol-4-yl)-2'-oxo-3,4-dihydro-1H-spiro[naphthalene-2,3'-pyrrolidine]-6-carboxamide | 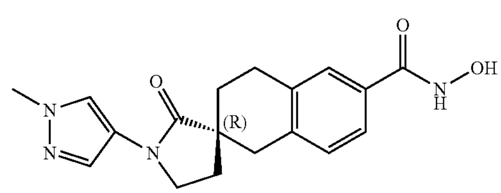 | 341 |
| I-114 | (R)-N-hydroxy-1'-(6-methoxypyridin-3-yl)-2'-oxo-3,4-dihydro-1H-spiro[naphthalene-2,3'-pyrrolidine]-6-carboxamide | 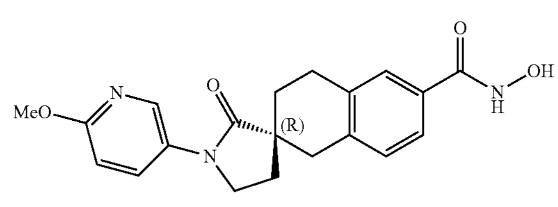 | 368 |

TABLE 14-continued

The following compounds were prepared according to the parallel synthesis method of Example 27.

| Ex. | Name | Structure | Found (ES, m/z) [M + H]+ |
|---|---|---|---|
| I-111 | (R)-N-hydroxy-1'-(2-methoxyphenyl)-2'-oxo-3,4-dihydro-1H-spiro[naphthalene-2,3'-pyrrolidine]-6-carboxamide | 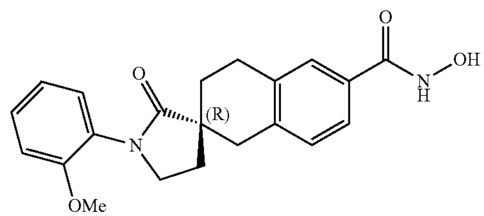 | 367 |
| I-125 | (2R)-1'-(2-fluoro-3-methoxyphenyl)-N-hydroxy-2'-oxo-3,4-dihydro-1H-spiro[naphthalene-2,3'-pyrrolidine]-6-carboxamide | 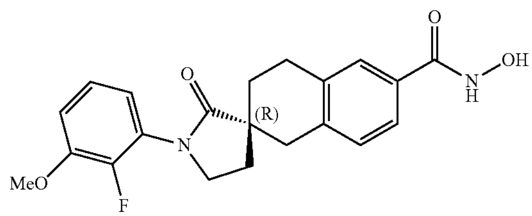 | 385 |
| I-128 | (2R)--(4-fluoro-3-methoxyphenyl)-N-hydroxy-2'-oxo-3,4-dihydro-1H-spiro[naphthalene-2,3'-pyrrolidine]-6-carboxamide | 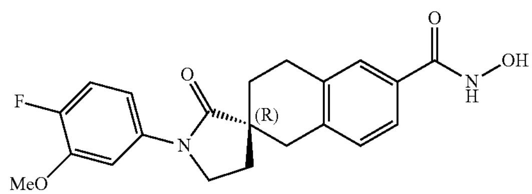 | 385 |
| I-151 | (2R)-1'-[6-(dimethylamino)pyridin-3-yl]-N-hydroxy-2'-oxo-3,4-dihydro-1H-spiro[naphthalene-2,3'-pyrrolidine]-6-carboxamide | 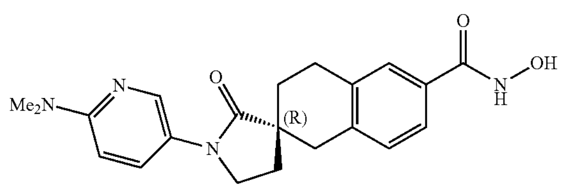 | 381 |

TABLE 15

The following compounds were prepared according to the parallel synthesis method of Example 27, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-100 | (S)-1'-(2,4-dimethylphenyl)-N-hydroxy-2'-oxo-3,4-dihydro-1H-spiro[naphthalene-2,3'-pyrrolidine]-6-carboxamide | 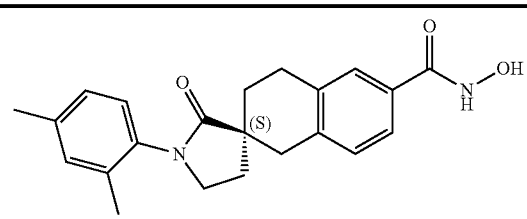 | 365 |
| I-101 | (S)-N-hydroxy-1'-(6-isopropylpyridin-3-yl)-2'-oxo-3,4-dihydro-1H-spiro[naphthalene-2,3'-pyrrolidine]-6-carboxamide | 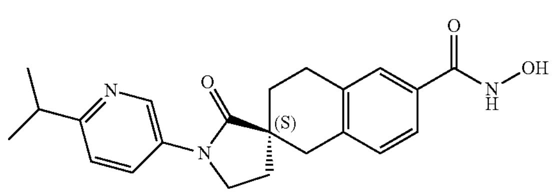 | 380 |

TABLE 15-continued

The following compounds were prepared according to the parallel synthesis method of Example 27, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-102 | (S)-N-hydroxy-2'-oxo-1'-(quinolin-3-yl)-3,4-dihydro-1H-spiro[naphthalene-2,3'-pyrrolidine]-6-carboxamide | 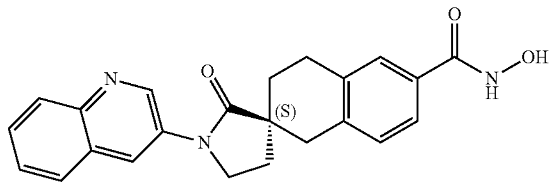 | 388 |
| I-103 | (S)-N-hydroxy-1'-(imidazo[1,2-a]pyridin-6-yl)-2'-oxo-3,4-dihydro-1H-spiro[naphthalene-2,3'-pyrrolidine]-6-carboxamide | 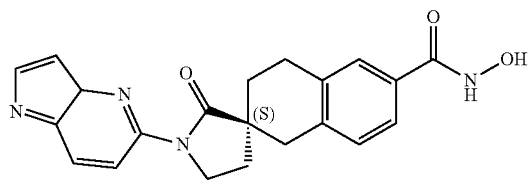 | 377 |
| I-130 | (S)-1'-(5-chloropyridin-2-yl)-N-hydroxy-2'-oxo-3,4-dihydro-1H-spiro[naphthalene-2,3'-pyrrolidine]-6-carboxamide | 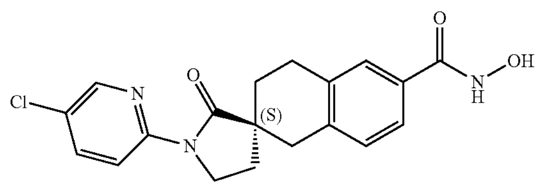 | 372 |
| I-132 | (S)-N-hydroxy-1'-(2-methylpyridin-3-yl)-2'-oxo-3,4-dihydro-1H-spiro[naphthalene-2,3'-pyrrolidine]-6-carboxamide | 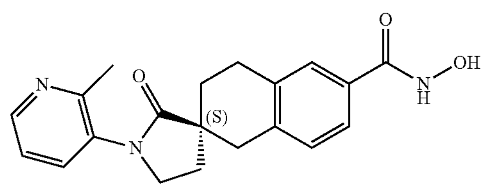 | 352 |
| I-134 | (S)-N-hydroxy-1'-(6-methylpyridin-3-yl)-2'-oxo-3,4-dihydro-1H-spiro[naphthalene-2,3'-pyrrolidine]-6-carboxamide | 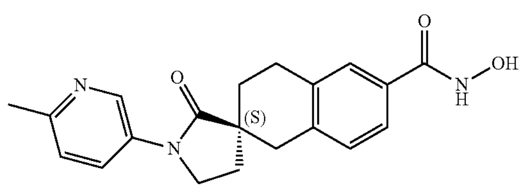 | 352 |
| I-138 | (S)-1'-(5-chloropyridin-3-yl)-N-hydroxy-2'-oxo-3,4-dihydro-1H-spiro[naphthalene-2,3'-pyrrolidine]-6-carboxamide | 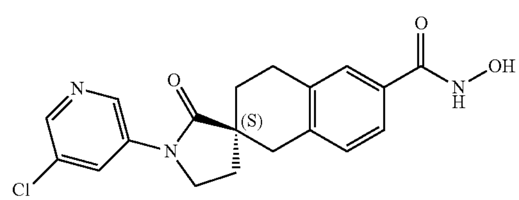 | 372 |
| I-141 | (S)-1'-(3-chloropyridin-4-yl)-N-hydroxy-2'-oxo-3,4-dihydro-1H-spiro[naphthalene-2,3'-pyrrolidine]-6-carboxamide | 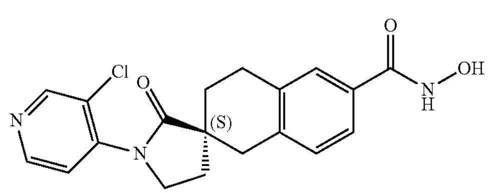 | 372 |

TABLE 15-continued

The following compounds were prepared according to the parallel synthesis method of Example 27, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-142 | (S)-N-hydroxy-1'-(4-methoxypyridin-3-yl)-2'-oxo-3,4-dihydro-1H-spiro[naphthalene-2,3'-pyrrolidine]-6-carboxamide | 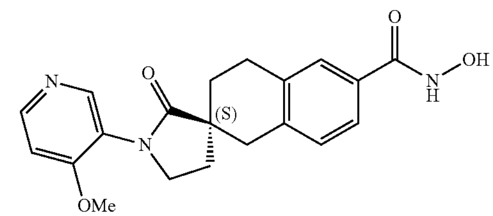 | 368 |
| I-146 | (S)-N-hydroxy-1'-(2-methoxypyridin-3-yl)-2'-oxo-3,4-dihydro-1H-spiro[naphthalene-2,3'-pyrrolidine]-6-carboxamide | 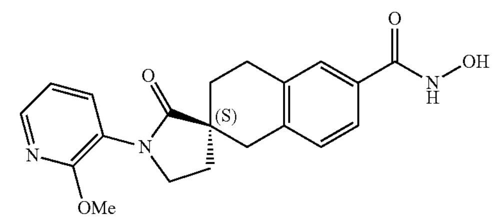 | 368 |
| I-150 | (S)-N-hydroxy-1'-(2-methoxypyridin-4-yl)-2'-oxo-3,4-dihydro-1H-spiro[naphthalene-2,3'-pyrrolidine]-6-carboxamide | 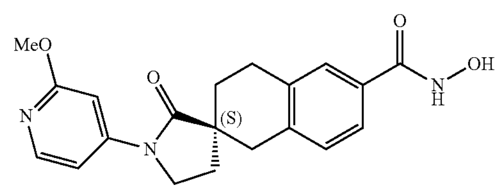 | 368 |
| I-170 | (S)-N-hydroxy-1'-(1-methyl-1H-pyrazol-4-yl)-2'-oxo-3,4-dihydro-1H-spiro[naphthalene-2,3-pyrrolidine]-6-carboxamide | 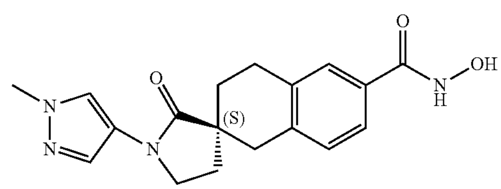 | 341 |
| I-118 | (S)-N-hydroxy-1'-(6-methoxypyridin-3-yl)-2'-oxo-3,4-dihydro-1H-spiro[naphthalene-2,3'-pyrrolidine]-6-carboxamide | 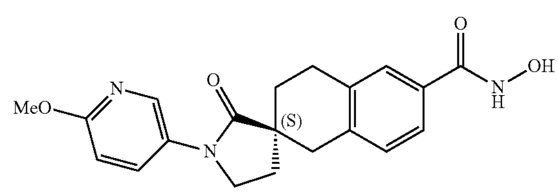 | 368 |
| I-115 | (S)-N-hydroxy-1'-(2-methoxyphenyl)-2'-oxo-3,4-dihydro-1H-spiro[naphthalene-2,3'-pyrrolidine]-6-carboxamide | 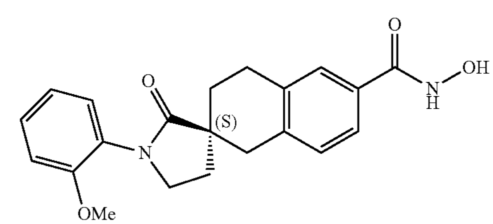 | 367 |
| I-126 | (2S)-1'-(2-fluoro-3-methoxyphenyl)-N-hydroxy-2'-oxo-3,4-dihydro-1H-spiro[naphthalene-2,3'-pyrrolidine]-6-carboxamide | 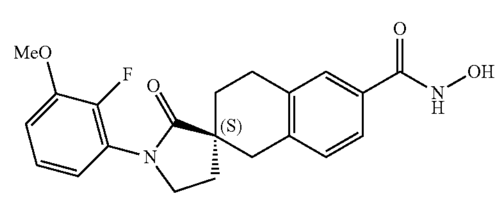 | 385 |

TABLE 15-continued

The following compounds were prepared according to the parallel synthesis method of Example 27, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]$^+$ |
|---|---|---|---|
| I-127 | (2S)-1'-(2-fluoro-4-methoxyphenyl)-N-hydroxy-2'-oxo-3,4-dihydro-1H-spiro[naphthalene-2,3'-pyrrolidine]-6-carboxamide | 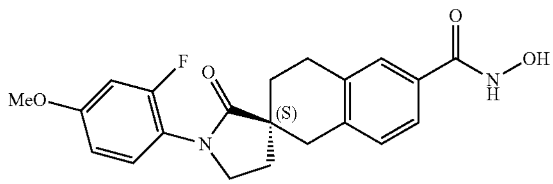 | 385 |
| I-129 | (2S)-1'-(4-fluoro-3-methoxyphenyl)-N-hydroxy-2'-oxo-3,4-dihydro-1H-spiro[naphthalene-2,3'-pyrrolidine]-6-carboxamide | 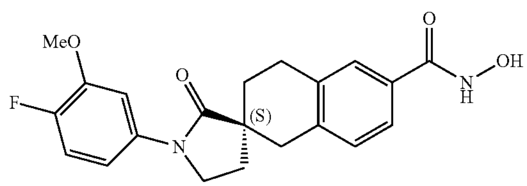 | 385 |
| I-137 | (S)-N-hydroxy-1'-(4-methylpyridin-3-yl)-2'-oxo-3,4-dihydro-1H-spiro[naphthalene-2,3'-pyrrolidine]-6-carboxamide | 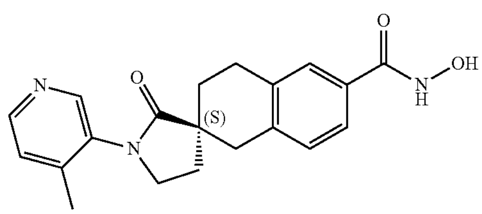 | 352 |
| I-144 | (2S)-N-hydroxy-1'-(5-methoxypyridin-3-yl)-2'-oxo-3,4-dihydro-1H-spiro[naphthalene-2,3'-pyrrolidine]-6-carboxamide | 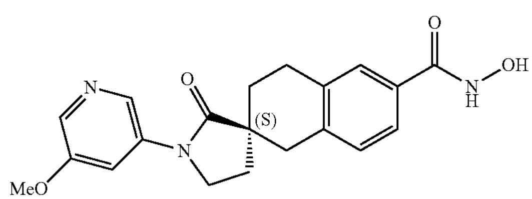 | 368 |
| I-147 | (2S)-1'-(2-fluoro-5-methoxyphenyl)-N-hydroxy-2'-oxo-3,4-dihydro-1H-spiro[naphthalene-2,3'-pyrrolidine]-6-carboxamide | 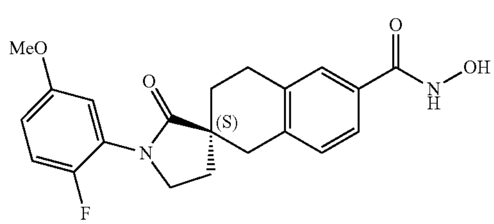 | 385 |
| I-148 | (2S)-1'-(3-fluoro-5-methoxyphenyl)-N-hydroxy-2'-oxo-3,4-dihydro-1H-spiro[naphthalene-2,3'-pyrrolidine]-6-carboxamide | 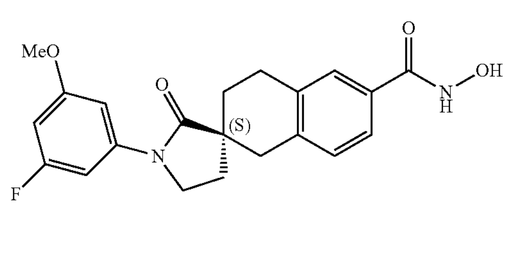 | 385 |

TABLE 15-continued

The following compounds were prepared according to the parallel synthesis method of
Example 27, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-152 | (2S)-1'-[6-(dimethylamino)pyridin-3-yl]-N-hydroxy-2'-oxo-3,4-dihydro-1H-spiro[naphthalene-2,3'-pyrrolidine]-6-carboxamide | 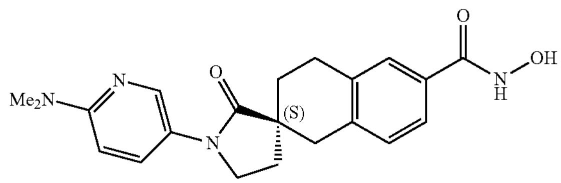 | 381 |
| I-153 | (2S)-1'-(5-fluoropyridin-3-yl)-N-hydroxy-2'-oxo-3,4-dihydro-1H-spiro[naphthalene-2,3'-pyrrolidine]-6-carboxamide | 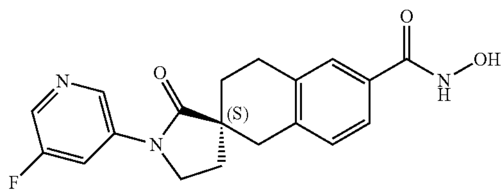 | 356 |

Example 28

Preparation of (R)-1'-(3,4-difluorophenyl)-N-hydroxy-2'-oxo-3,4-dihydro-1H-spiro[naphthalene-2,3'-pyrrolidine]-6-carboxamide (I-119)

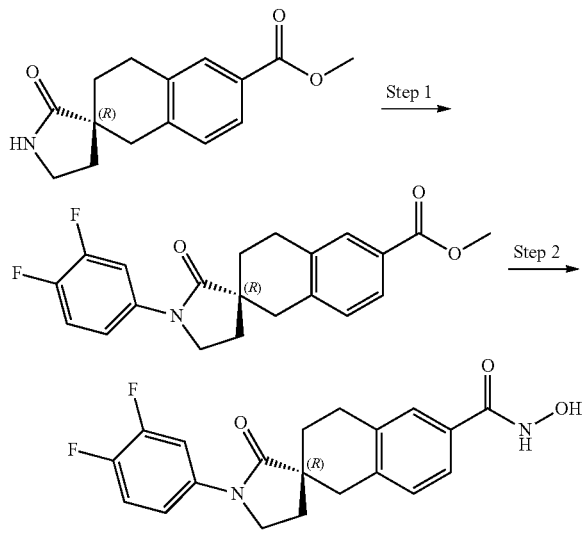

Step-1: Methyl (R)-1'-(3,4-difluorophenyl)-2'-oxo-3,4-dihydro-1H-spiro[naphthalene-2,3'-pyrrolidine]-6-carboxylate A 2-dram vial was charged with (Xantphos)PdCl$_2$ (0.02 M, 0.150 mL, 0.30 μmol) in CH$_2$Cl$_2$. The solvent was then evaporated under a stream of N$_2$. Next 4-bromo-1,2-difluorobenzene in 1,4-dioxane (0.2 M, 0.200 mL, 0.030 mmol) was added followed by Cs$_2$CO$_3$ (39 mg, 0.120 mmol). The vial was capped and carried into an inert atmosphere glovebox where a solution of methyl (R)-2'-oxo-3,4-dihydro-1H-spiro[naphthalene-2,3'-pyrrolidine]-6-carboxylate in dioxane/Et$_3$N (98:2, 0.20 M, 0.200 mL, 0.030 mmol) was added. The vial was capped and heated at 100° C. for 16 h. The solvent was removed under a stream of N$_2$. The residue was diluted with brine (0.50 mL) and extracted with EtOAc (2×0.50 mL). The combined organic layers were dried under a stream of N$_2$.

Step-2: (R)-1'-(3,4-difluorophenyl)-N-hydroxy-2'-oxo-3,4-dihydro-1H-spiro[naphthalene-2,3'-pyrrolidine]-6-carboxamide The residue was dissolved in THF/MeOH (3:1, 0.20 mL). The vial was sealed and shaken at 50° C. for 15 min to dissolve the residue, then cooled to room temperature. NH$_2$OH (50% v/v solution in water, 0.150 mL) was added, followed by 1N aq NaOH (0.10 mL). The mixture was sealed and then shaken at room temperature for 18 h. The reaction mixture was concentrated under a stream of N$_2$ at room temperature, then dissolved in 0.50 mL of DMSO and purified by reverse-phase chromatography HPLC Column: Waters Sunfire C18, 5 μm, 19×50 mm; Mobile Phase A: Water/0.1% Formic acid, Mobile Phase B: CH$_3$CN/0.1% Formic acid; Gradient: 15% B to 100% B in 6 min; Flow rate: 23 mL/min; Detector: UV 254 nm, 220 nm. The product-containing fractions were combined and concentrated in a Genevac to afford 3.3 mg (28% yield) of the title compound. $^1$H NMR (400 MHz, CDCl$_3$) δ (ppm): 8.70 (br s, 1H), 7.77 (ddd, J=12, 7.0, 2.7 Hz, 1H), 7.56 (s, 1H), 7.48 (d, J=7.8 Hz, 1H), 7.33-7.29 (m, 1H), 7.20 (d, J=10 Hz, 1H), 7.15 (d, J=10 Hz, 1H), 3.82 (t, J=6.6 Hz, 2H), 3.15 (d, J=17 Hz, 1H), 3.06-2.99 (m, 1H), 2.94-2.85 (m, 1H), 2.75 (d, J=17 Hz, 1H), 2.18-1.94 (m, 3H), 1.88-1.82 (m, 1H). MS: (ES, m z) 373 [M+H]+.

TABLE-16

The following compounds were prepared according to the parallel synthesis method of Example 28.

| Ex. | Name | Structure | Found (ES, m/z) [M + H]+ |
|---|---|---|---|
| I-167 | (R)-1'-(2,5-difluorophenyl)-N-hydroxy-2'-oxo-3,4-dihydro-1H-spiro[naphthalene-2,3'-pyrrolidine]-6-carboxamide | 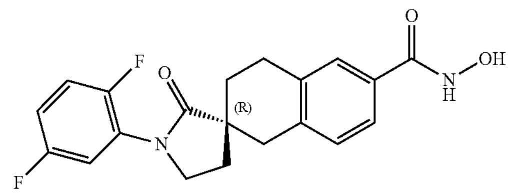 | 373 |
| I-120 | (R)-1'-(4-fluorophenyl)-N-hydroxy-2'-oxo-3,4-dihydro-1H-spiro[naphthalene-2,3'-pyrrolidine]-6-carboxamide | 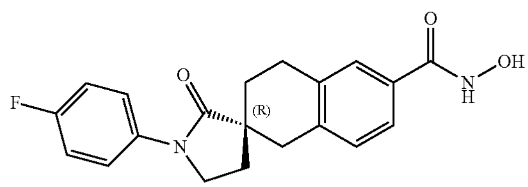 | 355 |
| I-113 | (R)-1'-(3-fluorophenyl)-N-hydroxy-2'-oxo-3,4-dihydro-1H-spiro[naphthalene-2,3'-pyrrolidine]-6-carboxamide | 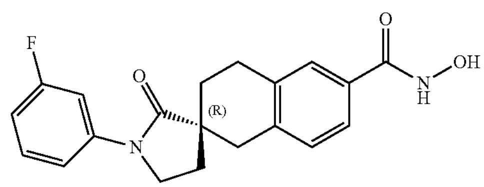 | 355 |
| I-121 | (R)-1'-(2-fluorophenyl)-N-hydroxy-2'-oxo-3,4-dihydro-1H-spiro[naphthalene-2,3'-pyrrolidine]-6-carboxamide | 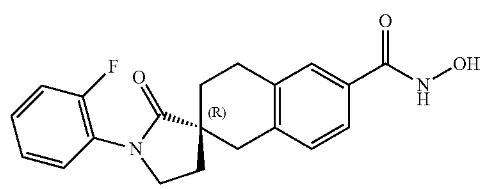 | 355 |
| I-123 | (R)-1'-(2,3-difluorophenyl)-N-hydroxy-2'-oxo-3,4-dihydro-1H-spiro[naphthalene-2,3'-pyrrolidine]-6-carboxamide | 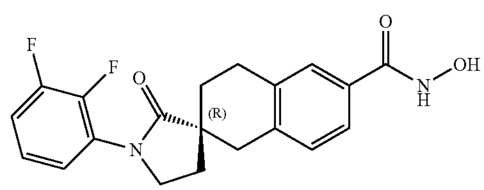 | 373 |

TABLE-17

The following compounds were prepared according to the synthesis method of Example 28, using methyl (S)-2'-oxo-3,4-dihydro-1H-spiro[naphthalene-2,3'-pyrrolidine]-6-carboxylate in Step 1.

| Ex. | Name | Structure | Found (ES, m/z) [M + H]+ |
|---|---|---|---|
| I-154 | (S)-1'-(4-fluorophenyl)-N-hydroxy-2'-oxo-3,4-dihydro-1H-spiro[naphthalene-2,3'-pyrrolidine]-6-carboxamide | 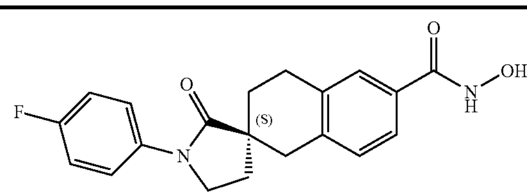 | 355 |

TABLE-17-continued

*The following compounds were prepared according to the synthesis method of Example 28, using methyl (S)-2'-oxo-3,4-dihydro-1H-spiro[naphthalene-2,3'-pyrrolidine]-6-carboxylate in Step 1.*

| Ex. | Name | Structure | Found (ES, m/z) [M + H]⁺ |
|---|---|---|---|
| I-156 | (S)-1'-(2,3-difluorophenyl)-N-hydroxy-2'-oxo-3,4-dihydro-1H-spiro[naphthalene-2,3'-pyrrolidine]-6-carboxamide | 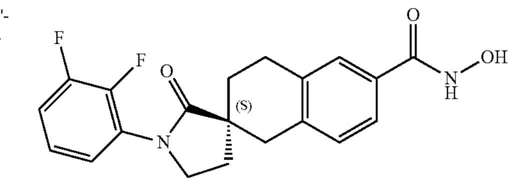 | 373 |
| I-155 | (S)-1'-(3,4-difluorophenyl)-N-hydroxy-2'-oxo-3,4-dihydro-1H-spiro[naphthalene-2,3'-pyrrolidine]-6-carboxamide | 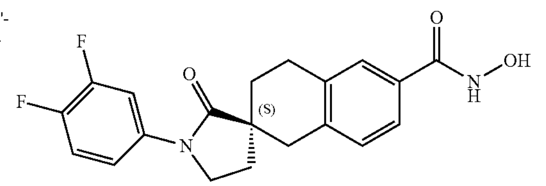 | 373 |
| I-157 | (S)-1'-(2-fluorophenyl)-N-hydroxy-2'-oxo-3,4-dihydro-1H-spiro[naphthalene-2,3'-pyrrolidine]-6-carboxamide | 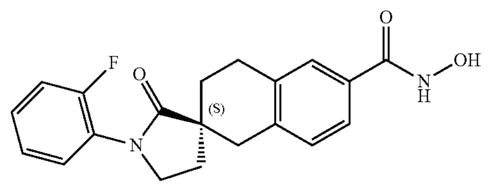 | 355 |
| I-158 | (S)-N-hydroxy-1'-(3-methoxyphenyl)-2'-oxo-3,4-dihydro-1H-spiro[naphthalene-2,3'-pyrrolidine]-6-carboxamide | 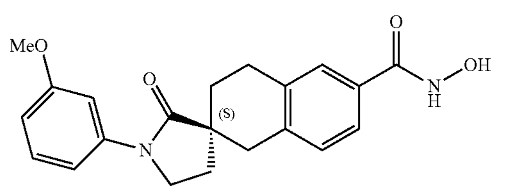 | 367 |
| I-169 | (S)-1'-(2,5-difluorophenyl)-N-hydroxy-2'-oxo-3,4-dihydro-1H-spiro[naphthalene-2,3'-pyrrolidine]-6-carboxamide | 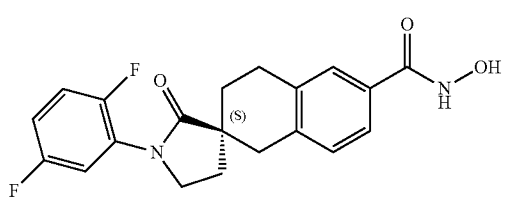 | 373 |
| I-117 | (S)-1'-(3-fluorophenyl)-N-hydroxy-2'-oxo-3,4-dihydro-1H-spiro[naphthalene-2,3'-pyrrolidine]-6-carboxamide | 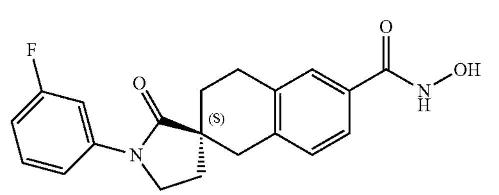 | 355 |

Example 29

Preparation of N-hydroxy-2-oxo-1-(pyridin-4-ylmethyl)spiro[pyrrolidine-3,2'-thiochromane]-6'-carboxamide 1',1'-dioxide (I-242)

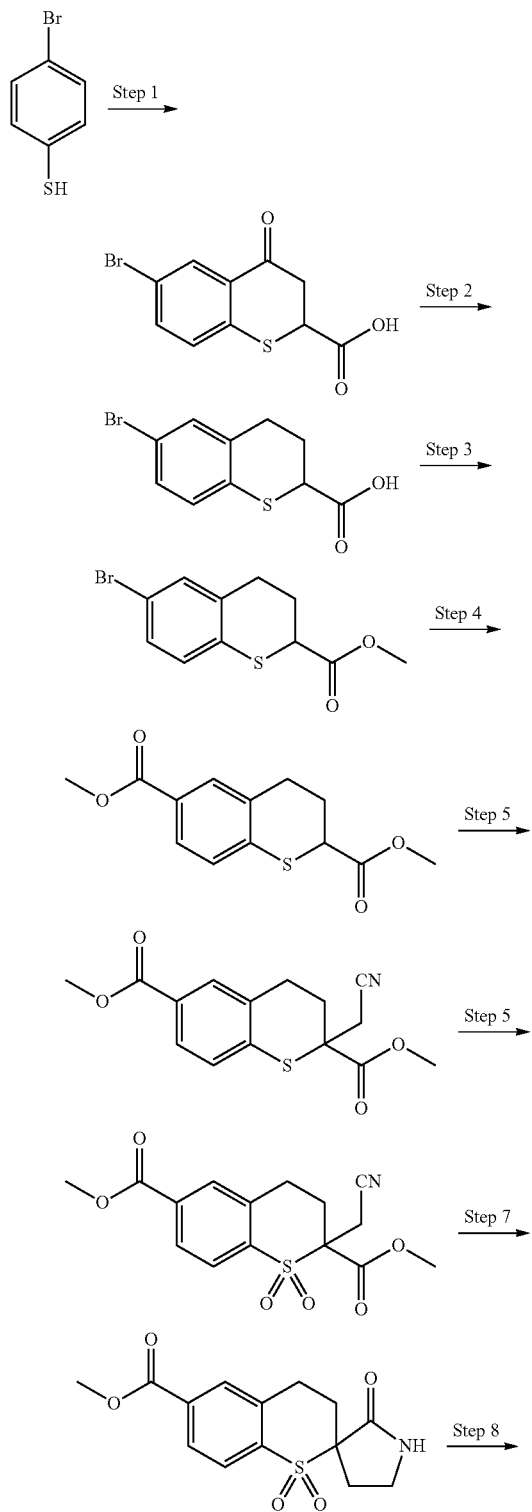

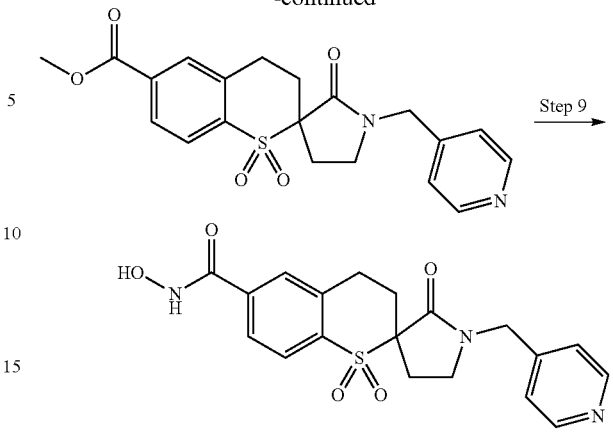

Step-1: 6-Bromo-4-oxothiochromane-2-carboxylic acid

In a 100-mL 3-necked round-bottom flask 4-bromobenzenethiol (20.0 g, 105.78 mmol, 1 equiv) in toluene (25 mL) and 2,5-dihydrofuran-2,5-dione (12.96 g, 132.17 mmol, 1 equiv) were stirred at 50° C. for 1 h. A solution of Et$_3$N (27.6 mg, 0.28 mmol) in toluene (0.4 mL) was then added, ensuring the reaction temperature did not increase over 60° C. The reaction was heated at 70° C. for 50 min. The reaction was then concentrated under high vacuum. The residue was dissolved in CH$_2$Cl$_2$ (109 mL), cooled to 0° C. in an ice bath and treated with AlCl$_3$ (14.52 g, 108.89 mmol, 1.03 equiv). The reaction was slowly warmed to room temperature. After stirring for 3 h the reaction mixture was then diluted with CH$_2$Cl$_2$ (18 mL) and slowly poured into vigorously stirred concentrated HCl (44 mL) and ice (44 g). The reaction was vigorously stirred and diluted with CH$_2$Cl$_2$ (500 mL) and isopropanol (72 mL). The CH$_2$Cl$_2$ layer was separated, dried over magnesium sulfate, filtered and concentrated in vacuum. The mixture was triturated with Et$_2$O and then filtered to give 6.64 g (22% yield) of the title compound as a light yellow solid. MS: (ES, m/z): 285 [M+H]$^+$.

Step-2: 6-Bromothiochromane-2-carboxylic acid

Into a 500-mL round-bottom flask was placed a solution of 6-bromo-4-oxothiochromane-2-carboxylic acid (4.0 g, 13.93 mmol, 1 equiv) in TFA (200 mL). This was followed by the addition of triethylsilane (16 g, 137.60 mmol, 10 equiv) at 0° C. The resulting solution was stirred for 19 h at room temperature. The resulting mixture was concentrated under vacuum. The residue was dissolved in 100 mL of CH$_2$Cl$_2$ and washed with 2×40 mL of H$_2$O, dried over anhydrous magnesium sulfate, filtered, and concentrated under vacuum. The residue was dissolved in 30 mL of H$_2$O. The pH of the solution was adjusted to 9 with aq. NaOH. The resulting solution was washed with 2×50 mL of CH$_2$Cl$_2$ and the aqueous layers combined. 6N aq. HCl was employed to adjust the pH to 4. The resulting solution was extracted with 3×70 mL of CH$_2$Cl$_2$. The combined organic layers were dried over anhydrous magnesium sulfate, filtered, and then concentrated under vacuum to give 1.42 g (37% yield) of the title compound as a light yellow solid. MS: (ES, m/z): 271 [M+H]$^+$.

Step-3: Methyl 6-bromothiochromane-2-carboxylate

Into a 50-mL round-bottom flask was placed a solution of 6-bromothiochromane-2-carboxylic acid (1.42 g, 5.20 mmol, 1 equiv) in MeOH (15 mL) and concentrated sulfuric acid (2.84 mL). The resulting solution was stirred for 15 h at 70° C. The resulting mixture was concentrated under vacuum. The residue was dissolved in 100 mL of $CH_2Cl_2$. The resulting mixture was washed with 2×50 mL of $H_2O$, washed with 3×50 mL of $NaHCO_3$ and 2×50 mL of brine. The organic layer was dried over anhydrous magnesium sulfate, filtered, and concentrated under vacuum to give 1.28 g (86% yield) of the title compound as a yellow solid. MS: (ES, m/z): 285 [M+H]$^+$.

Step-4: Dimethyl thiochromane-2,6-dicarboxylate

Into a 50-mL pressure tank reactor (30 atm), was placed a solution of methyl 6-bromothiochromane-2-carboxylate (1.28 g, 4.47 mmol, 1 equiv) in MeOH (15 mL), $Et_3N$ (1.85 mL), and Pd(dppf)Cl$_2$ (655 mg, 0.90 mmol, 0.20 equiv). CO (g) was introduced into the reactor. The resulting solution was stirred for 2 days at 100° C. The resulting mixture was concentrated under vacuum. The residue was purified by normal phase chromatography on silica gel with EtOAc/petroleum ether (1:3). The collected fractions were concentrated to give 811 mg (68% yield) of the title compound as a light brown solid. MS: (ES, m/z): 267 [M+H]$^+$.

Step-5: Dimethyl 2-(cyanomethyl)thiochromane-2,6-dicarboxylate

Into a 100-mL 3-necked round-bottom flask purged and maintained with an inert atmosphere of nitrogen, was placed a solution of dimethyl thiochromane-2,6-dicarboxylate (1.55 g, 5.83 mmol, 1 equiv) in THF (20 mL). This was followed by the addition of LDA (7 mL, 1.2 equiv) at −78° C. over 30 min. To this was added 2-bromoacetonitrile (910.6 mg, 7.59 mmol, 1.3 equiv) at −78° C. The resulting solution was stirred for 1.5 h at the same temperature. The reaction was then quenched by the addition of 35 mL of sat. aq. $NH_4Cl$. The resulting solution was extracted with 2×100 mL of EtOAc. The organic layers were combined and concentrated under vacuum. The residue was purified by normal phase chromatography on silica gel with EtOAc/petroleum ether (1:3). The collected fractions were concentrated to give 1.51 g (85% yield) of the title compound as a yellow oil. MS: (ES, m/z): 304 [M−H]$^-$.

Step-6: Dimethyl 2-(cyanomethyl)thiochromane-2,6-dicarboxylate 1,1-dioxide

Into a 250-mL round-bottom flask was placed a solution of dimethyl 2-(cyanomethyl)thiochromane-2,6-dicarboxylate (1.51 g, 4.95 mmol, 1 equiv) in $CH_2Cl_2$ (150 mL). This was followed by the addition of a solution of m-CPBA (2.57 g, 14.87 mmol, 3 equiv) in $CH_2Cl_2$ (10 mL) at 0° C. The resulting mixture was stirred for 14 h at room temperature. Then $K_2CO_3$ (1 g) was added and the reaction stirred for 1 h at room temperature. The solids were filtered out. The solid was washed with 100 mL of $CH_2Cl_2$. The filtrate was concentrated under vacuum to give 1.79 g (crude) of the title compound as a yellow oil. MS: (ES, m/z): 336 [M−H]$^-$.

Step-7: Methyl 2-oxospiro[pyrrolidine-3,2'-thiochromane]-6'-carboxylate 1',1'-dioxide Into a 500-mL round-bottom flask was placed a solution of dimethyl 2-(cyanomethyl)thiochromane-2,6-dicarboxylate 1,1-dioxide (1.79 g, 5.31 mmol, 1 equiv) in MeOH (150 mL), PtO$_2$ (675 mg, 2.97 mmol, 0.6 equiv), and acetic acid (33.4 mL). Hydrogen (g) was introduced. The resulting solution was stirred for 1 day at room temperature. The solids were filtered out and the filtrate was concentrated under vacuum. The pH of the solution was adjusted to 9 with aq. $Na_2CO_3$. The resulting solution was extracted with 3×100 mL of $CH_2Cl_2$, dried over anhydrous magnesium sulfate, filtered and concentrated under vacuum to give 1.27 g (78% yield) of the title compound as a gray solid. $^1$H-NMR (400 MHz, DMSO-d6) δ (ppm): 8.06-8.01 (m, 3H), 6.00 (s, 1H), 3.97 (s, 3H), 3.71-3.55 (m, 2H), 3.49-3.43 (m, 1H), 3.16-3.05 (m, 2H), 2.71-2.63 (m, 2H), 2.31-2.23 (m, 1H). MS: (ES, m/z): 310 [M+H]$^+$.

Step-8: 2-Oxo-1-(pyridin-4-ylmethyl)spiro[pyrrolidine-3,2'-thiochromane]-6'-carboxylic acid 1',1'-dioxide Into an 8-mL vial, was placed a solution of methyl 2-oxospiro[pyrrolidine-3,2'-thiochromane]-6'-carboxylate 1',1'-dioxide (100 mg, 0.32 mmol, 1 equiv) in DMF (3 mL). This was followed by the addition of NaH (60% dispersion in oil, 65 mg, 2.71 mmol, 5 equiv) at 0° C. over 10 min. To this was added 4-(bromomethyl) pyridine hydrobromide (163 mg, 0.64 mmol, 2 equiv). The resulting mixture was stirred for 18 h at room temperature. The reaction was then quenched by the addition of $NH_4Cl$ (aq.). The resulting solution was extracted with 2×20 mL of EtOAc and the aqueous layers combined. The pH of the aqueous layers was adjusted to 4 with 1N aq. HCl. The resulting solution was extracted with 3×20 mL of $CH_2Cl_2$, dried over anhydrous magnesium sulfate, filtered, and concentrated under vacuum to give 30 mg (24% yield) of the title compound as a light brown oil which was used in the next step without purification. MS: (ES, m/z): 387 [M+H]$^+$.

Step-9: N-Hydroxy-2-oxo-1-(pyridin-4-ylmethyl) spiro[pyrrolidine-3,2'-thiochromane]-6'-carboxamide 1',1'-dioxide Into an 8-mL vial, was placed a solution of 2-oxo-1-(pyridin-4-ylmethyl)spiro[pyrrolidine-3,2'-thiochromane]-6'-carboxylic acid 1',1'-dioxide (55 mg, 0.14 mmol, 1 equiv) in DMA (1.5 mL). This was followed by the dropwise addition of isopropyl chloroformate (90 mg, 0.71 mmol, 5 equiv) with stirring at 0° C. over 15 min. NMM (72 mg, 0.71 mmol, 5 equiv) was added dropwise with stirring at 0° C. The mixture was stirred for 15 min at 0° C. A solution of NH$_2$OH.HCl (50 mg, 0.71 mmol, 5 equiv) in DMA (0.5 mL) was added to the stirring mixture. The resulting solution was stirred for 19 h at room temperature. The crude product was purified by Prep-HPLC with the following conditions: Column: Sunfire Prep C18, 5 μm, 19×100 mm; Mobile Phase A: Water/0.05% TFA, Mobile Phase B: $CH_3CN$/0.05% TFA; Flow rate: 25 ml/min; Gradient: 4% B to 58% B in 7 min; Detector: UV 254 nm, 220 nm. The collected fractions were lyophilized to give 8 mg (11% yield) of the title compound as a brown solid. $^1$H-NMR (400 MHz, DMSO-d6) δ (ppm): 11.41 (br s, 1H), 8.66 (s, 2H), 7.90-7.88 (m, 1H), 7.80-7.74 (m, 2H), 7.48 (s, 2H), 4.74-4.70 (m, 1H), 4.52-4.44 (m, 1H), 3.42-3.33 (m, 2H), 3.16-3.04 (m, 2H), 2.75-2.67 (m, 3H), 2.37-2.29 (m, 1H). MS: (ES, m z): 402 [M+H]$^+$.

TABLE-18

The following compound was prepared according to the method of Example 29.

| Ex. | Structure | $^{1}$H-NMR δ (ppm) | Found (ES, m/z) [M + H]$^{+}$ |
|---|---|---|---|
| I-239 | 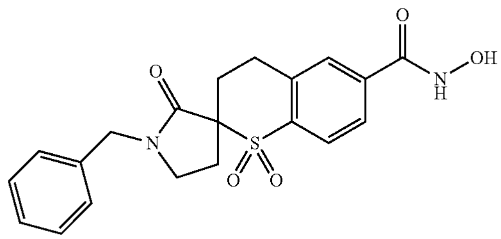 [SMILES: O=C(NO)c1ccc2c(c1)CCC1(CCN(Cc3ccccc3)C1=O)S2(=O)=O] | (400 MHz, DMSO-d6): 11.41 (br s, 1H), 7.89-7.87 (d, J = 8.0 Hz, 1H), 7.79-7.74 (m, 2H), 7.37-7.24 (m, 5H), 4.58-4.55 (d, J = 12.0 Hz, 1H), 4.35-4.31 (d, J = 16.0 Hz, 1H), 3.41-3.29 (m, 3H), 3.10-3.02 (m, 1H), 2.70-2.61 (m, 2H), 2.48-2.43 (m, 1H), 2.28-2.21 (m, 1H) | 401 |

Example 30

Preparation of N-hydroxy-2-oxo-1-phenylspiro[pyrrolidine-3,2'-thiochromane]-6'-carboxamide 1',1'-dioxide (I-238)

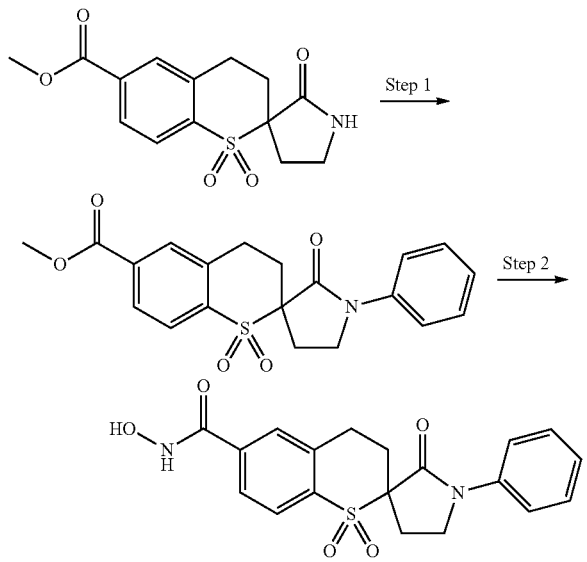

Step-1: Methyl 2-oxo-1-phenylspiro[pyrrolidine-3,2'-thiochromane]-6'-carboxylate 1',1'-dioxide Into a 25-mL vial purged and maintained with an inert atmosphere of nitrogen, were placed methyl 2-oxospiro[pyrrolidine-3,2'-thiochromane]-6'-carboxylate 1',1'-dioxide (100 mg, 0.32 mmol, 1 equiv), Cs$_2$CO$_3$ (211 mg, 0.65 mmol, 2 equiv) in 1,4-dioxane (6 mL), XantPhos (41 mg, 0.07 mmol, 0.22 equiv), iodobenzene (79 mg, 0.39 mmol, 1.2 equiv), and Pd(OAc)$_2$ (7.3 mg, 0.03 mmol, 0.1 equiv). The resulting mixture was stirred for 17 h at 100° C. and then concentrated under vacuum. The residue was dissolved in 30 mL of EtOAc and washed with 3×20 mL of H$_2$O. The organics were dried over anhydrous Na$_2$SO$_4$, filtered and concentrated under vacuum. The residue was purified by normal phase chromatography on silica gel with EtOAc/petroleum ether (5:6). The collected fractions were concentrated to give 60.5 mg (49% yield) of the title compound as a light brown oil. MS: (ES, m/z): 386 [M+H]$^{+}$.

Step-2: N-Hydroxy-2-oxo-1-phenylspiro[pyrrolidine-3,2'-thiochromane]-6'-carboxamide 1',1'-dioxide Into an 8-mL vial, was placed a solution of methyl 2-oxo-1-phenylspiro[pyrrolidine-3,2'-thiochromane]-6'-carboxylate 1',1'-dioxide (60.5 mg, 0.16 mmol, 1 equiv) in THF/MeOH (4:1, 2 mL), NH$_2$OH (50% in H$_2$O, 0.31 mL, 30 equiv) and 1N aq. NaOH (0.31 mL, 2 equiv). The resulting solution was stirred for 3 h at room temperature. The crude product was purified by Prep-HPLC with the following conditions: Column: Xbridge C18, 5 μm, 19×100 mm; Mobile Phase A: Water/0.05% TFA, Mobile Phase B: CH$_3$CN/0.05% TFA; Flow rate: 25 mL/min; Gradient: 5% B to 57% B in 7 min; Detector: UV 254 nm, 220 nm. The collected fractions were lyophilized to give 45.9 mg (76% yield) of the title compound as a pink solid. $^{1}$H-NMR (400 MHz, DMSO-d6) δ (ppm): 11.42 (br s, 1H), 7.90-7.87 (d, J=12.0 Hz, 1H), 7.80-7.76 (m, 2H), 7.66-7.64 (d, J=8.0 Hz, 2H), 7.43-7.38 (m, 2H), 7.26-7.18 (m, 1H), 4.09-3.89 (m, 2H), 3.40-3.30 (m, 1H), 3.19-3.05 (m, 1H), 2.84-2.75 (m, 2H), 2.57-2.55 (m, 1H), 2.44-2.39 (m, 1H). MS: (ES, m/z): 387 [M+H]$^{+}$.

TABLE-19

The following compound was prepared according to the method of Example 30.

| Ex. | Structure | $^{1}$H-NMR δ (ppm) | Found (ES, m/z) [M + H]$^{+}$ |
|---|---|---|---|
| I-240 | 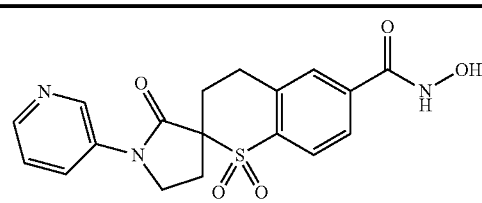 | (400 MHz, DMSO-d6): 11.43 (br s, 1H), 8.95-8.94 (d, J = 4.0 Hz, 1H), 8.46-8.45 (d, J = 4 Hz, 1H), 8.20-8.17 (d, J = 12 Hz, 1H), 7.91-7.88(d, J = 12 Hz, 1H), 7.81-7.77 (m, 2H), 7.57-7.52 (m, 1H), 4.06-4.01 (m, 2H), 3.40-3.29 (m, 1H), 3.16-3.06 (m, 1H), 2.89-2.77 (m 2H), 2.59-2.56 (m, 1H), 2.46-2.39 (m, 1H) | 388 |

Example 31

Preparation of N-hydroxy-2-oxo-1-((tetrahydro-2H-pyran-4-yl)methyl)spiro[pyrrolidine-3,2'-thiochromane]-6'-carboxamide 1',1'-dioxide (I-241)

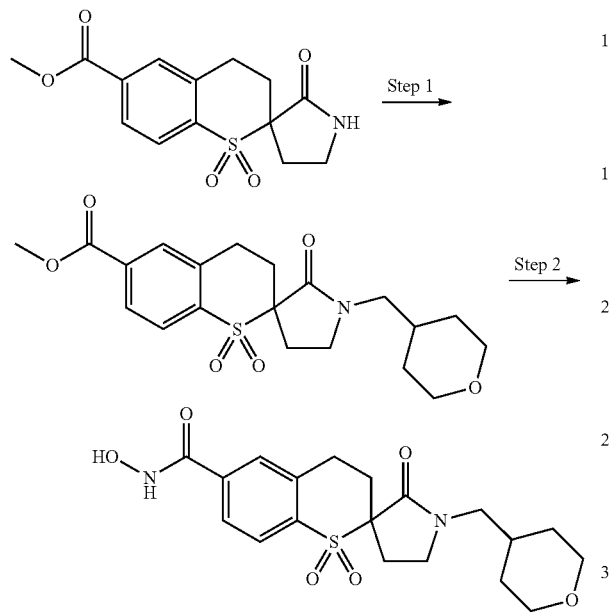

Step-1: Methyl 2-oxo-1-((tetrahydro-2H-pyran-4-yl)methyl)spiro[pyrrolidine-3,2'-thiochromane]-6'-carboxylate 1',1'-dioxide Into a 25-mL vial, was placed a solution of methyl 2-oxospiro[pyrrolidine-3,2'-thiochromane]-6'-carboxylate 1',1'-dioxide (150 mg, 0.48 mmol, 1 equiv) in DMF (4 mL). This was followed by the addition of NaH (60% dispersion in oil, 39 mg, 1.62 mmol, 2 equiv) at 0° C. over 10 min. 4-(Bromomethyl)oxane (261 mg, 1.46 mmol, 3 equiv) was then added. The resulting solution was stirred for 4 h at room temperature. The reaction was quenched with a solution of aq. NH$_4$Cl. The resulting solution was extracted with 3×20 mL of EtOAc. The combined organic layers were dried over anhydrous Na$_2$SO$_4$, filtered, and concentrated under vacuum to give 144.8 mg (73% yield) of the title compound as a light yellow oil. MS: (ES, m/z): 408 [M+H]$^+$.

Step-2: N-Hydroxy-2-oxo-1-((tetrahydro-2H-pyran-4-yl)methyl)spiro[pyrrolidine-3,2'-thiochromane]-6'-carboxamide 1',1'-dioxide Into an 8-mL vial, was placed a solution of methyl 2-oxo-1-((tetrahydro-2H-pyran-4-yl)methyl)spiro[pyrrolidine-3,2'-thiochromane]-6'-carboxylate 1',1'-dioxide (100 mg, 0.25 mmol, 1 equiv) in THF/MeOH (4:1, 3 mL), NH$_2$OH (50% in H$_2$O, 0.48 mL, 30 equiv), and aq. NaOH (1N, 0.49 mL, 2 equiv). The resulting solution was stirred for 5 h at room temperature. The crude product was purified by Prep-HPLC with the following conditions: Column: Xbridge C18, 19×150 mm, 5 μm; Mobile Phase A: Water/0.05% TFA, CH$_3$CN/0.05% TFA; Flow rate: 25 mL/min; Gradient: 5% B to 57% B in 6 min; Detector: UV 254 nm, 220 nm. The collected fractions were lyophilized to give 15 mg (15% yield) of the title compound as a pink solid. $^1$H-NMR (400 MHz, DMSO-d6) δ (ppm): 11.40 (br s, 1H), 7.85-7.83 (d, J=8.0 Hz, 1H), 7.77-7.71 (m, 2H), 3.83-3.80 (m, 2H), 3.50-3.44 (m, 3H), 3.35-3.24 (m, 3H), 3.05-2.98 (m, 2H), 2.67-2.63 (m, 2H), 2.42-2.40 (m, 1H), 2.24-2.22 (m, 1H), 1.89-1.79 (m, 1H), 1.56-1.48 (m, 2H), 1.14-1.05 (m, 2H). MS: (ES, m/z): 409 [M+H]$^+$.

Example 32

Preparation of N-hydroxy-2-oxospiro[pyrrolidine-3,2'-thiochromane]-6'-carboxamide 1',1'-dioxide (I-243)

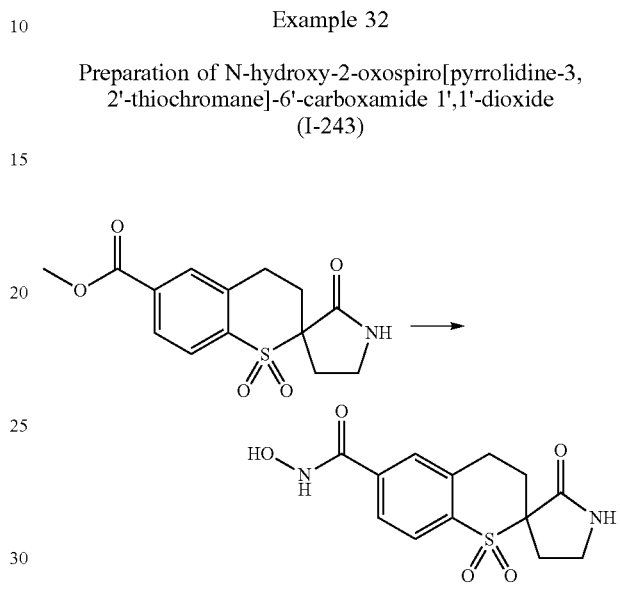

Into an 8-mL vial, was placed a solution of methyl 2-oxospiro[pyrrolidine-3,2'-thiochromane]-6'-carboxylate 1',1'-dioxide (50 mg, 0.16 mmol, 1 equiv) in THF/MeOH (4:1, 1 mL), NH$_2$OH (50% in H$_2$O, 0.48 mL, 30 equiv), and 1N aq. NaOH (0.32 mL, 2 equiv). The resulting solution was stirred for 2 h at room temperature. The crude product was purified by Prep-HPLC with the following conditions: Column: Xbridge C18, 19×150 mm, 5 μm; Mobile Phase A: Water/0.05% TFA, Mobile Phase B: CH$_3$CN/0.05% TFA; Flow rate: 25 mL/min; Gradient: 5% B to 57% B in 7 min; Detector: UV 254 nm, 220 nm. The collected fractions were lyophilized to give 4.6 mg (9% yield) of the title compound as a brown oil. $^1$H-NMR (400 MHz, DMSO-d6) δ (ppm): 11.39 (br s, 1H), 9.21 (br s, 1H), 8.35 (s, 1H), 7.86-7.84 (d, J=8.0 Hz, 1H), 7.77-7.75 (d, J=8.0 Hz, 1H), 7.70 (s, 1H), 3.33-3.27 (m, 3H), 3.05-2.98 (m, 1H), 2.71-2.60 (m, 2H), 2.43-2.32 (m, 1H), 2.27-2.20 (m, 1H). MS: (ES, m/z): 311 [M+H]$^+$.

Example 33

Preparation of N-hydroxy-1-methyl-2-oxospiro[pyrrolidine-3,2'-thiochromane]-6'-carboxamide 1',1'-dioxide (I-244)

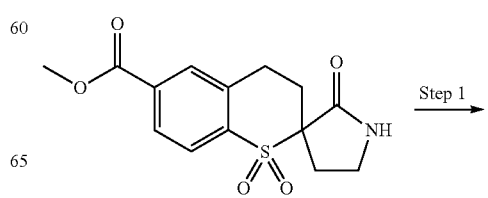

-continued

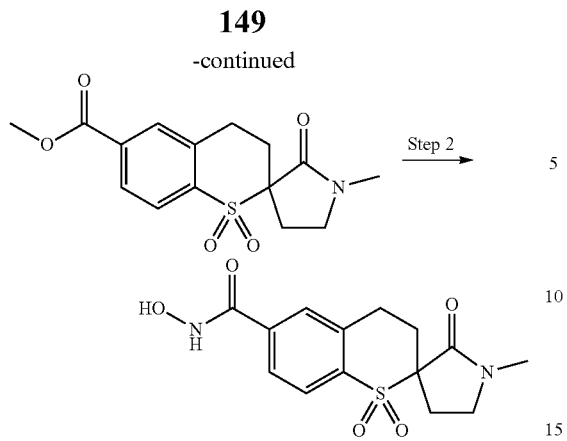

Step-1: Methyl 1-methyl-2-oxospiro[pyrrolidine-3, 2'-thiochromane]-6'-carboxylate 1',1'-dioxide Into an 8-mL vial, was placed a solution of methyl 2-oxospiro[pyrrolidine-3,2'-thiochromane]-6'-carboxylate 1',1'-dioxide (80 mg, 0.26 mmol, 1 equiv) in DMF (3 mL) and $Cs_2CO_3$ (104 mg, 0.75 mmol, 3 equiv). This was followed by the dropwise addition of $CH_3I$ (74 mg, 0.52 mmol, 2 equiv) with stirring at 0° C. The resulting mixture was stirred for 14 h at room temperature. The reaction was diluted with 20 mL of water and extracted with 2×20 mL of $CH_2Cl_2$. The organic layers were combined and washed with 3×10 mL of $H_2O$, dried over anhydrous $Na_2SO_4$, filtered and concentrated under vacuum. The residue was purified by normal phase chromatography on silica gel with $CH_2Cl_2$/MeOH (25:1) to give 46.4 mg (55% yield) of the title compound as a light yellow oil. MS: (ES, m/z): 324 [M+H]$^+$.

Step-2: N-Hydroxy-1-methyl-2-oxospiro[pyrrolidine-3,2'-thiochromane]-6'-carboxamide 1',1'-dioxide Into an 8-mL vial, was placed a solution of methyl 1-methyl-2-oxospiro[pyrrolidine-3,2'-thiochromane]-6'-carboxylate 1',1'-dioxide (46.4 mg, 0.14 mmol, 1 equiv) in THF/MeOH (4:1, 1.5 mL), $NH_2OH$ (50% in $H_2O$, 0.28 mL, 30 equiv), and 1N aq. NaOH (0.29 mL, 2 equiv). The resulting solution was stirred for 3 h at room temperature. The crude product was purified by Prep-HPLC with the following conditions: Column: Xbridge C18, 19×150 mm, 5 μm; Mobile Phase A: Water/0.05% TFA, Mobile Phase B: $CH_3CN$/0.05% TFA; Flow rate: 25 mL/min; Gradient: 4% B to 56% B in 7 min; Detector: UV 254 nm, 220 nm. The collected fractions were lyophilized to give 14.4 mg (23% yield) of the title compound as a brown oil. $^1$H-NMR (400 MHz, DMSO-d6) δ (ppm): 11.40 (br s, 1H), 9.21 (br s, 1H), 7.85-7.71 (m, 3H), 3.45-3.41 (m, 3H), 3.05-2.98 (m, 1H), 2.78 (s, 3H), 2.66-2.59 (m, 2H), 2.49-2.41 (m, 1H), 2.20-2.19 (m, 1H). MS: (ES, m/z): 325 [M+H]$^+$.

Example 34

Preparation of (R)-N-hydroxy-1'-methyl-5'-oxo-3,4-dihydro-1H-spiro[naphthalene-2,3'-pyrrolidine]-6-carboxamide (I-201)

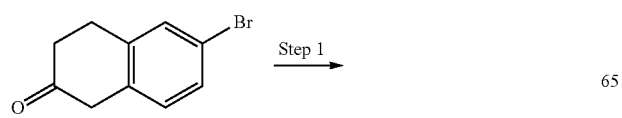

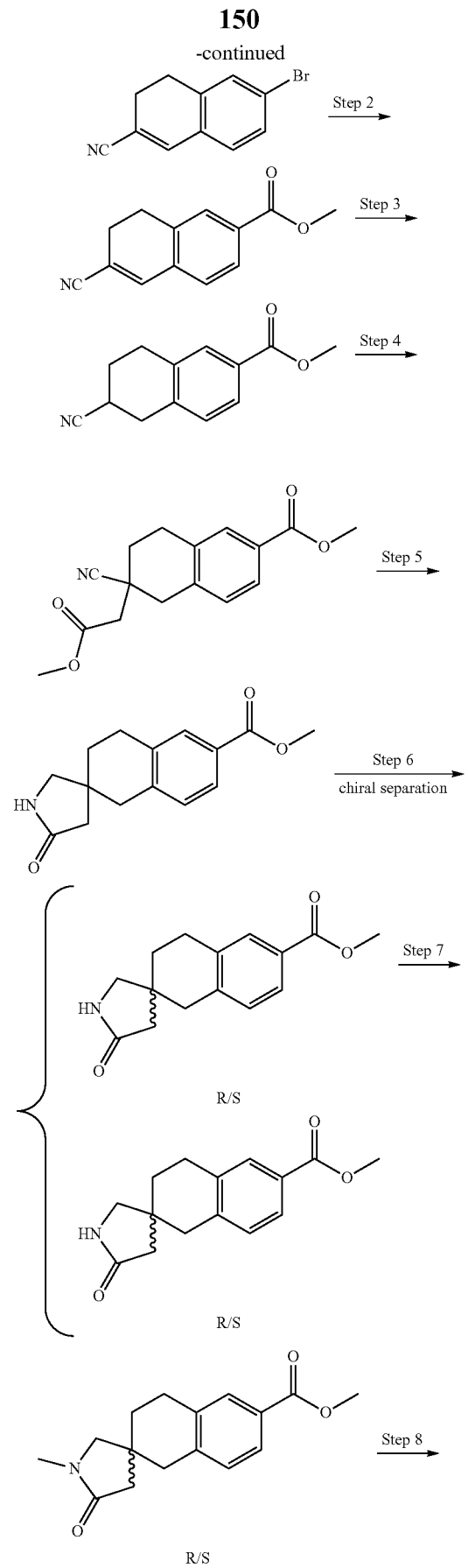

-continued

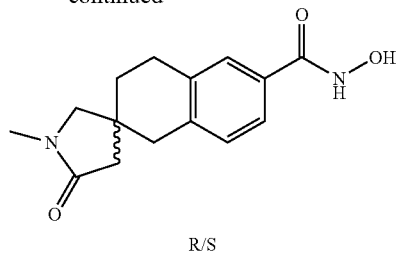

R/S

Step-1: 6-Bromo-3,4-dihydronaphthalene-2-carbonitrile

Into a 500-mL round-bottom flask, was placed a solution of 6-bromo-3,4-dihydronaphthalen-2(1H)-one (15.00 g, 66.64 mmol, 1 equiv) in toluene (150 mL), TMSCN (7.29 g, 1 equiv), and $ZnI_2$ (513 mg, 0.02 equiv). The resulting solution was stirred overnight at 25° C. Then pyrazine (100 mL) and $POCl_3$ (30 mL) were added to the solution and allowed to react with stirring for 4 h at 110° C. The reaction was then quenched by the addition of 1000 mL of 10% HCl aqueous solution at 0° C. The resulting solution was extracted with 3×500 mL of EtOAc. The combined organics were dried over anhydrous $Na_2SO_4$, filtered and concentrated under vacuum. The residue was purified by normal phase column chromatography on silica gel with EtOAc/petroleum ether (1:10). The collected fractions were concentrated under vacuum to give 6 g (38% yield) of the title compound as a yellow solid. MS: (ES, m/z): 234 $[M+H]^+$.

Step-2: Methyl 6-cyano-7,8-dihydronaphthalene-2-carboxylate

Into a 100-mL pressure tank reactor (60 atm), was placed a solution of 6-bromo-3,4-dihydronaphthalene-2-carbonitrile (6.00 g, 25.63 mmol, 1 equiv) in MeOH (40 mL), Pd(dppf)$Cl_2$ (1.88 g, 2.57 mmol, 0.10 equiv) and $Et_3N$ (7.80 g, 77.08 mmol, 3 equiv). CO (g) was introduced to the flask. The resulting solution was stirred overnight at 130° C. The resulting mixture was concentrated under vacuum. The residue was purified by normal phase column chromatography on silica gel with EtOAc/petroleum ether (1:3). The collected fractions were concentrated under vacuum to give 4.0 g (73% yield) of the title compound as a yellow solid. MS: (ES, m/z): 214 $[M+H]^+$.

Step-3: Methyl 6-cyano-5,6,7,8-tetrahydronaphthalene-2-carboxylate

Into a 500-mL round-bottom flask, was placed a solution of methyl 6-cyano-7,8-dihydronaphthalene-2-carboxylate (3.00 g, 14.07 mmol, 1 equiv) in MeOH (200 mL). Then magnesium (3.38 g, 139.07 mmol, 10 equiv) was added at 0° C. The resulting solution was stirred for 30 min at 0° C. The resulting mixture was the poured into 100 mL of water and MeOH was evaporated under vacuum. The pH of the solution was adjusted to 3 with 2N HCl at 0° C. The resulting solution was extracted with 3×100 mL of $CH_2Cl_2$, dried over anhydrous $Na_2SO_4$, filtered and concentrated under vacuum. The residue was purified by normal phase column chromatography on silica gel with EtOAc/petroleum ether (1:10). The collected fractions were concentrated under vacuum to give 1.9 g (63% yield) of the title compound as a white solid. MS: (ES, m/z): 216 $[M+H]^+$.

Step-4: Methyl 6-cyano-6-(2-methoxy-2-oxoethyl)-5,6,7,8-tetrahydronaphthalene-2-carboxylate Into a 250-mL 3-necked round-bottom flask purged and maintained with an inert atmosphere of nitrogen, was placed a solution of methyl 6-cyano-5,6,7,8-tetrahydronaphthalene-2-carboxylate (1.50 g, 6.97 mmol, 1 equiv) in THF (90 mL). LDA (2M in THF, 13.95 mL, 2 equiv) was added dropwise into the solution at −78° C. The resulting solution was stirred for 1 h at −78° C. 2-Bromoacetate (2.12 g, 1 equiv) was the added dropwise into the solution at −78° C. The resulting solution was allowed to react with stirring for 3 h at 25° C. The reaction was then quenched by the addition of 150 mL of aq. $NH_4Cl$ solution, then extracted with 3×100 mL of EtOAc. The combined organics were dried over anhydrous $Na_2SO_4$, filtered and concentrated under vacuum. The residue was purified by normal phase column chromatography on silica gel with EtOAc/petroleum ether (1:5). The collected fractions were concentrated under vacuum to give 450 mg (22% yield) of the title compound as a yellow solid. MS: (ES, m/z): 288 $[M+H]^+$.

Step-5: Methyl 5'-oxo-3,4-dihydro-1H-spiro[naphthalene-2,3'-pyrrolidine]-6-carboxylate Into a 100-mL round-bottom flask, was placed a solution of methyl 6-cyano-6-(2-methoxy-2-oxoethyl)-5,6,7,8-tetrahydronaphthalene-2-carboxylate (550 mg, 1.91 mmol, 1 equiv) in MeOH (25 mL), $PtO_2$ (225 mg, 0.99 mmol), and AcOH (5 mL, 87.26 mmol). Hydrogen gas was introduced into the flask and the resulting solution was stirred for 1 h at 25° C. The solids were filtered out and the filtrate was concentrated under vacuum. The residue was dissolved in 7M $NH_3$ in MeOH (25 mL) and allowed to react with stirring for 1 h at 25° C. The resulting mixture was concentrated under vacuum and the residue was purified by normal phase column chromatography on silica gel with $CH_2Cl_2$/MeOH (100:1). The collected fractions were concentrated under vacuum to give 250 mg (50% yield) of the title compound as a white solid. MS: (ES, m/z): 260 $[M+H]^+$.

Step-6: Chiral separation of methyl (R)-5'-oxo-3,4-dihydro-1H-spiro[naphthalene-2,3'-pyrrolidine]-6-carboxylate and methyl (S)-5'-oxo-3,4-dihydro-1H-spiro[naphthalene-2,3'-pyrrolidine]-6-carboxylate 250 mg of the racemate methyl 5'-oxo-3,4-dihydro-1H-spiro[naphthalene-2,3'-pyrrolidine]-6-carboxylate was separated by Chiral-Prep-HPLC with the following conditions: Column: Phenomenex Lux 5u Cellulose-4AXIA Packed, 250×21.2 mm, 5 μm; Mobile Phase A: Hexanes, Mobile Phase B: EtOH; Gradient: hold 30% B in 25 min; Detector: UV 254 nm, 220 nm. The first eluting isomer (Rt 3.626 min) was collected and concentrated under vacuum to give 105 mg (42% yield) of a white solid which was assigned as the R isomer of methyl 5'-oxo-3,4-dihydro-1H-spiro[naphthalene-2,3'-pyrrolidine]-6-carboxylate. MS: (ES, m/z): 260 $[M+H]^+$. The second eluting isomer (Rt 4.410 min) was collected and concentrated under vacuum to give 100 mg (40% yield) of a white solid which was assigned as the S isomer of methyl 5'-oxo-3,4-dihydro-1H-spiro[naphthalene-2,3'-pyrrolidine]-6-carboxylate as a white solid. MS: (ES, m/z): 260 $[M+H]^+$.

Step-7: Methyl (R)-1'-methyl-5'-oxo-3,4-dihydro-1H-spiro[naphthalene-2,3'-pyrrolidine]-6-carboxylate Into a 10-mL round-bottom flask, was placed a solution of the first eluted isomer from Step 6, which was assigned as methyl (R)-5'-oxo-3,4-dihydro-1H-spiro[naphthalene-2,3'-pyrrolidine]-6-carboxylate as described above, (50 mg, 0.19 mmol, 1 equiv) in DMF (2 mL). NaH (60% dispersion in oil, 9 mg, 2 equiv) was added into the solution at 0° C. The resulting mixture was stirred for 1 h at 25° C. Iodomethane (55 mg, 0.39 mmol, 2 equiv) was added into the solution and the resulting solution was allowed to react with stirring for 1 h at 25° C. The reaction was then quenched by the addition of 15 mL of water, extracted with 3×15 mL of EtOAc. The combined extracts were dried over anhydrous $Na_2SO_4$, filtered and concentrated under vacuum to give 50 mg (90% yield) of the title compound as a yellow solid. MS: (ES, m/z): 274 $[M+H]^+$.

Step-8: (R)-N-Hydroxy-1'-methyl-5'-oxo-3,4-dihydro-1H-spiro[naphthalene-2,3'-pyrrolidine]-6-carboxamide Into a 10-mL round-bottom flask, was placed a solution of the product from Step 7, which was assigned as methyl (R)-1'-methyl-5'-oxo-3,4-dihydro-1H-spiro[naphthalene-2,3'-pyrrolidine]-6-carboxylate as described above, (50 mg, 0.18 mmol, 1 equiv) in THF/MeOH (4:1, 2 mL), $NH_2OH$ (50% in water, 725 mg, 14.20 mmol, 120 equiv), and 1N aq. NaOH (14.4 mg, 0.36 mmol, 2 equiv). The resulting solution was stirred for 2 h at 25° C. The crude product was purified by Prep-HPLC with the following conditions: Column: XBridge Prep C18 OBD, 19×150 mm 5 µm; Mobile Phase A: Water/0.1% Formic acid, Mobile Phase B: $CH_3CN$; Gradient: 5% B to 30% B in 7 min; Detector: UV 254 nm, 220 nm. The collected fractions were lyophilized to give 17.9 mg (36% yield) of the title compound as a light pink solid. $^1$H-NMR (400 MHz, DMSO-d6) δ (ppm): 11.08 (s, 1H), 8.95 (s, 1H), 7.51 (s, 1H), 7.47-7.45 (d, J=8.0 Hz, 1H), 7.13-7.11 (d, J=8.0 Hz, 1H), 3.24-3.22 (d, J=9.6 Hz, 1H), 3.08-3.05 (d, J=9.6 Hz, 1H), 2.86-2.82 (m, 2H), 2.78-2.76 (d, J=8.4 Hz, 2H), 2.71 (s, 3H), 2.27-2.23 (d, J=16.4 Hz, 1H), 2.03-1.99 (d, J=16.4 Hz, 1H), 1.80-1.76 (m, 2H). MS: (ES, m/z): 275 $[M+H]^+$.

TABLE-20

The following compounds were prepared according to the method of Example 34, with the following modifications: (1) In Step 7, the first eluted product from Step 6 was used; (2) in Step 7, the halide can be an iodide, a chloride, or a bromide.

| Ex. | Structure | $^1$H-NMR δ (ppm) | Found (ES, m/z) [M + H]$^+$ |
|---|---|---|---|
| I-215 | (R/S, spiro[naphthalene-pyrrolidine] with N-(oxetan-3-ylmethyl), N-hydroxy carboxamide) | (300 MHz, DMSO-d6): 7.51 (s, 1H), 7.48 (d, J = 8.1 Hz, 1H), 7.13 (d, J = 8.1 Hz, 1H), 4.64-4.59 (m, 2H), 4.31-4.26 (m, 2H), 3.49 (d, J = 7.5 Hz, 2H), 3.21-3.11 (m, 2H), 3.05 (d, J = 9.6 Hz, 1H), 2.86-2.82 (m, 2H), 2.75 (s, 2H), 2.27 (d, J = 16.5 Hz, 1H), 2.04 (d, J = 16.5 Hz, 1H), 1.79-1.75 (m, 2H) | 331 |
| I-219 | (R/S, spiro[naphthalene-pyrrolidine] with N-(3-methoxypropyl), N-hydroxy carboxamide) | (300 MHz, DMSO-d6 + D$_2$O): 7.51 (s, 1H), 7.47 (d, J = 8.1 Hz, 1H), 7.13 (d, J = 8.1 Hz, 1H), 3.29-3.18 (m, 8H), 3.08 (d, J = 9.6 Hz, 1H), 2.87-2.83 (m, 2H), 2.77-2.76 (m, 2H), 2.27 (d, J = 16.2 Hz, 1H), 2.04 (d, J = 16.5 Hz, 1H), 1.81-1.77 (m, 2H), 1.70-1.61 (m, 2H) | 333 |
| I-206 | (R/S, spiro[naphthalene-pyrrolidine] with N-ethyl, N-hydroxy carboxamide) | (300 MHz, DMSO-d6): 10.95 (s, 1H), 8.95 (s, 1H), 7.52 (s, 1H), 7.48 (d, J = 8.1 Hz, 1H), 7.13 (d, J = 8.1 Hz, 1H), 3.32-3.17 (m, 3H), 3.08 (d, J = 9.9 Hz, 1H), 2.87-2.76 (m, 4H), 2.26 (d, J = 16.2 Hz, 1H), 2.03 (d, J = 16.5 Hz, 1H), 1.81-1.79 (m, 2H), 1.03-1.00 (m, 3H) | 289 |

TABLE-20-continued

The following compounds were prepared according to the method of Example 34,
with the following modifications: (1) In Step 7, the first eluted product from Step 6 was used; (2)
in Step 7, the halide can be an iodide, a chloride, or a bromide.

| Ex. | Structure | $^1$H-NMR δ (ppm) | Found (ES, m/z) [M + H]$^+$ |
|---|---|---|---|
| I-220 | R/S | (300 MHz, DMSO-d6): 10.80 (s, 1H), 9.00 (s, 1H), 7.52 (s, 1H), 7.48 (d, J = 7.8 Hz, 1H), 7.13 (d, J = 7.8 Hz, 1H), 4.11-4.02 (m, 2H), 3.38-3.35 (m, 1H), 3.25-3.22 (m, 1H), 2.87-2.83 (m, 2H), 2.80-1.73 (m, 2H), 2.37 (d, J = 16.8 Hz, 1H), 2.15 (d, J = 16.8 Hz, 1H), 1.81-1.79 (m, 2H) | 343 |
| I-207 | R/S | (400 MHz, DMSO-d6): 11.11 (s, 1H), 8.98 (s, 1H), 7.53-7.47 (m, 2H), 7.14 (d, J = 8.0 Hz, 1H), 3.24 (d, J = 9.6 Hz, 1H), 3.09 (d, J = 9.6 Hz, 1H), 2.99 (d, J = 7.6 Hz, 2H), 2.88-2.78 (m, 4H), 2.30 (d, J = 16.4 Hz, 1H), 2.07 (d, J = 16.4 Hz, 1H), 1.85-1.79 (m, 3H), 0.85-0.83 (m, 6H) | 317 |
| I-208 | R/S | (400 MHz, DMSO-d6): 11.11 (s, 1H), 8.96 (s, 1H), 7.52-7.46 (m, 2H), 7.13 (d, J = 8.0 Hz, 1H), 4.19-4.15 (m, 1H), 3.15 (d, J = 10.0 Hz, 1H), 3.03 (d, J = 9.6 Hz, 1H), 2.87-2.74 (m, 4H), 2.25 (d, J = 16.4 Hz, 1H), 2.03 (d, J = 16.4 Hz, 1H), 1.80-1.76 (m, 2H), 1.05-1.02 (m, 6H) | 303 |
| I-216 | R/S | (400 MHz, DMSO-d6): 11.05 (s, 1H), 8.96 (s, 1H), 7.47 (s, 1H), 7.44 (d, J = 8.0 Hz, 1H), 7.38-7.21 (m, 5H), 7.06 (d, J = 8.0 Hz, 1H), 7.37 (s, 2H), 3.11 (d, J = 9.6 Hz, 1H), 2.96 (d, J = 9.6 Hz, 1H), 2.87-2.71 (m, 4H), 2.35 (d, J = 16.8 Hz, 1H), 2.13 (d, J = 16.8 Hz, 1H), 1.75 (s, 2H) | 351 |
| I-225 | R/S | (400 MHz, DMSO-d6): 11.04 (br s, 1H), 8.96 (br s, 1H), 7.48-7.43 (m, 2H), 7.18-7.14 (m, 4H), 7.09 (d, J = 8 Hz, 1H), 4.39 (s, 2H), 3.05 (d, J = 10 Hz, 1H), 2.92 (d, J = 9.6 Hz, 1H), 2.87-2.71 (m, 4H), 2.37 (d, J = 16.4 Hz, 1H), 2.24 (s, 3H), 2.14 (d, J = 16.4 Hz, 1H), 1.79-1.74 (m, 2H) | 365 |

TABLE-21

The following compounds were prepared according to the method of Example 34,
with the following modifications: (1) In Step 7, the second eluted product from Step 6 was used;
(2) In Step 7, the halide can be an iodide, a chloride, or a bromide.

| Ex. | Structure | ¹H-NMR δ (ppm) | Found (ES, m/z) [M + H]⁺ |
|---|---|---|---|
| I-202 | R/S | (300 MHz, DMSO-d6): 11.01 (s, 1H), 8.94 (s, 1H), 7.51 (s, 1H), 7.47 (d, J = 7.8 Hz, 1H), 7.11 (d, J = 7.8 Hz, 1H), 3.23 (d, J = 9.9 Hz, 1H), 3.07 (d, J = 9.9 Hz, 1H), 2.84 (m, 2H), 2.77-2.76 (m, 2H), 2.71 (s, 3H), 2.25 (d, J = 16.5 Hz, 1H), 2.02 (d, J = 16.5 Hz, 1H), 1.80-1.76 (m, 2H) | 275 |
| I-210 | R/S | (300 MHz, DMSO-d6): 11.08 (br s, 1H), 8.95 (br s, 1H), 7.51-7.45 (m, 2H), 7.12 (d, J = 8.1 Hz, 1H), 3.21-3.17 (m, 3H), 3.04 (d, J = 9.9 Hz, 1H), 2.85-2.81 (m, 2H), 2.75-2.65 (m, 2H), 2.50-2.41 (m, 1H), 2.25 (d, J = 16.5 Hz, 1H), 2.05-1.84 (m, 3H), 1.82-1.75 (m, 4H), 1.73-1.58 (m, 2H) | 329 |
| I-217 | R/S | (300 MHz, DMSO-d6): 7.50-7.45 (m, 2H), 7.06 (d, J = 7.8 Hz, 1H), 4.63-4.58 (m, 2H), 4.30-4.25 (m, 2H), 3.49 (d, J = 7.5 Hz, 2H), 3.20-3.02 (m, 3H), 2.84-2.80 (m, 2H), 2.72 (s, 2H), 2.28-2.23 (m, 1H), 2.03 (d, J = 16.5 Hz, 1H), 1.77-1.73 (m, 2H) | 331 |
| I-222 | R/S | (400 MHz, DMSO-d6): 7.50-7.45 (m, 2H), 7.15 (d, J = 7.6 Hz, 1H), 3.74-3.20 (m, 8H), 3.10 (d, J = 9.6 Hz, 1H), 2.87-2.83 (m, 2H), 2.78 (d, J = 7.2 Hz, 2H), 2.29 (d, J = 16.4 Hz, 1H), 2.06 (d, J = 16.4 Hz, 1H), 1.80-1.78 (m, 2H), 1.70-1.63 (m, 2H) | 333 |
| I-211 | R/S | (300 MHz, DMSO-d6): 11.09 (br s, 1H), 8.95 (br s, 1H), 7.51-7.45 (m, 2H), 7.13 (d, J = 8.1 Hz, 1H), 3.25-3.16 (m, 3H), 3.08 (d, J = 9.6 Hz, 1H), 2.87-2.82 (m, 2H), 2.77-2.76 (m, 2H), 2.26 (d, J = 16.2 Hz, 1H), 2.02 (d, J = 16.5 Hz, 1H0, 1.81-1.76 (m, 2H), 1.02-0.97 (m, 3H) | 289 |

TABLE-21-continued

The following compounds were prepared according to the method of Example 34, with the following modifications: (1) In Step 7, the second eluted product from Step 6 was used; (2) In Step 7, the halide can be an iodide, a chloride, or a bromide.

| Ex. | Structure | $^1$H-NMR δ (ppm) | Found (ES, m/z) [M + H]$^+$ |
|---|---|---|---|
| I-223 | R/S | (300 MHz, DMSO-d6): 11.01 (br s, 1H), 9.04 (br s, 1H), 7.52-7.34 (m, 2H), 7.13 (d, J = 7.8 Hz, 1H), 4.11-4.01 (m, 2H), 3.38 (s, 1H), 3.24 (d, J = 9.3 Hz, 1H), 2.85-2.78 (m, 4H), 2.37 (d, J = 16.5 Hz, 1H), 2.14 (d, J = 16.8 Hz, 1H), 1.83-1.79 (m, 2H) | 343 |
| I-212 | R/S | (300 MHz, DMSO-d6): 11.10 (br s, 1H), 8.95 (br s, 1H), 7.51-7.45 (m, 2H), 7.13 (d, J = 8.1 Hz, 1H), 3.22 (d, J = 9.9 Hz, 1H), 3.07 (d, J = 9.6 Hz, 1H), 2.98-2.91 (m, 2H), 2.87-2.83 (m, 2H), 2.77 (s, 2H), 2.29 (d, J = 16.5 Hz, 1H), 2.06 (d, J = 16.2 Hz, 1H), 1.88-1.69 (m, 3H), 0.83-0.80 (m, 6H) | 317 |
| I-213 | R/S | (400 MHz, DMSO-d6): 11.10 (s, 1H), 8.95 (s, 1H), 7.52-7.46 (m, 2H), 7.13 (d, J = 8 Hz, 1H), 4.19-4.15 (m, 1H), 3.15 (d, J = 10 Hz, 1H), 3.03 (d, J = 9.6 Hz, 1H), 2.87-2.83 (m, 2H), 2.76-2.74 (m, 2H), 2.25 (d, J = 16.4 Hz, 1H), 2.03 (d, J = 16.4 Hz, 2H), 1.80-1.76 (m, 2H), 1.05-1.02 (m, 6H) | 303 |
| I-218 | R/S | (300 MHz, DMSO-d6): 11.07 (br s, 1H), 8.97 (br s, 1H), 7.47-7.42 (m, 2H), 7.36-7.21 (m, 5H), 7.08 (d, J = 8.1 Hz, 1H), 4.37 (s, 2H), 3.11 (d, J = 9.9 Hz, 1H), 2.96 (d, J = 9.9 Hz, 1H), 2.89-2.74 (m, 4H), 2.36 (d, J = 16.5 Hz, 1H), 2.13 (d, J = 16.5 Hz, 1H), 1.78-1.73 (m, 2H) | 351 |

Example 35

Preparation of (R)-1'-(cyclobutylmethyl)-N-hydroxy-5'-oxo-3,4-dihydro-1H-spiro[naphthalene-2,3'-pyrrolidine]-6-carboxamide (I-205)

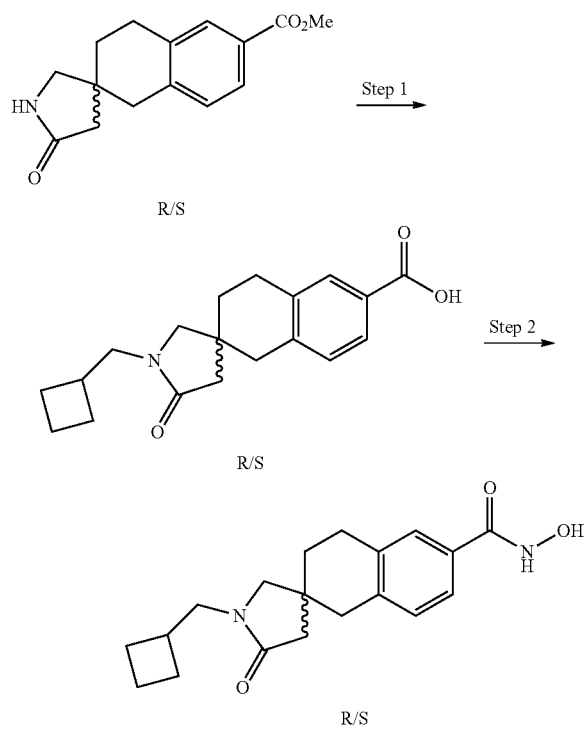

Step-1: (R)-1'-(Cyclobutylmethyl)-5'-oxo-3,4-dihydro-H-spiro[naphthalene-2,3'-pyrrolidine]-6-carboxylic acid Into a 10-mL round-bottom flask purged and maintained with an inert atmosphere of nitrogen was placed a solution of the first eluted isomer from Example 34, Step 6, which was assigned as methyl (R)-5'-oxo-3,4-dihydro-1H-spiro[naphthalene-2,3'-pyrrolidine]-6-carboxylate as described above, (50 mg, 0.19 mmol, 1 equiv) in DMF (2 mL). This was followed by the portionwise addition of NaH (60% dispersion in oil, 30 mg, 0.75 mmol, 3.89 equiv) at 0° C. The mixture was stirred for 30 min at 25° C. To this was added (bromomethyl)cyclobutane (115 mg, 0.77 mmol, 4 equiv). The resulting solution was stirred for 2 h at 25° C. The reaction was then poured into 10 mL of ice/water. The resulting solution was extracted with 10 mL of EtOAc. The pH of the aqueous layer was adjusted to 3 with 6N HCl. The resulting solution was extracted with 3×50 mL of $CH_2Cl_2$, dried over anhydrous $Na_2SO_4$, filtered and concentrated under vacuum. The residue was purified by normal phase chromatography on silica gel column with $CH_2Cl_2$/MeOH (10:1). The collected fractions were concentrated under vacuum to give 67 mg (crude) of the title compound as a yellow oil. MS: (ES, m/z): 314 $[M+H]^+$.

Step-2: (R)-1'-(Cyclobutylmethyl)-N-hydroxy-5'-oxo-3,4-dihydro-1H-spiro[naphthalene-2,3'-pyrrolidine]-6-carboxamide Into a 25-mL round-bottom flask was placed a solution of the product from Step 1, which was assigned as (R)-1'-(cyclobutylmethyl)-5'-oxo-3,4-dihydro-1H-spiro[naphthalene-2,3'-pyrrolidine]-6-carboxylic acid as described above, (67 mg, 0.21 mmol, 1 equiv) in DMA (3 mL). This was followed by the dropwise addition of isopropyl chloroformate (135 mg, 1.10 mmol, 5.15 equiv) with stirring at 0° C. NMM (128 mg, 1.27 mmol, 5.92 equiv) was added to the solution dropwise with stirring at 0° C. The mixture was stirred for 30 min at 0° C. Next, a solution of $NH_2OH·HCl$ (75 mg, 1.08 mmol, 5.05 equiv) in DMA (2 mL) was added dropwise with stirring at 0° C. The resulting solution was stirred overnight at room temperature. The solids were filtered out and the crude product was purified by Prep-HPLC with the following conditions: Column: XBridge Prep C18 OBD, 19×150 mm 5 μm; Mobile Phase A: Water/0.1% Formic Acid, Mobile Phase B: $CH_3CN$/0.1% Formic Acid; Gradient: 25% B up to 55% B in 7 min; Detector: UV 254, 220 nm. The collected fractions were lyophilized to give 10.5 mg (15% yield) of the title compound as a pink solid. $^1$H-NMR (400 MHz, DMSO-d6) δ (ppm): 11.17 (br s, 1H), 8.97 (br s, 1H), 7.46-7.44 (m, 2H), 7.10 (d, J=8.0 Hz, 1H), 3.19-3.16 (m, 3H), 3.03 (d, J=9.6 Hz, 1H), 2.84-2.80 (m, 2H), 2.78-2.72 (m, 2H), 2.48-2.41 (m, 1H), 2.24 (d, J=16.4 Hz, 1H), 2.03-1.91 (m, 3H), 1.83-1.74 (m, 4H), 1.68-1.60 (m, 2H). MS: (ES, m/z): 329 $[M+H]^+$.

Example 36

Preparation of (R)-N-hydroxy-5'-oxo-1'-(pyridin-3-ylmethyl)-3,4-dihydro-1H-spiro[naphthalene-2,3'-pyrrolidine]-6-carboxamide (I-226)

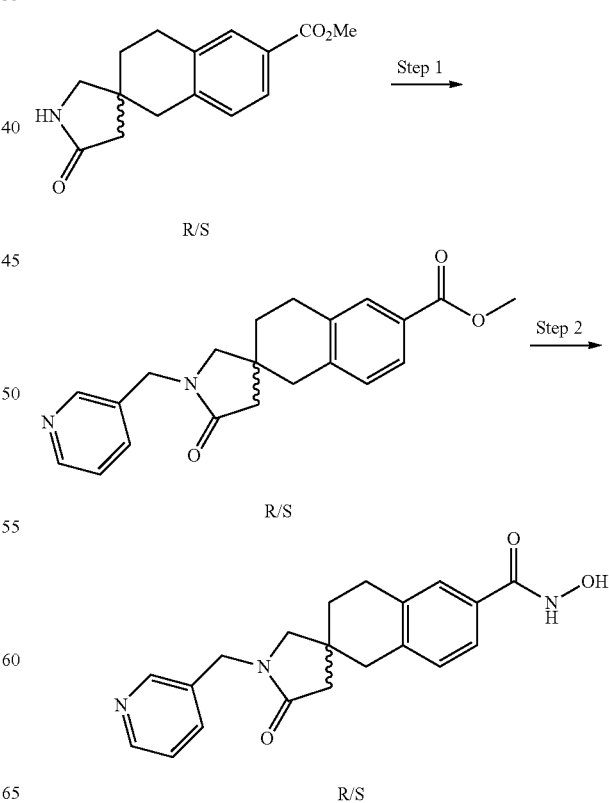

Step-1: Methyl (R)-5'-oxo-1'-(pyridin-3-ylmethyl)-3,4-dihydro-1H-spiro[naphthalene-2,3'-pyrrolidine]-6-carboxylate Into a 10-mL vial was placed a solution of the first eluted isomer from Example 34, Step 6, which was assigned as methyl (R)-5'-oxo-3,4-dihydro-1H-spiro[naphthalene-2,3'-pyrrolidine]-6-carboxylate as described above, (60 mg, 0.23 mmol, 1 equiv) in DMF (5 mL). This was followed by the portionwise addition of NaH (60% in oil, 56 mg, 1.40 mmol, 6 equiv) at 0° C. The resulting solution was stirred for 30 min at room temperature. Next, a solution of Et$_3$N (93 mg, 0.92 mmol, 4 equiv) and 3-(bromomethyl)pyridine hydrobromide (232 mg, 0.92 mmol, 4 equiv) in DMF (1 mL) were added dropwise at 0° C. The resulting solution was stirred for 2 h at 25° C. The reaction mixture was poured into 20 mL of water/ice. The resulting solution was extracted with 3×20 mL of EtOAc, dried over anhydrous Na$_2$SO$_4$, filtered and concentrated under vacuum to give 47 mg (58% yield) of the title compound as a yellow oil. MS: (ES, m/z): 351 [M+H]$^+$.

Step-2: (R)-N-Hydroxy-5'-oxo-1'-(pyridin-3-ylmethyl)-3,4-dihydro-1H-spiro[naphthalene-2,3'-pyrrolidine]-6-carboxamide Into a 25-mL round-bottom flask was placed a solution of the product from Step 1, which was assigned as methyl (R)-5'-oxo-1'-(pyridin-3-ylmethyl)-3,4-dihydro-1H-spiro[naphthalene-2,3'-pyrrolidine]-6-carboxylate as described above, (47 mg, 0.13 mmol, 1 equiv) in THF/MeOH (4:1, 2 mL), and NH$_2$OH (50% in water, 531 mg, 8.04 mmol, 60 equiv). This was followed by the dropwise addition of 1N aq. NaOH (0.3 mL, 0.27 mmol, 2 equiv). The resulting solution was stirred for 2 h at 25° C. The solids were filtered and the crude product was purified by Prep-HPLC with the following conditions: Column: XBridge Prep C18 OBD, 19×150 mm 5 μm; Mobile Phase A: Water/0.01% NH$_4$HCO$_3$, Mobile Phase B: CH$_3$CN/0.01% NH$_4$HCO$_3$; Gradient: 5% B up to 20% B in 6 min; Detector: UV 254, 220 nm. The collected fractions were lyophilized to give 13.7 mg (29% yield) of the title compound as a brown solid. $^1$H-NMR (400 MHz, DMSO-d6) δ (ppm): 10.90 (br s, 1H), 9.07 (br s, 1H), 8.50-8.47 (m, 2H), 7.65 (d, J=8 Hz, 1H), 7.49-7.44 (m, 2H), 7.40-7.36 (m, 1H), 7.08 (d, J=8 Hz, 1H), 4.42 (s, 2H), 3.15 (d, J=10 Hz, 1H), 3.00 (d, J=10 Hz, 1H), 2.90-2.74 (m, 4H), 2.37 (d, J=16.4 Hz, 1H), 2.14 (d, J=16.8 Hz, 1H), 1.81-1.76 (m, 2H). MS: (ES, m/z): 352 [M+H]$^+$.

Example 37

Preparation of (R)-N-hydroxy-5'-oxo-1'-phenyl-3,4-dihydro-1H-spiro[naphthalene-2,3'-pyrrolidine]-6-carboxamide (I-203)

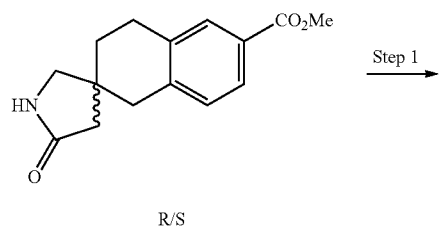

R/S

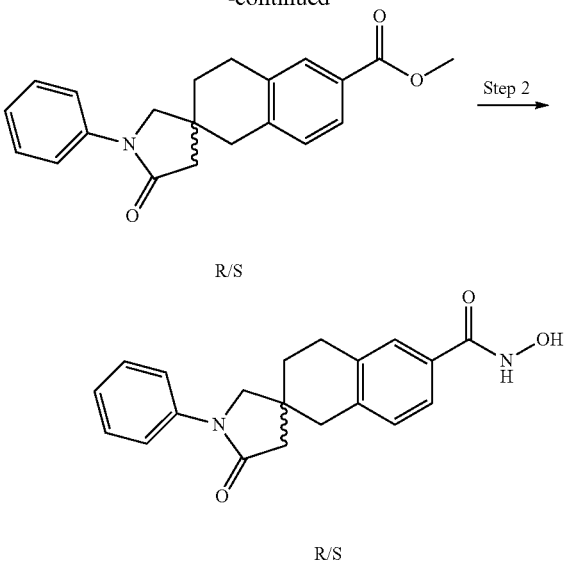

Step-1: Methyl (R)-5'-oxo-1'-phenyl-3,4-dihydro-1H-spiro[naphthalene-2,3'-pyrrolidine]-6-carboxylate Into a 50-mL round-bottom flask, was placed a solution of the first eluted isomer from Example 34, Step 6, which was assigned as methyl (R)-5'-oxo-3,4-dihydro-1H-spiro[naphthalene-2,3'-pyrrolidine]-6-carboxylate as described above, (50 mg, 0.19 mmol, 1 equiv) in CH$_2$Cl$_2$ (15 mL), Et$_3$N (58 mg, 0.57 mmol, 3 equiv), phenylboronic acid (48 mg, 0.39 mmol, 2 equiv), Cu(OAc)$_2$ (38 mg, 0.21 mmol, 1 equiv), and 4 Å molecular sieves (100 mg). O$_2$ was introduced into the flask and the resulting solution was stirred overnight at 25° C. The reaction was then quenched by the addition of 20 mL of water and diluted with 20 mL of CH$_2$Cl$_2$. The solids were filtered out and the filtrate was extracted with 2×20 mL of CH$_2$Cl$_2$. The combined organics were dried over anhydrous Na$_2$SO$_4$, filtered and concentrated under vacuum. The residue was purified by normal phase column chromatography on silica gel with EtOAc/petroleum ether (1:3). The collected fractions were concentrated under vacuum to give 60 mg (92% yield) of the title compound as a yellow oil. MS: (ES, m/z): 336 [M+H]$^+$.

Step-2: (R)-N-Hydroxy-5'-oxo-1'-phenyl-3,4-dihydro-1H-spiro[naphthalene-2,3'-pyrrolidine]-6-carboxamide Into a 10-mL round-bottom flask, was placed a solution of the product from Step 1, which was assigned as methyl (R)-5'-oxo-1'-phenyl-3,4-dihydro-1H-spiro[naphthalene-2,3'-pyrrolidine]-6-carboxylate as described above, (60 mg, 0.18 mmol, 1 equiv) in THF/MeOH (4:1, 2 mL), NH$_2$OH (50% in water, 709 mg, 120 equiv), and 1N aq. NaOH (14.4 mg, 0.36 mmol, 2 equiv). The resulting solution was stirred for 2 h at 25° C. The crude product was purified by Prep-HPLC with the following conditions: Column: XBridge Prep C18 OBD, 19×150 μm 5 μm; Mobile Phase A: Water/0.1% Formic acid, Mobile Phase B: CH$_3$CN; Gradient: 20% B to 45% B in 7 min; Detector: UV 254 nm, 220 nm. The collected fractions were lyophilized to give 23.9 mg (40% yield) of the title compound as a white solid. $^1$H-NMR (400 MHz, DMSO-d6) δ (ppm): 11.06 (s, 1H), 8.94 (s, 1H), 7.63-7.61 (m, 2H), 7.52 (s, 1H), 7.47-7.44 (m, 1H), 7.35-7.31 (m, 2H), 7.14-7.08 (m, 2H), 3.77-3.74 (d, J=9.6 Hz, 1H), 3.57-3.55 (d, J=9.6 Hz, 1), 2.96-2.80 (m, 4H), 2.58-2.54 (d, J=16.8 Hz, 1H), 2.33-2.28 (d, J=16.8 Hz, 1H), 1.89-1.85 (m, 2H). MS: (ES, m/z): 337 [M+H]$^+$.

TABLE-22

The following compounds were prepared according to the method of Example 37 with the first eluted product from Example 34, Step 6.

| Ex. | Structure | $^1$H-NMR δ (ppm) | Found (ES, m/z) [M + H]$^+$ |
|---|---|---|---|
| I-209 | 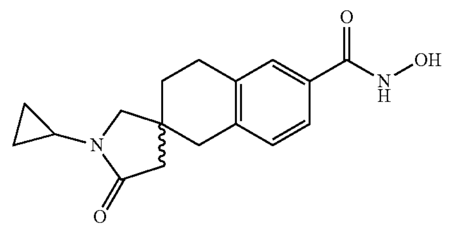 | (400 MHz, DMSO-d6): 11.08 (s, 1H), 8.93 (s, 1H), 7.49-7.44 (m, 2H), 7.10 (d, J = 8.0 Hz, 1H), 3.13 (d, J = 9.6 Hz, 1H), 2.96 (d, J = 9.6 Hz, 1H), 2.83-2.60 (m, 5H), 2.25 (d, J = 16.4 Hz, 1H), 2.01 (d, J = 16.8 Hz, 1H), 1.75-1.72 (m, 2H), 0.64-0.52 (m, 4H) | 301 |
| I-221 | 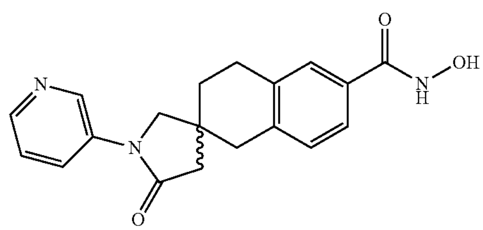 | (300 MHz, DMSO-d6): 11.16 (s, 1H), 8.96 (s, 1H), 8.87 (d, J = 2.4 Hz, 1H), 8.33 (d, J = 3.3 Hz, 1H), 8.07 (d, J = 7.5 Hz, 1H), 7.54 (s, 1H), 7.48 (d, J = 7.8 Hz, 1H), 7.39 (m, 1H), 7.14 (d, J = 7.8 Hz, 1H), 3.82 (d, J = 9.9 Hz, 1H), 3.63 (d, J = 9.9 Hz, 1H), 2.90-2.88 (m, 4H), 2.60 (d, J = 16.5 Hz, 1H), 2.35 (d, J = 16.5 Hz, 1H), 1.89 (s, 2H) | 338 |
| I-227 | 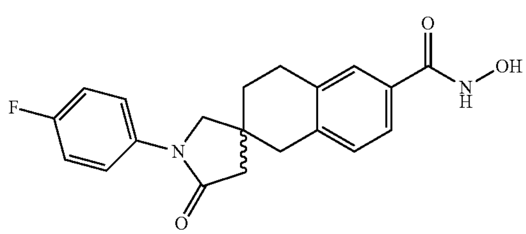 | (400 MHz, DMSO-d6): 11.11 (br s, 1H), 8.99 (br s, 1H), 7.70-7.64 (m, 2H), 7.54 (s, 1H), 7.49-7.41 (m, 1H), 7.23-7.08 (m, 3H), 3.77 (d, J = 10 Hz, 1H), 3.57 (d, J = 9.6 Hz, 1H), 3.98-2.86 (m, 4H), 2.8 (d, J = 16.8 Hz, 1H), 2.32 (d, J = 16.4 Hz, 1H), 1.90-1.87 (m, 2H) | 355 |

TABLE-23

The following compounds were prepared according to the method of Example 37, with the following modification: In Step 1, the second eluted product from Example 34, Step 6 was used.

| Ex. | Structure | $^1$H-NMR δ (ppm) | Found (ES, m/z) [M + H]$^+$ |
|---|---|---|---|
| I-204 | 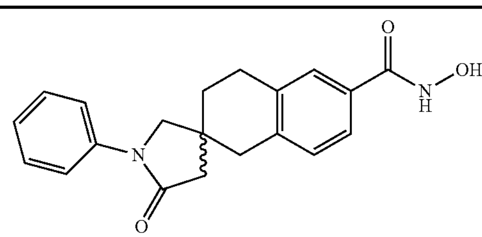 | (300 MHz, DMSO-d6): 11.09 (s, 1H), 9.00 (s, 1H), 7.64 (d, J = 7.8 Hz, 2H), 7.54 (s, 1H), 7.48 (d, J = 7.8 Hz, 1H), 7.37-7.32 (m, 2H), 7.16-7.09 (m, 2H), 3.78 (d, J = 9.9 Hz, 1H), 3.58 (d, J = 9.9 Hz, 1H), 2.94-2.86 (m, 4H), 2.58 (d, J = 16.8 Hz, 1H), 2.32 (d, J = 16.8 Hz, 1H), 1.91-1.86 (m, 2H) | 337 |

TABLE-23-continued

The following compounds were prepared according to the method of Example 37, with the following modification: In Step 1, the second eluted product from Example 34, Step 6 was used.

| Ex. | Structure | ¹H-NMR δ (ppm) | Found (ES, m/z) [M + H]⁺ |
|---|---|---|---|
| I-214 | (R/S) | (300 MHz, DMSO-d6): 11.06 (br s, 1H), 8.94 (s, 1H), 7.50-7.45 (m, 2H), 7.12 (d, J = 7.8 Hz, 1H), 3.14 (d, J = 9.6 Hz, 1H), 2.97 (d, J = 9.6 Hz, 1H), 2.85-2.80 (m, 2H), 2.73-2.72 (m, 1H), 2.66-2.61 (m, 2H), 2.26 (d, J = 16.2 Hz, 1H), 2.02 (d, J = 16.5 Hz, 1H), 1.77-1.73 (m, 2H), 0.66-0.56 (m, 4H) | 301 |
| I-224 | (R/S) | (300 MHz, DMSO-d6): 11.12 (br s, 1H), 9.01 (br s, 1H), 8.88 (d, J = 1.8 Hz, 2H), 8.33 (d, J = 4.2 Hz, 1H), 8.08 (d, J = 8.4 Hz, 1H), 7.55 (s, 1H), 7.49 (d, J = 8.1 Hz, 1H), 7.42-7.37 (m, 1H), 7.15 (d, J = 8.1 Hz, 1H), 3.82 (d, J = 9.9Hz, 1H), 3.63 (d, J = 9.9 Hz, 1H), 2.99-2.89 (m, 4H), 2.61 (d, J = 16.8 Hz, 1H), 2.35 (d, J = 16.8 Hz, 1H), 1.92-1.88(m, 2H) | 338 |

Example 38

Preparation of (R)-N-hydroxy-5'-oxo-1'-(pyridin-4-yl)-3,4-dihydro-1H-spiro[naphthalene-2,3'-pyrrolidine]-6-carboxamide (I-228)

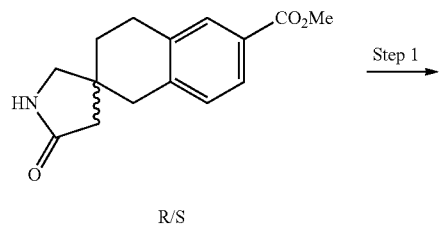

R/S

Step 1

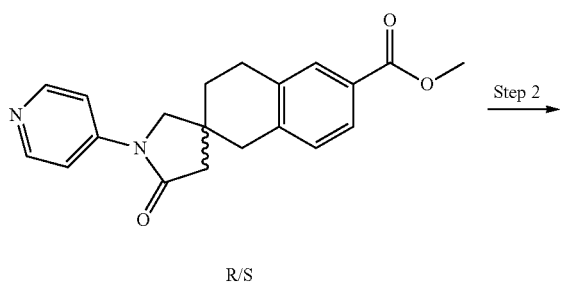

R/S

Step 2

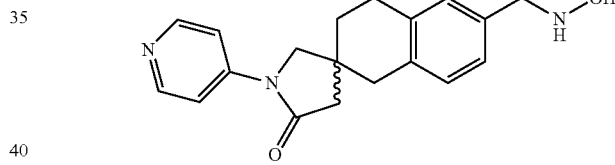

R/S

Step-1: Methyl (R)-5'-oxo-1'-(pyridin-4-yl)-3,4-dihydro-1H-spiro[naphthalene-2,3'-pyrrolidine]-6-carboxylate Into a 10-mL sealed tube purged and maintained with an inert atmosphere of nitrogen was placed the first eluted isomer from Example 34, Step 6, which was assigned as methyl (R)-5'-oxo-3,4-dihydro-1H-spiro[naphthalene-2,3'-pyrrolidine]-6-carboxylate as described above, (50 mg, 0.19 mmol, 1 equiv), toluene (4 mL), 4-bromopyridine (60.6 mg, 0.38 mmol, 2 equiv), RuPhos Pd G2 (15 mg, 0.02 mmol, 0.1 equiv), RuPhos (18 mg, 0.04 mmol, 0.20 equiv), and $Cs_2CO_3$ (189 mg, 0.58 mmol, 3 equiv). The resulting solution was stirred for 16 h at 100° C. in an oil bath. The reaction mixture was cooled to room temperature. The resulting solution was poured into 20 mL of water, extracted with 2×10 mL of EtOAc, dried over anhydrous $Na_2SO_4$, filtered and concentrated under vacuum. The residue was purified by preparative TLC with $CH_2Cl_2$/MeOH (20:1). The collected band was dissolved in $CH_2Cl_2$/MeOH (20:1), filtered and was concentrated under vacuum to give 60 mg (93% yield) of the title compound as a yellow oil. MS: (ES, m/z): 337 [M+H]⁺.

Step-2: (R)-N-Hydroxy-5'-oxo-1'-(pyridin-4-yl)-3,4-dihydro-1H-spiro[naphthalene-2,3'-pyrrolidine]-6-carboxamide Into a 8-mL vial was placed a solution of the product from Step 1, which was assigned as methyl (R)-5'-oxo-1'-(pyridin-4-yl)-3,4-dihydro-1H-spiro[naphthalene-2,3'-pyrrolidine]-6-carboxylate as described above, (60 mg, 0.18 mmol, 1 equiv) in THF/MeOH (4:1, 2 mL), NH$_2$OH (50% in water, 1.4 g, 21.43 mmol, 120 equiv) and 1N aq. NaOH (0.35 mL, 0.35 mmol, 2 equiv). The resulting solution was stirred for 3 h at room temperature. The solids were filtered out and the crude product was purified by Prep-HPLC with the following conditions: Column: XBridge Shield RP18 OBD, 5 μm, 19×150 mm; Mobile Phase A: Water/0.1% Formic Acid, Mobile Phase B: CH$_3$CN/0.1% Formic Acid; Gradient: 3% B up to 23% B in 5 min; Detector: UV 220, 254 nm. The collected fractions were lyophilized with 1M HCl (1 mL) to give 23.4 mg (39% yield) of the title compound as the HCl salt as a pink solid. $^1$H-NMR (300 MHz, DMSO-d6) δ (ppm): 11.14 (br s, 1H), 8.96 (br s, 1H), 8.67 (d, J=6.3 Hz, 2H), 8.04 (d, J=6 Hz, 2H), 7.56-7.47 (m, 2H), 7.13 (d, J=8.1 Hz, 1H), 3.86 (d, J=10.2 Hz, 1H), 3.71 (d, J=10.2 Hz, 1H), 2.99-2.82 (m, 4H), 2.74 (d, J=17.1 Hz, 1H), 2.49 (d, J=16.8 Hz, 1H), 1.92-1.87 (m, 2H). MS: (ES, m/z): 338 [M+H]$^+$.

TABLE-24

The following compound was prepared according to the method of Example 38.

| Ex. | Structure | $^1$H-NMR δ (ppm) | Found (ES, m/z) [M + H]$^+$ |
|---|---|---|---|
| I-229 | <br>R/S | (300 MHz, DMSO-d6): 11.10 (br s, 1H), 8.99 (br s, 1H), 8.33-8.30 (m, 2H), 7.84-7.78 (m, 1H), 7.54-7.41 (m, 2H), 7.14-7.10 (m, 2H), 3.87 (s, 1H), 2.92-2.85 (m, 4H), 2.68 (d, J = 16.8 Hz, 1H), 2.41 (d, J = 17.1 Hz, 1H), 1.91-1.87 (m, 2H) | 338 |

Example 39

Preparation of N-hydroxy-2'-oxo-1'-(pyridin-4-ylmethyl)spiro[chromane-2,3'-pyrrolidine]-6-carboxamide (I-230)

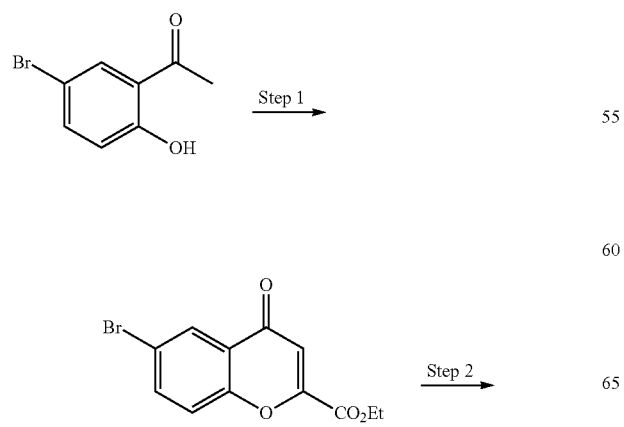

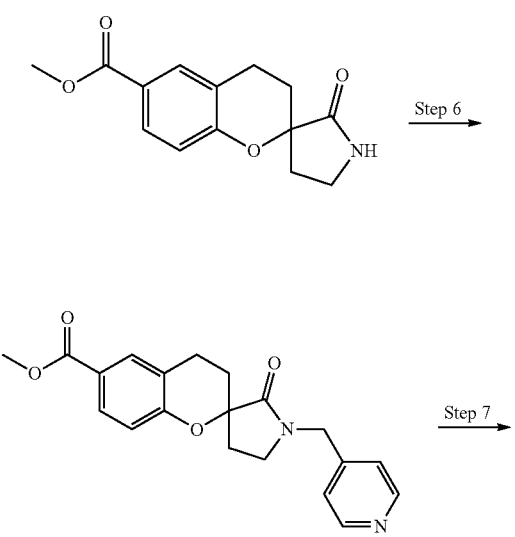

-continued

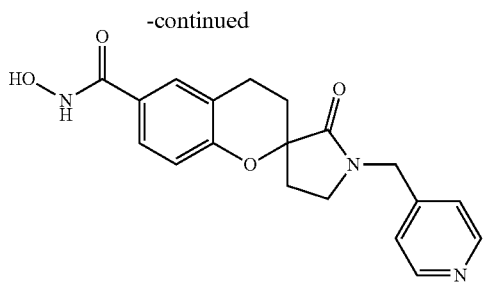

Step-1: Ethyl 6-bromo-4-oxo-4H-chromene-2-carboxylate

Into a 250-mL 3-necked round-bottom flask was placed NaH (28 g, 3 equiv) in THF (800 mL) at 0° C. Then 1-(5-bromo-2-hydroxyphenyl)ethan-1-one (50 g, 232.51 mmol, 1 equiv) and diethyl oxalate (65 mL, 2 equiv) were added at 0° C. The resulting mixture was stirred overnight at 25° C. The reaction was then quenched by the addition of NH$_4$Cl. The resulting solution was extracted with 3×500 mL of EtOAc. The organic layers were combined and dried over anhydrous Na$_2$SO$_4$, filtered and concentrated under vacuum. The residue was taken up in toluene (800 mL) and PTSA (1.5 g, 0.05 equiv) was added. The resulting mixture was allowed to react with stirring, using a Dean-Stark Separator, for an additional overnight while the temperature was maintained at 120° C. in an oil bath. The solution was concentrated under vacuum. The residue was purified by normal phase chromatography on silica gel with EtOAc/petroleum ether (1:20). The collected fractions were concentrated to give 38 g (55% yield) of the title compound as a yellow solid. MS: (ES, m/z): 297 [M+H]$^+$.

Step-2: Dimethyl 4-oxo-4H-chromene-2,6-dicarboxylate

Into a 150-mL pressure tank reactor, was placed ethyl 6-bromo-4-oxo-4H-chromene-2-carboxylate (20 g, 67.32 mmol, 1 equiv) in MeOH (150 mL), Et$_3$N (28.3 mL, 3 equiv) and Pd(dppf)Cl$_2$.CH$_2$Cl$_2$ (2.8 g, 0.05 equiv). The resulting mixture was stirred for 4 days at 80° C. under CO (g) (20 atm). The reaction mixture was cooled to room temperature. The solids were filtered out and the resulting mixture was concentrated under vacuum. The residue was purified by normal phase chromatography on silica gel with EtOAc/petroleum ether (1:10). The collected fractions were concentrated to give 4 g (23% yield) of the title compound as a white solid. MS: (ES, m/z): 263 [M+H]$^+$.

Step-3: Dimethyl chromane-2,6-dicarboxylate

Into a 250-mL pressure tank reactor, was placed dimethyl 4-oxo-4H-chromene-2,6-dicarboxylate (15 g, 57.20 mmol, 1 equiv), palladium on carbon (3 g, 0.2 equiv), MeOH (150 mL) and AcOH (15 mL, 10 equiv). The resulting mixture was stirred for 2 days at 80° C. under H$_2$ (g). The reaction mixture was cooled to room temperature. The solids were filtered out and the filtrate was concentrated under vacuum. The residue was purified by normal phase chromatography on silica gel with EtOAc/petroleum ether (1:10). The collected fractions were concentrated to give 10 g (70% yield) of the title compound as a white solid. MS: (ES, m/z): 251 [M+H]$^+$.

Step-4: Dimethyl 2-(cyanomethyl)chromane-2,6-dicarboxylate

Into a 100-mL 3-necked round-bottom flask purged and maintained with an inert atmosphere of nitrogen, were placed a solution of dimethyl chroman-2,6-dicarboxylate (2 g, 7.99 mmol, 1 equiv) in THF (20 mL). This was followed by the dropwise addition of LDA (10.4 mL, 1.30 equiv) with stirring at −78° C. The resulting solution was stirred for 1 h at −78° C. 2-Bromoacetonitrile (0.84 mL, 1.5 equiv) was added dropwise with stirring at −78° C. The reaction was stirred for 1 h at −60° C. The reaction was then quenched by the addition of 20 mL of sat aq. NH$_4$Cl. The resulting solution was extracted with 3×50 mL of EtOAc. The organics were combined, dried over anhydrous Na$_2$SO$_4$, filtered and concentrated under vacuum. The residue was purified by normal phase chromatography on silica gel with EtOAc/petroleum ether (1:3). The collected fractions were concentrated to give 0.7 g (30% yield) of the title compound as a white solid. MS: (ES, m/z): 290 [M+H]$^+$.

Step-5: Methyl 2'-oxospiro[chroman-2,3'-pyrrolidine]-6-carboxylate

Into a 50-mL round-bottom flask were placed dimethyl 2-(cyanomethyl)chroman-2,6-dicarboxylate (700 mg, 2.42 mmol, 1 equiv) in MeOH (15 mL), 7M NH$_3$ in MeOH (1 mL) and PtO$_2$ (160 mg, 0.70 mmol, 0.13 equiv). H$_2$ (g) was introduced to the flask. The resulting mixture was stirred overnight at room temperature. The solids were filtered out and the filtrate was concentrated under vacuum. The residue was purified by normal phase chromatography on silica gel with EtOAc/petroleum ether (1:1). The collected fractions were concentrated to give 0.22 g (35% yield) of the title compound as a white solid. MS: (ES, m/z): 262 [M+H]$^+$.

Step-6: Methyl 2'-oxo-1'-(pyridin-4-ylmethyl)spiro[chromane-2,3'-pyrrolidine]-6-carboxylate Into a 25-mL round-bottom flask was placed methyl 2'-oxospiro[chromane-2,3'-pyrrolidine]-6-carboxylate (50 mg, 0.19 mmol, 1 equiv) in DMF (5 mL), NaH (23 mg, 0.96 mmol, 3 equiv) and 4-(bromomethyl)pyridine (73 mg, 0.43 mmol, 1.5 equiv). The resulting mixture was stirred for 4 h at room temperature. The reaction was then quenched by the addition of NH$_4$Cl. The resulting solution was extracted with 3×30 mL of EtOAc. The combined organics were dried over anhydrous Na$_2$SO$_4$, filtered, and concentrated under vacuum. The residue was purified by normal phase chromatography on silica gel with CH$_3$Cl/MeOH (50:1). The collected fractions were concentrated to give 30 mg (45% yield) of the title compound as a light yellow solid. MS: (ES, m/z): 353 [M+H]$^+$.

Step-7: N-Hydroxy-2'-oxo-1'-(pyridin-4-ylmethyl)spiro[chromane-2,3'-pyrrolidine]-6-carboxamide Into a 25-mL round-bottom flask was placed a solution of methyl 2'-oxo-1'-(pyridin-4-ylmethyl)spiro[chromane-2,3'-pyrrolidine]-6-carboxylate (30 mg, 0.09 mmol, 1 equiv) in THF/MeOH (4:1, 2 mL), NH$_2$OH (50% in water, 168 mg, 30 equiv) and 1N aq. NaOH (1.7 mL, 2 equiv). The resulting solution was stirred for 5 h at 25° C. The pH of the solution was adjusted to 6 with 3N aq. HCl. The crude product was purified by Prep-HPLC with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 1.3 mg (3% yield) of the title compound as a white solid. $^1$H-NMR (300 MHz, DMSO-d6) δ (ppm): 11.04 (s, 1H), 8.63-8.65 (d, 2H), 7.50-7.56 (t, 2H), 7.37-7.39 (d, 2H), 6.82-6.84 (d, 1H), 4.54-4.55 (d, 2H), 2.96 (s, 2H), 2.73-2.83 (d, 2H), 2.21-2.27 (m, 2H), 1.98-2.13 (m, 2H). MS: (ES, m/z): 354 [M+H]$^+$.

TABLE-25

The following compounds were prepared according to the method of Example 39, with the following modification: In Step 6, the halide can be an iodide, a chloride, or a bromide.

| Ex. | Structure | $^1$H-NMR δ (ppm) | Found (ES, m/z) [M + H]$^+$ |
|---|---|---|---|
| I-232 | 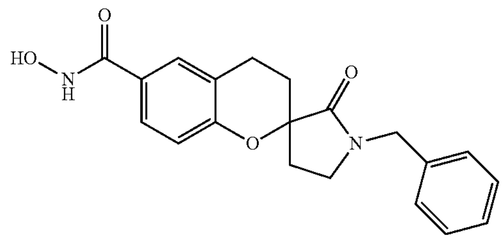 [SMILES: O=C(NO)c1ccc2c(c1)CCC1(CCN(Cc3ccccc3)C1=O)O2] | (300 MHz, DMSO-d6): 11.01 (s, 1H), 7.55 (s, 1H), 7.49-7.52 (d, 1H), 7.23-7.38 (m, 4H), 6.79-6.82 (d, 1H), 4.43-4.44 (d, 2H), 3.21-3.35 (m, 2H), 2.95-3.05 (m, 1H), 2.72-2.83 (m, 1H), 2.04-2.27 (m, 3H), 1.92-1.94 (d, 1H) | 353 |
| I-234 | 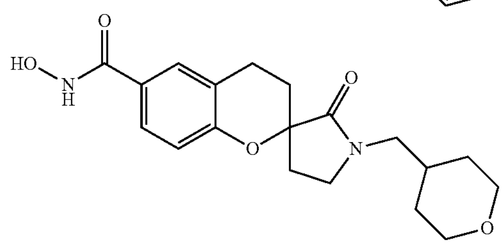 | (300 MHz, DMSO-d6): 11.00 (s, 1H), 7.47-7.54 (m, 2H), 6.76-6.79 (d, 1H), 3.81-3.86 (m, 2H), 3.38-3.50 (m, 2H), 3.23-3.35 (m, 2H), 3.10-3.13 (m, 2H), 2.90 (s, 1H), 2.80 (s, 1H), 2.02-2.20 (m, 3H), 1.85-1.93 (m, 2H), 1.49-1.53 (t, 2H), 1.13-1.17 (m, 2H) | 361 |
| I-237 | 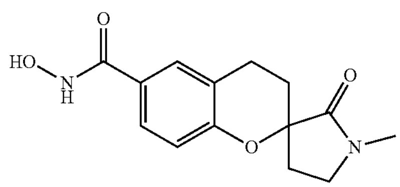 [SMILES: CN1CCC2(CCc3cc(C(=O)NO)ccc3O2)C1=O] | (400 MHz, DMSO-d6): 10.99 (br s, 1H), 8.85 (br s, 1H), 7.53 (s, 1H), 7.50-7.45 (m, 1H), 6.78-6.73 (m, 1H), 3.43-3.38 (m, 2H), 3.01-2.89 (m, 1H), 2.85-2.75 (m, 1H), 2.79 (s, 3H), 2.23-1.97 (m, 3H), 1.96-1.80 (m, 1H) | 277 |

Example 40

Preparation of N-hydroxy-2'-oxo-1'-phenylspiro[chromane-2,3'-pyrrolidine]-6-carboxamide (I-231)

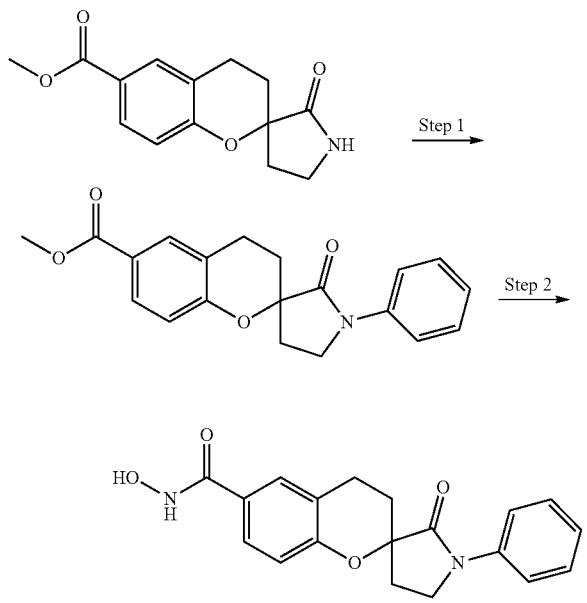

Step-1: Methyl 2'-oxo-1'-phenylspiro[chromane-2,3'-pyrrolidine]-6-carboxylate

Into a 50-mL 3-necked round-bottom flask was placed a solution of methyl 2'-oxospiro[chromane-2,3'-pyrrolidine]-6-carboxylate (80 mg, 0.31 mmol, 1 equiv) in 1,4-dioxane (10 mL), iodobenzene (76 mg, 0.37 mmol, 1.2 equiv), Pd(OAc)$_2$ (6.8 mg, 0.1 equiv), XantPhos (39.2 mg, 0.07 mmol, 0.2 equiv) and Cs$_2$CO$_3$ (200 mg, 0.61 mmol, 2 equiv). The resulting mixture was stirred for 3 h at 100° C. under N$_2$. The solids were filtered out and the filtrate was concentrated under vacuum. The residue was purified by normal phase chromatography on silica gel with EtOAc/petroleum ether (1:2). The collected fractions were concentrated to give 40 mg (39% yield) of the title compound as a brown solid. MS: (ES, m/z): 338 [M+H]$^+$.

Step-2: N-Hydroxy-2'-oxo-1'-phenylspiro[chromane-2,3'-pyrrolidine]-6-carboxamide Into a 25-mL round-bottom flask was placed a solution of methyl 2'-oxo-1'-phenylspiro[chromane-2,3'-pyrrolidine]-6-carboxylate (40 mg, 0.12 mmol, 1 equiv) in THF/MeOH (4:1, 2 mL), NH$_2$OH (50% in water, 235 mg, 30 equiv), and 1N aq. NaOH (0.238 mL, 2 equiv). The resulting solution was stirred for 1 h at 25° C. The crude product was purified by Prep-HPLC with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 26.1 mg (65% yield) of the title compound as an off-white solid. $^1$H-NMR (300 MHz, DMSO-d6) δ (ppm): 11.02 (s, 1H), 7.70-7.23 (d, 2H), 7.50-7.57 (m, 2H), 7.39-7.44 (t, 2H), 7.17-7.22 (t, 1H), 6.83-6.86 (d, 1H), 3.87-3.92 (m, 2H), 2.83-2.93 (m, 2H), 2.29-2.39 (m, 2H), 2.17-2.22 (t, 1H), 2.00-2.05 (t, 1H). MS: (ES, m/z): 339 [M+H]$^+$.

TABLE-26

The following compound was prepared according to the method of Example 40.

| Ex. | Structure | ¹H-NMR δ (ppm) | Found (ES, m/z) [M + H]⁺ |
|---|---|---|---|
| I-233 | 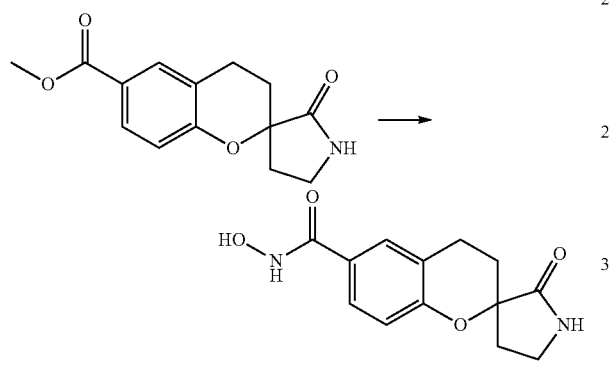 | (300 MHz, DMSO-d6): 11.05 (s, 1H), 8.93 (s, 1H), 8.39-8.43 (m, 1H), 8.13-8.17 (m, 1H), 7.44-7.58 (m, 3H), 6.83-6.86 (d, 1H), 3.92-3.97 (m, 2H), 2.73-2.92 (m, 2H), 2.34-2.43 (m, 2H), 2.19-2.29 (m, 1H), 2.04-2.07 (d, 1H) | 340 |

Example 41

Preparation of N-hydroxy-2'-oxospiro[chromane-2,3'-pyrrolidine]-6-carboxamide (I-236)

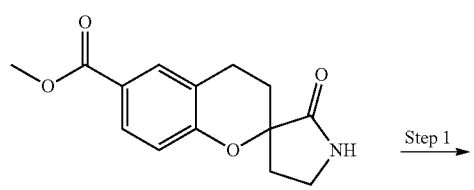

Into an 8-mL vial, was placed a solution of methyl 2'-oxospiro[chromane-2,3'-pyrrolidine]-6-carboxylate (70 mg, 0.27 mmol, 1 equiv) in THF/MeOH (4:1, 2.5 mL), NH₂OH (in 50% water, 0.53 mL, 30 equiv), and 1N aq. NaOH (0.54 mL, 2 equiv). The resulting solution was stirred for 2 h at room temperature. The crude product was purified by Prep-HPLC with the following conditions: Column: Sunfire C18, 19×150 mm, 5 µm; Mobile Phase A: Water/0.05% TFA, Mobile Phase B: CH₃CN/0.05% TFA; Gradient: 5% B to 65% B in 8 min; Detector: UV 254 nm. The collected fractions were lyophilized to give 22.8 mg (32% yield) as a pink solid. ¹H-NMR (400 MHz, DMSO-d6) δ (ppm): 10.99 (s, 1H), 8.88 (m, 1H), 8.06 (s, 1H), 7.52-7.46 (m, 2H), 6.79-6.77 (d, J=8.0 Hz, 1H), 3.31-3.28 (m, 2H), 2.97-2.93 (m, 1H), 2.79-2.73 (m, 1H), 2.21-2.19 (m, 2H), 2.17-2.00 (m, 1H), 1.89-1.83 (m, 1H). MS: (ES, m/z): 263 [M+H]⁺.

Example 42

Preparation of N-hydroxy-1'-isopropyl-2'-oxospiro[chromane-2,3'-pyrrolidine]-6-carboxamide (I-235)

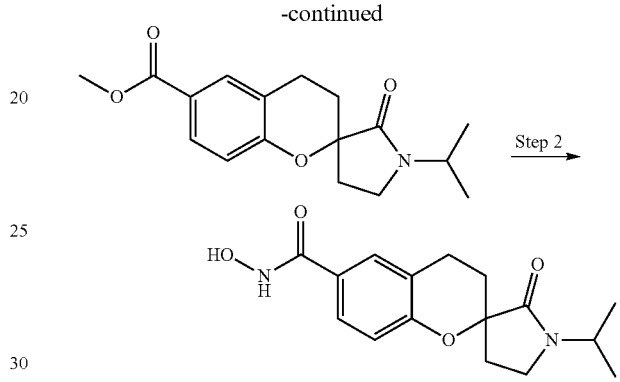

Step-1: Methyl 1'-isopropyl-2'-oxospiro[chromane-2,3'-pyrrolidine]-6-carboxylate Into a 25-mL round-bottom flask was placed a solution of methyl 2'-oxospiro[chromane-2,3'-pyrrolidine]-6-carboxylate (100 mg, 0.38 mmol, 1 equiv) in CH₃CN (6 mL), 2-iodopropane (326 mg, 1.92 mmol, 5 equiv), Cs₂CO₃ (375 mg, 1.15 mmol, 3 equiv). The resulting solution was stirred for 18 h at 70° C. The resulting mixture was concentrated under vacuum. The residue was dissolved in 20 mL of EtOAc. The resulting mixture was washed with 2×15 mL of H₂O. The organics were dried over anhydrous Na₂SO₄, filtered and concentrated. The residue was purified by normal phase chromatography on silica gel with EtOAc/petroleum ether (1:1). The collected fractions were concentrated to give 44.2 mg (38% yield) of the title compound as a solid. MS: (ES, m/z): 304 [M+H]⁺.

Step-2: N-Hydroxy-1'-isopropyl-2'-oxospiro[chromane-2,3'-pyrrolidine]-6-carboxamide Into an 8-mL vial, was placed a solution of methyl 1'-isopropyl-2'-oxospiro[chromane-2,3'-pyrrolidine]-6-carboxylate (44.2 mg, 0.15 mmol, 1 equiv) in THF/MeOH (4:1, 1 mL), NH₂OH (50% in water, 0.29 mL, 30 equiv), and 1N aq. NaOH (0.29 mL, 2 equiv). The resulting solution was stirred for 2.5 h at room temperature. The crude product was purified by Prep-HPLC with the following conditions: Column: Xbridge C18, 19×150 mm, 5 µm; Mobile Phase A: Water/0.05% TFA, Mobile Phase B: CH₃CN/0.05% TFA; Flow rate: 25 mL/min; Gradient: 5% B to 57% B in 7 min; Detector: UV 254 nm, 220 nm. The collected fractions were lyophilized to give 15.8 mg (36% yield) of the title compound as a pink solid. ¹H-NMR (400 MHz, DMSO-d6) δ

(ppm): 11.00 (br s, 1H), 8.87 (s, 1H), 7.53-7.47 (s, 2H), 6.79-6.76 (d, J=12 Hz, 1H), 4.11 (m, 1H), 3.36-3.35 (m, 1H), 3.30-3.28 (m, 1H), 2.98-2.88 (m, 1H), 2.79-2.73 (m, 1H), 2.18-1.99 (m, 3H), 1.88-1.83 (m, 1H), 1.13-1.08 (m, 6H). MS: (ES, m/z): 305 [M+H]$^+$.

Example 43

Preparation of N-hydroxy-1'-(4-methoxybenzyl) spiro[chromane-2,4'-piperidine]-6-carboxamide (II-1)

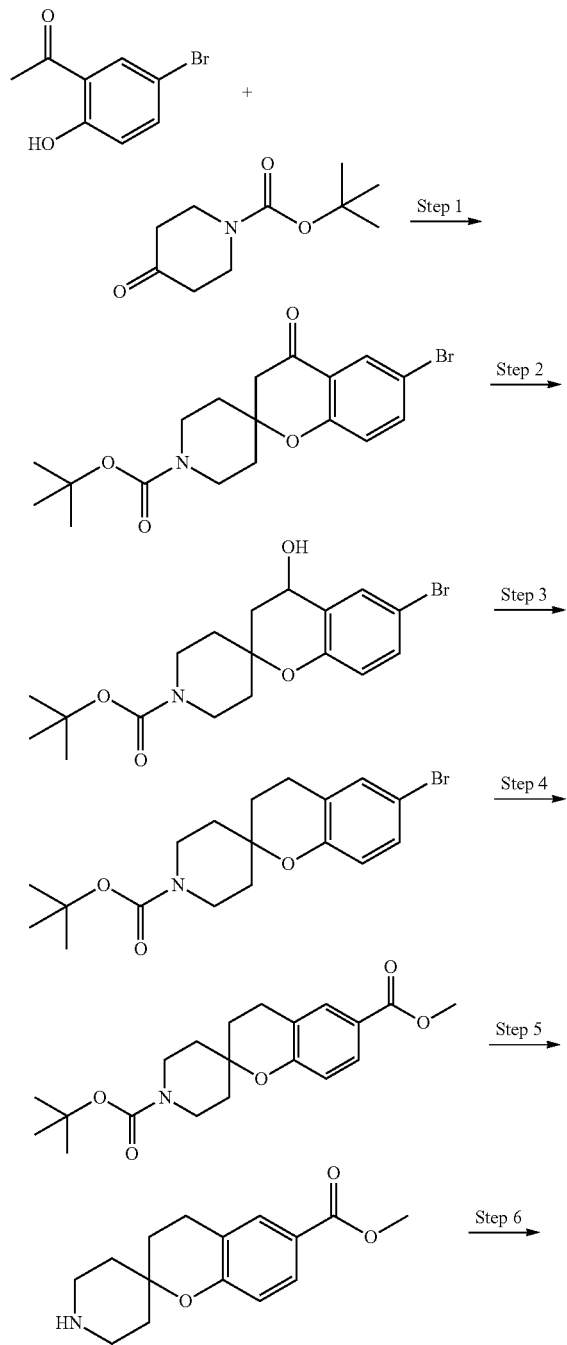

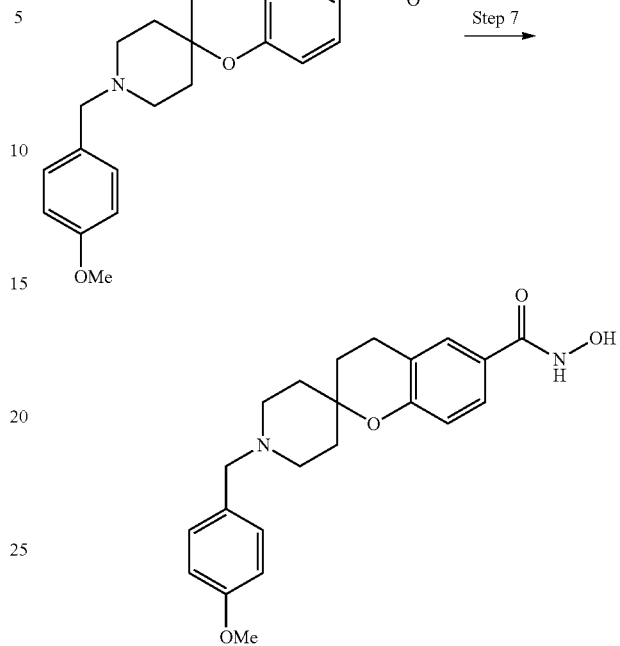

Step-1: tert-Butyl 6-bromo-4-oxospiro[chromane-2,4'-piperidine]-1'-carboxylate 1-(5-Bromo-2-hydroxyphenyl)ethan-1-one (10.0 g, 45.5 mmol), tert-butyl 4-oxopiperidine-1-carboxylate (9.27 g, 46.5 mmol) and pyrrolidine (1.91 mL, 23.3 mmol) were combined in 75 mL of MeOH and refluxed for 12 h. After cooling down to room temperature the reaction mixture was concentrated to dryness and purified by normal phase chromatography on silica gel (EtOAc/hexanes gradient). After purification 17.1 g (92% yield) of the title compound was obtained. $^1$H NMR (300 MHz, CDCl$_3$) δ (ppm): 7.96 (d, J=2.5 Hz, 1H), 7.55 (dd, J$_1$=8.8 Hz, J$_2$=2.5 Hz, 1H), 7.88 (d, J=8.8 Hz, 1H), 3.86 (br s, 2H), 3.20-3.10 (m, 2H), 2.71 (s, 2H), 2.05-1.90 (m, 2H), 1.70-1.55 (m, 2H), 1.45 (s, 9H). MS: (ES, m/z): 296/298 [M−Boc]$^+$.

Step-2: tert-Butyl 6-bromo-4-hydroxyspiro[chromane-2,4'-piperidine]-1'-carboxylate Sodium borohydride (0.120 g, 3.15 mmol, 1 equiv) was added to a suspension of tert-butyl 6-bromo-4-oxospiro[chromane-2,4'-piperidine]-1'-carboxylate (1.25 g, 3.15 mmol, 1 equiv) in EtOH (25 mL). The reaction was stirred at room temperature for 16 h. The reaction was concentrated under vacuum to afford 1 g (crude) of the title compound and was used without further purification.

Step-3: 1'-(tert-Butyl) 6-methyl spiro[chromane-2,4'-piperidine]-1',6-dicarboxylate To a solution of tert-butyl 6-bromo-4-hydroxyspiro[chromane-2,4'-piperidine]-1'-carboxylate (1 g, 2.51 mmol, 1 equiv) in CH$_2$Cl$_2$ (14.5 ml) was added TFA (6.38 ml, 83 mmol, 33.07 equiv) and triethylsilane (3.21 ml, 20.09 mmol, 8 equiv). The reaction was concentrated to afford 882 mg of the title compound, which was used without further purification.

Step-4: 1'-(tert-Butyl) 6-methyl spiro[chromane-2,4'-piperidine]-1',6-dicarboxylate To a solution of tert-butyl 6-bromospiro[chromane-2,4'-piperidine]-1'-carboxylate (249 mg, 0.651 mmol, 1 equiv) in THF (5 mL) cooled to −78° C. (dry ice/acetone bath), was added n-Butyl lithium (1.6M, 0.602 mL, 0.964 mmol, 1.48 equiv). The resulting mixture was stirred at −78° C. for 45 min when methyl chloroformate (1.0 mL, 13.02 mmol, 20 equiv) was added. The resulting mixture was stirred and slowly warmed to room temperature and then stirred for 1 h. The reaction was concentrated under reduced pressure. The light pink residue was partitioned between EtOAc and water. The aqueous layer was extracted with EtOAc. The organic layers were combined and dried over $Na_2SO_4$, concentrated and purified by normal phase chromatography on silica gel (10-50% EtOAc/hexanes) to provide 243 mg of the title compound. MS: (ES, m/z): 362 [M+H]$^+$.

Step-5: Methyl spiro[chromane-2,4'-piperidine]-6-carboxylate

To a solution of 1'-(tert-butyl) 6-methyl spiro[chromane-2,4'-piperidine]-1',6-dicarboxylate (243 mg, 0.672 mmol, 1 equiv) in $CH_2Cl_2$ (0.5 mL) was added TFA (0.259 mL, 3.36 mmol, 5 equiv). The reaction mixture was stirred at room temperature for 40 min. The reaction mixture was then concentrated under vacuum and azeotroped with toluene 3 times. The crude mixture was used in the next step without further purification. MS: (ES, m/z): 262 [M+H]$^+$.

Step-6: Methyl 1'-(4-methoxybenzyl)spiro[chromane-2,4'-piperidine]-6-carboxylate Methyl spiro[chromane-2,4'-piperidine]-6-carboxylate (126.3 mg, 0.336 mmol, 1 equiv) was combined with $Et_3N$ (0.094 mL, 0.671 mmol, 2 equiv) and 4-methoxybenzaldehyde (0.041 mL, 0.336 mmol, 1 equiv) in DCE (2.0 mL). The reaction was stirred at room temperature for 1.5 h. Then $NaBH(OAc)_3$ (92 mg, 0.436 mmol, 1.3 equiv) was added and the reaction was allowed to stir at room temperature for 16 h. The reaction mixture was directly purified by normal phase chromatography on silica gel (10%-60% EtOAc/hexanes) to afford 37 mg (28% yield) of the title compound. MS: (ES m/z) 382 [M+H]$^+$.

Step-7: N-hydroxy-1'-(4-methoxybenzyl)spiro[chromane-2,4'-piperidine]-6-carboxamide Methyl 1'-(4-methoxybenzyl)spiro[chromane-2,4'-piperidine]-6-carboxylate (36 mg, 0.095 mmol, 1 equiv) was dissolved in a solution of THF/MeOH (4:1, 1.25 mL). $NH_2OH$ (50% in water, 0.263 mL, 8.59 mmol, 90 equiv) was added followed by 2N aq. NaOH (0.095 mL, 2 equiv). The reaction was allowed to stir at room temperature for 18 h and was purified directly by reverse-phase chromatography using the following conditions: Column: XTerra Prep MS C18 OBD, 5 μm, 19×100 mm; Mobile Phase A: Water/0.05% Formic Acid, Mobile Phase B: $CH_3CN$/0.05% Formic Acid; Flow rate: 20 mL/min; Gradient: 15% B to 85% B in 10 min; Detector: UV 254 nm, 220 nm. Combined fractions were lyophilized to afford 30 mg (83% yield) of the title compound. $^1$H NMR (300 MHz, $CD_3OD$) δ (PPM): 8.26-8.58 (m, 1H), 7.39-7.67 (m, 4H), 6.87-7.15 (m, 3H), 4.30 (br s, 2H), 3.82 (s, 3H), 3.27-3.44 (m, 6H), 2.82-3.02 (m, 2H), 1.87-2.20 (m, 6H). MS: (ES m/z) 383 [M+H]$^+$.

TABLE-27

The following compound was prepared according to the method of Example 43.

| Ex. | Structure | $^1$H-NMR δ (ppm) | Found (ES, m/z) [M + H]$^+$ |
|---|---|---|---|
| II-2 | ![structure] | (300 MHz, $CD_3OD$): 8.08-8.22 (m, 2H), 7.40-7.71 (m, 4H), 7.29 (br dd, J = 5.9, 2.9 Hz, 2H), 6.67-6.97 (m, 1H), 4.12 (s, 2H), 3.32 (dt, J = 3.2, 1.6 Hz, 6H), 2.75-3.01 (m, 4H), 1.80-1.96 (m, 4H) | 393 |

Example 44

Preparation of 1'-(cyclohexanecarbonyl)-N-hydroxyspiro[chromane-2,4'-piperidine]-6-carboxamide (II-3)

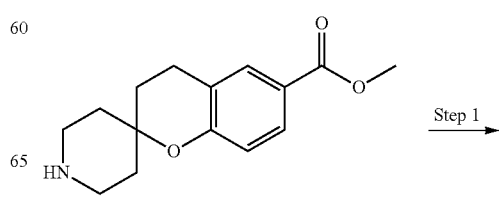

Step 1

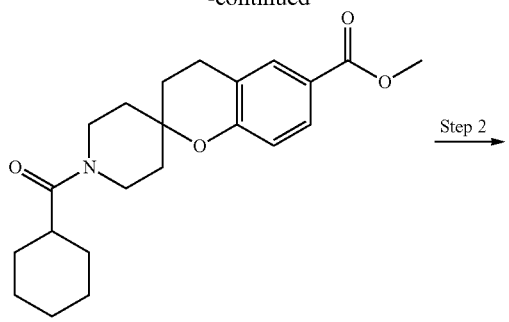

Step-1: Methyl 1'-(cyclohexanecarbonyl)spiro[chromane-2,4'-piperidine]-6-carboxylate To a solution of methyl spiro[chromane-2,4'-piperidine]-6-carboxylate (78 mg, 0.196 mmol, 1 equiv) in CH$_2$Cl$_2$ (1 mL) was added cyclohexane carboxylic acid (26 mg, 0.206 mmol, 1.05 equiv), DIEA (0.137 mL, 0.589 mmol, 3 equiv) and HBTU (86 mg, 0.226 mmol, 1.50 equiv). The reaction was stirred at room temperature for 18 h. The reaction mixture was concentrated and purified by normal phase chromatography on silica gel (10%-50% EtOAc/hexanes) to afford 57 mg (78% yield) of the title compound. MS: (ES, m/z): 372 [M+H]$^+$.

Step-2: 1'-(Cyclohexanecarbonyl)-N-hydroxyspiro[chromane-2,4'-piperidine]-6-carboxamide Methyl 1'-(cyclohexanecarbonyl)spiro[chromane-2,4'-piperidine]-6-carboxylate (57 mg, 0.154 mmol, 1 equiv) was dissolved in a solution of THF/MeOH (4:1, 1.25 mL). NH$_2$OH (50% in water, 0.801 mL, 13.07 mmol, 85 equiv) was added, followed by 2N aq. NaOH (0.154 mL, 2 equiv). The reaction was stirred at room temperature for 18 h and was purified directly by reverse-phase chromatography using the following conditions: Column: XTerra Prep MS C18 OBD 5 μm, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyophilized to afford 18 mg (31% yield) of the title compound. $^1$H NMR (300 MHz, DMSO-d6) δ (ppm): 10.92 (br s, 1H), 8.81 (s, 1H), 7.17-7.52 (m, 2H), 6.59-6.85 (m, 1H), 4.02 (br d, J=13.2 Hz, 1H), 3.67 (br d, J=14.1 Hz, 1H), 2.93 (br t, J=11.6 Hz, 2H), 2.60-2.78 (m, 2H), 1.67-1.85 (m, 3H), 1.49-1.67 (m, 7H), 0.97-1.33 (m, 6H). MS: (ES, m/z): 373 [M+H]$^+$.

TABLE-28

The following compound was prepared according to the method of Example 44.

| Ex. | Structure | $^1$H-NMR δ (ppm) | Found (ES, m/z) [M + H]$^+$ |
|---|---|---|---|
| II-4 | 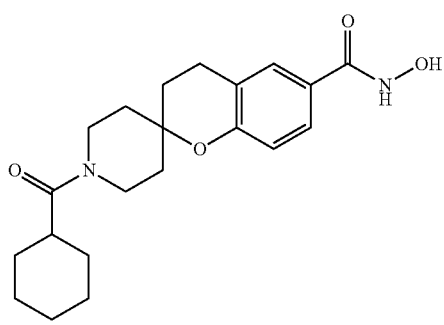 | | 397 |

Example 45

Preparation of N-hydroxy-1'-((4-methoxyphenyl)sulfonyl)spiro[chromane-2,4'-piperidine]-6-carboxamide (II-5)

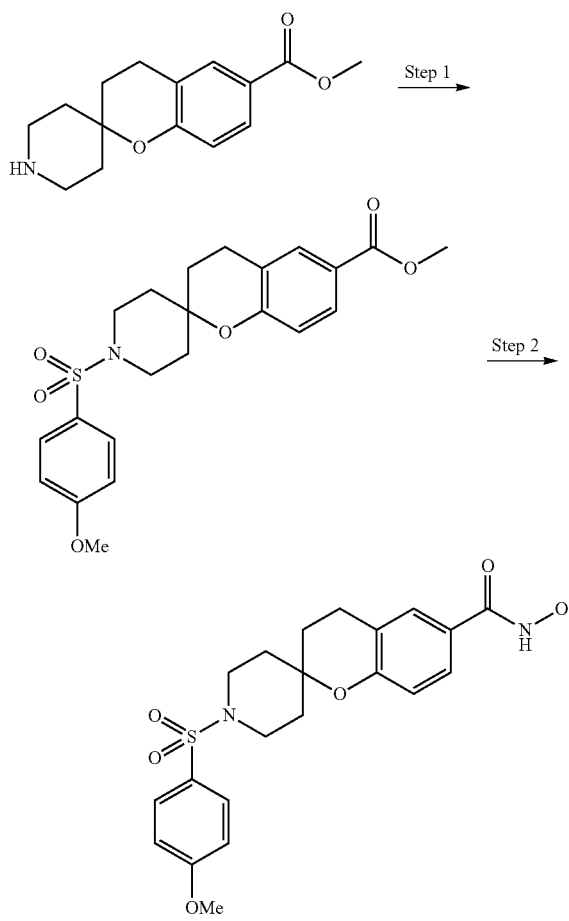

Step-1: Methyl 1'-((4-methoxyphenyl)sulfonyl)spiro[chromane-2,4'-piperidine]-6-carboxylate Methyl spiro[chromane-2,4'-piperidine]-6-carboxylate (75.8 mg, 0.189 mmol, 1 equiv) was combined with DIEA (0.115 mL, 0.660 mmol, 3.5 equiv) in THF (2.0 ml). After several min, 4-methoxybenzene-1-sulfonyl chloride (47 mg, 0.226 mmol, 1.20 equiv) was added and the resulting mixture was left to stir at room temperature for 16 h. The reaction mixture was partitioned between sat. aq. NaHCO$_3$ and EtOAc. Water was added to dissolve salts. The organic phase was separated and the aqueous layer was extracted with several portions of EtOAc. The combined organic layers were washed with brine, dried over Na$_2$SO$_4$, filtered and concentrated. The resulting residue was purified by normal phase chromatography on silica gel to afford 68 mg (84% yield) of the title compound. MS: (ES, m/z) 431 [M+H]$^+$.

Step-2: N-Hydroxy-1'-((4-methoxyphenyl)sulfonyl)spiro[chromane-2,4'-piperidine]-6-carboxamide Methyl 1'-((4-methoxyphenyl)sulfonyl)spiro[chromane-2,4'-piperidine]-6-carboxylate (63 mg, 0.147 mmol, 1 equiv) was dissolved in a solution of THF/MeOH (4:1, 1.25 mL). NH$_2$OH (50% in water, 0.76 mL, 12.47 mmol, 85 equiv) was added, followed by 1N aq. NaOH (0.015 mL, 2 equiv). The reaction was allowed to stir at room temperature for 2 h and was directly purified by reverse-phase chromatography using the following conditions: Column: XTerra Prep MS C18 OBD, 5 μm, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyophilized to afford 14 mg (22% yield) of the title compound. $^1$H NMR (300 MHz, DMSO-d6) δ (ppm): 10.90 (br s, 1H), 8.80 (s, 1H), 7.59-7.67 (m, 2H), 7.41-7.59 (m, 1H), 7.35 (dd, J=8.4, 2.2 Hz, 1H), 6.99-7.15 (m, 2H), 6.51 (d, J=8.5 Hz, 1H), 3.81 (s, 3H), 3.32-3.40 (m, 2H), 2.65 (br t, J=6.3 Hz, 2H), 2.51 (br t, J=10.8 Hz, 2H), 1.38-1.76 (m, 6H). MS: (ES, m/z) 432 [M+H]$^+$.

Example 46

Preparation of 1'-(cyclohexylsulfonyl)-N-hydroxyspiro[chromane-2,4'-piperidine]-6-carboxamide (II-6)

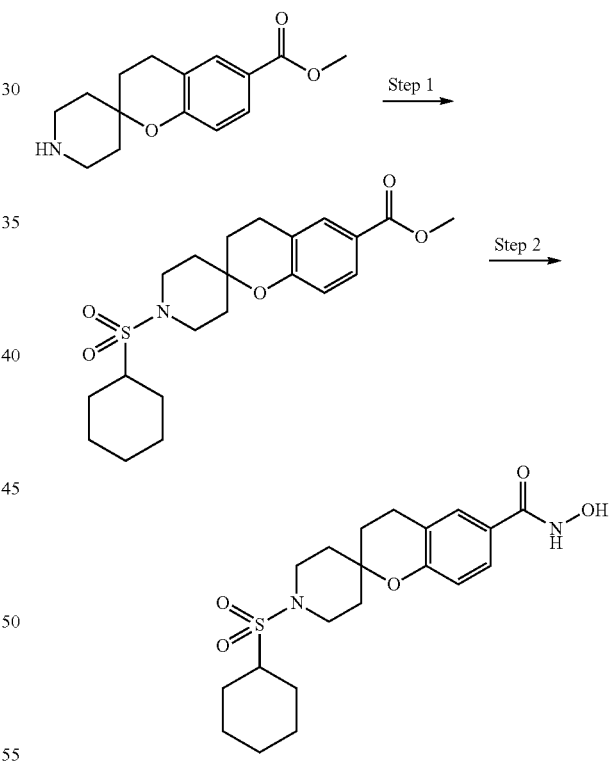

Step-1: Methyl 1'-(cyclohexylsulfonyl)spiro[chromane-2,4'-piperidine]-6-carboxylate Into a 50-mL round-bottom flask, was placed a solution of methyl 3,4-dihydrospiro[1-benzopyran-2,4'-piperidine]-6-carboxylate (70 mg, 0.24 mmol, 1 equiv) in CH$_2$Cl$_2$ (2 mL). This was followed by the addition of Et$_3$N (95 mg, 0.94 mmol, 4 equiv) dropwise with stirring at 0° C. To this was added cyclohexanesulfonyl chloride (74 mg, 0.41 mmol, 1.73 equiv) dropwise with stirring at 0° C. The resulting solution was stirred overnight at room temperature. The residue was purified by preparative TLC with EtOAc/petroleum ether (1:2). The collected fractions were combined and concentrated under vacuum to afford 60 mg (63% yield) of the title compound as a yellow solid. MS: (ES, m/z) 408 [M+H]$^+$.

Step-2: 1'-(Cyclohexylsulfonyl)-N-hydroxyspiro[chromane-2,4'-piperidine]-6-carboxamide Into a 25-mL round-bottom flask, was placed a solution of methyl 1'-(cyclohexylsulfonyl)spiro[chromane-2,4'-piperidine]-6-carboxylate (60 mg, 0.15 mmol, 1 equiv) in THF/MeOH (1.5 mL), NH$_2$OH (35.12 mmol, 234 equiv), and aq. 1N NaOH (0.29 mL, 2 equiv). The resulting solution was stirred for 7 h at room temperature. The crude product was purified by Prep-HPLC with the following conditions: Column: XBridge Shield RP18 OBD 5 μm, 19×150 mm; Mobile Phase A: Water/0.05% TFA, Mobile Phase B: CH$_3$CN/0.05% TFA; Gradient: 10% B to 80% B in 7 min; Detector: UV 254 nm, 220 nm. The product fractions were dried by lyophilization to afford 4.9 mg (6% yield) of the title compound as a orange solid. $^1$H NMR (400 MHz, DMSO-d6) δ (ppm): 11.00 (br s, 1H), 8.90 (br s, 1H), 7.55 (s, 1H), 7.51 (m, 2H), 6.85 (d, J=8 Hz, 1H), 3.50 (m, 2H), 3.24-3.10 (m, 3H), 2.78 (t, J=6.8 Hz, 2H), 2.02 (m, 2H), 1.86-1.62 (m, 9H), 1.42-1.11 (m, 5H) 11.00 (br s, 1H), 8.90 (br s, 1H), 7.55 (s, 1H), 7.51 (m, 2H), 6.85 (d, J=8 Hz, 1H), 3.50 (m, 2H), 3.24-3.10 (m, 3H), 2.78 (t, J=6.8 Hz, 2H), 2.02 (m, 2H), 1.86-1.62 (m, 9H), 1.42-1.11 (m, 5H). MS: (ES, m/z): 409 [M+H]$^+$.

Example 47

Preparation of N6-hydroxy-N1'-phenylspiro[chromane-2,4'-piperidine]-1',6-dicarboxamidedicarboxamide (II-7)

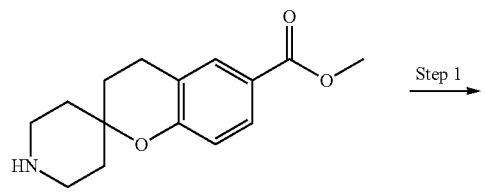

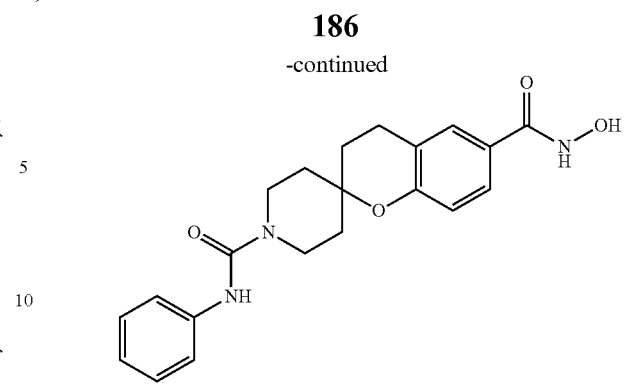

Step-1: Methyl 1'-(phenylcarbamoyl)spiro[chromane-2,4'-piperidine]-6-carboxylate Into a 100-mL round-bottom flask was placed a solution of methyl spiro[chromane-2,4'-piperidine]-6-carboxylate (70 mg, 0.24 mmol, 1 equiv) in CH$_2$Cl$_2$ (10 mL), This was followed by the addition of Et$_3$N (81.26 mg, 0.80 mmol, 3 equiv) and isocyanatobenzene (40 mg, 0.34 mmol, 1.5 equiv). The resulting solution was stirred for 2 h at 0° C. The resulting mixture was concentrated under vacuum and the residue was purified by normal phase chromatography on silica gel with EtOAc/petroleum ether (1:3). The collected fractions were concentrated to give 72 mg (81% yield) of the title compound as a light yellow solid. MS: (ES, m/z): 381 [M+H]$^+$.

Step-2: N6-Hydroxy-N1'-phenylspiro[chromane-2,4'-piperidine]-1',6-dicarboxamidedicarboxamide Into a 100-mL round-bottom flask was placed a solution of methyl 1'-(phenylcarbamoyl)spiro[chromane-2,4'-piperidine]-6-carboxylate (72 mg, 0.19 mmol, 1 equiv) in THF/MeOH (4:1, 2.5 mL), NH$_2$OH (50% in water, 0.5 mL, 60 equiv), and 1N aq. NaOH (0.25 mL, 2 equiv). The resulting solution was stirred for 6 h at room temperature. The crude product was purified by Prep-HPLC with the following conditions: Column: Waters HSS C18, 2.1×50 mm, 1.8 μm; Mobile Phase, A: Water/0.05% TFA, Mobile Phase B: CH$_3$CN/0.05% TFA; Flow rate: 0.7 mL/min; Gradient: 5% B to 95% B in 2 min, hold 0.6 min; Detector: UV 254 nm. The collected fractions were lyophilized to give 22.1 mg (31% yield) of the title compound as a pink solid. $^1$H-NMR (400 MHz, DMSO-d6) δ (ppm): 10.99 (br s, 1H), 8.54 (s, 1H), 7.45-7.56 (m, 4H), 7.21-7.25 (d, J=8 Hz, 2H), 6.83-6.90 (m, 2H), 3.90-3.86 (m, 2H), 3.28-3.22 (t, J=11.2 Hz, 2H), 2.80-2.77 (t, J=6.4 Hz, 2H), 1.86-1.83 (t, J=6.8 Hz, 2H), 1.75-1.59 (m, 4H) MS: (ES, m/z): 382 [M+H]$^+$.

Example 48

Preparation of 1'-cyclohexyl-N-hydroxyspiro[chromane-2,4'-piperidine]-6-carboxamide (II-8)

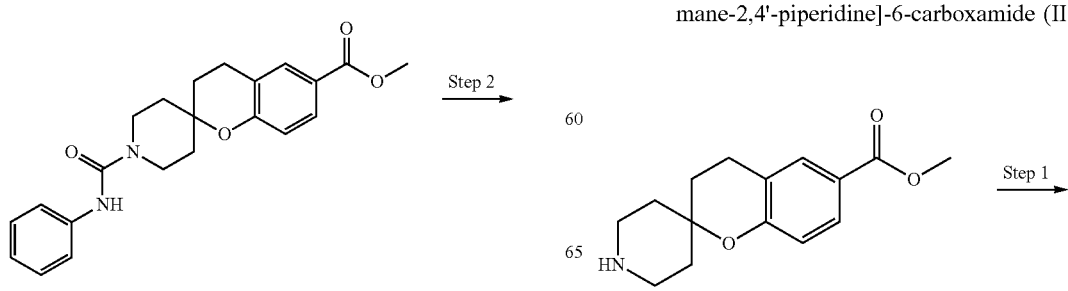

187

-continued

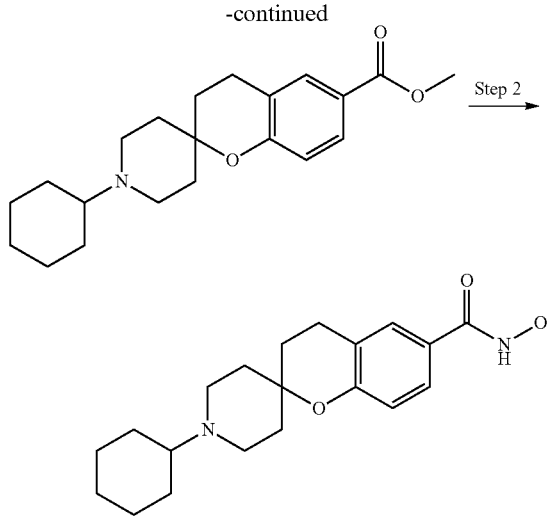

Step-1: Methyl 1'-cyclohexylspiro[chromane-2,4'-piperidine]-6-carboxylate

Into a 100-mL round-bottom flask was placed a solution of methyl spiro[chromane-2,4'-piperidine]-6-carboxylate (50 mg, 0.17 mmol, 1 equiv) in $CH_2Cl_2$ (5 mL). This was followed by the addition of cyclohexanone (18.77 mg, 0.19 mmol, 1 equiv) and $NaBH(OAc)_3$ (60.9 mg, 0.29 mmol, 1.5 equiv). The resulting solution was stirred for 3 days at room temperature. The resulting mixture was concentrated under vacuum. The residue was purified by reverse-phase chromatography using the following conditions: C18 column; Mobile Phase A: Water/0.05% TFA, Mobile Phase B: $CH_3CN$/0.05% TFA; Gradient: 3% B to 50% B in 30 min. The collected fractions were concentrated to give 35 mg (61% yield) of the title compound as a light yellow oil. MS: (ES, m/z): 344 $[M+H]^+$.

Step-2: 1'-Cyclohexyl-N-hydroxyspiro[chromane-2, 4'-piperidine]-6-carboxamide

Into a 100-mL round-bottom flask was placed a solution of methyl 1'-cyclohexylspiro[chromane-2,4'-piperidine]-6-carboxylate (35 mg, 0.10 mmol, 1 equiv) in THF/MeOH (4:1, 2.5 mL), $NH_2OH$ (50% in water, 0.7 mL, 60 equiv), and 1N aq. NaOH (0.3 ml, 7.50 mmol, 2 equiv). The resulting solution was stirred for 8 h at room temperature. The crude product was purified by Prep-HPLC with the following conditions: Column: Waters HSS C18, 2.1×50 mm, 1.8 μm; Mobile Phase A: Water/0.05% TFA, Mobile Phase B: $CH_3CN$/0.05% TFA; Flow rate: 0.7 mL/min; Gradient: 5% B to 95% B in 2 min, hold 0.6 min; Detector: UV 254 nm. The collected fractions were lyophilized to give 10.9 mg (22% yield) of the title compound as a pink solid. $^1$H-NMR (300 MHz, DMSO-d6) δ (ppm): 11.02 (br s, 1H), 9.25 (br s, 1H), 8.90 (br s, 1H), 7.58-7.52 (m, 2H), 6.90-6.80 (m, 1H), 3.41-3.22 (m, 3H), 3.14-3.10 (m, 3H), 2.82-2.78 (t, J=6.6 Hz, 2H), 2.27-2.05 (m, 3H), 1.97-1.82 (m, 7H), 1.65-1.61 (m, 1H), 1.49-1.22 (m, 4H), 1.17-1.09 (m, 1H). MS: (ES, m/z): 345 $[M+H]^+$.

188

Example 49

Preparation of N-hydroxy-1'-(2',3',5',6'-tetrahydrospiro[indoline-3,4'-pyran]-1-carbonyl)spiro[chromane-2,4'-piperidine]-6-carboxamide (II-9)

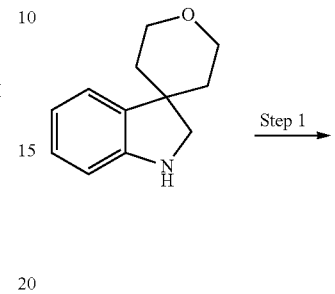

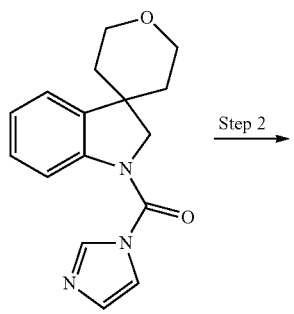

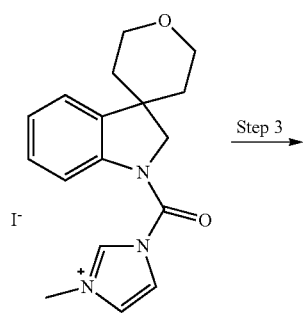

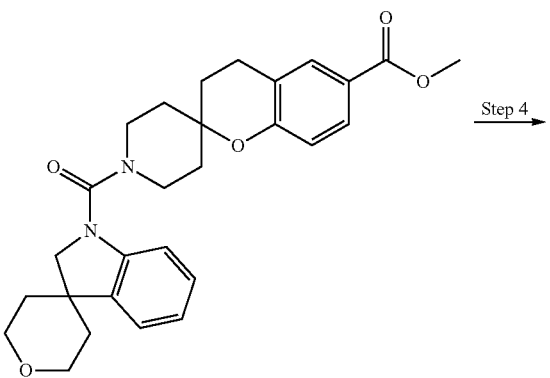

-continued

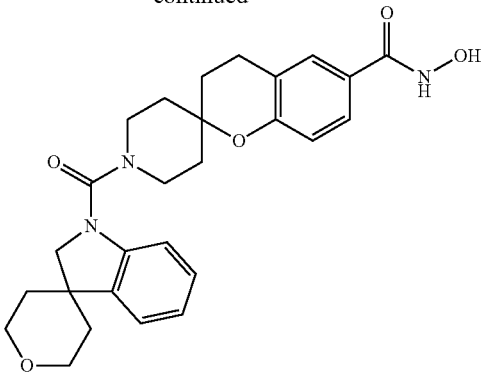

Step-1: (1H-Imidazol-1-yl)(2',3',5',6'-tetrahydrospiro[indoline-3,4'-pyran]-1-yl)methanone In a 20-mL scintillation vial, 1,1'-carbonyldiimidazole (236 mg, 1.453 mmol, 1.09 equiv) was taken up in THF (10 mL) and 2',3',5',6'-tetrahydrospiro[indoline-3,4'-pyran](250 mg, 1.321 mmol, 1 equiv) was added. The resulting solution was heated at 50° C. with agitation for 3 h. The reaction was cooled to ambient temperature, and then concentrated to dryness. The residue was dissolved in 20 mL of $CH_2Cl_2$ and washed with 20 mL of brine. The organic layer was passed through an Isolute© phase separator, and then concentrated to dryness to afford the title compound as a white solid which was used without further purification. MS: (ES, m/z): 284 $[M+H]^+$.

Step-2: 3-Methyl-1-(2',3',5',6'-tetrahydrospiro[indoline-3,4'-pyran]-1-carbonyl)-1H-imidazol-3-ium iodide In a 20-mL scintillation vial (1H-imidazol-1-yl)(2',3',5',6'-tetrahydrospiro[indoline-3,4'-pyran]-1-yl)methanone (400 mg, 1.412 mmol, 1 equiv) was taken up in $CH_3CN$ (10 mL). $CH_3I$ (0.53 mL, 8.47 mmol, 5.96 equiv) was added and the reaction was stirred at ambient temperature for 24 h. The reaction was concentrated to dryness to afford the title compound as a yellow solid which was used without further purification. MS: (ES, m/z): 299 $[M-I+H]^+$.

Step-3: Methyl 1'-(2',3',5',6'-tetrahydrospiro[indoline-3,4'-pyran]-1-carbonyl)spiro[chromane-2,4'-piperidine]-6-carboxylate In a 20-mL scintillation vial 3-methyl-1-(2',3',5',6'-tetrahydrospiro[indoline-3,4'-pyran]-1-carbonyl)-1H-imidazol-3-ium iodide (30 mg, 0.071 mmol, 1 equiv) and methyl spiro[chromane-2,4'-piperidine]-6-carboxylate (18 mg, 0.071 mmol, 1 equiv) were taken up in $CH_3Cl$ (2 mL). $Et_3N$ (0.029 ml, 0.212 mmol, 3 equiv) was added. The resulting solution was stirred at ambient temperature for 18 h. The reaction was diluted with 10 mL of $CH_2Cl_2$ and washed with 20 mL of brine. The organic layer was passed through an Isolute© phase separator, and then concentrated to dryness to afford the title compound as an orange oil which was used without further purification. MS: (ES, m/z): 477 $[M+H]^+$.

Step-4: N-Hydroxy-1'-(2',3',5',6'-tetrahydrospiro[indoline-3,4'-pyran]-1-carbonyl)spiro[chromane-2,4'-piperidine]-6-carboxamide Into a 20-mL scintillation vial was placed a solution of methyl 2-(2',3',5',6'-tetrahydrospiro[indoline-3,4'-pyran]-1-ylcarbonyl)-5-thia-2-azaspiro[3.4]octane-7-carboxylate 5,5-dioxide (30 mg, 0.069 mmol, 1 equiv) in THF/MeOH (1:1, 2 mL), $NH_2OH$ (50% in water, 0.5 mL, 7.57 mmol, 110 equiv), and 1N aq. NaOH (0.5 mL, 0.5 mmol, 7.24 equiv). The resulting solution was stirred for 2 h at ambient temperature and concentrated to dryness. The crude product was purified by Prep-HPLC using the following conditions: Column: XBridge Prep C18 OBD 5 μm, 19×50 mm; Mobile Phase A: Water/0.05% Formic acid, Mobile Phase B: $CH_3CN$/0.05% Formic Acid; Flow Rate: 23 mL/min; Gradient: 15% B to 65% B in 8 min; Detector: UV 254 nm, 220 nm. The collected fractions were lyophilized to obtain 5 mg (16% yield) of the title compound as an off-white solid. $^1H$ NMR (300 MHz, DMSO-d6) δ (ppm): 11.00 (s, 1H), 8.89 (s, 1H), 8.36 (s, 1H), 7.39-7.63 (m, 2H), 7.12-7.30 (m, 2H), 7.03 (d, J=8.21 Hz, 1H), 6.78-6.97 (m, 2H), 3.83 (s, 4H), 3.44-3.58 (m, 4H), 2.75 (br d, J=15.24 Hz, 4H), 1.73-1.89 (m, 6H), 1.54 (s, 2H). MS: (ES, m/z): 478 $[M+H]^+$.

Example 50

Preparation of 1'-((1H-benzo[d]imidazol-2-yl)methyl)-N-hydroxy-3,4-dihydro-1H-spiro[naphthalene-2,3'-pyrrolidine]-6-carboxamide (I-1)

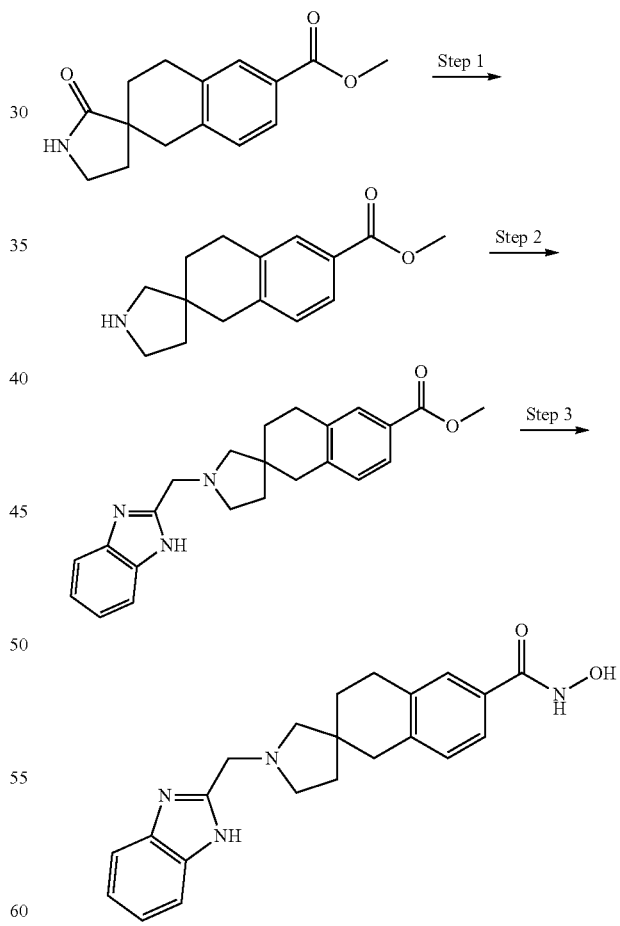

Step-1: Methyl 3,4-dihydro-1H-spiro[naphthalene-2,3'-pyrrolidine]-6-carboxylate A solution of methyl-2'-oxo-3,4-dihydro-1H-spiro[naphthalene-2,3'-pyrrolidine]-6-carboxylate (0.100 g, 0.386 mmol, 1 equiv) in 3 mL of THF was cooled to −10° C. (ice/acetone) when borane-THF complex (1M in THF; 0.58 mL, 0.58 mmol, 1.5 equiv) was added drop wise over 5 min. The mixture was stirred at −10° C. for 5 min, then heated up to 52° C. for about 7 days and an additional 0.5 eq borane-THF complex was added after 24 and 48 h; THF was added as needed to maintain volume. The resulting mixture was cooled to room temperature and quenched with 0.3 mL 2 N HCl, heated to 52° C. for 1 h, then concentrated. The residue was loaded onto a 10 g (70 mL) SCX-2 cartridge with MeOH (with some CH$_2$Cl$_2$), flushed with MeOH (with some CH$_2$Cl$_2$), and eluted with 2 M NH$_3$ in MeOH (with some CH$_2$Cl$_2$). The fractions from the NH$_3$ elution were combined and concentrated. Purification by silica gel chromatography with CH$_2$Cl$_2$/MeOH/NH$_4$OH (90/20/1) afforded 134 mg (50% yield) of the title compound. $^1$H NMR (300 MHz, DMSO-d6) δ (ppm): 7.73-7.63 (m, 2H), 7.23-7.14 (m, 1H), 3.82 (s, 3H), 3.12-3.05 (dd, 2H), 2.90-2.62 (m, 6H), 2.50 (br s, 1H), 1.78-1.45 (m, 4H). MS: (APCI, m/z): 246 [M+H]$^+$.

Step-2: Methyl 1'-((1H-benzo[d]imidazol-2-yl)methyl)-3,4-dihydro-1H-spiro[naphthalene-2,3'-pyrrolidine]-6-carboxylate To a 20 mL vial was added methyl 3,4-dihydro-1H-spiro[naphthalene-2,3'-pyrrolidine]-6-carboxylate (0.045 g, 0.183 mmol, 1 equiv), K$_2$CO$_3$ (0.051 g, 0.367 mmol, 2 equiv) and DMF (1 mL). Next, 2-(chloromethyl)-1H-benzo[d]imidazole (0.035 g, 0.211 mmol, 1.15 equiv) was added and the mixture was stirred at 50° C. overnight. Water was added to the reaction mixture and extracted with two portions of EtOAc. The organic layers were combined and dried over anhydrous Na$_2$SO$_4$, filtered and concentrated. Purification by column chromatography on silica gel (0-5% MeOH/CH$_2$Cl$_2$) afforded 39 mg (57% yield) of the title compound as a colourless glassy solid. MS: (ES, m/z): 376 [M+H]+.

Step-3: 1'-((1H-Benzo[d]imidazol-2-yl)methyl)-N-hydroxy-3,4-dihydro-1H-spiro[naphthalene-2,3'-pyrrolidine]-6-carboxamide Methyl 1'-((1H-benzo[d]imidazol-2-yl)methyl)-3,4-dihydro-1H-spiro[naphthalene-2,3'-pyrrolidine]-6-carboxylate (0.039 g, 0.104 mmol, 1 equiv) was dissolved in a solution of THF/MeOH (4:1, 1.38 mL). Hydroxylamine (50% in water, 0.58 mL, 9.4 mmol, 90 equiv) was added followed by 1N aq. NaOH (0.157 mL, 3 equiv). The reaction was stirred at room temperature for 1 h and was purified directly by reverse-phase chromatography using the following conditions: Column: XTerra Prep MS C18 OBD 5 μm, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyohpilized to afford 0.016 g (41% yield) of the title compound. $^1$H NMR (300 MHz, CD$_3$OD) δ (ppm): 8.29 (s, 2H), 7.58 (br dd, J=5.9, 3.2 Hz, 3H), 7.39-7.49 (m, 2H), 7.21-7.34 (m, 2H), 7.04-7.18 (m, 1H), 4.28 (br s, 2H), 3.29-3.35 (m, 4H), 2.77-3.02 (m, 8H), 1.81-1.99 (m, 4H). MS: (ES, m/z): 377 [M+H]$^+$.

TABLE-29

The following compound was prepared according to the method of Example 50.

| Ex. | Structure | $^1$H-NMR δ (ppm) | Found (ES, m/z) [M + H]$^+$ |
|---|---|---|---|
| I-2 | 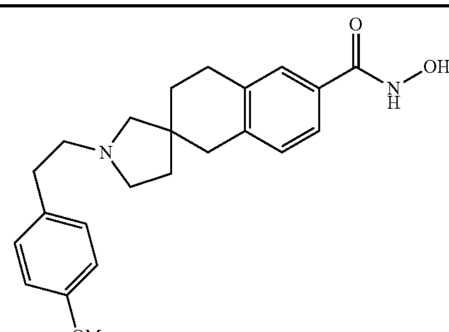 | (300 MHz, CD$_3$OD): 8.47 (s, 1H), 7.34-7.69 (m, 3H), 7.11-7.29 (m, 3H), 6.88 (d, J = 8.5 Hz, 2H), 3.76 (s, 3H), 3.46-3.64 (m, 2H), 3.16-3.46 (m, 6H), 2.87-3.14 (m, 4H), 1.83-2.11 (m, 4H) | 381 |

Example 51

Preparation of N-hydroxy-1'-(4-methoxybenzyl)-3,4-dihydro-1H-spiro[naphthalene-2,3'-pyrrolidine]-6-carboxamide (I-3)

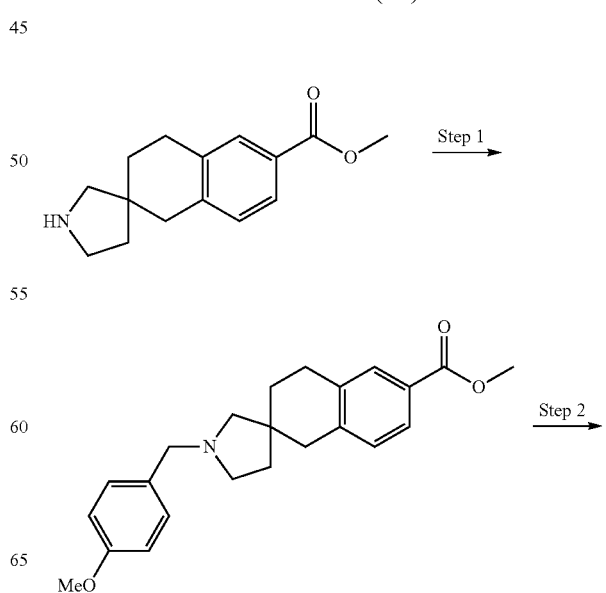

-continued

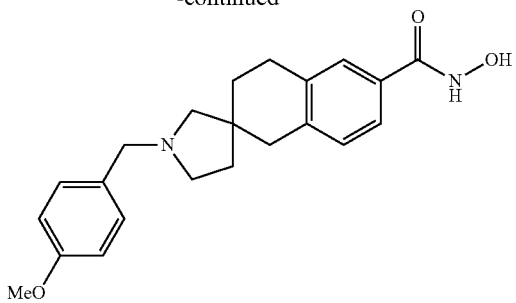

Step-1: Methyl 1'-(4-methoxybenzyl)-3,4-dihydro-1H-spiro[naphthalene-2,3'-pyrrolidine]-7-carboxylate Methyl 3,4-dihydro-H-spiro[naphthalene-2,3'-pyrrolidine]-6-carboxylate (0.043 g, 0.177 mmol, 1 equiv) was combined with Et$_3$N (0.025 mL, 0.179 mmol, 1 equiv) and 4-methoxybenzaldehyde (0.024 mL, 0.195 mmol, 1.1 equiv) in DCE (2.0 mL). The reaction was stirred at room temperature for 1 hour. Then NaBH(OAc)$_3$ (0.049 g, 0.23 mmol, 1.3 equiv) was added and the reaction was stirred at room temperature for 16 h. The reaction mixture was quenched with sat. aq. NaHCO$_3$ and the organic layer was separated and directly purified by normal phase chromatography on silica gel (30% to 100% EtOAc/hexanes) to afford 0.045 g (70% yield) of the title compound as a colorless, glassy solid. MS: (ES, m/z): 366 [M+H]$^+$.

Step-2: N-Hydroxy-1'-(4-methoxybenzyl)-3,4-dihydro-1H-spiro[naphthalene-2,3'-pyrrolidine]-6-carboxamide Methyl 1'-(4-methoxybenzyl)-3,4-dihydro-1H-spiro[naphthalene-2,3'-pyrrolidine]-7-carboxylate (0.045 g, 0.123 mmol, 1 equiv) was dissolved in a solution of THF/MeOH (4:1, 1.25 mL). Hydroxylamine (50% in water, 0.68 mL, 11.1 mmol, 90 equiv) was added followed by 2N aq. NaOH (0.185 mL, 3 equiv). The reaction was stirred at room temperature for 48 h and was purified directly by reverse-phase chromatography using the following conditions: Column: XTerra Prep MS C18 OBD 5 μm, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyohpilized to afford 27 mg (61% yield) of the title compound. $^1$H NMR (300 MHz, CD$_3$OD) δ (ppm): 8.44 (s, 2H), 7.37-7.56 (m, 4H), 7.14 (d, J=7.9 Hz, 1H), 6.84-7.09 (m, 2H), 4.32 (s, 2H), 3.79 (s, 3H), 3.10-3.61 (m, 8H), 2.84-3.08 (m, 4H), 1.86-2.11 (m, 4H). MS: (ES, m/z): 367 [M+H]$^+$.

Example 52

Small Molecule X-ray Crystallography Experiment for methyl (R)-1'-[(4-methanesulfonylphenyl)methyl]-2'-oxo-3,4-dihydro-1H-spiro[naphthalene-2,3'-pyrrolidine]-6-carboxylate Low-temperature diffraction data (ω-scans) were collected on a Rigaku MicroMax-007HF diffractometer coupled to a Saturn994+ CCD detector with Cu Kβ (λ=1.54178 Å). All structures were solved by direct methods and were refined against F$^2$ on all data by full-matrix least squares. All non-hydrogen atoms were refined anisotropically. Hydrogen atoms were included in the model at geometrically calculated positions and refined using a riding model. The isotropic displacement parameters of all hydrogen atoms were fixed to 1.2 times the U value of the atoms to which they are linked (1.5 times for methyl groups). All atoms shown are depicted with 50% thermal contours. The hydrogen atoms are shown as arbitrary spheres. Carbon atoms C11 and C34 both have R stereochemistry (FIG. 1).

TABLE 30

Crystal data and structure refinement for methyl (R)-1'-[(4-methanesulfonylphenyl)methyl]-2'-oxo-3,4-dihydro-1H-spiro[naphthalene-2,3'-pyrrolidine]-6-carboxylate.

| | | |
|---|---|---|
| Empirical formula | C$_{23}$H$_{25}$NO$_5$S | |
| Formula weight | 427.50 | |
| Temperature | 93(2) K | |
| Wavelength | 1.54187 Å | |
| Crystal system | Monoclinic | |
| Space group | P 2$_1$ | |
| Unit cell dimensions | a = 19.8815(6) Å | α = 90° |
| | b = 5.6009(2) Å | β = 113.941(8)° |
| | c = 20.4656(14) Å | γ = 90° |
| Volume | 2082.9(2) Å$^3$ | |
| Z | 4 | |
| Density (calculated) | 1.363 Mg/m$^3$ | |
| Absorption coefficient | 1.680 mm$^{-1}$ | |
| F(000) | 904 | |
| Crystal size | 0.140 × 0.040 × 0.010 mm$^3$ | |
| Crystal color and habit | Colorless Plate | |
| Diffractometer | Rigaku Saturn 944+ CCD | |
| Θ range for data collection | 2.362 to 68.068°. | |
| Index ranges | −21 ≤ h ≤ 22, −6 ≤ k ≤ 6, −24 ≤ l ≤ 23 | |
| Reflections collected | 34368 | |
| Independent reflections | 7110 [R(int) = 0.1679] | |
| Observed reflections (I > 2σ (I)) | 3779 | |
| Completeness to θ = 67.687° | 97.6% | |
| Absorption correction | Semi-empirical from equivalents | |
| Max. and min. transmission | 0.983 and 0.775 | |
| Solution method | SHELXL-2014/7 (Sheldrick, 2014) | |
| Refinement method | SHELXL-2014/7 (Sheldrick, 2014) | |
| Data/restraints/parameters | 7110/1/545 | |
| Goodness-of-fit on F$^2$ | 0.933 | |
| Final R indices [I > 2σ(I)] | R1 = 0.0633, wR2 = 0.1111 | |
| R indices (all data) | R1 = 0.1253, wR2 = 0.1362 | |
| Absolute structure parameter | 0.05(3) | |
| Largest diff. peak and hole | 0.381 and −0.629 e.Å$^{-3}$ | |

Example 53

In vitro Histone Deacetylase Assay

The enzymatic HDAC6 assay was performed using electrophoretic mobility shift assay. Full length human recombinant HDAC6 protein was expressed in baculoviral system and purified by affinity chromatography. The enzymatic reactions were assembled in 384 well plates in a total volume of 25 μL in a reaction buffer composing: 100 mM HEPES, pH7.5, 25 mM KCl, 0.1% bovine serum albumin, 0.01% Triton X-100, 1% DMSO (from compounds) 2 μM of the fluorescently labeled peptide substrate and enzyme. The enzyme was added at a final concentration of 1 nM. The peptide substrate RHKK(Ac)—NH2 was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 μL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition (Pinh) is determined using the following equation:

Pinh=(PSR0%−PSRinh)/(PSR0%−PSR100%)*100, where PSRinh is the product sum ratio in the presence of inhibitor, PSR0% is the average product sum ration in the absence of inhibitor and PSR100% is the average product sum ratio in 100%-inhibition control samples. The IC50 values of inhibitors were determined by fitting the %-inhibition curves with 4 parameter dose-response model using XLfit 4 software.

As set forth in Table-31, below, $IC_{50}$ values are defined as follows: IC50≤0.1 μM (+++); IC50>0.1 μM and ≤0.5 μM (++); IC50>0.5 μM (+).

TABLE 31

Inhibitory Concentration (IC50) Values for Representative Compounds against HDAC6

| ChemDraw Name | Number | HDAC6 activity range |
|---|---|---|
| 1'-((1H-benzo[d]imidazol-2-yl)methyl)-N-hydroxy-3,4-dihydro-1H-spiro[naphthalene-2,3'-pyrrolidine]-6-carboxamide | (I-1) | +++ |
| N-hydroxy-1'-(4-methoxyphenethyl)-3,4-dihydro-1H-spiro[naphthalene-2,3'-pyrrolidine]-6-carboxamide | (I-2) | ++ |
| N-hydroxy-1'-(4-methoxybenzyl)-3,4-dihydro-1H-spiro[naphthalene-2,3'-pyrrolidine]-6-carboxamide | (I-3) | ++ |
| N-hydroxy-1'-(4-methoxyphenethyl)-2'-oxo-3,4-dihydro-1H-spiro[naphthalene-2,3'-pyrrolidine]-6-carboxamide | (I-4) | +++ |
| 1'-(1H-benzo[d]imidazol-2-yl)-N-hydroxy-2'-oxo-3,4-dihydro-1H-spiro[naphthalene-2,3'-pyrrolidine]-6-carboxamide | (I-5) | +++ |
| 1'-(3,4-dichlorobenzyl)-N-hydroxy-2'-oxo-3,4-dihydro-1H-spiro[naphthalene-2,3'-pyrrolidine]-6-carboxamide | (I-6) | +++ |
| 1'-(cyclohexylmethyl)-N-hydroxy-2'-oxo-3,4-dihydro-1H-spiro[naphthalene-2,3'-pyrrolidine]-6-carboxamide | (I-7) | ++ |
| N-hydroxy-1'-(4-methylbenzyl)-2'-oxo-3,4-dihydro-1H-spiro[naphthalene-2,3'-pyrrolidine]-6-carboxamide | (I-8) | ++ |
| 1'-(3-(dimethylamino)propyl)-N-hydroxy-2'-oxo-3,4-dihydro-1H-spiro[naphthalene-2,3'-pyrrolidine]-6-carboxamide | (I-9) | ++ |
| (R)-N-hydroxy-2'-oxo-1'-(pyridin-3-yl)-3,4-dihydro-1H-spiro[naphthalene-2,3'-pyrrolidine]-6-carboxamide | (I-10) | +++ |
| (S)-N-hydroxy-2'-oxo-1'-(pyridin-3-yl)-3,4-dihydro-1H-spiro[naphthalene-2,3'-pyrrolidine]-6-carboxamide | (I-11) | +++ |
| (R)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide | (I-12) | ++ |
| (S)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide | (I-13) | +++ |
| (R)-N-hydroxy-2'-oxo-1'-(pyridin-4-ylmethyl)-3,4-dihydro-1H-spiro[naphthalene-2,3'-pyrrolidine]-6-carboxamide | (I-14) | + |
| (S)-N-hydroxy-2'-oxo-1'-(pyridin-4-ylmethyl)-3,4-dihydro-1H-spiro[naphthalene-2,3'-pyrrolidine]-6-carboxamide | (I-15) | +++ |
| (R)-N-hydroxy-2'-oxo-1'-(pyridin-4-yl)-3,4-dihydro-1H-spiro[naphthalene-2,3'-pyrrolidine]-6-carboxamide | (I-16) | ++ |
| (S)-N-hydroxy-2'-oxo-1'-(pyridin-4-yl)-3,4-dihydro-1H-spiro[naphthalene-2,3'-pyrrolidine]-6-carboxamide | (I-17) | +++ |
| (R)-N-hydroxy-2'-oxo-1'-(pyridin-3-ylmethyl)-3,4-dihydro-1H-spiro[naphthalene-2,3'-pyrrolidine]-6-carboxamide | (I-18) | +++ |
| (S)-N-hydroxy-2'-oxo-1'-(pyridin-3-ylmethyl)-3,4-dihydro-1H-spiro[naphthalene-2,3'-pyrrolidine]-6-carboxamide | (I-19) | +++ |
| (R)-N-hydroxy-2'-oxo-1'-(pyridin-2-yl)-3,4-dihydro-1H-spiro[naphthalene-2,3'-pyrrolidine]-6-carboxamide | (I-20) | +++ |
| (S)-N-hydroxy-2'-oxo-1'-(pyridin-2-yl)-3,4-dihydro-1H-spiro[naphthalene-2,3'-pyrrolidine]-6-carboxamide | (I-21) | +++ |
| (R)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide | (I-22) | +++ |
| (S)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide | (I-23) | +++ |

TABLE 31-continued

Inhibitory Concentration (IC50) Values for
Representative Compounds against HDAC6

| ChemDraw Name | Number | HDAC6 activity range |
|---|---|---|
| (R)-N-hydroxy-1'-isopropyl-2'-oxo-3,4-dihydro-1H-spiro[naphthalene-2,3'-pyrrolidine]-6-carboxamide | (I-24) | +++ |
| (S)-N-hydroxy-1'-isopropyl-2'-oxo-3,4-dihydro-1H-spiro[naphthalene-2,3'-pyrrolidine]-6-carboxamide | (I-25) | +++ |
| (R)-N-hydroxy-2'-oxo-1'-phenyl-3,4-dihydro-1H-spiro[naphthalene-2,3'-pyrrolidine]-6-carboxamide | (I-26) | +++ |
| (R)-N-hydroxy-2'-oxo-3,4-dihydro-1H-spiro[naphthalene-2,3'-pyrrolidine]-6-carboxamide | (I-27) | +++ |
| (S)-N-hydroxy-2'-oxo-3,4-dihydro-1H-spiro[naphthalene-2,3'-pyrrolidine]-6-carboxamide | (I-28) | +++ |
| (S)-N-hydroxy-2'-oxo-1'-phenyl-3,4-dihydro-1H-spiro[naphthalene-2,3'-pyrrolidine]-6-carboxamide | (I-29) | +++ |
| (R)-1'-((2-chlorothiazol-5-yl)methyl)-N-hydroxy-2'-oxo-3,4-dihydro-1H-spiro[naphthalene-2,3'-pyrrolidine]-6-carboxamide | (I-30) | +++ |
| (R)-N-hydroxy-1'-((2-hydroxythiazol-5-yl)methyl)-2'-oxo-3,4-dihydro-1H-spiro[naphthalene-2,3'-pyrrolidine]-6-carboxamide | (I-31) | +++ |
| (R)-N-hydroxy-2'-oxo-1'-propyl-3,4-dihydro-1H-spiro[naphthalene-2,3'-pyrrolidine]-6-carboxamide | (I-32) | +++ |
| (R)-1'-(cyclobutylmethyl)-N-hydroxy-2'-oxo-3,4-dihydro-1H-spiro[naphthalene-2,3'-pyrrolidine]-6-carboxamide | (I-33) | +++ |
| (R)-N-hydroxy-1'-isopentyl-2'-oxo-3,4-dihydro-1H-spiro[naphthalene-2,3'-pyrrolidine]-6-carboxamide | (I-34) | +++ |
| (R)-1'-(but-2-yn-1-yl)-N-hydroxy-2'-oxo-3,4-dihydro-1H-spiro[naphthalene-2,3'-pyrrolidine]-6-carboxamide | (I-35) | +++ |
| (R)-N-hydroxy-1'-(2-methoxyethyl)-2'-oxo-3,4-dihydro-1H-spiro[naphthalene-2,3'-pyrrolidine]-6-carboxamide | (I-36) | +++ |
| (R)-1'-cinnamyl-N-hydroxy-2'-oxo-3,4-dihydro-1H-spiro[naphthalene-2,3'-pyrrolidine]-6-carboxamide | (I-37) | +++ |
| (R)-N-hydroxy-1'-(2-methylbenzyl)-2'-oxo-3,4-dihydro-1H-spiro[naphthalene-2,3'-pyrrolidine]-6-carboxamide | (I-38) | +++ |
| (R)-N-hydroxy-2'-oxo-1'-(2-(trifluoromethyl)benzyl)-3,4-dihydro-1H-spiro[naphthalene-2,3'-pyrrolidine]-6-carboxamide | (I-39) | +++ |
| (R)-1'-(2-chlorobenzyl)-N-hydroxy-2'-oxo-3,4-dihydro-1H-spiro[naphthalene-2,3'-pyrrolidine]-6-carboxamide | (I-40) | +++ |
| (R)-N-hydroxy-2'-oxo-1'-(2-(trifluoromethoxy)benzyl)-3,4-dihydro-1H-spiro[naphthalene-2,3'-pyrrolidine]-6-carboxamide | (I-41) | +++ |
| (R)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide | (I-42) | +++ |
| (R)-N-hydroxy-1'-(2-morpholino-2-oxoethyl)-2'-oxo-3,4-dihydro-1H-spiro[naphthalene-2,3'-pyrrolidine]-6-carboxamide | (I-43) | +++ |
| (R)-N-hydroxy-1'-(2-methoxybenzyl)-2'-oxo-3,4-dihydro-1H-spiro[naphthalene-2,3'-pyrrolidine]-6-carboxamide | (I-44) | +++ |
| (R)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide | (I-45) | +++ |
| (R)-N-hydroxy-1'-((1-methyl-1H-benzo[d]imidazol-2-yl)methyl)-2'-oxo-3,4-dihydro-1H-spiro[naphthalene-2,3'-pyrrolidine]-6-carboxamide | (I-46) | +++ |
| (R)-N-hydroxy-1'-(2-methylallyl)-2'-oxo-3,4-dihydro-1H-spiro[naphthalene-2,3'-pyrrolidine]-6-carboxamide | (I-47) | +++ |
| (R)-1'-(2,5-dichlorobenzyl)-N-hydroxy-2'-oxo-3,4-dihydro-1H-spiro[naphthalene-2,3'-pyrrolidine]-6-carboxamide | (I-48) | +++ |
| (R)-1'-(2,6-dichlorobenzyl)-N-hydroxy-2'-oxo-3,4-dihydro-1H-spiro[naphthalene-2,3'-pyrrolidine]-6-carboxamide | (I-49) | +++ |
| (R)-1'-benzyl-N-hydroxy-2'-oxo-3,4-dihydro-1H-spiro[naphthalene-2,3'-pyrrolidine]-6-carboxamide | (I-50) | +++ |
| (R)-N-hydroxy-1'-(3-methoxybenzyl)-2'-oxo-3,4-dihydro-1H-spiro[naphthalene-2,3'-pyrrolidine]-6-carboxamide | (I-51) | +++ |
| (R)-N-hydroxy-2'-oxo-1'-(pyridin-2-ylmethyl)-3,4-dihydro-1H-spiro[naphthalene-2,3'-pyrrolidine]-6-carboxamide | (I-52) | +++ |
| (R)-1'-(3-fluorobenzyl)-N-hydroxy-2'-oxo-3,4-dihydro-1H-spiro[naphthalene-2,3'-pyrrolidine]-6-carboxamide | (I-53) | +++ |
| (R)-1'-(3-chlorobenzyl)-N-hydroxy-2'-oxo-3,4-dihydro-1H-spiro[naphthalene-2,3'-pyrrolidine]-6-carboxamide | (I-54) | +++ |
| (R)-1'-(4-chlorobenzyl)-N-hydroxy-2'-oxo-3,4-dihydro-1H-spiro[naphthalene-2,3'-pyrrolidine]-6-carboxamide | (I-55) | +++ |
| (R)-N-hydroxy-1'-(4-methoxybenzyl)-2'-oxo-3,4-dihydro-1H-spiro[naphthalene-2,3'-pyrrolidine]-6-carboxamide | (I-56) | +++ |
| (R)-1'-(2-fluorobenzyl)-N-hydroxy-2'-oxo-3,4-dihydro-1H-spiro[naphthalene-2,3'-pyrrolidine]-6-carboxamide | (I-57) | +++ |
| (R)-N-hydroxy-1'-(naphthalen-2-ylmethyl)-2'-oxo-3,4-dihydro-1H-spiro[naphthalene-2,3'-pyrrolidine]-6-carboxamide | (I-58) | +++ |

TABLE 31-continued

Inhibitory Concentration (IC50) Values for
Representative Compounds against HDAC6

| ChemDraw Name | Number | HDAC6 activity range |
|---|---|---|
| (R)-1'-(2-(difluoromethoxy)benzyl)-N-hydroxy-2'-oxo-3,4-dihydro-1H-spiro[naphthalene-2,3'-pyrrolidine]-6-carboxamide | (I-59) | +++ |
| (S)-N-hydroxy-2'-oxo-1'-propyl-3,4-dihydro-1H-spiro[naphthalene-2,3'-pyrrolidine]-6-carboxamide | (I-60) | ++ |
| (S)-1'-(cyclobutylmethyl)-N-hydroxy-2'-oxo-3,4-dihydro-1H-spiro[naphthalene-2,3'-pyrrolidine]-6-carboxamide | (I-61) | ++ |
| (S)-N-hydroxy-1'-isopentyl-2'-oxo-3,4-dihydro-1H-spiro[naphthalene-2,3'-pyrrolidine]-6-carboxamide | (I-62) | ++ |
| (S)-1'-(but-2-yn-1-yl)-N-hydroxy-2'-oxo-3,4-dihydro-1H-spiro[naphthalene-2,3'-pyrrolidine]-6-carboxamide | (I-63) | +++ |
| (S)-N-hydroxy-1'-(2-methoxyethyl)-2'-oxo-3,4-dihydro-1H-spiro[naphthalene-2,3'-pyrrolidine]-6-carboxamide | (I-64) | ++ |
| (S)-1'-cinnamyl-N-hydroxy-2'-oxo-3,4-dihydro-1H-spiro[naphthalene-2,3'-pyrrolidine]-6-carboxamide | (I-65) | +++ |
| (S)-N-hydroxy-1'-(2-methylbenzyl)-2'-oxo-3,4-dihydro-1H-spiro[naphthalene-2,3'-pyrrolidine]-6-carboxamide | (I-66) | +++ |
| (S)-N-hydroxy-2'-oxo-1'-(2-(trifluoromethyl)benzyl)-3,4-dihydro-1H-spiro[naphthalene-2,3'-pyrrolidine]-6-carboxamide | (I-67) | ++ |
| (S)-1'-(2-chlorobenzyl)-N-hydroxy-2'-oxo-3,4-dihydro-1H-spiro[naphthalene-2,3'-pyrrolidine]-6-carboxamide | (I-68) | ++ |
| (S)-N-hydroxy-2'-oxo-1'-(2-(trifluoromethoxy)benzyl)-3,4-dihydro-1H-spiro[naphthalene-2,3'-pyrrolidine]-6-carboxamide | (I-69) | ++ |
| (S)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide | (I-70) | +++ |
| (S)-N-hydroxy-1'-(2-morpholino-2-oxoethyl)-2'-oxo-3,4-dihydro-1H-spiro[naphthalene-2,3'-pyrrolidine]-6-carboxamide | (I-71) | ++ |
| (S)-N-hydroxy-1'-(2-methoxybenzyl)-2'-oxo-3,4-dihydro-1H-spiro[naphthalene-2,3'-pyrrolidine]-6-carboxamide | (I-72) | +++ |
| (S)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide | (I-73) | +++ |
| (S)-1'-(2,5-dichlorobenzyl)-N-hydroxy-2'-oxo-3,4-dihydro-1H-spiro[naphthalene-2,3'-pyrrolidine]-6-carboxamide | (I-74) | ++ |
| (S)-1'-(2,6-dichlorobenzyl)-N-hydroxy-2'-oxo-3,4-dihydro-1H-spiro[naphthalene-2,3'-pyrrolidine]-6-carboxamide | (I-75) | ++ |
| (S)-1'-benzyl-N-hydroxy-2'-oxo-3,4-dihydro-1H-spiro[naphthalene-2,3'-pyrrolidine]-6-carboxamide | (I-76) | +++ |
| (S)-N-hydroxy-1'-(3-methoxybenzyl)-2'-oxo-3,4-dihydro-1H-spiro[naphthalene-2,3'-pyrrolidine]-6-carboxamide | (I-77) | +++ |
| (S)-N-hydroxy-2'-oxo-1'-(pyridin-2-ylmethyl)-3,4-dihydro-1H-spiro[naphthalene-2,3'-pyrrolidine]-6-carboxamide | (I-78) | +++ |
| (S)-1'-(3-fluorobenzyl)-N-hydroxy-2'-oxo-3,4-dihydro-1H-spiro[naphthalene-2,3'-pyrrolidine]-6-carboxamide | (I-79) | +++ |
| (S)-N-hydroxy-2'-oxo-1'-(4-(trifluoromethoxy)benzyl)-3,4-dihydro-1H-spiro[naphthalene-2,3'-pyrrolidine]-6-carboxamide | (I-80) | ++ |
| (S)-1'-(3-chlorobenzyl)-N-hydroxy-2'-oxo-3,4-dihydro-1H-spiro[naphthalene-2,3'-pyrrolidine]-6-carboxamide | (I-81) | +++ |
| (S)-1'-(4-chlorobenzyl)-N-hydroxy-2'-oxo-3,4-dihydro-1H-spiro[naphthalene-2,3'-pyrrolidine]-6-carboxamide | (I-82) | +++ |
| (S)-N-hydroxy-1'-(4-methoxybenzyl)-2'-oxo-3,4-dihydro-1H-spiro[naphthalene-2,3'-pyrrolidine]-6-carboxamide | (I-83) | +++ |
| (S)-1'-(2-fluorobenzyl)-N-hydroxy-2'-oxo-3,4-dihydro-1H-spiro[naphthalene-2,3'-pyrrolidine]-6-carboxamide | (I-84) | +++ |
| (S)-1'-(4-(tert-butyl)benzyl)-N-hydroxy-2'-oxo-3,4-dihydro-1H-spiro[naphthalene-2,3'-pyrrolidine]-6-carboxamide | (I-85) | ++ |
| (S)-N-hydroxy-1'-(naphthalen-2-ylmethyl)-2'-oxo-3,4-dihydro-1H-spiro[naphthalene-2,3'-pyrrolidine]-6-carboxamide | (I-86) | +++ |
| (S)-1'-(2-(difluoromethoxy)benzyl)-N-hydroxy-2'-oxo-3,4-dihydro-1H-spiro[naphthalene-2,3'-pyrrolidine]-6-carboxamide | (I-87) | +++ |
| (R)-N-hydroxy-1'-(4-(methylsulfonyl)benzyl)-2'-oxo-3,4-dihydro-1H-spiro[naphthalene-2,3'-pyrrolidine]-6-carboxamide | (I-88) | +++ |
| (R)-N-hydroxy-1'-(naphthalen-1-yl)-2'-oxo-3,4-dihydro-1H-spiro[naphthalene-2,3'-pyrrolidine]-6-carboxamide | (I-89) | +++ |
| (R)-1'-(3-fluoro-4-methoxyphenyl)-N-hydroxy-2'-oxo-3,4-dihydro-1H-spiro[naphthalene-2,3'-pyrrolidine]-6-carboxamide | (I-90) | +++ |
| (R)-1'-(benzo[d][1,3]dioxol-5-yl)-N-hydroxy-2'-oxo-3,4-dihydro-1H-spiro[naphthalene-2,3'-pyrrolidine]-6-carboxamide | (I-91) | +++ |
| (R)-N-hydroxy-1'-(3-(methylthio)phenyl)-2'-oxo-3,4-dihydro-1H-spiro[naphthalene-2,3'-pyrrolidine]-6-carboxamide | (I-92) | +++ |
| (R)-1'-(4-(dimethylamino)phenyl)-N-hydroxy-2'-oxo-3,4-dihydro-1H-spiro[naphthalene-2,3'-pyrrolidine]-6-carboxamide | (I-93) | +++ |
| (R)-N-hydroxy-1'-(6-isopropylpyridin-3-yl)-2'-oxo-3,4-dihydro-1H-spiro[naphthalene-2,3'-pyrrolidine]-6-carboxamide | (I-94) | +++ |

TABLE 31-continued

Inhibitory Concentration (IC50) Values for
Representative Compounds against HDAC6

| ChemDraw Name | Number | HDAC6 activity range |
|---|---|---|
| (R)-N-hydroxy-2'-oxo-1'-(quinolin-3-yl)-3,4-dihydro-1H-spiro[naphthalene-2,3'-pyrrolidine]-6-carboxamide | (I-95) | +++ |
| (R)-1'-(2,3-dihydrobenzofuran-7-yl)-N-hydroxy-2'-oxo-3,4-dihydro-1H-spiro[naphthalene-2,3'-pyrrolidine]-6-carboxamide | (I-96) | +++ |
| (R)-1'-(6-(tert-butylamino)pyrimidin-4-yl)-N-hydroxy-2'-oxo-3,4-dihydro-1H-spiro[naphthalene-2,3'-pyrrolidine]-6-carboxamide | (I-97) | +++ |
| (R)-1'-(1,3-dimethyl-1H-pyrazol-4-yl)-N-hydroxy-2'-oxo-3,4-dihydro-1H-spiro[naphthalene-2,3'-pyrrolidine]-6-carboxamide | (I-98) | +++ |
| (R)-N-hydroxy-1'-(imidazo[1,2-a]pyridin-6-yl)-2'-oxo-3,4-dihydro-1H-spiro[naphthalene-2,3'-pyrrolidine]-6-carboxamide | (I-99) | +++ |
| (S)-1'-(2,4-dimethylphenyl)-N-hydroxy-2'-oxo-3,4-dihydro-1H-spiro[naphthalene-2,3'-pyrrolidine]-6-carboxamide | (I-100) | +++ |
| (S)-N-hydroxy-1'-(6-isopropylpyridin-3-yl)-2'-oxo-3,4-dihydro-1H-spiro[naphthalene-2,3'-pyrrolidine]-6-carboxamide | (I-101) | +++ |
| (S)-N-hydroxy-2'-oxo-1'-(quinolin-3-yl)-3,4-dihydro-1H-spiro[naphthalene-2,3'-pyrrolidine]-6-carboxamide | (I-102) | +++ |
| (S)-N-hydroxy-1'-(imidazo[1,2-a]pyridin-6-yl)-2'-oxo-3,4-dihydro-1H-spiro[naphthalene-2,3'-pyrrolidine]-6-carboxamide | (I-103) | +++ |
| (R)-N-hydroxy-1'-methyl-2'-oxo-3,4-dihydro-1H-spiro[naphthalene-2,3'-pyrrolidine]-6-carboxamide | (I-104) | +++ |
| (S)-N-hydroxy-1'-methyl-2'-oxo-3,4-dihydro-1H-spiro[naphthalene-2,3'-pyrrolidine]-6-carboxamide | (I-105) | +++ |
| (R)-N-hydroxy-2'-oxo-1'-(4-((trifluoromethyl)sulfonyl)benzyl)-3,4-dihydro-1H-spiro[naphthalene-2,3'-pyrrolidine]-6-carboxamide | (I-106) | +++ |
| (S)-N-hydroxy-2'-oxo-1'-(4-((trifluoromethyl)sulfonyl)benzyl)-3,4-dihydro-1H-spiro[naphthalene-2,3'-pyrrolidine]-6-carboxamide | (I-107) | ++ |
| (R)-N-hydroxy-1'-(3-methoxyphenyl)-2'-oxo-3,4-dihydro-1H-spiro[naphthalene-2,3'-pyrrolidine]-6-carboxamide | (I-108) | +++ |
| (R)-1'-cyclopropyl-N-hydroxy-2'-oxo-3,4-dihydro-1H-spiro[naphthalene-2,3'-pyrrolidine]-6-carboxamide | (I-109) | +++ |
| (R)-1'-(5-fluoropyridin-3-yl)-N-hydroxy-2'-oxo-3,4-dihydro-1H-spiro[naphthalene-2,3'-pyrrolidine]-6-carboxamide | (I-110) | +++ |
| (R)-N-hydroxy-1'-(2-methoxyphenyl)-2'-oxo-3,4-dihydro-1H-spiro[naphthalene-2,3'-pyrrolidine]-6-carboxamide | (I-111) | +++ |
| (R)-1'-(3-cyanophenyl)-N-hydroxy-2'-oxo-3,4-dihydro-1H-spiro[naphthalene-2,3'-pyrrolidine]-6-carboxamide | (I-112) | +++ |
| (R)-1'-(3-fluorophenyl)-N-hydroxy-2'-oxo-3,4-dihydro-1H-spiro[naphthalene-2,3'-pyrrolidine]-6-carboxamide | (I-113) | +++ |
| (R)-N-hydroxy-1'-(6-methoxypyridin-3-yl)-2'-oxo-3,4-dihydro-1H-spiro[naphthalene-2,3'-pyrrolidine]-6-carboxamide | (I-114) | +++ |
| (S)-N-hydroxy-1'-(2-methoxyphenyl)-2'-oxo-3,4-dihydro-1H-spiro[naphthalene-2,3'-pyrrolidine]-6-carboxamide | (I-115) | +++ |
| (S)-1'-(3-cyanophenyl)-N-hydroxy-2'-oxo-3,4-dihydro-1H-spiro[naphthalene-2,3'-pyrrolidine]-6-carboxamide | (I-116) | +++ |
| (S)-1'-(3-fluorophenyl)-N-hydroxy-2'-oxo-3,4-dihydro-1H-spiro[naphthalene-2,3'-pyrrolidine]-6-carboxamide | (I-117) | +++ |
| (S)-N-hydroxy-1'-(6-methoxypyridin-3-yl)-2'-oxo-3,4-dihydro-1H-spiro[naphthalene-2,3'-pyrrolidine]-6-carboxamide | (I-118) | +++ |
| (R)-1'-(3,4-difluorophenyl)-N-hydroxy-2'-oxo-3,4-dihydro-1H-spiro[naphthalene-2,3'-pyrrolidine]-6-carboxamide | (I-119) | +++ |
| (R)-1'-(4-fluorophenyl)-N-hydroxy-2'-oxo-3,4-dihydro-1H-spiro[naphthalene-2,3'-pyrrolidine]-6-carboxamide | (I-120) | +++ |
| (R)-1'-(2-fluorophenyl)-N-hydroxy-2'-oxo-3,4-dihydro-1H-spiro[naphthalene-2,3'-pyrrolidine]-6-carboxamide | (I-121) | |
| (S)-N-hydroxy-1'-(oxetan-3-ylmethyl)-2'-oxo-3,4-dihydro-1H-spiro[naphthalene-2,3'-pyrrolidine]-6-carboxamide | (I-122) | ++ |
| (R)-1'-(2,3-difluorophenyl)-N-hydroxy-2'-oxo-3,4-dihydro-1H-spiro[naphthalene-2,3'-pyrrolidine]-6-carboxamide | (I-123) | +++ |
| (R)-N-hydroxy-1'-(4-methoxyphenyl)-2'-oxo-3,4-dihydro-1H-spiro[naphthalene-2,3'-pyrrolidine]-6-carboxamide | (I-124) | +++ |
| (R)-1'-(2-fluoro-3-methoxyphenyl)-N-hydroxy-2'-oxo-3,4-dihydro-1H-spiro[naphthalene-2,3'-pyrrolidine]-6-carboxamide | (I-125) | +++ |
| (S)-1'-(2-fluoro-3-methoxyphenyl)-N-hydroxy-2'-oxo-3,4-dihydro-1H-spiro[naphthalene-2,3'-pyrrolidine]-6-carboxamide | (I-126) | +++ |
| (S)-1'-(2-fluoro-4-methoxyphenyl)-N-hydroxy-2'-oxo-3,4-dihydro-1H-spiro[naphthalene-2,3'-pyrrolidine]-6-carboxamide | (I-127) | +++ |
| (R)-1'-(4-fluoro-3-methoxyphenyl)-N-hydroxy-2'-oxo-3,4-dihydro-1H-spiro[naphthalene-2,3'-pyrrolidine]-6-carboxamide | (I-128) | +++ |
| (S)-1'-(4-fluoro-3-methoxyphenyl)-N-hydroxy-2'-oxo-3,4-dihydro-1H-spiro[naphthalene-2,3'-pyrrolidine]-6-carboxamide | (I-129) | +++ |

TABLE 31-continued

Inhibitory Concentration (IC50) Values for Representative Compounds against HDAC6

| ChemDraw Name | Number | HDAC6 activity range |
|---|---|---|
| (S)-1'-(5-chloropyridin-2-yl)-N-hydroxy-2'-oxo-3,4-dihydro-1H-spiro[naphthalene-2,3'-pyrrolidine]-6-carboxamide | (I-130) | +++ |
| (R)-N-hydroxy-1'-(2-methylpyridin-3-yl)-2'-oxo-3,4-dihydro-1H-spiro[naphthalene-2,3'-pyrrolidine]-6-carboxamide | (I-131) | +++ |
| (S)-N-hydroxy-1'-(2-methylpyridin-3-yl)-2'-oxo-3,4-dihydro-1H-spiro[naphthalene-2,3'-pyrrolidine]-6-carboxamide | (I-132) | +++ |
| (R)-N-hydroxy-1'-(6-methylpyridin-3-yl)-2'-oxo-3,4-dihydro-1H-spiro[naphthalene-2,3'-pyrrolidine]-6-carboxamide | (I-133) | +++ |
| (S)-N-hydroxy-1'-(6-methylpyridin-3-yl)-2'-oxo-3,4-dihydro-1H-spiro[naphthalene-2,3'-pyrrolidine]-6-carboxamide | (I-134) | +++ |
| (R)-N-hydroxy-1'-(5-methylpyridin-3-yl)-2'-oxo-3,4-dihydro-1H-spiro[naphthalene-2,3'-pyrrolidine]-6-carboxamide | (I-135) | +++ |
| (R)-N-hydroxy-1'-(4-methylpyridin-3-yl)-2'-oxo-3,4-dihydro-1H-spiro[naphthalene-2,3'-pyrrolidine]-6-carboxamide | (I-136) | +++ |
| (S)-N-hydroxy-1'-(4-methylpyridin-3-yl)-2'-oxo-3,4-dihydro-1H-spiro[naphthalene-2,3'-pyrrolidine]-6-carboxamide | (I-137) | +++ |
| (R)-1'-(5-chloropyridin-3-yl)-N-hydroxy-2'-oxo-3,4-dihydro-1H-spiro[naphthalene-2,3'-pyrrolidine]-6-carboxamide | (I-138) | +++ |
| (S)-1'-(5-chloropyridin-3-yl)-N-hydroxy-2'-oxo-3,4-dihydro-1H-spiro[naphthalene-2,3'-pyrrolidine]-6-carboxamide | (I-139) | +++ |
| (R)-1'-(3-chloropyridin-4-yl)-N-hydroxy-2'-oxo-3,4-dihydro-1H-spiro[naphthalene-2,3'-pyrrolidine]-6-carboxamide | (I-140) | +++ |
| (S)-1'-(3-chloropyridin-4-yl)-N-hydroxy-2'-oxo-3,4-dihydro-1H-spiro[naphthalene-2,3'-pyrrolidine]-6-carboxamide | (I-141) | +++ |
| (S)-N-hydroxy-1'-(4-methoxypyridin-3-yl)-2'-oxo-3,4-dihydro-1H-spiro[naphthalene-2,3'-pyrrolidine]-6-carboxamide | (I-142) | +++ |
| (R)-N-hydroxy-1'-(5-methoxypyridin-3-yl)-2'-oxo-3,4-dihydro-1H-spiro[naphthalene-2,3'-pyrrolidine]-6-carboxamide | (I-143) | +++ |
| (S)-N-hydroxy-1'-(5-methoxypyridin-3-yl)-2'-oxo-3,4-dihydro-1H-spiro[naphthalene-2,3'-pyrrolidine]-6-carboxamide | (I-144) | +++ |
| (R)-N-hydroxy-1'-(2-methoxypyridin-3-yl)-2'-oxo-3,4-dihydro-1H-spiro[naphthalene-2,3'-pyrrolidine]-6-carboxamide | (I-145) | +++ |
| (S)-N-hydroxy-1'-(2-methoxypyridin-3-yl)-2'-oxo-3,4-dihydro-1H-spiro[naphthalene-2,3'-pyrrolidine]-6-carboxamide | (I-146) | +++ |
| (S)-1'-(2-fluoro-5-methoxyphenyl)-N-hydroxy-2'-oxo-3,4-dihydro-1H-spiro[naphthalene-2,3'-pyrrolidine]-6-carboxamide | (I-147) | +++ |
| (S)-1'-(3-fluoro-5-methoxyphenyl)-N-hydroxy-2'-oxo-3,4-dihydro-1H-spiro[naphthalene-2,3'-pyrrolidine]-6-carboxamide | (I-148) | +++ |
| (R)-N-hydroxy-1'-(2-methoxypyridin-4-yl)-2'-oxo-3,4-dihydro-1H-spiro[naphthalene-2,3'-pyrrolidine]-6-carboxamide | (I-149) | +++ |
| (S)-N-hydroxy-1'-(2-methoxypyridin-4-yl)-2'-oxo-3,4-dihydro-1H-spiro[naphthalene-2,3'-pyrrolidine]-6-carboxamide | (I-150) | +++ |
| (R)-1'-(6-(dimethylamino)pyridin-3-yl)-N-hydroxy-2'-oxo-3,4-dihydro-1H-spiro[naphthalene-2,3'-pyrrolidine]-6-carboxamide | (I-151) | +++ |
| (S)-1'-(6-(dimethylamino)pyridin-3-yl)-N-hydroxy-2'-oxo-3,4-dihydro-1H-spiro[naphthalene-2,3'-pyrrolidine]-6-carboxamide | (I-152) | ++ |
| (S)-1'-(5-fluoropyridin-3-yl)-N-hydroxy-2'-oxo-3,4-dihydro-1H-spiro[naphthalene-2,3'-pyrrolidine]-6-carboxamide | (I-153) | +++ |
| (S)-1'-(4-fluorophenyl)-N-hydroxy-2'-oxo-3,4-dihydro-1H-spiro[naphthalene-2,3'-pyrrolidine]-6-carboxamide | (I-154) | +++ |
| (S)-1'-(3,4-difluorophenyl)-N-hydroxy-2'-oxo-3,4-dihydro-1H-spiro[naphthalene-2,3'-pyrrolidine]-6-carboxamide | (I-155) | +++ |
| (S)-1'-(2,3-difluorophenyl)-N-hydroxy-2'-oxo-3,4-dihydro-1H-spiro[naphthalene-2,3'-pyrrolidine]-6-carboxamide | (I-156) | +++ |
| (S)-1'-(2-fluorophenyl)-N-hydroxy-2'-oxo-3,4-dihydro-1H-spiro[naphthalene-2,3'-pyrrolidine]-6-carboxamide | (I-157) | +++ |
| (S)-N-hydroxy-1'-(3-methoxyphenyl)-2'-oxo-3,4-dihydro-1H-spiro[naphthalene-2,3'-pyrrolidine]-6-carboxamide | (I-158) | +++ |
| (R)-N-hydroxy-1'-isobutyl-2'-oxo-3,4-dihydro-1H-spiro[naphthalene-2,3'-pyrrolidine]-6-carboxamide | (I-159) | +++ |
| (S)-N-hydroxy-1'-isobutyl-2'-oxo-3,4-dihydro-1H-spiro[naphthalene-2,3'-pyrrolidine]-6-carboxamide | (I-160) | ++ |
| (R)-1'-ethyl-N-hydroxy-2'-oxo-3,4-dihydro-1H-spiro[naphthalene-2,3'-pyrrolidine]-6-carboxamide | (I-161) | +++ |
| (S)-1'-ethyl-N-hydroxy-2'-oxo-3,4-dihydro-1H-spiro[naphthalene-2,3'-pyrrolidine]-6-carboxamide | (I-162) | +++ |
| (R)-1'-cyclopentyl-N-hydroxy-2'-oxo-3,4-dihydro-1H-spiro[naphthalene-2,3'-pyrrolidine]-6-carboxamide | (I-163) | +++ |
| (S)-1'-cyclopentyl-N-hydroxy-2'-oxo-3,4-dihydro-1H-spiro[naphthalene-2,3'-pyrrolidine]-6-carboxamide | (I-164) | ++ |
| (R)-N-hydroxy-2'-oxo-1'-(2,2,2-trifluoroethyl)-3,4-dihydro-1H-spiro[naphthalene-2,3'-pyrrolidine]-6-carboxamide | (I-165) | +++ |
| (S)-N-hydroxy-2'-oxo-1'-(2,2,2-trifluoroethyl)-3,4-dihydro-1H-spiro[naphthalene-2,3'-pyrrolidine]-6-carboxamide | (I-166) | ++ |

TABLE 31-continued

Inhibitory Concentration (IC50) Values for
Representative Compounds against HDAC6

| ChemDraw Name | Number | HDAC6 activity range |
|---|---|---|
| (R)-1'-(2,5-difluorophenyl)-N-hydroxy-2'-oxo-3,4-dihydro-1H-spiro[naphthalene-2,3'-pyrrolidine]-6-carboxamide | (I-167) | +++ |
| (R)-N-hydroxy-1'-(1-methyl-1H-pyrazol-4-yl)-2'-oxo-3,4-dihydro-1H-spiro[naphthalene-2,3'-pyrrolidine]-6-carboxamide | (I-168) | +++ |
| (S)-1'-(2,5-difluorophenyl)-N-hydroxy-2'-oxo-3,4-dihydro-1H-spiro[naphthalene-2,3'-pyrrolidine]-6-carboxamide | (I-169) | +++ |
| (S)-N-hydroxy-1'-(1-methyl-1H-pyrazol-4-yl)-2'-oxo-3,4-dihydro-1H-spiro[naphthalene-2,3'-pyrrolidine]-6-carboxamide | (I-170) | +++ |
| (R)-1'-cyclobutyl-N-hydroxy-2'-oxo-3,4-dihydro-1H-spiro[naphthalene-2,3'-pyrrolidine]-6-carboxamide | (I-171) | +++ |
| (S)-1'-cyclobutyl-N-hydroxy-2'-oxo-3,4-dihydro-1H-spiro[naphthalene-2,3'-pyrrolidine]-6-carboxamide | (I-172) | +++ |
| (S)-1'-(4-cyanophenyl)-N-hydroxy-2'-oxo-3,4-dihydro-1H-spiro[naphthalene-2,3'-pyrrolidine]-6-carboxamide | (I-173) | +++ |
| (S)-1'-(2-cyanophenyl)-N-hydroxy-2'-oxo-3,4-dihydro-1H-spiro[naphthalene-2,3'-pyrrolidine]-6-carboxamide | (I-174) | +++ |
| (R)-1'-(2-cyanophenyl)-N-hydroxy-2'-oxo-3,4-dihydro-1H-spiro[naphthalene-2,3'-pyrrolidine]-6-carboxamide | (I-175) | +++ |
| 1'-benzyl-N-hydroxy-2'-oxo-3,4-dihydro-1H-spiro[naphthalene-2,3'-piperidine]-6-carboxamide | (I-176) | +++ |
| N-hydroxy-2'-oxo-3,4-dihydro-1H-spiro[naphthalene-2,3'-piperidine]-6-carboxamide | (I-177) | +++ |
| N-hydroxy-1'-methyl-2'-oxo-3,4-dihydro-1H-spiro[naphthalene-2,3'-piperidine]-6-carboxamide | (I-178) | +++ |
| (R)-N-hydroxy-1'-methyl-2'-oxo-3,4-dihydro-1H-spiro[naphthalene-2,3'-piperidine]-6-carboxamide | (I-179) | +++ |
| (S)-N-hydroxy-1'-methyl-2'-oxo-3,4-dihydro-1H-spiro[naphthalene-2,3'-piperidine]-6-carboxamide | (I-180) | +++ |
| (R)-N-hydroxy-2'-oxo-1'-phenyl-3,4-dihydro-1H-spiro[naphthalene-2,3'-piperidine]-6-carboxamide | (I-181) | +++ |
| (S)-N-hydroxy-2'-oxo-1'-phenyl-3,4-dihydro-1H-spiro[naphthalene-2,3'-piperidine]-6-carboxamide | (I-182) | +++ |
| (S)-1'-cyclopropyl-N-hydroxy-2'-oxo-3,4-dihydro-1H-spiro[naphthalene-2,3'-piperidine]-6-carboxamide | (I-183) | +++ |
| (S)-1'-ethyl-N-hydroxy-2'-oxo-3,4-dihydro-1H-spiro[naphthalene-2,3'-piperidine]-6-carboxamide | (I-184) | +++ |
| (R)-1'-(cyclobutylmethyl)-N-hydroxy-2'-oxo-3,4-dihydro-1H-spiro[naphthalene-2,3'-piperidine]-6-carboxamide | (I-185) | +++ |
| (S)-1'-(cyclobutylmethyl)-N-hydroxy-2'-oxo-3,4-dihydro-1H-spiro[naphthalene-2,3'-piperidine]-6-carboxamide | (I-186) | +++ |
| (R)-N-hydroxy-1'-(3-methoxypropyl)-2'-oxo-3,4-dihydro-1H-spiro[naphthalene-2,3'-piperidine]-6-carboxamide | (I-187) | +++ |
| (S)-N-hydroxy-1'-(3-methoxypropyl)-2'-oxo-3,4-dihydro-1H-spiro[naphthalene-2,3'-piperidine]-6-carboxamide | (I-188) | +++ |
| (R)-N-hydroxy-1'-isobutyl-2'-oxo-3,4-dihydro-1H-spiro[naphthalene-2,3'-piperidine]-6-carboxamide | (I-189) | +++ |
| (S)-N-hydroxy-1'-isobutyl-2'-oxo-3,4-dihydro-1H-spiro[naphthalene-2,3'-piperidine]-6-carboxamide | (I-190) | +++ |
| (R)-N-hydroxy-1'-isopropyl-2'-oxo-3,4-dihydro-1H-spiro[naphthalene-2,3'-piperidine]-6-carboxamide | (I-191) | +++ |
| (S)-N-hydroxy-1'-isopropyl-2'-oxo-3,4-dihydro-1H-spiro[naphthalene-2,3'-piperidine]-6-carboxamide | (I-192) | +++ |
| (R)-1'-cyclopropyl-N-hydroxy-2'-oxo-3,4-dihydro-1H-spiro[naphthalene-2,3'-piperidine]-6-carboxamide | (I-193) | +++ |
| (R)-1'-ethyl-N-hydroxy-2'-oxo-3,4-dihydro-1H-spiro[naphthalene-2,3'-piperidine]-6-carboxamide | (I-194) | +++ |
| (S)-N-hydroxy-1'-(oxetan-3-ylmethyl)-2'-oxo-3,4-dihydro-1H-spiro[naphthalene-2,3'-piperidine]-6-carboxamide | (I-195) | +++ |
| (R)-N-hydroxy-1'-(oxetan-3-ylmethyl)-2'-oxo-3,4-dihydro-1H-spiro[naphthalene-2,3'-piperidine]-6-carboxamide | (I-196) | +++ |
| (R)-1'-cyclobutyl-N-hydroxy-2'-oxo-3,4-dihydro-1H-spiro[naphthalene-2,3'-piperidine]-6-carboxamide | (I-197) | +++ |
| (S)-1'-cyclobutyl-N-hydroxy-2'-oxo-3,4-dihydro-1H-spiro[naphthalene-2,3'-piperidine]-6-carboxamide | (I-198) | +++ |
| (R)-1'-cyclopentyl-N-hydroxy-2'-oxo-3,4-dihydro-1H-spiro[naphthalene-2,3'-piperidine]-6-carboxamide | (I-199) | +++ |
| (S)-1'-cyclopentyl-N-hydroxy-2'-oxo-3,4-dihydro-1H-spiro[naphthalene-2,3'-piperidine]-6-carboxamide | (I-200) | +++ |
| (R)-N-hydroxy-1'-methyl-5'-oxo-3,4-dihydro-1H-spiro[naphthalene-2,3'-pyrrolidine]-6-carboxamide | (I-201) | +++ |
| (S)-N-hydroxy-1'-methyl-5'-oxo-3,4-dihydro-1H-spiro[naphthalene-2,3'-pyrrolidine]-6-carboxamide | (I-202) | +++ |
| (R)-N-hydroxy-5'-oxo-1'-phenyl-3,4-dihydro-1H-spiro[naphthalene-2,3'-pyrrolidine]-6-carboxamide | (I-203) | +++ |

TABLE 31-continued

Inhibitory Concentration (IC50) Values for
Representative Compounds against HDAC6

| ChemDraw Name | Number | HDAC6 activity range |
|---|---|---|
| (S)-N-hydroxy-5'-oxo-1'-phenyl-3,4-dihydro-1H-spiro[naphthalene-2,3'-pyrrolidine]-6-carboxamide | (I-204) | +++ |
| (R)-1'-(cyclobutylmethyl)-N-hydroxy-5'-oxo-3,4-dihydro-1H-spiro[naphthalene-2,3'-pyrrolidine]-6-carboxamide | (I-205) | +++ |
| (R)-1'-ethyl-N-hydroxy-5'-oxo-3,4-dihydro-1H-spiro[naphthalene-2,3'-pyrrolidine]-6-carboxamide | (I-206) | +++ |
| (R)-N-hydroxy-1'-isobutyl-5'-oxo-3,4-dihydro-1H-spiro[naphthalene-2,3'-pyrrolidine]-6-carboxamide | (I-207) | +++ |
| (R)-N-hydroxy-1'-isopropyl-5'-oxo-3,4-dihydro-1H-spiro[naphthalene-2,3'-pyrrolidine]-6-carboxamide | (I-208) | +++ |
| (R)-1'-cyclopropyl-N-hydroxy-5'-oxo-3,4-dihydro-1H-spiro[naphthalene-2,3'-pyrrolidine]-6-carboxamide | (I-209) | +++ |
| (S)-1'-(cyclobutylmethyl)-N-hydroxy-5'-oxo-3,4-dihydro-1H-spiro[naphthalene-2,3'-pyrrolidine]-6-carboxamide | (I-210) | +++ |
| (S)-1'-ethyl-N-hydroxy-5'-oxo-3,4-dihydro-1H-spiro[naphthalene-2,3'-pyrrolidine]-6-carboxamide | (I-211) | +++ |
| (S)-N-hydroxy-1'-isobutyl-5'-oxo-3,4-dihydro-1H-spiro[naphthalene-2,3'-pyrrolidine]-6-carboxamide | (I-212) | +++ |
| (S)-N-hydroxy-1'-isopropyl-5'-oxo-3,4-dihydro-1H-spiro[naphthalene-2,3'-pyrrolidine]-6-carboxamide | (I-213) | +++ |
| (S)-1'-cyclopropyl-N-hydroxy-5'-oxo-3,4-dihydro-1H-spiro[naphthalene-2,3'-pyrrolidine]-6-carboxamide | (I-214) | +++ |
| (R)-N-hydroxy-1'-(oxetan-3-ylmethyl)-5'-oxo-3,4-dihydro-1H-spiro[naphthalene-2,3'-pyrrolidine]-6-carboxamide | (I-215) | +++ |
| (R)-1'-benzyl-N-hydroxy-5'-oxo-3,4-dihydro-1H-spiro[naphthalene-2,3'-pyrrolidine]-6-carboxamide | (I-216) | +++ |
| (S)-N-hydroxy-1'-(oxetan-3-ylmethyl)-5'-oxo-3,4-dihydro-1H-spiro[naphthalene-2,3'-pyrrolidine]-6-carboxamide | (I-217) | ++ |
| (S)-1'-benzyl-N-hydroxy-5'-oxo-3,4-dihydro-1H-spiro[naphthalene-2,3'-pyrrolidine]-6-carboxamide | (I-218) | +++ |
| (R)-N-hydroxy-1'-(3-methoxypropyl)-5'-oxo-3,4-dihydro-1H-spiro[naphthalene-2,3'-pyrrolidine]-6-carboxamide | (I-219) | +++ |
| (R)-N-hydroxy-5'-oxo-1'-(2,2,2-trifluoroethyl)-3,4-dihydro-1H-spiro[naphthalene-2,3'-pyrrolidine]-6-carboxamide | (I-220) | +++ |
| (R)-N-hydroxy-5'-oxo-1'-(pyridin-3-yl)-3,4-dihydro-1H-spiro[naphthalene-2,3'-pyrrolidine]-6-carboxamide | (I-221) | +++ |
| (S)-N-hydroxy-1'-(3-methoxypropyl)-5'-oxo-3,4-dihydro-1H-spiro[naphthalene-2,3'-pyrrolidine]-6-carboxamide | (I-222) | +++ |
| (S)-N-hydroxy-5'-oxo-1'-(2,2,2-trifluoroethyl)-3,4-dihydro-1H-spiro[naphthalene-2,3'-pyrrolidine]-6-carboxamide | (I-223) | +++ |
| (S)-N-hydroxy-5'-oxo-1'-(pyridin-3-yl)-3,4-dihydro-1H-spiro[naphthalene-2,3'-pyrrolidine]-6-carboxamide | (I-224) | +++ |
| (R)-N-hydroxy-1'-(2-methylbenzyl)-5'-oxo-3,4-dihydro-1H-spiro[naphthalene-2,3'-pyrrolidine]-6-carboxamide | (I-225) | +++ |
| (R)-N-hydroxy-5'-oxo-1'-(pyridin-3-ylmethyl)-3,4-dihydro-1H-spiro[naphthalene-2,3'-pyrrolidine]-6-carboxamide | (I-226) | +++ |
| (R)-1'-(4-fluorophenyl)-N-hydroxy-5'-oxo-3,4-dihydro-1H-spiro[naphthalene-2,3'-pyrrolidine]-6-carboxamide | (I-227) | +++ |
| (R)-N-hydroxy-5'-oxo-1'-(pyridin-4-yl)-3,4-dihydro-1H-spiro[naphthalene-2,3'-pyrrolidine]-6-carboxamide | (I-228) | +++ |
| (R)-N-hydroxy-5'-oxo-1'-(pyridin-2-yl)-3,4-dihydro-1H-spiro[naphthalene-2,3'-pyrrolidine]-6-carboxamide | (I-229) | +++ |
| N-hydroxy-2'-oxo-1'-(pyridin-4-ylmethyl)spiro[chromane-2,3'-pyrrolidine]-6-carboxamide | (I-230) | + |
| N-hydroxy-2'-oxo-1'-phenylspiro[chromane-2,3'-pyrrolidine]-6-carboxamide | (I-231) | ++ |
| 1'-benzyl-N-hydroxy-2'-oxospiro[chromane-2,3'-pyrrolidine]-6-carboxamide | (I-232) | ++ |
| N-hydroxy-2'-oxo-1'-(pyridin-3-yl)spiro[chromane-2,3'-pyrrolidine]-6-carboxamide | (I-233) | ++ |
| N-hydroxy-2'-oxo-1'-((tetrahydro-2H-pyran-4-yl)methyl)spiro[chromane-2,3'-pyrrolidine]-6-carboxamide | (I-234) | + |
| N-hydroxy-1'-isopropyl-2'-oxospiro[chromane-2,3'-pyrrolidine]-6-carboxamide | (I-235) | + |
| N-hydroxy-2'-oxospiro[chromane-2,3'-pyrrolidine]-6-carboxamide | (I-236) | ++ |
| N-hydroxy-1'-methyl-2'-oxospiro[chromane-2,3'-pyrrolidine]-6-carboxamide | (I-237) | ++ |
| N-hydroxy-2-oxo-1-phenylspiro[pyrrolidine-3,2'-thiochromane]-6'-carboxamide 1',1'-dioxide | (I-238) | ++ |
| 1-benzyl-N-hydroxy-2-oxospiro[pyrrolidine-3,2'-thiochromane]-6'-carboxamide 1',1'-dioxide | (I-239) | ++ |
| N-hydroxy-2-oxo-1-(pyridin-3-yl)spiro[pyrrolidine-3,2'-thiochromane]-6'-carboxamide 1',1'-dioxide | (I-240) | ++ |

TABLE 31-continued

Inhibitory Concentration (IC50) Values for
Representative Compounds against HDAC6

| ChemDraw Name | Number | HDAC6 activity range |
|---|---|---|
| N-hydroxy-2-oxo-1-((tetrahydro-2H-pyran-4-yl)methyl)spiro[pyrrolidine-3,2'-thiochromane]-6'-carboxamide 1',1'-dioxide | (I-241) | + |
| N-hydroxy-2-oxo-1-(pyridin-4-ylmethyl)spiro[pyrrolidine-3,2'-thiochromane]-6'-carboxamide 1',1'-dioxide | (I-242) | + |
| N-hydroxy-2-oxospiro[pyrrolidine-3,2'-thiochromane]-6'-carboxamide 1',1'-dioxide | (I-243) | + |
| N-hydroxy-1-methyl-2-oxospiro[pyrrolidine-3,2'-thiochromane]-6'-carboxamide 1',1'-dioxide | (I-244) | + |
| N-hydroxy-1'-(4-methoxybenzyl)spiro[chromane-2,4'-piperidine]-6-carboxamide | (II-1) | + |
| 1'-((1H-benzo[d]imidazol-2-yl)methyl)-N-hydroxyspiro[chromane-2,4'-piperidine]-6-carboxamide | (II-2) | + |
| 1'-(cyclohexanecarbonyl)-N-hydroxyspiro[chromane-2,4'-piperidine]-6-carboxamide | (II-3) | + |
| N-hydroxy-1'-(4-methoxybenzoyl)spiro[chromane-2,4'-piperidine]-6-carboxamide | (II-4) | + |
| N-hydroxy-1'-((4-methoxyphenyl)sulfonyl)spiro[chromane-2,4'-piperidine]-6-carboxamide | (II-5) | + |
| 1'-(cyclohexylsulfonyl)-N-hydroxyspiro[chromane-2,4'-piperidine]-6-carboxamide | (II-6) | ++ |
| N6-hydroxy-N1'-phenylspiro[chromane-2,4'-piperidine]-1',6-dicarboxamide | (II-7) | ++ |
| 1'-cyclohexyl-N-hydroxyspiro[chromane-2,4'-piperidine]-6-carboxamide | (II-8) | + |
| N-hydroxy-1'-(2',3',5',6'-tetrahydrospiro[indoline-3,4'-pyran]-1-carbonyl)spiro[chromane-2,4'-piperidine]-6-carboxamide | (II-9) | + |

Equivalents

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:
1. A compound of the Formula I:

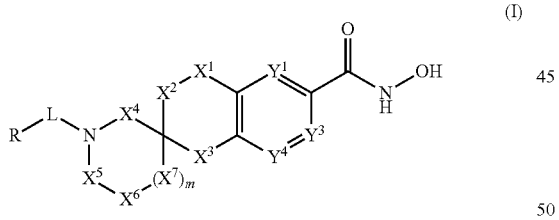

(I)

or a pharmaceutically acceptable salt, prodrug, solvate, hydrate, tautomer, or isomer or thereof, wherein:

$X^1$, $X^2$, $X^3$, $X^6$, and $X^7$ are each independently —$CR^1R^2$—, —$NR^3$—, —O—, —C(O)—, —$SO_2$—, —S(O)—, or —S—;

$X^4$ and $X^5$ are each independently —$CR^1R^2$—, —C(O)—, —$SO_2$—, —S(O)—, or —S—;

$Y^1$, $Y^3$ and $Y^4$ are each independently N or $CR^1$;

L is a bond, —$(CR^1R^2)_n$—, —$C(O)NR^3$—, —$S(O)_2$—, —$S(O)_2NR^3$—, —S(O)—, —$S(O)NR^3$—, —C(O)$(CR^1R^2)_nO$—, or —$C(O)(CR^1R^2)_n$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl;

$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —$NO_2$, —CN, —$NHC_1$-$C_6$alkyl, —$N(C_1$-$C_6$alkyl$)_2$, —$S(O)_2N(C_1$-$C_6$alkyl$)_2$, —$N(C_1$-$C_6$alkyl)$S(O)_2R^5$, —$S(O)_2(C_1$-$C_6$alkyl), —$(C_1$-$C_6$alkyl)$S(O)_2R^5$, —$C(O)C_1$-$C_6$alkyl, —$CO_2C_1$-$C_6$alkyl, —$N(C_1$-$C_6$alkyl)$S(O)_2C_1$-$C_6$alkyl, or $(CHR^5)_nNR^3R^4$, wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —$C(O)R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or $R^1$ and $R^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —CO$_2$C$_1$-C$_6$alkyl, or —(CHR$^5$)$_n$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkly)$_2$, —S(O)$_2$N(C$_1$-C$_6$alkyl)$_2$, —S(O)$_2$NHC$_1$-C$_6$alkyl, —C(O)C$_1$-C$_6$alkyl, —CO$_2$C$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —CO$_2$C$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_n$N(C$_1$-C$_6$alkyl)$_2$;

n is an integer from 0 to 6; and m is 0, 1, 2 or 3.

2. The compound of claim 1, wherein X$^4$ is —C(O)—.

3. The compound of claim 1, wherein m is 0 or 1.

4. The compound of claim 1, wherein the compound is of the Formula I-a:

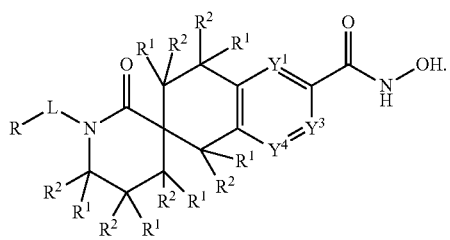

(I-a)

5. The compound of claim 1, wherein the compound is of the Formula I-b:

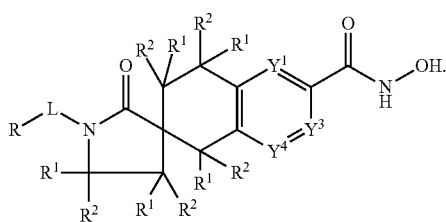

(I-b)

6. The compound of claim 1, wherein the compound is of the Formula I-c:

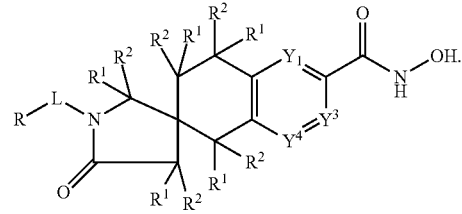

(I-c)

7. The compound of claim 1, wherein the compound is of the Formula I-d:

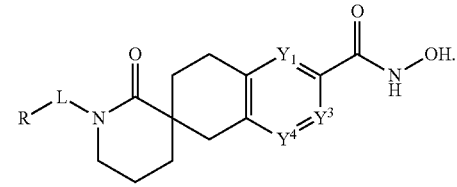

(I-d)

8. The compound of claim 1, wherein the compound is of the Formula I-e:

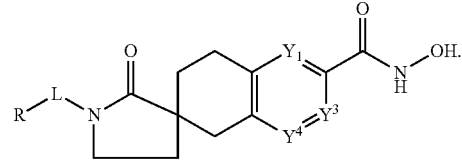

(I-e)

9. The compound of claim 1, wherein the compound is of the Formula I-f:

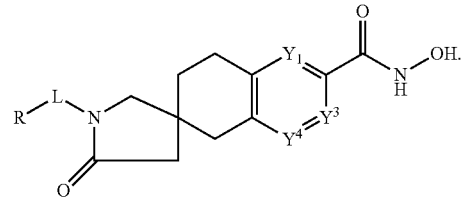

(I-f)

10. The compound of claim 1, wherein the compound is of the Formula I-g:

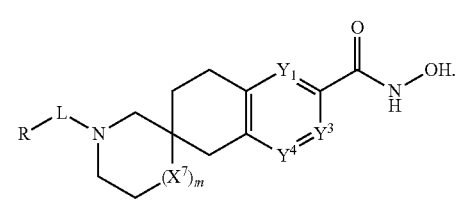

(I-g)

11. The compound of claim 1, wherein the compound is of the Formula I-h:

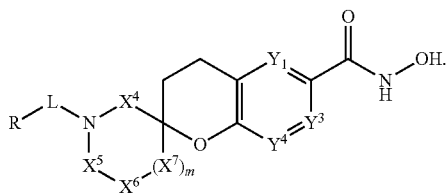
(I-h)

12. The compound of claim 1, wherein the compound is of the Formula I-j:

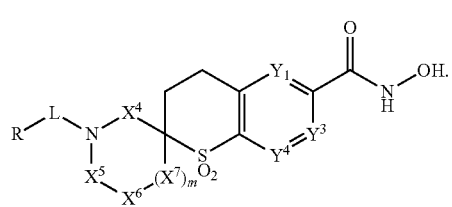
(I-j)

13. The compound of claim 1, wherein the compound is of the Formula I-k:

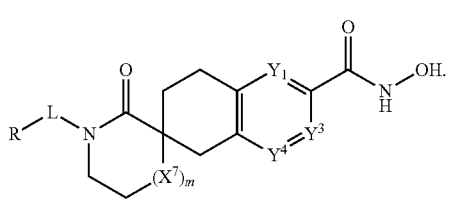
(I-k)

14. The compound of claim 1, wherein the compound is of the Formula I-m:

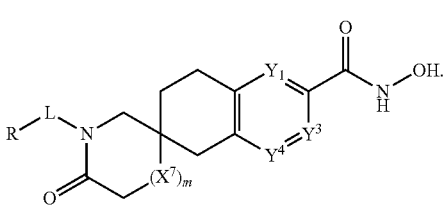
(I-m)

15. A compound of the Formula II:

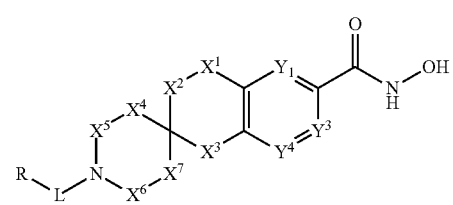
(II)

or a pharmaceutically acceptable salt, prodrug, solvate, hydrate, tautomer, or isomer or thereof, wherein:

$X^1$ is independently —$CR^1R^2$—, —$NR^3$—, —O—, —$SO_2$—, —S(O)—, or —S—;

$X^2$, $X^3$, $X^4$, and $X^7$ are each independently —$CR^1R^2$—, —$NR^3$—, —O—, —C(O)—, —$SO_2$—, —S(O)—, or —S—;

$X^5$ and $X^6$ are each independently —$CR^1R^2$—, —C(O)—, —$SO_2$—, —S(O)—, or —S—;

$Y^1$, $Y^3$ and $Y^4$ are each independently N or $CR^1$;

L is a bond, —$(CR^1R^2)_n$—, —$C(O)NR^3$—, —$S(O)_2$—, —$S(O)_2NR^3$—, —S(O)—, —$S(O)NR^3$—, —C(O)($CR^1R^2)_nO$—, or —C(O)($CR^1R^2)_n$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each -alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —C(O)$R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl;

$R^1$ and $R^2$ are independently, and at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P, or O, —OH, halogen, —$NO_2$, —CN, —$NHC_1$-$C_6$alkyl, —$N(C_1$-$C_6$alkyl$)_2$, —$S(O)_2N(C_1$-$C_6$alkyl$)_2$, —$N(C_1$-$C_6$alkyl$)S(O)_2R^5$, —$S(O)_2(C_1$-$C_6$alkyl), —$(C_1$-$C_6$alkyl$)S(O)_2R^5$, —$C(O)C_1$-$C_6$alkyl, —$CO_2C_1$-$C_6$alkyl, —$N(C_1$-$C_6$alkyl$)S(O)_2C_1$-$C_6$alkyl, or $(CHR^5)_nNR^3R^4$, wherein each alkyl, alkenyl, cycloalkenyl, alkynyl, cycloalkyl, heterocyclyl, aryl, or heteroaryl is optionally substituted with one or more substituents selected from —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —C(O)$R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or $R^1$ and $R^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —$S(O)_2N(C_1$-$C_6$alkyl$)_2$, —$S(O)_2(C_1$-$C_6$alkyl), —$(C_1$-$C_6$alkyl$)S(O)_2R^5$, —$C(O)C_1$-$C_6$alkyl, —$CO_2C_1$-$C_6$alkyl, or —$(CHR^5)_nN(C_1$-$C_6$alkyl$)_2$, wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, oxo, —CN, —$R^5$, —O($C_1$-$C_6$)alkyl, —NH($C_1$-$C_6$)alkyl, —$N(C_1$-$C_6$alkly$)_2$, —$S(O)_2N(C_1$-$C_6$alkyl$)_2$, —$S(O)_2NHC_1$-$C_6$alkyl, —$C(O)C_1$-$C_6$alkyl, —$CO_2C_1$-$C_6$alkyl, —$N(C_1$-$C_6$alkyl$)S(O)_2C_1$-$C_6$alkyl, —$S(O)R^5$, —$S(O)N(C_1$-$C_6$alkyl$)_2$, —$N(C_1$-$C_6$alkyl$)S(O)R^5$, heterocycle, aryl, or heteroaryl;

each $R^5$ is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, O and P, —OH, halogen, —$NO_2$, —CN, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$CO_2C_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6$alkyl$)_2$, —$N(C_1$-$C_6$alkyl)$S(O)(C_1$-$C_6$alkyl) or —$(CH_2)_nN(C_1$-$C_6$alkyl$)_2$; and n is an integer from 0 to 6.

16. The compound of claim 15, wherein $X^5$ is C(O).

17. The compound of claim 15 wherein the compound is of the Formula II-a:

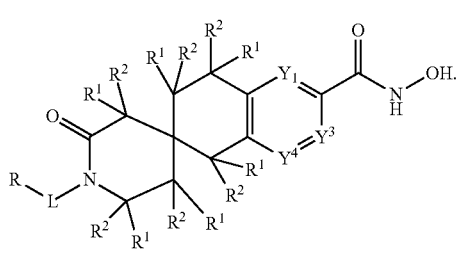

(II-a)

18. The compound of claim 15, wherein the compound is of the Formula II-b:

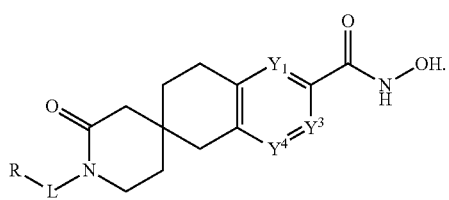

(II-b)

19. The compound of claim 15, wherein the compound is of the Formula II-c:

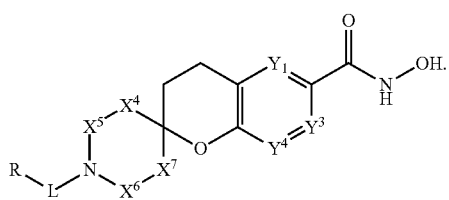

(II-c)

20. The compound of claim 15, wherein the compound is of the Formula II-d:

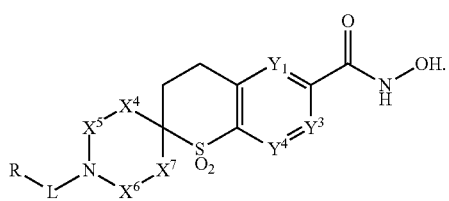

(II-d)

21. The compound of claim 15, wherein the compound is of the Formula II-e:

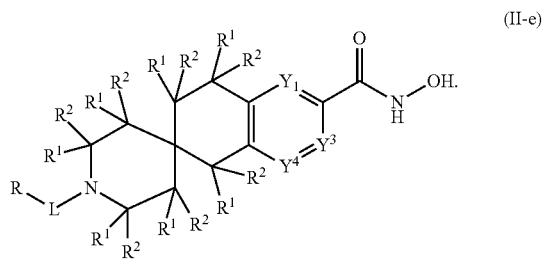

(II-e)

22. A compound of claim 1 selected from:

1'-((1H-benzo[d]imidazol-2-yl)methyl)-N-hydroxy-3,4-dihydro-1H-spiro[naphthalene-2,3'-pyrrolidine]-6-carboxamide (I-1);

N-hydroxy-1'-(4-methoxyphenethyl)-3,4-dihydro-1H-spiro[naphthalene-2,3'-pyrrolidine]-6-carboxamide (I-2);

N-hydroxy-1'-(4-methoxybenzyl)-3,4-dihydro-1H-spiro[naphthalene-2,3'-pyrrolidine]-6-carboxamide (I-3);

N-hydroxy-1'-(4-methoxyphenethyl)-2'-oxo-3,4-dihydro-1H-spiro[naphthalene-2,3'-pyrrolidine]-6-carboxamide (I-4);

1'-(1H-benzo[d]imidazol-2-yl)-N-hydroxy-2'-oxo-3,4-dihydro-1H-spiro[naphthalene-2,3'-pyrrolidine]-6-carboxamide (I-5);

1'-(3,4-dichlorobenzyl)-N-hydroxy-2'-oxo-3,4-dihydro-1H-spiro[naphthalene-2,3'-pyrrolidine]-6-carboxamide (I-6);

1'-(cyclohexylmethyl)-N-hydroxy-2'-oxo-3,4-dihydro-1H-spiro[naphthalene-2,3'-pyrrolidine]-6-carboxamide (I-7);

N-hydroxy-1'-(4-methylbenzyl)-2'-oxo-3,4-dihydro-1H-spiro[naphthalene-2,3'-pyrrolidine]-6-carboxamide (I-8);

1'-(3-(dimethylamino)propyl)-N-hydroxy-2'-oxo-3,4-dihydro-1H-spiro[naphthalene-2,3'-pyrrolidine]-6-carboxamide (I-9);

(R)-N-hydroxy-2'-oxo-1'-(pyridin-3-yl)-3,4-dihydro-1H-spiro[naphthalene-2,3'-pyrrolidine]-6-carboxamide (I-10);

(S)-N-hydroxy-2'-oxo-1'-(pyridin-3-yl)-3,4-dihydro-1H-spiro[naphthalene-2,3'-pyrrolidine]-6-carboxamide (I-11);

(R)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-12);

(S)-N-hydroxy-1'-(1-(2-methoxyethyl)-1H-benzo[d]imidazol-2-yl)-2'-oxo-3,4-dihydro-1H-spiro[naphthalene-2,3'-pyrrolidine]-6-carboxamide (I-13);

(R)-N-hydroxy-2'-oxo-1'-(pyridin-4-ylmethyl)-3,4-dihydro-1H-spiro[naphthalene-2,3'-pyrrolidine]-6-carboxamide (I-14);

(S)-N-hydroxy-2'-oxo-1'-(pyridin-4-ylmethyl)-3,4-dihydro-1H-spiro[naphthalene-2,3'-pyrrolidine]-6-carboxamide (I-15);

(R)-N-hydroxy-2'-oxo-1'-(pyridin-4-yl)-3,4-dihydro-1H-spiro[naphthalene-2,3'-pyrrolidine]-6-carboxamide (I-16);

(S)-N-hydroxy-2'-oxo-1'-(pyridin-4-yl)-3,4-dihydro-1H-spiro[naphthalene-2,3'-pyrrolidine]-6-carboxamide (I-17);

(R)-N-hydroxy-2'-oxo-1'-(pyridin-3-ylmethyl)-3,4-dihydro-1H-spiro[naphthalene-2,3'-pyrrolidine]-6-carboxamide (I-18);
(S)-N-hydroxy-2'-oxo-1'-(pyridin-3-ylmethyl)-3,4-dihydro-1H-spiro[naphthalene-2,3'-pyrrolidine]-6-carboxamide (I-19);
(R)-N-hydroxy-2'-oxo-1'-(pyridin-2-yl)-3,4-dihydro-1H-spiro[naphthalene-2,3'-pyrrolidine]-6-carboxamide (I-20);
(S)-N-hydroxy-2'-oxo-1'-(pyridin-2-yl)-3,4-dihydro-1H-spiro[naphthalene-2,3'-pyrrolidine]-6-carboxamide (I-21);
(R)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide (I-22);
(S)-N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-6-carboxamide (I-23);
(R)-N-hydroxy-1'-isopropyl-2'-oxo-3,4-dihydro-1H-spiro[naphthalene-2,3'-pyrrolidine]-6-carboxamide (I-24);
(S)-N-hydroxy-1'-isopropyl-2'-oxo-3,4-dihydro-1H-spiro[naphthalene-2,3'-pyrrolidine]-6-carboxamide (I-25);
(R)-N-hydroxy-2'-oxo-1'-phenyl-3,4-dihydro-1H-spiro[naphthalene-2,3'-pyrrolidine]-6-carboxamide (I-26);
(R)-N-hydroxy-2'-oxo-3,4-dihydro-1H-spiro[naphthalene-2,3'-pyrrolidine]-6-carboxamide (I-27);
(S)-N-hydroxy-2'-oxo-3,4-dihydro-1H-spiro[naphthalene-2,3'-pyrrolidine]-6-carboxamide (I-28);
(S)-N-hydroxy-2'-oxo-1'-phenyl-3,4-dihydro-1H-spiro[naphthalene-2,3'-pyrrolidine]-6-carboxamide (I-29);
(R)-1'-((2-chlorothiazol-5-yl)methyl)-N-hydroxy-2'-oxo-3,4-dihydro-1H-spiro[naphthalene-2,3'-pyrrolidine]-6-carboxamide (I-30);
(R)-N-hydroxy-1'-((2-hydroxythiazol-5-yl)methyl)-2'-oxo-3,4-dihydro-1H-spiro[naphthalene-2,3'-pyrrolidine]-6-carboxamide (I-31);
(R)-N-hydroxy-2'-oxo-1'-propyl-3,4-dihydro-1H-spiro[naphthalene-2,3'-pyrrolidine]-6-carboxamide (I-32);
(R)-1'-(cyclobutylmethyl)-N-hydroxy-2'-oxo-3,4-dihydro-1H-spiro[naphthalene-2,3'-pyrrolidine]-6-carboxamide (I-33);
(R)-N-hydroxy-1'-isopentyl-2'-oxo-3,4-dihydro-1H-spiro[naphthalene-2,3'-pyrrolidine]-6-carboxamide (I-34);
(R)-1'-(but-2-yn-1-yl)-N-hydroxy-2'-oxo-3,4-dihydro-1H-spiro[naphthalene-2,3'-pyrrolidine]-6-carboxamide (I-35);
(R)-N-hydroxy-1'-(2-methoxyethyl)-2'-oxo-3,4-dihydro-1H-spiro[naphthalene-2,3'-pyrrolidine]-6-carboxamide (I-36);
(R)-1'-cinnamyl-N-hydroxy-2'-oxo-3,4-dihydro-1H-spiro[naphthalene-2,3'-pyrrolidine]-6-carboxamide (I-37);
(R)-N-hydroxy-1'-(2-methylbenzyl)-2'-oxo-3,4-dihydro-1H-spiro[naphthalene-2,3'-pyrrolidine]-6-carboxamide (I-38);
(R)-N-hydroxy-2'-oxo-1'-(2-(trifluoromethyl)benzyl)-3,4-dihydro-1H-spiro[naphthalene-2,3'-pyrrolidine]-6-carboxamide (I-39);
(R)-1'-(2-chlorobenzyl)-N-hydroxy-2'-oxo-3,4-dihydro-1H-spiro[naphthalene-2,3'-pyrrolidine]-6-carboxamide (I-40);
(R)-N-hydroxy-2'-oxo-1'-(2-(trifluoromethoxy)benzyl)-3,4-dihydro-1H-spiro[naphthalene-2,3'-pyrrolidine]-6-carboxamide (I-41);
(R)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide (I-42);
(R)-N-hydroxy-1'-(2-morpholino-2-oxoethyl)-2'-oxo-3,4-dihydro-1H-spiro[naphthalene-2,3'-pyrrolidine]-6-carboxamide (I-43);
(R)-N-hydroxy-1'-(2-methoxybenzyl)-2'-oxo-3,4-dihydro-1H-spiro[naphthalene-2,3'-pyrrolidine]-6-carboxamide (I-44);
(R)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide (I-45);
(R)-N-hydroxy-1'-((1-methyl-1H-benzo[d]imidazol-2-yl)methyl)-2'-oxo-3,4-dihydro-1H-spiro[naphthalene-2,3'-pyrrolidine]-6-carboxamide (I-46);
(R)-N-hydroxy-1'-(2-methylallyl)-2'-oxo-3,4-dihydro-1H-spiro[naphthalene-2,3'-pyrrolidine]-6-carboxamide (I-47);
(R)-1'-(2,5-dichlorobenzyl)-N-hydroxy-2'-oxo-3,4-dihydro-H-spiro[naphthalene-2,3'-pyrrolidine]-6-carboxamide (I-48);
(R)-1'-(2,6-dichlorobenzyl)-N-hydroxy-2'-oxo-3,4-dihydro-1H-spiro[naphthalene-2,3'-pyrrolidine]-6-carboxamide (I-49);
(R)-1'-benzyl-N-hydroxy-2'-oxo-3,4-dihydro-1H-spiro[naphthalene-2,3'-pyrrolidine]-6-carboxamide (I-50);
(R)-N-hydroxy-1'-(3-methoxybenzyl)-2'-oxo-3,4-dihydro-1H-spiro[naphthalene-2,3'-pyrrolidine]-6-carboxamide (I-51);
(R)-N-hydroxy-2'-oxo-1'-(pyridin-2-ylmethyl)-3,4-dihydro-1H-spiro[naphthalene-2,3'-pyrrolidine]-6-carboxamide (I-52);
(R)-1'-(3-fluorobenzyl)-N-hydroxy-2'-oxo-3,4-dihydro-1H-spiro[naphthalene-2,3'-pyrrolidine]-6-carboxamide (I-53);
(R)-1'-(3-chlorobenzyl)-N-hydroxy-2'-oxo-3,4-dihydro-1H-spiro[naphthalene-2,3'-pyrrolidine]-6-carboxamide (I-54);
(R)-1'-(4-chlorobenzyl)-N-hydroxy-2'-oxo-3,4-dihydro-1H-spiro[naphthalene-2,3'-pyrrolidine]-6-carboxamide (I-55);
(R)-N-hydroxy-1'-(4-methoxybenzyl)-2'-oxo-3,4-dihydro-1H-spiro[naphthalene-2,3'-pyrrolidine]-6-carboxamide (I-56);
(R)-1'-(2-fluorobenzyl)-N-hydroxy-2'-oxo-3,4-dihydro-1H-spiro[naphthalene-2,3'-pyrrolidine]-6-carboxamide (I-57);
(R)-N-hydroxy-1'-(naphthalen-2-ylmethyl)-2'-oxo-3,4-dihydro-1H-spiro[naphthalene-2,3'-pyrrolidine]-6-carboxamide (I-58);
(R)-1'-(2-(difluoromethoxy)benzyl)-N-hydroxy-2'-oxo-3,4-dihydro-1H-spiro[naphthalene-2,3'-pyrrolidine]-6-carboxamide (I-59);
(S)-N-hydroxy-2'-oxo-1'-propyl-3,4-dihydro-1H-spiro[naphthalene-2,3'-pyrrolidine]-6-carboxamide (I-60);
(S)-1'-(cyclobutylmethyl)-N-hydroxy-2'-oxo-3,4-dihydro-1H-spiro[naphthalene-2,3'-pyrrolidine]-6-carboxamide (I-61);
(S)-N-hydroxy-1'-isopentyl-2'-oxo-3,4-dihydro-1H-spiro[naphthalene-2,3'-pyrrolidine]-6-carboxamide (I-62);
(S)-1'-(but-2-yn-1-yl)-N-hydroxy-2'-oxo-3,4-dihydro-1H-spiro[naphthalene-2,3'-pyrrolidine]-6-carboxamide (I-63);
(S)-N-hydroxy-1'-(2-methoxyethyl)-2'-oxo-3,4-dihydro-1H-spiro[naphthalene-2,3'-pyrrolidine]-6-carboxamide (I-64);
(S)-1'-cinnamyl-N-hydroxy-2'-oxo-3,4-dihydro-1H-spiro[naphthalene-2,3'-pyrrolidine]-6-carboxamide (I-65);

(S)-N-hydroxy-1'-(2-methylbenzyl)-2'-oxo-3,4-dihydro-1H-spiro[naphthalene-2,3'-pyrrolidine]-6-carboxamide (I-66);

(S)-N-hydroxy-2'-oxo-1'-(2-(trifluoromethyl)benzyl)-3,4-dihydro-1H-spiro[naphthalene-2,3'-pyrrolidine]-6-carboxamide (I-67);

(S)-1'-(2-chlorobenzyl)-N-hydroxy-2'-oxo-3,4-dihydro-1H-spiro[naphthalene-2,3'-pyrrolidine]-6-carboxamide (I-68);

(S)-N-hydroxy-2'-oxo-1'-(2-(trifluoromethoxy)benzyl)-3,4-dihydro-1H-spiro[naphthalene-2,3'-pyrrolidine]-6-carboxamide (I-69);

(S)-1'-(benzo[c][1,2,5]oxadiazol-5-ylmethyl)-N-hydroxy-2'-oxo-3,4-dihydro-1H-spiro[naphthalene-2,3'-pyrrolidine]-6-carboxamide (I-70);

(S)-N-hydroxy-1'-(2-morpholino-2-oxoethyl)-2'-oxo-3,4-dihydro-1H-spiro[naphthalene-2,3'-pyrrolidine]-6-carboxamide (I-71);

(S)-N-hydroxy-1'-(2-methoxybenzyl)-2'-oxo-3,4-dihydro-1H-spiro[naphthalene-2,3'-pyrrolidine]-6-carboxamide (I-72);

(S)-N-hydroxy-1'-((1-isopropyl-1H-benzo[d]imidazol-2-yl)methyl)-2'-oxo-3,4-dihydro-1H-spiro[naphthalene-2,3'-pyrrolidine]-6-carboxamide (I-73);

(S)-1'-(2,5-dichlorobenzyl)-N-hydroxy-2'-oxo-3,4-dihydro-1H-spiro[naphthalene-2,3'-pyrrolidine]-6-carboxamide (I-74);

(S)-1'-(2,6-dichlorobenzyl)-N-hydroxy-2'-oxo-3,4-dihydro-1H-spiro[naphthalene-2,3'-pyrrolidine]-6-carboxamide (I-75);

(S)-1'-benzyl-N-hydroxy-2'-oxo-3,4-dihydro-1H-spiro[naphthalene-2,3'-pyrrolidine]-6-carboxamide (I-76);

(S)-N-hydroxy-1'-(3-methoxybenzyl)-2'-oxo-3,4-dihydro-1H-spiro[naphthalene-2,3'-pyrrolidine]-6-carboxamide (I-77);

(S)-N-hydroxy-2'-oxo-1'-(pyridin-2-ylmethyl)-3,4-dihydro-1H-spiro[naphthalene-2,3'-pyrrolidine]-6-carboxamide (I-78);

(S)-1'-(3-fluorobenzyl)-N-hydroxy-2'-oxo-3,4-dihydro-1H-spiro[naphthalene-2,3'-pyrrolidine]-6-carboxamide (I-79);

(S)-N-hydroxy-2'-oxo-1'-(4-(trifluoromethoxy)benzyl)-3,4-dihydro-1H-spiro[naphthalene-2,3'-pyrrolidine]-6-carboxamide (I-80);

(S)-1'-(3-chlorobenzyl)-N-hydroxy-2'-oxo-3,4-dihydro-1H-spiro[naphthalene-2,3'-pyrrolidine]-6-carboxamide (I-81);

(S)-1'-(4-chlorobenzyl)-N-hydroxy-2'-oxo-3,4-dihydro-1H-spiro[naphthalene-2,3'-pyrrolidine]-6-carboxamide (I-82);

(S)-N-hydroxy-1'-(4-methoxybenzyl)-2'-oxo-3,4-dihydro-1H-spiro[naphthalene-2,3'-pyrrolidine]-6-carboxamide (I-83);

(S)-1'-(2-fluorobenzyl)-N-hydroxy-2'-oxo-3,4-dihydro-1H-spiro[naphthalene-2,3'-pyrrolidine]-6-carboxamide (I-84);

(S)-1'-(4-(tert-butyl)benzyl)-N-hydroxy-2'-oxo-3,4-dihydro-1H-spiro[naphthalene-2,3'-pyrrolidine]-6-carboxamide (I-85);

(S)-N-hydroxy-1'-(naphthalen-2-ylmethyl)-2'-oxo-3,4-dihydro-1H-spiro[naphthalene-2,3'-pyrrolidine]-6-carboxamide (I-86);

(S)-1'-(2-(difluoromethoxy)benzyl)-N-hydroxy-2'-oxo-3,4-dihydro-1H-spiro[naphthalene-2,3'-pyrrolidine]-6-carboxamide (I-87);

(R)-N-hydroxy-1'-(4-(methylsulfonyl)benzyl)-2'-oxo-3,4-dihydro-1H-spiro[naphthalene-2,3'-pyrrolidine]-6-carboxamide (I-88);

(R)-N-hydroxy-1'-(naphthalen-1-yl)-2'-oxo-3,4-dihydro-1H-spiro[naphthalene-2,3'-pyrrolidine]-6-carboxamide (I-89);

(R)-1'-(3-fluoro-4-methoxyphenyl)-N-hydroxy-2'-oxo-3,4-dihydro-1H-spiro[naphthalene-2,3'-pyrrolidine]-6-carboxamide (I-90);

(R)-1'-(benzo[d][1,3]dioxol-5-yl)-N-hydroxy-2'-oxo-3,4-dihydro-1H-spiro[naphthalene-2,3'-pyrrolidine]-6-carboxamide (I-91);

(R)-N-hydroxy-1'-(3-(methylthio)phenyl)-2'-oxo-3,4-dihydro-1H-spiro[naphthalene-2,3'-pyrrolidine]-6-carboxamide (I-92);

(R)-1'-(4-(dimethylamino)phenyl)-N-hydroxy-2'-oxo-3,4-dihydro-1H-spiro[naphthalene-2,3'-pyrrolidine]-6-carboxamide (I-93);

(R)-N-hydroxy-1'-(6-isopropylpyridin-3-yl)-2'-oxo-3,4-dihydro-1H-spiro[naphthalene-2,3'-pyrrolidine]-6-carboxamide (I-94);

(R)-N-hydroxy-2'-oxo-1'-(quinolin-3-yl)-3,4-dihydro-1H-spiro[naphthalene-2,3'-pyrrolidine]-6-carboxamide (I-95);

(R)-1'-(2,3-dihydrobenzofuran-7-yl)-N-hydroxy-2'-oxo-3,4-dihydro-1H-spiro[naphthalene-2,3'-pyrrolidine]-6-carboxamide (I-96);

(R)-1'-(6-(tert-butylamino)pyrimidin-4-yl)-N-hydroxy-2'-oxo-3,4-dihydro-1H-spiro[naphthalene-2,3'-pyrrolidine]-6-carboxamide (I-97);

(R)-1'-(1,3-dimethyl-1H-pyrazol-4-yl)-N-hydroxy-2'-oxo-3,4-dihydro-1H-spiro[naphthalene-2,3'-pyrrolidine]-6-carboxamide (I-98);

(R)-N-hydroxy-1'-(imidazo[1,2-a]pyridin-6-yl)-2'-oxo-3,4-dihydro-1H-spiro[naphthalene-2,3'-pyrrolidine]-6-carboxamide (I-99);

(S)-1'-(2,4-dimethylphenyl)-N-hydroxy-2'-oxo-3,4-dihydro-1H-spiro[naphthalene-2,3'-pyrrolidine]-6-carboxamide (I-100);

(S)-N-hydroxy-1'-(6-isopropylpyridin-3-yl)-2'-oxo-3,4-dihydro-1H-spiro[naphthalene-2,3'-pyrrolidine]-6-carboxamide (I-101);

(S)-N-hydroxy-2'-oxo-1'-(quinolin-3-yl)-3,4-dihydro-1H-spiro[naphthalene-2,3'-pyrrolidine]-6-carboxamide (I-102);

(S)-N-hydroxy-1'-(imidazo[1,2-a]pyridin-6-yl)-2'-oxo-3,4-dihydro-1H-spiro[naphthalene-2,3'-pyrrolidine]-6-carboxamide (I-103);

(R)-N-hydroxy-1'-methyl-2'-oxo-3,4-dihydro-1H-spiro[naphthalene-2,3'-pyrrolidine]-6-carboxamide (I-104);

(S)-N-hydroxy-1'-methyl-2'-oxo-3,4-dihydro-1H-spiro[naphthalene-2,3'-pyrrolidine]-6-carboxamide (I-105);

(R)-N-hydroxy-2'-oxo-1'-(4-((trifluoromethyl)sulfonyl)benzyl)-3,4-dihydro-1H-spiro[naphthalene-2,3'-pyrrolidine]-6-carboxamide (I-106);

(S)-N-hydroxy-2'-oxo-1'-(4-((trifluoromethyl)sulfonyl)benzyl)-3,4-dihydro-1H-spiro[naphthalene-2,3'-pyrrolidine]-6-carboxamide (I-107);

(R)-N-hydroxy-1'-(3-methoxyphenyl)-2'-oxo-3,4-dihydro-1H-spiro[naphthalene-2,3'-pyrrolidine]-6-carboxamide (I-108);

(R)-1'-cyclopropyl-N-hydroxy-2'-oxo-3,4-dihydro-1H-spiro[naphthalene-2,3'-pyrrolidine]-6-carboxamide (I-109);

(R)-1'-(5-fluoropyridin-3-yl)-N-hydroxy-2'-oxo-3,4-dihydro-1H-spiro[naphthalene-2,3'-pyrrolidine]-6-carboxamide (I-110);

(R)-N-hydroxy-1'-(2-methoxyphenyl)-2'-oxo-3,4-dihydro-1H-spiro[naphthalene-2,3'-pyrrolidine]-6-carboxamide (I-111);
(R)-1'-(3-cyanophenyl)-N-hydroxy-2'-oxo-3,4-dihydro-1H-spiro[naphthalene-2,3'-pyrrolidine]-6-carboxamide (I-112);
(R)-1'-(3-fluorophenyl)-N-hydroxy-2'-oxo-3,4-dihydro-1H-spiro[naphthalene-2,3'-pyrrolidine]-6-carboxamide (I-113);
(R)-N-hydroxy-1'-(6-methoxypyridin-3-yl)-2'-oxo-3,4-dihydro-1H-spiro[naphthalene-2,3'-pyrrolidine]-6-carboxamide (I-114);
(S)-N-hydroxy-1'-(2-methoxyphenyl)-2'-oxo-3,4-dihydro-1H-spiro[naphthalene-2,3'-pyrrolidine]-6-carboxamide (I-115);
(S)-1'-(3-cyanophenyl)-N-hydroxy-2'-oxo-3,4-dihydro-1H-spiro[naphthalene-2,3'-pyrrolidine]-6-carboxamide (I-116);
(S)-1'-(3-fluorophenyl)-N-hydroxy-2'-oxo-3,4-dihydro-1H-spiro[naphthalene-2,3'-pyrrolidine]-6-carboxamide (I-117);
(S)-N-hydroxy-1'-(6-methoxypyridin-3-yl)-2'-oxo-3,4-dihydro-1H-spiro[naphthalene-2,3'-pyrrolidine]-6-carboxamide (I-118);
(R)-1'-(3,4-difluorophenyl)-N-hydroxy-2'-oxo-3,4-dihydro-1H-spiro[naphthalene-2,3'-pyrrolidine]-6-carboxamide (I-119);
(R)-1'-(4-fluorophenyl)-N-hydroxy-2'-oxo-3,4-dihydro-1H-spiro[naphthalene-2,3'-pyrrolidine]-6-carboxamide (I-120);
(R)-1'-(2-fluorophenyl)-N-hydroxy-2'-oxo-3,4-dihydro-1H-spiro[naphthalene-2,3'-pyrrolidine]-6-carboxamide (I-121);
(S)-N-hydroxy-1'-(oxetan-3-ylmethyl)-2'-oxo-3,4-dihydro-1H-spiro[naphthalene-2,3'-pyrrolidine]-6-carboxamide (I-122);
(R)-1'-(2,3-difluorophenyl)-N-hydroxy-2'-oxo-3,4-dihydro-1H-spiro[naphthalene-2,3'-pyrrolidine]-6-carboxamide (I-123);
(R)-N-hydroxy-1'-(4-methoxyphenyl)-2'-oxo-3,4-dihydro-1H-spiro[naphthalene-2,3'-pyrrolidine]-6-carboxamide (I-124);
(R)-1'-(2-fluoro-3-methoxyphenyl)-N-hydroxy-2'-oxo-3,4-dihydro-1H-spiro[naphthalene-2,3'-pyrrolidine]-6-carboxamide (I-125);
(S)-1'-(2-fluoro-3-methoxyphenyl)-N-hydroxy-2'-oxo-3,4-dihydro-1H-spiro[naphthalene-2,3'-pyrrolidine]-6-carboxamide (I-126);
(S)-1'-(2-fluoro-4-methoxyphenyl)-N-hydroxy-2'-oxo-3,4-dihydro-1H-spiro[naphthalene-2,3'-pyrrolidine]-6-carboxamide (I-127);
(R)-1'-(4-fluoro-3-methoxyphenyl)-N-hydroxy-2'-oxo-3,4-dihydro-1H-spiro[naphthalene-2,3'-pyrrolidine]-6-carboxamide (I-128);
(S)-1'-(4-fluoro-3-methoxyphenyl)-N-hydroxy-2'-oxo-3,4-dihydro-1H-spiro[naphthalene-2,3'-pyrrolidine]-6-carboxamide (I-129);
(S)-1'-(5-chloropyridin-2-yl)-N-hydroxy-2'-oxo-3,4-dihydro-1H-spiro[naphthalene-2,3'-pyrrolidine]-6-carboxamide (I-130);
(R)-N-hydroxy-1'-(2-methylpyridin-3-yl)-2'-oxo-3,4-dihydro-1H-spiro[naphthalene-2,3'-pyrrolidine]-6-carboxamide (I-131);
(S)-N-hydroxy-1'-(2-methylpyridin-3-yl)-2'-oxo-3,4-dihydro-1H-spiro[naphthalene-2,3'-pyrrolidine]-6-carboxamide (I-132);
(R)-N-hydroxy-1'-(6-methylpyridin-3-yl)-2'-oxo-3,4-dihydro-1H-spiro[naphthalene-2,3'-pyrrolidine]-6-carboxamide (I-133);
(S)-N-hydroxy-1'-(6-methylpyridin-3-yl)-2'-oxo-3,4-dihydro-1H-spiro[naphthalene-2,3'-pyrrolidine]-6-carboxamide (I-134);
(R)-N-hydroxy-1'-(5-methylpyridin-3-yl)-2'-oxo-3,4-dihydro-1H-spiro[naphthalene-2,3'-pyrrolidine]-6-carboxamide (I-135);
(R)-N-hydroxy-1'-(4-methylpyridin-3-yl)-2'-oxo-3,4-dihydro-1H-spiro[naphthalene-2,3'-pyrrolidine]-6-carboxamide (I-136);
(S)-N-hydroxy-1'-(4-methylpyridin-3-yl)-2'-oxo-3,4-dihydro-1H-spiro[naphthalene-2,3'-pyrrolidine]-6-carboxamide (I-137);
(R)-1'-(5-chloropyridin-3-yl)-N-hydroxy-2'-oxo-3,4-dihydro-1H-spiro[naphthalene-2,3'-pyrrolidine]-6-carboxamide (I-138);
(S)-1'-(5-chloropyridin-3-yl)-N-hydroxy-2'-oxo-3,4-dihydro-1H-spiro[naphthalene-2,3'-pyrrolidine]-6-carboxamide (I-139);
(R)-1'-(3-chloropyridin-4-yl)-N-hydroxy-2'-oxo-3,4-dihydro-1H-spiro[naphthalene-2,3'-pyrrolidine]-6-carboxamide (I-140);
(S)-1'-(3-chloropyridin-4-yl)-N-hydroxy-2'-oxo-3,4-dihydro-1H-spiro[naphthalene-2,3'-pyrrolidine]-6-carboxamide (I-141);
(S)-N-hydroxy-1'-(4-methoxypyridin-3-yl)-2'-oxo-3,4-dihydro-1H-spiro[naphthalene-2,3'-pyrrolidine]-6-carboxamide (I-142);
(R)-N-hydroxy-1'-(5-methoxypyridin-3-yl)-2'-oxo-3,4-dihydro-1H-spiro[naphthalene-2,3'-pyrrolidine]-6-carboxamide (I-143);
(S)-N-hydroxy-1'-(5-methoxypyridin-3-yl)-2'-oxo-3,4-dihydro-1H-spiro[naphthalene-2,3'-pyrrolidine]-6-carboxamide (I-144);
(R)-N-hydroxy-1'-(2-methoxypyridin-3-yl)-2'-oxo-3,4-dihydro-1H-spiro[naphthalene-2,3'-pyrrolidine]-6-carboxamide (I-145);
(S)-N-hydroxy-1'-(2-methoxypyridin-3-yl)-2'-oxo-3,4-dihydro-1H-spiro[naphthalene-2,3'-pyrrolidine]-6-carboxamide (I-146);
(S)-1'-(2-fluoro-5-methoxyphenyl)-N-hydroxy-2'-oxo-3,4-dihydro-1H-spiro[naphthalene-2,3'-pyrrolidine]-6-carboxamide (I-147);
(S)-1'-(3-fluoro-5-methoxyphenyl)-N-hydroxy-2'-oxo-3,4-dihydro-1H-spiro[naphthalene-2,3'-pyrrolidine]-6-carboxamide (I-148);
(R)-N-hydroxy-1'-(2-methoxypyridin-4-yl)-2'-oxo-3,4-dihydro-1H-spiro[naphthalene-2,3'-pyrrolidine]-6-carboxamide (I-149);
(S)-N-hydroxy-1'-(2-methoxypyridin-4-yl)-2'-oxo-3,4-dihydro-1H-spiro[naphthalene-2,3'-pyrrolidine]-6-carboxamide (I-150);
(R)-1'-(6-(dimethylamino)pyridin-3-yl)-N-hydroxy-2'-oxo-3,4-dihydro-1H-spiro[naphthalene-2,3'-pyrrolidine]-6-carboxamide (I-151);
(S)-1'-(6-(dimethylamino)pyridin-3-yl)-N-hydroxy-2'-oxo-3,4-dihydro-1H-spiro[naphthalene-2,3'-pyrrolidine]-6-carboxamide (I-152);
(S)-1'-(5-fluoropyridin-3-yl)-N-hydroxy-2'-oxo-3,4-dihydro-1H-spiro[naphthalene-2,3'-pyrrolidine]-6-carboxamide (I-153);
(S)-1'-(4-fluorophenyl)-N-hydroxy-2'-oxo-3,4-dihydro-1H-spiro[naphthalene-2,3'-pyrrolidine]-6-carboxamide (I-154);

(S)-1'-(3,4-difluorophenyl)-N-hydroxy-2'-oxo-3,4-dihydro-1H-spiro[naphthalene-2,3'-pyrrolidine]-6-carboxamide (I-155);
(S)-1'-(2,3-difluorophenyl)-N-hydroxy-2'-oxo-3,4-dihydro-1H-spiro[naphthalene-2,3'-pyrrolidine]-6-carboxamide (I-156);
(S)-1'-(2-fluorophenyl)-N-hydroxy-2'-oxo-3,4-dihydro-1H-spiro[naphthalene-2,3'-pyrrolidine]-6-carboxamide (I-157);
(S)-N-hydroxy-1'-(3-methoxyphenyl)-2'-oxo-3,4-dihydro-1H-spiro[naphthalene-2,3'-pyrrolidine]-6-carboxamide (I-158);
(R)-N-hydroxy-1'-isobutyl-2'-oxo-3,4-dihydro-1H-spiro[naphthalene-2,3'-pyrrolidine]-6-carboxamide (I-159);
(S)-N-hydroxy-1'-isobutyl-2'-oxo-3,4-dihydro-1H-spiro[naphthalene-2,3'-pyrrolidine]-6-carboxamide (I-160);
(R)-1'-ethyl-N-hydroxy-2'-oxo-3,4-dihydro-1H-spiro[naphthalene-2,3'-pyrrolidine]-6-carboxamide (I-161);
(S)-1'-ethyl-N-hydroxy-2'-oxo-3,4-dihydro-1H-spiro[naphthalene-2,3'-pyrrolidine]-6-carboxamide (I-162);
(R)-1'-cyclopentyl-N-hydroxy-2'-oxo-3,4-dihydro-1H-spiro[naphthalene-2,3'-pyrrolidine]-6-carboxamide (I-163);
(S)-1'-cyclopentyl-N-hydroxy-2'-oxo-3,4-dihydro-H-spiro[naphthalene-2,3'-pyrrolidine]-6-carboxamide (I-164);
(R)-N-hydroxy-2'-oxo-1'-(2,2,2-trifluoroethyl)-3,4-dihydro-1H-spiro[naphthalene-2,3'-pyrrolidine]-6-carboxamide (I-165);
(S)-N-hydroxy-2'-oxo-1'-(2,2,2-trifluoroethyl)-3,4-dihydro-1H-spiro[naphthalene-2,3'-pyrrolidine]-6-carboxamide (I-166);
(R)-1'-(2, 5-difluorophenyl)-N-hydroxy-2'-oxo-3,4-dihydro-1H-spiro[naphthalene-2,3'-pyrrolidine]-6-carboxamide (I-167);
(R)-N-hydroxy-1'-(1-methyl-1H-pyrazol-4-yl)-2'-oxo-3,4-dihydro-1H-spiro[naphthalene-2,3'-pyrrolidine]-6-carboxamide (I-168);
(S)-1'-(2,5-difluorophenyl)-N-hydroxy-2'-oxo-3,4-dihydro-1H-spiro[naphthalene-2,3'-pyrrolidine]-6-carboxamide (I-169);
(S)-N-hydroxy-1'-(1-methyl-1H-pyrazol-4-yl)-2'-oxo-3,4-dihydro-1H-spiro[naphthalene-2,3'-pyrrolidine]-6-carboxamide (I-170);
(R)-1'-cyclobutyl-N-hydroxy-2'-oxo-3,4-dihydro-1H-spiro[naphthalene-2,3'-pyrrolidine]-6-carboxamide (I-171);
(S)-1'-cyclobutyl-N-hydroxy-2'-oxo-3,4-dihydro-1H-spiro[naphthalene-2,3'-pyrrolidine]-6-carboxamide (I-172);
(S)-1'-(4-cyanophenyl)-N-hydroxy-2'-oxo-3,4-dihydro-1H-spiro[naphthalene-2,3'-pyrrolidine]-6-carboxamide (I-173);
(S)-1'-(2-cyanophenyl)-N-hydroxy-2'-oxo-3,4-dihydro-1H-spiro[naphthalene-2,3'-pyrrolidine]-6-carboxamide (I-174);
(R)-1'-(2-cyanophenyl)-N-hydroxy-2'-oxo-3,4-dihydro-1H-spiro[naphthalene-2,3'-pyrrolidine]-6-carboxamide (I-175);
1'-benzyl-N-hydroxy-2'-oxo-3,4-dihydro-1H-spiro[naphthalene-2,3'-piperidine]-6-carboxamide (I-176);
N-hydroxy-2'-oxo-3,4-dihydro-1H-spiro[naphthalene-2,3'-piperidine]-6-carboxamide (I-177);
N-hydroxy-1'-methyl-2'-oxo-3,4-dihydro-1H-spiro[naphthalene-2,3'-piperidine]-6-carboxamide (I-178);
(R)-N-hydroxy-1'-methyl-2'-oxo-3,4-dihydro-1H-spiro[naphthalene-2,3'-piperidine]-6-carboxamide (I-179);
(S)-N-hydroxy-1'-methyl-2'-oxo-3,4-dihydro-1H-spiro[naphthalene-2,3'-piperidine]-6-carboxamide (I-180);
(R)-N-hydroxy-2'-oxo-1'-phenyl-3,4-dihydro-1H-spiro[naphthalene-2,3'-piperidine]-6-carboxamide (I-181);
(S)-N-hydroxy-2'-oxo-1'-phenyl-3,4-dihydro-1H-spiro[naphthalene-2,3'-piperidine]-6-carboxamide (I-182);
(S)-1'-cyclopropyl-N-hydroxy-2'-oxo-3,4-dihydro-1H-spiro[naphthalene-2,3'-piperidine]-6-carboxamide (I-183);
(S)-1'-ethyl-N-hydroxy-2'-oxo-3,4-dihydro-1H-spiro[naphthalene-2,3'-piperidine]-6-carboxamide (I-184);
(R)-1'-(cyclobutylmethyl)-N-hydroxy-2'-oxo-3,4-dihydro-1H-spiro[naphthalene-2,3'-piperidine]-6-carboxamide (I-185);
(S)-1'-(cyclobutylmethyl)-N-hydroxy-2'-oxo-3,4-dihydro-1H-spiro[naphthalene-2,3'-piperidine]-6-carboxamide (I-186);
(R)-N-hydroxy-1'-(3-methoxypropyl)-2'-oxo-3,4-dihydro-1H-spiro[naphthalene-2,3'-piperidine]-6-carboxamide (I-187);
(S)-N-hydroxy-1'-(3-methoxypropyl)-2'-oxo-3,4-dihydro-1H-spiro[naphthalene-2,3'-piperidine]-6-carboxamide (I-188);
(R)-N-hydroxy-1'-isobutyl-2'-oxo-3,4-dihydro-1H-spiro[naphthalene-2,3'-piperidine]-6-carboxamide (I-189);
(S)-N-hydroxy-1'-isobutyl-2'-oxo-3,4-dihydro-1H-spiro[naphthalene-2,3'-piperidine]-6-carboxamide (I-190);
(R)-N-hydroxy-1'-isopropyl-2'-oxo-3,4-dihydro-1H-spiro[naphthalene-2,3'-piperidine]-6-carboxamide (I-191);
(S)-N-hydroxy-1'-isopropyl-2'-oxo-3,4-dihydro-1H-spiro[naphthalene-2,3'-piperidine]-6-carboxamide (I-192);
(R)-1'-cyclopropyl-N-hydroxy-2'-oxo-3,4-dihydro-1H-spiro[naphthalene-2,3'-piperidine]-6-carboxamide (I-193);
(R)-1'-ethyl-N-hydroxy-2'-oxo-3,4-dihydro-1H-spiro[naphthalene-2,3'-piperidine]-6-carboxamide (I-194);
(S)-N-hydroxy-1'-(oxetan-3-ylmethyl)-2'-oxo-3,4-dihydro-1H-spiro[naphthalene-2,3'-piperidine]-6-carboxamide (I-195);
(R)-N-hydroxy-1'-(oxetan-3-ylmethyl)-2'-oxo-3,4-dihydro-1H-spiro[naphthalene-2,3'-piperidine]-6-carboxamide (I-196);
(R)-1'-cyclobutyl-N-hydroxy-2'-oxo-3,4-dihydro-1H-spiro[naphthalene-2,3'-piperidine]-6-carboxamide (I-197);
(S)-1'-cyclobutyl-N-hydroxy-2'-oxo-3,4-dihydro-1H-spiro[naphthalene-2,3'-piperidine]-6-carboxamide (I-198);
(R)-1'-cyclopentyl-N-hydroxy-2'-oxo-3,4-dihydro-1H-spiro[naphthalene-2,3'-piperidine]-6-carboxamide (I-199);
(S)-1'-cyclopentyl-N-hydroxy-2'-oxo-3,4-dihydro-1H-spiro[naphthalene-2,3'-piperidine]-6-carboxamide (I-200);
(R)-N-hydroxy-1'-methyl-5'-oxo-3,4-dihydro-1H-spiro[naphthalene-2,3'-pyrrolidine]-6-carboxamide (I-201);
(S)-N-hydroxy-1'-methyl-5'-oxo-3,4-dihydro-1H-spiro[naphthalene-2,3'-pyrrolidine]-6-carboxamide (I-202);
(R)-N-hydroxy-5'-oxo-1'-phenyl-3,4-dihydro-1H-spiro[naphthalene-2,3'-pyrrolidine]-6-carboxamide (I-203);
(S)-N-hydroxy-5'-oxo-1'-phenyl-3,4-dihydro-1H-spiro[naphthalene-2,3'-pyrrolidine]-6-carboxamide (I-204);
(R)-1'-(cyclobutylmethyl)-N-hydroxy-5'-oxo-3,4-dihydro-1H-spiro[naphthalene-2,3'-pyrrolidine]-6-carboxamide (I-205);
(R)-1'-ethyl-N-hydroxy-5'-oxo-3,4-dihydro-1H-spiro[naphthalene-2,3'-pyrrolidine]-6-carboxamide (I-206);

(R)-N-hydroxy-1'-isobutyl-5'-oxo-3,4-dihydro-1H-spiro[naphthalene-2,3'-pyrrolidine]-6-carboxamide (I-207);
(R)-N-hydroxy-1'-isopropyl-5'-oxo-3,4-dihydro-1H-spiro[naphthalene-2,3'-pyrrolidine]-6-carboxamide (I-208);
(R)-1'-cyclopropyl-N-hydroxy-5'-oxo-3,4-dihydro-H-spiro[naphthalene-2,3'-pyrrolidine]-6-carboxamide (I-209);
(S)-1'-(cyclobutylmethyl)-N-hydroxy-5'-oxo-3,4-dihydro-1H-spiro[naphthalene-2,3'-pyrrolidine]-6-carboxamide (I-210);
(S)-1'-ethyl-N-hydroxy-5'-oxo-3,4-dihydro-1H-spiro[naphthalene-2,3'-pyrrolidine]-6-carboxamide (I-211);
(S)-N-hydroxy-1'-isobutyl-5'-oxo-3,4-dihydro-1H-spiro[naphthalene-2,3'-pyrrolidine]-6-carboxamide (I-212);
(S)-N-hydroxy-1'-isopropyl-5'-oxo-3,4-dihydro-1H-spiro[naphthalene-2,3'-pyrrolidine]-6-carboxamide (I-213);
(S)-1'-cyclopropyl-N-hydroxy-5'-oxo-3,4-dihydro-1H-spiro[naphthalene-2,3'-pyrrolidine]-6-carboxamide (I-214);
(R)-N-hydroxy-1'-(oxetan-3-ylmethyl)-5'-oxo-3,4-dihydro-1H-spiro[naphthalene-2,3'-pyrrolidine]-6-carboxamide (I-215);
(R)-1'-benzyl-N-hydroxy-5'-oxo-3,4-dihydro-1H-spiro[naphthalene-2,3'-pyrrolidine]-6-carboxamide (I-216);
(S)-N-hydroxy-1'-(oxetan-3-ylmethyl)-5'-oxo-3,4-dihydro-1H-spiro[naphthalene-2,3'-pyrrolidine]-6-carboxamide (I-217);
(S)-1'-benzyl-N-hydroxy-5'-oxo-3,4-dihydro-1H-spiro[naphthalene-2,3'-pyrrolidine]-6-carboxamide (I-218);
(R)-N-hydroxy-1'-(3-methoxypropyl)-5'-oxo-3,4-dihydro-1H-spiro[naphthalene-2,3'-pyrrolidine]-6-carboxamide (I-219);
(R)-N-hydroxy-5'-oxo-1'-(2,2,2-trifluoroethyl)-3,4-dihydro-1H-spiro[naphthalene-2,3'-pyrrolidine]-6-carboxamide (I-220);
(R)-N-hydroxy-5'-oxo-1'-(pyridin-3-yl)-3,4-dihydro-1H-spiro[naphthalene-2,3'-pyrrolidine]-6-carboxamide (I-221);
(S)-N-hydroxy-1'-(3-methoxypropyl)-5'-oxo-3,4-dihydro-1H-spiro[naphthalene-2,3'-pyrrolidine]-6-carboxamide (I-222);
(S)-N-hydroxy-5'-oxo-1'-(2,2,2-trifluoroethyl)-3,4-dihydro-1H-spiro[naphthalene-2,3'-pyrrolidine]-6-carboxamide (I-223);
(S)-N-hydroxy-5'-oxo-1'-(pyridin-3-yl)-3,4-dihydro-1H-spiro[naphthalene-2,3'-pyrrolidine]-6-carboxamide (I-224);
(R)-N-hydroxy-1'-(2-methylbenzyl)-5'-oxo-3,4-dihydro-1H-spiro[naphthalene-2,3'-pyrrolidine]-6-carboxamide (I-225);
(R)-N-hydroxy-5'-oxo-1'-(pyridin-3-ylmethyl)-3,4-dihydro-1H-spiro[naphthalene-2,3'-pyrrolidine]-6-carboxamide (I-226);
(R)-1'-(4-fluorophenyl)-N-hydroxy-5'-oxo-3,4-dihydro-1H-spiro[naphthalene-2,3'-pyrrolidine]-6-carboxamide (I-227);
(R)-N-hydroxy-5'-oxo-1'-(pyridin-4-yl)-3,4-dihydro-1H-spiro[naphthalene-2,3'-pyrrolidine]-6-carboxamide (I-228);
(R)-N-hydroxy-5'-oxo-1'-(pyridin-2-yl)-3,4-dihydro-1H-spiro[naphthalene-2,3'-pyrrolidine]-6-carboxamide (I-229);
N-hydroxy-2'-oxo-1'-(pyridin-4-ylmethyl)spiro[chromane-2,3'-pyrrolidine]-6-carboxamide (I-230);
N-hydroxy-2'-oxo-1'-phenylspiro[chromane-2,3'-pyrrolidine]-6-carboxamide (I-231);
1'-benzyl-N-hydroxy-2'-oxospiro[chromane-2,3'-pyrrolidine]-6-carboxamide (I-232);
N-hydroxy-2'-oxo-1'-(pyridin-3-yl)spiro[chromane-2,3'-pyrrolidine]-6-carboxamide (I-233);
N-hydroxy-2'-oxo-1'-((tetrahydro-2H-pyran-4-yl)methyl)spiro[chromane-2,3'-pyrrolidine]-6-carboxamide (I-234);
N-hydroxy-1'-isopropyl-2'-oxospiro[chromane-2,3'-pyrrolidine]-6-carboxamide (I-235);
N-hydroxy-2'-oxospiro[chromane-2,3'-pyrrolidine]-6-carboxamide (I-236);
N-hydroxy-1'-methyl-2'-oxospiro[chromane-2,3'-pyrrolidine]-6-carboxamide (I-237);
N-hydroxy-2-oxo-1-phenylspiro[pyrrolidine-3,2'-thiochromane]-6'-carboxamide 1',1'-dioxide (I-238);
1-benzyl-N-hydroxy-2-oxospiro[pyrrolidine-3,2'-thiochromane]-6'-carboxamide 1',1'-dioxide (I-239);
N-hydroxy-2-oxo-1-(pyridin-3-yl)spiro[pyrrolidine-3,2'-thiochromane]-6'-carboxamide 1',1'-dioxide (I-240);
N-hydroxy-2-oxo-1-((tetrahydro-2H-pyran-4-yl)methyl)spiro[pyrrolidine-3,2'-thiochromane]-6'-carboxamide 1',1'-dioxide (I-241);
N-hydroxy-2-oxo-1-(pyridin-4-ylmethyl)spiro[pyrrolidine-3,2'-thiochromane]-6'-carboxamide 1',1'-dioxide (I-242);
N-hydroxy-2-oxospiro[pyrrolidine-3,2'-thiochromane]-6'-carboxamide 1',1'-dioxide (I-243); or
N-hydroxy-1-methyl-2-oxospiro[pyrrolidine-3,2'-thiochromane]-6'-carboxamide 1',1'-dioxide (I-244).

23. A compound of claim 15 selected from:
N-hydroxy-1'-(4-methoxybenzyl)spiro[chromane-2,4'-piperidine]-6-carboxamide (II-1);
1'-(((1H-benzo[d]imidazol-2-yl)methyl)-N-hydroxyspiro[chromane-2,4'-piperidine]-6-carboxamide (II-2);
1'-(cyclohexanecarbonyl)-N-hydroxyspiro[chromane-2,4'-piperidine]-6-carboxamide (II-3);
N-hydroxy-1'-(4-methoxybenzoyl)spiro[chromane-2,4'-piperidine]-6-carboxamide (II-4);
N-hydroxy-1'-(((4-methoxyphenyl)sulfonyl)spiro[chromane-2,4'-piperidine]-6-carboxamide (II-5);
1'-(cyclohexylsulfonyl)-N-hydroxyspiro[chromane-2,4'-piperidine]-6-carboxamide (II-6);
N6-hydroxy-N1'-phenylspiro[chromane-2,4'-piperidine]-1',6-dicarboxamide (II-7);
1'-cyclohexyl-N-hydroxyspiro[chromane-2,4'-piperidine]-6-carboxamide (II-8); or
N-hydroxy-1'-(2',3',5',6'-tetrahydrospiro[indoline-3,4'-pyran]-1-carbonyl)spiro[chromane-2,4'-piperidine]-6-carboxamide (II-9).

24. A compound of claim 1 selected from:
N-hydroxy-1'-methyl-3,4-dihydro-1H-spiro[naphthalene-2,3'-piperidine]-6-carboxamide (I-245);
N-hydroxy-1-methyl-3',4'-dihydro-1'H-spiro[azepane-3,2'-naphthalene]-6'-carboxamide (I-246);
N-hydroxy-1-methyl-3',4'-dihydro-1'H-spiro[azocane-3,2'-naphthalene]-6'-carboxamide (I-247);
N-hydroxy-1-methyl-2-oxo-3',4'-dihydro-1'H-spiro[azepane-3,2'-naphthalene]-6'-carboxamide (I-248);
N-hydroxy-1-methyl-2-oxo-3',4'-dihydro-1'H-spiro[azocane-3,2'-naphthalene]-6'-carboxamide (I-249);
N-hydroxy-1'-methyl-6'-oxo-3,4-dihydro-1H-spiro[naphthalene-2,3'-piperidine]-6-carboxamide (I-250);
N-hydroxy-1-methyl-7-oxo-3',4'-dihydro-1'H-spiro[azepane-3,2'-naphthalene]-6'-carboxamide (I-251);
N-hydroxy-1-methyl-8-oxo-3',4'-dihydro-1'H-spiro[azocane-3,2'-naphthalene]-6'-carboxamide (I-252);

N-hydroxy-1'-methyl-2'-oxospiro[chromane-2,3'-piperidine]-6-carboxamide (I-253);

N-hydroxy-1-methyl-2-oxospiro[azepane-3,2'-chromane]-6'-carboxamide (I-254);

N-hydroxy-1-methyl-2-oxospiro[azocane-3,2'-chromane]-6'-carboxamide (I-255);

N-hydroxy-1-methyl-2-oxospiro[piperidine-3,2'-thiochromane]-6'-carboxamide 1',1'-dioxide (I-256);

N-hydroxy-1-methyl-2-oxospiro[azepane-3,2'-thiochromane]-6'-carboxamide 1',1'-dioxide (I-257); or N-hydroxy-1-methyl-2-oxospiro[azocane-3,2'-thiochromane]-6'-carboxamide 1',1'-dioxide (I-258).

25. A pharmaceutical composition comprising a compound of claim 1 or claim 15 and a pharmaceutically acceptable carrier.

26. A method of treating a cancer selected from melanoma, cutaneous T-cell lymphoma, peripheral T-cell lymphoma, multiple myeloma, leukemia, lung cancer, ovarian cancer, breast cancer, prostate cancer, pancreatic cancer, hepatocellular cancer, renal cancer, squamous cell carcinoma, lymphoma, non-small cell lung cancer, myeloproliferative neoplasm, metastatic solid tumor, myelodysplastic syndrome, urothelial cancer, or myelofibrosis in a subject in need thereof, comprising administering to the subject an effective amount of a compound of claim 1 or claim 15.

27. A method of treating a neurodegenerative disease selected from Alzheimer's, Huntington's, Parkinson's, Amyotrophic Lateral Sclerosis, Charcot-Marie-Tooth Disease, depression, Rett Syndrome, or spinal muscular atrophy in a subject in need thereof, comprising administering to the subject an effective amount of a compound of claim 1 or claim 15.

28. A method of treating an immunological disease selected from rheumatoid arthritis, spondylitis arthritis, psoriatic arthritis, psoriasis, multiple sclerosis, systemic lupus erythematosus, inflammatory bowel diseases, graft versus host disease, transplant rejection or fibrotic disease in a subject in need thereof, comprising administering to the subject an effective amount of a compound of claim 1 or claim 15.

29. A method of inhibiting a histone deacetylase, comprising administering to a subject in need thereof a compound of claim 1 or claim 15.

30. The method of claim 29, wherein the compound inhibits a zinc-dependent histone deacetylase.

31. The method of claim 30, wherein the compound inhibits the HDAC6 isozyme zinc-dependent histone deacetylase.

32. The method of claim 26, wherein the lymphoma is selected from B-cell lymphoma or non-Hodgkin's lymphoma.

33. The method of claim 26, wherein the leukemia is selected from acute myeloid leukemia and chronic lymphocytotic leukemia.

* * * * *